US009333272B2

(12) United States Patent
Aime et al.

(10) Patent No.: US 9,333,272 B2
(45) Date of Patent: *May 10, 2016

(54) FIBRIN BINDING PEPTIDE CONJUGATES FOR DIAGNOSTIC AND THERAPEUTIC APPLICATIONS

(75) Inventors: Silvio Aime, Carignano (IT); Linda Chaabane, Ivrea (IT); Luciano Lattuada, Bussero (IT); Vito Lorusso, Bussero (IT); Edmund R. Marinelli, Lawrenceville, NJ (US); Pierfrancesco Morosini, Lodi (IT); Kondareddiar Ramalingam, Dayton, NJ (US); Bo Song, Princeton, NJ (US); Rolf E. Swenson, Princeton, NJ (US); Fulvio Uggeri, Codogno (IT)

(73) Assignee: Bracco Imaging SpA, Milan (IT)

( * ) Notice: Subject to any disclaimer, the term of this patent is extended or adjusted under 35 U.S.C. 154(b) by 791 days.

This patent is subject to a terminal disclaimer.

(21) Appl. No.: 12/448,102

(22) PCT Filed: Dec. 11, 2007

(86) PCT No.: PCT/EP2007/063659
§ 371 (c)(1),
(2), (4) Date: Jun. 8, 2009

(87) PCT Pub. No.: WO2008/071679
PCT Pub. Date: Jun. 19, 2008

(65) Prior Publication Data
US 2010/0202967 A1 Aug. 12, 2010

Related U.S. Application Data

(60) Provisional application No. 60/869,472, filed on Dec. 11, 2006.

(51) Int. Cl.
| *A61K 38/36* | (2006.01) |
| *A61K 49/14* | (2006.01) |
| *A61K 49/00* | (2006.01) |
| *A61K 49/08* | (2006.01) |
| *A61K 49/12* | (2006.01) |
| *C07K 7/06* | (2006.01) |
| *G01N 33/532* | (2006.01) |
| *G01N 33/574* | (2006.01) |
| *G01N 33/86* | (2006.01) |

(52) U.S. Cl.
CPC ............. *A61K 49/14* (2013.01); *A61K 49/0043* (2013.01); *A61K 49/0056* (2013.01); *A61K 49/085* (2013.01); *A61K 49/124* (2013.01); *C07K 7/06* (2013.01); *G01N 33/532* (2013.01); *G01N 33/574* (2013.01); *G01N 33/86* (2013.01); *G01N 2500/04* (2013.01)

(58) Field of Classification Search
None
See application file for complete search history.

(56) References Cited

U.S. PATENT DOCUMENTS

| 5,021,556 A | 6/1991 | Srinivasan |
| 5,075,099 A | 12/1991 | Srinivasan et al. |
| 5,118,797 A | 6/1992 | Jurisson et al. |
| 5,143,718 A * | 9/1992 | Bar-Shalom .................... 424/47 |
| 5,183,653 A | 2/1993 | Linder et al. |
| 5,362,476 A | 11/1994 | Sherry et al. |
| 5,364,613 A | 11/1994 | Sieving et al. |
| 5,367,080 A | 11/1994 | Toner et al. |
| 5,387,409 A | 2/1995 | Nunn et al. |
| 5,409,689 A | 4/1995 | Winchell et al. |
| 5,574,140 A | 11/1996 | Pollack et al. |
| 5,608,110 A | 3/1997 | Ramalingam et al. |
| 5,627,286 A | 5/1997 | Ramalingam et al. |
| 5,656,254 A | 8/1997 | Ramalingam et al. |
| 5,659,041 A | 8/1997 | Pollak et al. |
| 5,662,885 A | 9/1997 | Pollak et al. |
| 5,665,329 A | 9/1997 | Ramalingam et al. |
| 5,688,487 A | 11/1997 | Linder et al. |
| 5,720,934 A | 2/1998 | Dean et al. |
| 5,780,006 A | 7/1998 | Pollak et al. |
| 5,886,142 A | 3/1999 | Thakur et al. |
| 5,910,300 A | 6/1999 | Tournier et al. |
| 5,976,495 A | 11/1999 | Pollak et al. |
| 6,051,207 A | 4/2000 | Klaveness et al. |
| 6,083,485 A | 7/2000 | Licha et al. |

(Continued)

FOREIGN PATENT DOCUMENTS

| JP | 2003-508027 A | 3/2003 |
| JP | 2004-523514 A | 8/2004 |

(Continued)

OTHER PUBLICATIONS

Mosley et al ('Determination of the minimum polypeptide lengths of the functionally active sites of human interleukins 1alpha and 1beta' PNAS v84 Jul. 1987 pp. 4572-4576).*
Wang et al ('A systematic assessment of MHC class II peptide binding predictions and evaluation of a consensus approach' PLOS computational biology v4(4) 2008 pp. 1-10).*
'Definition of Moiety' retrieved from http://chemistry.about.com/od/chemistryglossary/g/Moiety-Definition.htm on Aug. 11, 2014, 1 page.*
Pao et al ('Effect of serine o-glycosylation on cis-trans proline isomerization' Biochemical and Biophysical Research Communications v219 1996 pp. 157-162).*
Registry No. 147342-61-8 (Registry No. 147342-61-8 entered May 4, 1993, 3 pages).*
PCT Search Report for PCT/EP2007/063659, mail date Apr. 14, 2008.

(Continued)

Primary Examiner — Christina Bradley
Assistant Examiner — Ronald Niebauer
(74) Attorney, Agent, or Firm — Vivicar Law, PLLC

(57) ABSTRACT

The present invention relates to a novel class of diagnostically or therapeutically effective compounds comprising novel peptides able to bind fibrin, to a process for their preparation and to compositions thereof for use in therapy and diagnostics. The compounds of the invention bind, in particular, to fibrin present in the extracellular matrix (EC) of tumor or connective tissue of stroma thus acting as targeting moieties able to bring and successfully bound an active moiety linked thereto to fibrin depositions inside solid tumors.

24 Claims, 13 Drawing Sheets

(56) References Cited

U.S. PATENT DOCUMENTS

| | | | |
|---|---|---|---|
| 6,093,382 | A | 7/2000 | Wedeking et al. |
| 6,143,274 | A | 11/2000 | Tweedle et al. |
| 6,509,324 | B1 | 1/2003 | Franzini et al. |
| 6,534,041 | B1 | 3/2003 | Licha et al. |
| 8,466,107 | B2 * | 6/2013 | Bussat ............ A61K 49/0043 514/13.6 |
| 2003/0143158 | A1 | 7/2003 | Wescott et al. |
| 2006/0034773 | A1 * | 2/2006 | Giovenzana ....... A61K 49/0002 424/9.361 |
| 2006/0148683 | A1 | 7/2006 | McMurry et al. |

FOREIGN PATENT DOCUMENTS

| | | |
|---|---|---|
| WO | 96-23524 A1 | 8/1996 |
| WO | 01-09188 A1 | 2/2001 |
| WO | 02/055544 A2 | 7/2002 |
| WO | 02/055544 A3 | 7/2002 |
| WO | 03-008390 A1 | 1/2003 |

OTHER PUBLICATIONS

PCT Written Opinion for PCT/EP2007/063659, mail date Apr. 14, 2008.
PCT Written Opinion of the International Searching Authority for PCT/US2007/25403, mail date Aug. 5, 2008.
PCT International Search Report for PCT/US2007/25403, mail date Aug. 5, 2008.
PCT International Preliminary Report on Patentability for PCT/US2007/25403, mail date Aug. 12, 2009.
Botnar, Rene M. et al., "In vivo molecular imaging of acute and subacute thrombosis using a fibrin-binding magnetic resonance imaging contrast agent," Circulation, Lippincott Williams & Wilkins, US, vol. 109, No. 16, Jan. 1, 2004, pp. 2023-2029, XP009039993, ISSN: 0009-7322.
Extended European Search Report for EP07862810.4, mail date Mar. 11, 2011.
Moskowitz, Keith A., Biochemistry, vol. 33, No. 44, Nov. 8, 1994, pp. 12937-12944.
Office Action, mail date Oct. 16, 2012 for Japanese application No. 2009-541359.
Office Action, mail date Oct. 16, 2012 for Japanese application No. 2009-540744.
Office Action for European application No. 07848047.2, mail date Jun. 25, 2013.
Office Action for Chinese application No. 200780045892.5, mail date Nov. 29, 2013 (English translation).
Office Action for European application No. 07848047.2, mail date Jul. 3, 2014.
Liu, Shuang et al., "99mTc-Labeled Small Peptides as Diagnostic Radiopharmaceuticals", Chemical Reviews, 1999, vol. 99, No. 9, pp. 2235-2268, American Chemical Society.
Veprek, Pavel et al., "Peptide and Glycopeptide Dendrivers. Part II", Journal of Peptide Science, 1999, vol. 5, pp. 203-220, European Peptide Society and John Wiley & Sons, Ltd.
Office Action-1st for Chinese application No. 200780045892.5, mail date Aug. 3, 2011 (English translation) [B0574 CN-B].
Office Action-2nd for Chinese application No. 200780045892.5, mail date Aug. 3, 2012 (English translation) [B0574 CN-B].
Office Action-3rd for Chinese application No. 200780045892.5, mail date Apr. 28, 2013 (English translation) [B0574 CN-B].
Office Action-5th for Chinese application No. 200780045892.5, mail date Mar. 24, 2014 (English translation) [B0574 CN-B].
Office Action for European application No. 07848047.2, mail date Nov. 9, 2009 [B0574 EP-B].

* cited by examiner

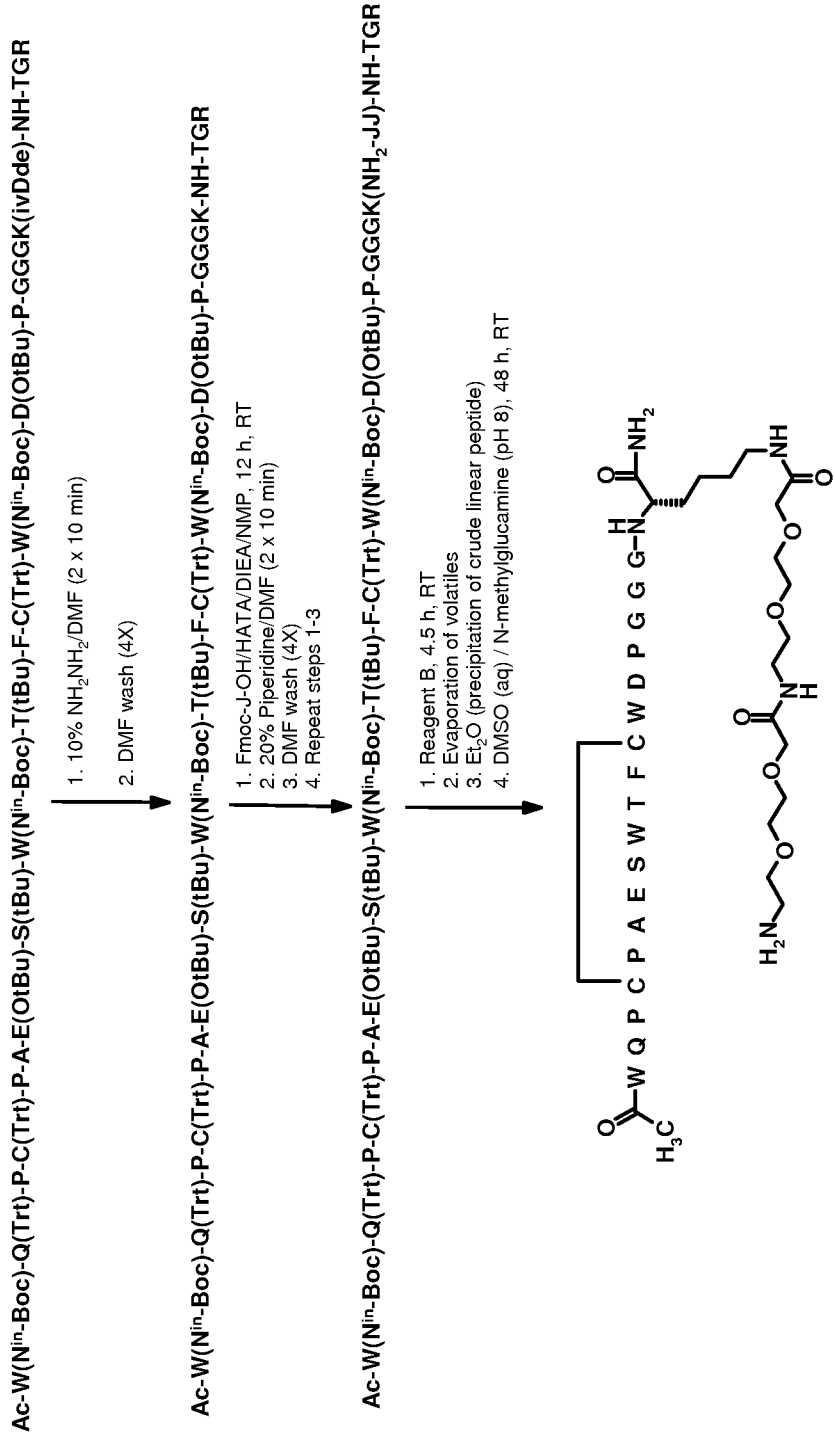
Figure 1 (SEQ ID NO:001)

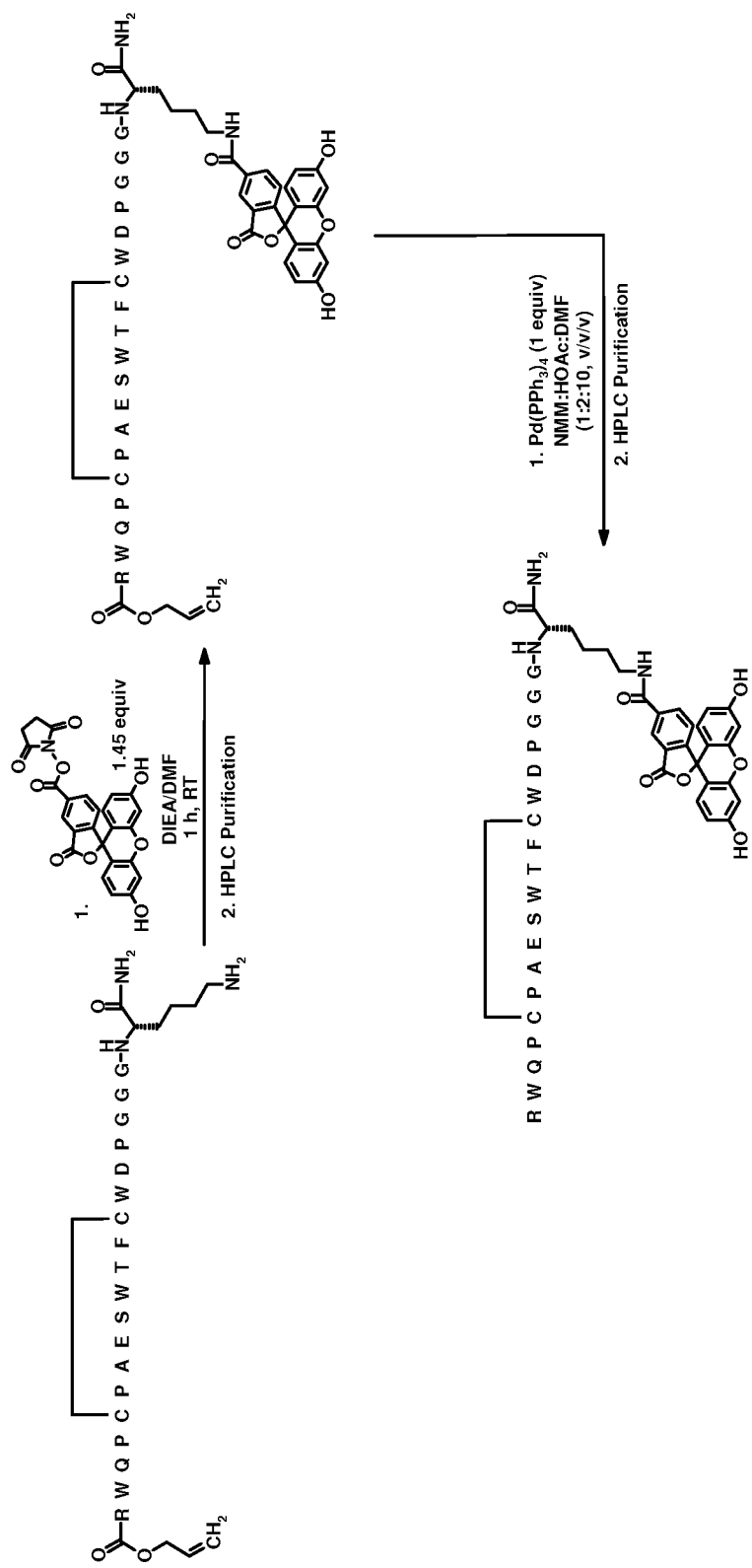
Figure 2 (SEQ ID NO:036)

Figure 3a
Chelators
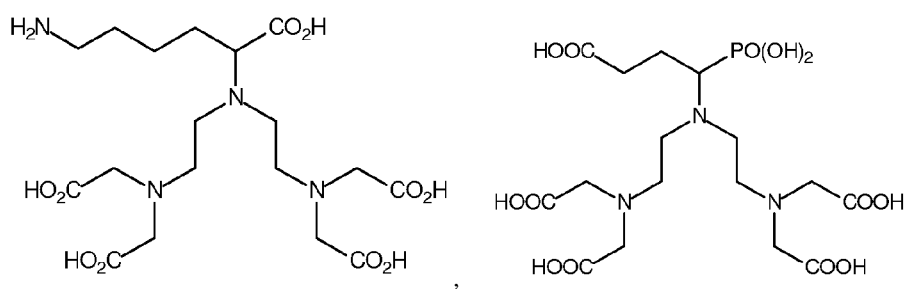
1
*Bioconj. Chem* (1999), *10*, 137
2
WO 01/46207
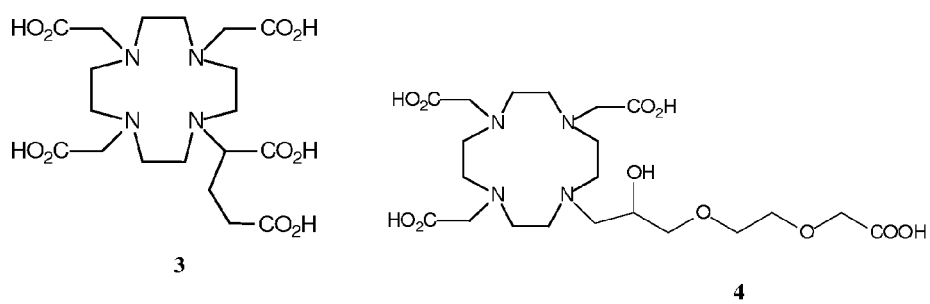
3
*Bioorg. Chemm. Lett.* (2000), *10*, 2133
4
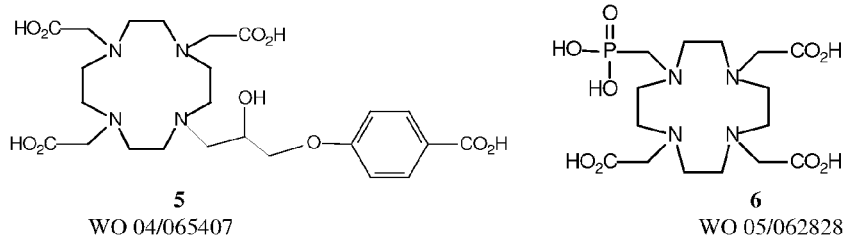
5
WO 04/065407
6
WO 05/062828

Figure 3b
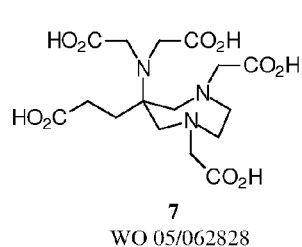
7
WO 05/062828
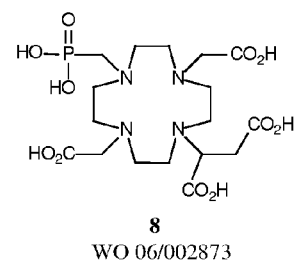
8
WO 06/002873
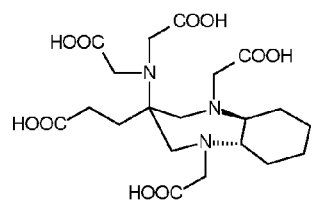
9
WO 06/002873
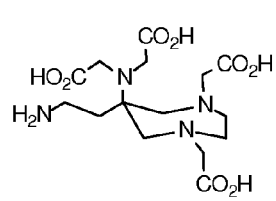
10
WO 06/002873
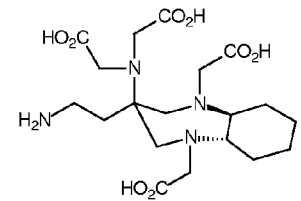
11
WO 06/002873
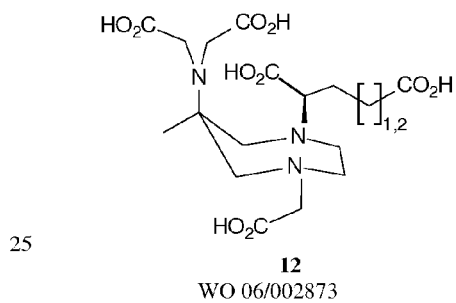
12
WO 06/002873
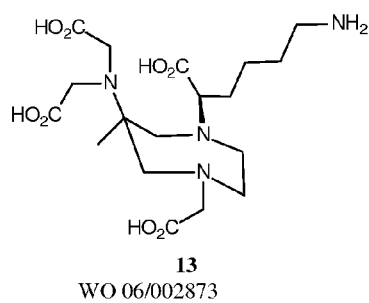
13
WO 06/002873

Figure 4a
Radionuclide chelants
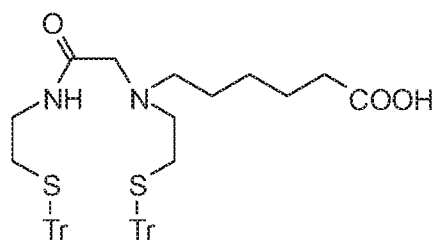
22
*Bioconjugate Chem.* 1999, *10*, 489
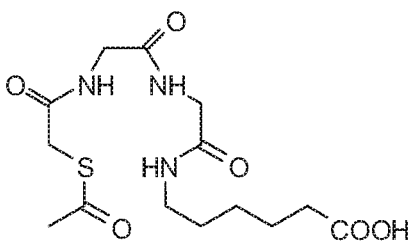
23
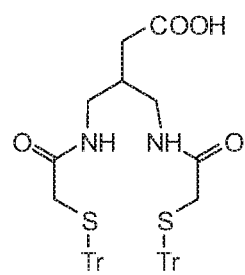
24
*Bioconjugate Chem.* 1999, *10*, 470
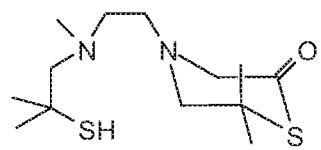
25
*Bioconjugate Chem.* 1990, *1*, 132
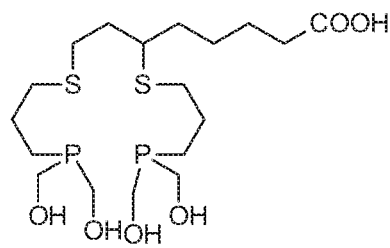
26
*Bioconjugate Chem.* 1999, *10*, 254
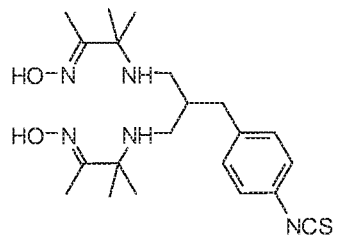
27
*Eur. J. Nucl. Med.* 1994, *21*, 437
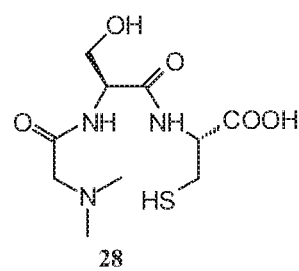
28
*Inorg. Chem.* 1997, *36*, 5799

Figure 4b
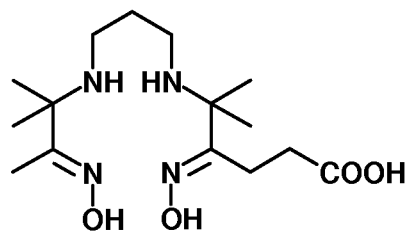
29
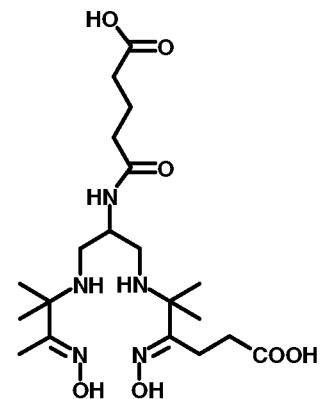
30
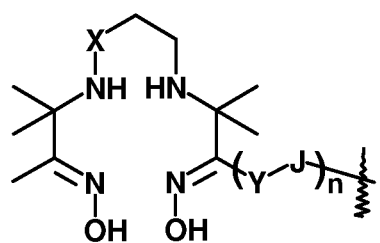
31
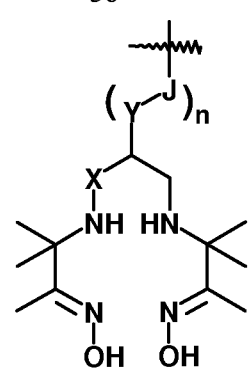
32
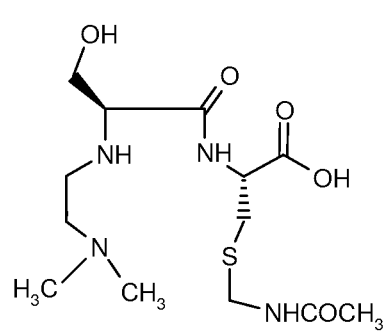
33

ProHance
100 μmol/kg

Chelate
Complex 5
25 μmol/kg

FIBRIN BINDING PEPTIDE CONJUGATES FOR DIAGNOSTIC AND THERAPEUTIC APPLICATIONS

This application is the national stage application of corresponding international application number PCT/EP2007/063659 filed Dec. 11, 2007, which claims priority to and the benefit of the U.S. provisional application No. 60/869,472, filed Dec. 11, 2006, all of which are hereby incorporated by reference.

The instant application contains a Sequence Listing which is being submitted in compliance with the code set forth in the tables in WIPO Standard ST.25 (1998), Appendix 2 via EFS-WEB and is hereby incorporated by reference in its entirety.

FIELD OF THE INVENTION

The present invention is in the technical field of diagnostic imaging and therapy and relates, in particular, to peptide-based fibrin-targeted compounds for diagnostic or therapeutic applications.

The invention further relates to a method of making the above compounds, to pharmaceutical compositions comprising them and to their use in targeted imaging or therapy of solid tumors or, more in general, of all the pathological conditions associated with fibrin deposition or accumulation.

BACKGROUND OF THE INVENTION

Thrombus associated diseases such as, for instance, pulmonary embolism (PE), deep-vein thrombosis (DVT), stroke and atherosclerosis are all examples of pathological vascular conditions known to develop in the presence of a clot.

In DVT, as an example, blood clots forming in the deep blood vessels of the legs and groin can block the blood flow from the legs back to the heart. In some occurrences, e.g. embolism, clot particulate is detached and carried by the bloodstream to a blood vessel where it lodges and reduces, or even blocks, the blood flow to vascular tissues. If such a clot lodges in pulmonary blood vessels the embolism can be even fatal.

In the United States alone an estimated 600,000 patients suffer from PE's each year. In approximately 378,000 of these patients, PE goes undetected and approximately 114,000 of these patients later die due to complications associated with the disease. This high mortality is due to the absence of clinical symptoms, in many cases, and to significant limitations associated with currently available methods of investigation and detection.

As the above diseases represent a major cause of mortality, the development of thrombus-specific treatments and detection methodologies is of utmost importance in clinical practice.

In recent years it has been acknowledged that fibrin deposition or accumulation may be associated with various cancer forms, especially solid tumors. The existence of a heterogeneous pattern of fibrin/fibrinogen deposition in various tumor types is a fact supported by a substantial body of correlative and indirect evidence suggesting that fibrin/fibrinogen plays an important role in tumor stroma formation (see, for instance: Costantini V et al., Fibrin and Cancer, *Thromb Haemost.* 1993; 69:406; Dvorak H F et al. Thrombosis and cancer, *Hum Pathol.* 1987; 18:275; Dvorak H F et al. Vascular permeability factor, fibrin, and the pathogenesis of tumor stroma formation, *Ann N Y Acad Sci.* 1992; 667:101; Cavanagh P G et al., Role of the coagulation system in tumor-cell-induced platelet aggregation and metastasis, *Hemostasis.* 1988; 18:37; and Bardos H et al., Fibrin deposition in primary and metastatic human brain tumours, *Blood Coagul Fibrinolysis.* 1996; 7:536).

Several significant hemostatic abnormalities have been also described in patients with cancer including, for instance, disseminated intravascular coagulation, hemorrhagic events and migratory thrombophlebitis. Tumor-mediated activation of the coagulation cascade has been also implicated in both the formation of tumor stroma and the promotion of hematogenous metastasis. Fibrin matrix, moreover, is known to promote the migration of a substantial number of distinct cells types including transformed cells, macrophages and fibroblasts. In particular, much like in a healing wound, the deposition of fibrin/fibrinogen along with other adhesive glycoproteins into the extracellular matrix (ECM) have been shown to serve as a scaffold to support binding of growth factors and to promote the cellular response of adhesion, proliferation and migration during angiogenesis and tumor cells growth (see, for instance: Dvorak H F et al., Vascular permeability factor, fibrin, and the pathogenesis of tumor stroma formation, *Ann N Y Acad Sci.* 1992; 667:101; Rickles F R et al., Tissue Factor, Thrombin, and Cancer, *Chest.* 2003; 124:58S-68S; Brown H F et al., Fibrinogen influx and accumulation of cross-linked fibrin in healing wounds and in tumor stroma, *Am J Pathol.* 1988; 130:4559; Dvorak H F et al., Fibrin containing gels induce angiogenesis: implication for tumor stroma generation and wound healing, *Lab Invest.* 1987; 57:673; and Rickles F R et al., Tissue Factor, Thrombin and Cancer, *Cest.* 2003; 124:58S-68S).

Most of the solid tumors, in humans, contain considerable amounts of cross-linked fibrin, thus suggesting its role in tumor stroma formation. To this extent, recent techniques such as immunofluorescence, immunohistochemical and immunoelectron microscopy techniques indicated that fibrin deposition occurs within the stroma of a majority of tumor types and enabled to localize both fibrinogen and fibrin to the tumor-host cell interface (see, for instance: Rickles F R et al, Tissue Factor, Thrombin and Cancer, *Cest.* 2003; 124: 58S-68S; Costantini V et al., Fibrinogen deposition without trombine generation in primary human breast cancer, *Cancer Res.* 1991; 51: 349-353; and Simpson-Haidaris P J et al., Tumors and Fibrinogen: The Role of Fibrinogen as an Extracellular Matrix Protein, *Ann. N.Y. Acad. Sci.,* 2001 936(1): 406-425).

Moreover, a correlation seems to exist between plasma fibrinogen levels and tumor size, depth of tumor invasion and metastasis (see, for instance, Lee J H et al., Preoperative plasma fibrinogen levels in gastric cancer patients correlate with extent of tumor, *Hepatogastroenterology* 2004; 51:1860-3). In addition, it is known that fibrin/platelets are involved in protecting tumor cells from the action of the circulating natural killer units provided by the human immune system, thus improving the survival of circulating tumors (see, for instance, Palumbo J S, et al. Platelets and fibrin(ogen) increase metastatic potential by impeding natural killer cell-mediated elimination of tumor cells, *Blood,* 2005; 105:178). This implies, for example, that a conventional tumor therapy employing antibodies that target tumors may not be effective in the treatment of fibrin containing tumors as the latter are somehow protected by fibrin itself.

Thus, visualization of fibrin deposition and targeted inhibition/destruction of established vasculature and clotted fibrin is considered an important tool against malignant disease progression. In this respect, there remains the need for improved fibrin-binding compounds to be used in sensitive diagnosis and specific therapy of pathological conditions associated with fibrin deposition, particularly of solid tumors.

The search for thrombus-specific imaging agents began three decades ago when radiolabelled fibrinogen was first evaluated (see, for instance, Kakkar et al., *Lancet.* 1970, 1:540-542).

A number of MRI based imaging approaches are also described in the literature (see, for instance, Winter P M, et al. Improved molecular imaging contrast agent for detection of human thrombus, *Magn Reson Med. August;* 2003 50(2):411-6; Botnar R M et al., In vivo molecular imaging of acute and subacute thrombosis using a fibrin-binding magnetic resonance imaging contrast agent, *Circulation.* 2004, Apr. 27; 109(16):2023-9; Yu X et al., High-resolution MRI characterization of human thrombus using a novel fibrin-targeted paramagnetic nanoparticle contrast agent, *Magn Reson Med.* 2000; 44:867-872; Flacke S et al., Novel MRI contrast agent for molecular imaging of fibrin: implications for detecting vulnerable plaques, *Circulation.* 2001; 104:1280-1285).

Radiolabelled platelets and anti-platelet antibodies that bind to forming thrombi, anti-fibrin antibodies, anti-activated platelet antibodies and activated or inactivated tissue type plasminogen activator (tPA) have been also disclosed (see, for instance, Thakur et al., *Throm. Res.,* 1976 9:345-357 and Palabrica et al., *Proc. Natl. Acad. Sci.,* 1989; 86:1036-1040).

Platelet affinity peptides are also known (see, for instance Bautovich et al., *J. Nucl. Med.,* 1994, 35:195-202 and Muto et al., *Radiology,* 1993; 189 (suppl):303).

The international patent application WO 01/09188 discloses fibrin binding polypeptides useful, when detectably labelled, for localization and imaging of fibrin clots.

WO 02/055544 relates to a class of fibrin-binding polypeptides that are said to be endowed with a lower dissociation rate over those peptides of the aforementioned WO 01/09188, and equally useful for detection, imaging and localization of fibrin-containing clots and, more in general, for the diagnosis/treatment of coronary conditions where fibrin plays a key role.

Among the preferred polypeptides of WO 02/055544 is, for instance, the polypeptide comprising the amino acid sequence WQPCPWESWTFCWDP (see page 9, line 25 of the said international patent application), SEQ ID NO:037, wherein the cysteine "C" residues are believed to form a disulfide bond (see bottom of page 19).

U.S. Pat. No. 5,792,742 discloses fibrin-binding peptides, their preparation and the use of labelled derivatives thereof for the imaging or therapy of clots, thrombi, microthrombi, pulmonary emboli, atherosclerotic lesions or tumors, and for the targeted delivery of therapeutic agents to thrombi, cancer cells and/or sites of given bacterial infections. In vivo test data are therein reported to assess the targeted ability of the claimed peptides towards thrombi.

U.S. Pat. No. 6,991,775 discloses peptide-based multimeric targeted contrast agents that are said to be useful for the diagnosis of thrombosis of deep vein, coronary and carotid, as well as of intracranial, arterial and ventricular aortic thrombi. A wide number of peptide-based MRI contrast agents is disclosed therein and one of them has been used for thrombolysis target assays.

In US 2006/0034773 two AAZA moieties have been conjugated with the fibrin targeted peptides of WO 02/055544 so as to provide an example of biologically active AAZA derivatives. The use of these conjugates for targeting and treating cardiovascular diseases, fibrin containing blood clots/thrombus, plaques or tumors is also claimed.

SUMMARY OF THE INVENTION

With respect to the need for improved materials and methods for detecting, localizing, measuring and treating fibrin deposition, and pathological processes associated thereto, the present invention provides a novel class of therapeutically or diagnostically active compounds comprising an improved fibrin-binding peptide that is conjugated, through suitable linker(s), with one or more diagnostically or therapeutically effective moieties.

The peptide moiety the compounds of the invention include exhibits, unexpectedly, a high degree of fibrin-specific binding in comparison to previously known peptides.

In addition, the compounds of the invention are endowed with improved physical properties, such as solubility, that render them particularly advantageous in clinical practice.

Importantly, the said peptide moiety is able to selectively bind fibrin, in particular fibrin being present in the extracellular matrix (EC) of tumor or in the connective tissue of stroma, thus acting as a targeting moiety able to bring and successfully bound a diagnostically or therapeutically active moiety linked thereto to those fibrin depositions, particularly to fibrin depositions inside solid tumors or metastatic tissues.

The novel diagnostic or therapeutic agents of the invention may thus find application for the diagnosis, prevention and treatment of pathological conditions associated with fibrin deposition or accumulation such as, for instance, solid malignant tumors and related disorders.

As detailed in the following paragraphs, the present invention relates to this novel class of compounds, to a manufacturing process for their preparation, to these same compounds for use as therapeutic or diagnostic agents, to their use in the preparation of pharmaceutical compositions for detecting and localizing fibrin containing thrombi or, in general, pathological conditions associated with fibrin deposition, in particular cancer and metastatic processes.

The invention further relates to a method for the treatment and prevention of disorders associated with fibrin deposition, as well as to a method for in vitro and in vivo fibrin imaging, through the administration and use of the compounds of the invention.

These and other aspects of the invention will become apparent with reference to the following detailed description.

DEFINITIONS

In the present description, unless otherwise provided, the term "polypeptide" is used to refer to a compound of two or more amino acids joined through the main chain (as opposed to side chain) by a peptide amido bond [—C(O)NH—]. The term "peptide", herein used interchangeably with "polypeptide", is generally used to refer to polypeptides having fewer than 25 amino acids.

The term "fibrin-derived polypeptide" refers to any subcomponent of fibrin or fragment of fibrin that is immunologically cross-reactive with fibrin, including immunologically reactive fragments of the protein.

The term "binding" refers to the capability that a polypeptide has to recognize and binds reversibly to a given target, that may be determined by standard assays, including those described herein. Such standard assays include, but are not limited to equilibrium dialysis, gel filtration, and the monitoring of spectroscopic changes that result from binding.

The term "specificity" refers to a binding polypeptide having a higher binding affinity for one target over another. Binding specificity may be characterized by a dissociation equilibrium constant ($K_D$) or by an association equilibrium constant ($K_a$) for the two tested target materials. The term "fibrin specificity" refers to a fibrin binding moiety having a higher affinity for fibrin than for an irrelevant target. In a preferred embodiment, binding polypeptides according to the present invention are specific for fibrin, and preferably have a dissociation constant that is lower than about 10 µM, more preferably less than about 1 µM, most preferably less than about 0.5 µM or even lower.

The term "binding moiety" as used herein refers to any molecule capable of forming a binding complex with another molecule. "Fibrin binding moiety" is a binding moiety that forms a complex with a clot, soluble or insoluble fibrin, or a soluble or insoluble fragment of fibrin having a structure or characteristic exhibited by fibrin but not fibrinogen. Included among such soluble or insoluble fragments of fibrin are fragments defined as "fibrin-derived" polypeptides, typically generated by proteolytic treatment of crosslinked fibrin but retaining structural features unique to fibrin.

Specific fibrin-binding peptides are described herein as including those of Table 1 below.

The terms "therapeutic agent" or "therapeutically effective moiety" as used herein interchangeably, refer to a compound or an agent having a beneficial, therapeutic or cytotoxic effect in vivo. Therapeutic agents include those compositions referred to as, for example, bioactive agents, cytotoxic agents, drugs, chemotherapeutic agents, radiotherapeutic agents, genetic material, etc.

The term "patient" as used herein refers to any mammal, especially humans. The term "pharmaceutically acceptable" carrier or excipient refers to a non-toxic carrier or excipient that can be administered to a patient, together with a compound of this invention, such that it does not destroy the biological or pharmacological activity thereof.

Having provided the above definitions, and unless otherwise provided in the present description, with the term "fibrin-binding peptide moiety" or, simply, "peptide moiety", as used herein interchangeably, we refer to a suitable residue of the corresponding fibrin-binding peptide as defined by each of the above sequences of Table 1.

DETAILED DESCRIPTION OF THE INVENTION

It is thus a first object of the invention a compound of general formula (I)

$$A[-Y(-T)_r]_s \qquad (I)$$

wherein
A is a fibrin-binding peptide moiety comprising an amino acid sequence selected from the group of Table 1, consisting of:

TABLE 1

Fibrin-binding peptide sequences

| Seq. ID | Amino acid sequence |
|---|---|
| Seq001 | WQPC*P<u>A</u>ESWTFC*WDP |
| Seq002 | GPPGWQPC*PWESWTFC*WDP |
| Seq003 | <u>GGR</u>GWQPC*PWESWTFC*WDP |
| Seq004 | <u>G</u>WQPC*PWESWTFC*WDP |
| Seq005 | <u>SGSGJ</u>WQPC*PWESWTFC*WDP |
| Seq006 | WQPC*PWESWT-<u>Cha</u>-C*WDP |
| Seq007 | WQPC*PWESWT-<u>Ffe4</u>-C*WDP |
| Seq008 | WQPC*PWESWT-<u>F34fe</u>-C*WDP |
| Seq009 | <u>RG</u>WQPC*PWESWTFC*WDP |

TABLE 1-continued

Fibrin-binding peptide sequences

| Seq. ID | Amino acid sequence |
|---|---|
| Seq010 | <u>RW</u>QPC*PWESWTFC*WDP |
| Seq011 | <u>SGSGSGSG</u>WQPC*PWESWTFC*WDP |
| Seq012 | <u>KKG</u>WQPC*PWESWTFC*WDP |
| Seq013 | <u>KGKGKG</u>WQPC*PWESWTFC*WDP |
| Seq014 | <u>S(Galnac)</u>-WQPC*PWESWTFC*WDP |
| Seq015 | <u>Thf2ca</u>-WQPC*PWESWTFC*WDP |
| Seq016 | <u>RRGG</u>WQPC*PWESWTFC*WDP |
| Seq017 | <u>S(Galnac)-J</u>WQPC*PWESWTFC*WDP |
| Seq018 | WQPC*-<u>Hypt4</u>-WESWTFC*WDP |
| Seq019 | GPPGWQPC*P<u>A</u>ESWTFC*WDP |
| Seq020 | <u>GGR</u>GWQPC*P<u>A</u>ESWTFC*WDP |
| Seq021 | <u>KKG</u>WQPC*P<u>A</u>ESWTFC* WDP |
| Seq022 | <u>KGKGKG</u>WQPC*P<u>A</u>ESWTFC*WDP |
| Seq023 | <u>G</u>WQPC*P<u>A</u>ESWTFC*WDP |
| Seq024 | <u>SGSGSGSG</u>WQPC*P<u>A</u>ESWTFC*WDP |
| Seq025 | WQPC*P<u>A</u>ESWT-<u>Ffe4</u>-C*WDP |
| Seq026 | WQPC*P<u>A</u>ESWT-<u>Cha</u>-C*WDP |
| Seq027 | WQPC*P<u>A</u>ESWT-<u>F34fe</u>-C*WDP |
| Seq028 | <u>Thf2ca</u>-WQPC*P<u>A</u>ESWTFC*WDP |
| Seq029 | <u>SGSGJ</u>WQPC*P<u>A</u>ESWTFC*WDP |
| Seq030 | <u>RRGG</u>WQPC*P<u>A</u>ESWTFC*WDP |
| Seq031 | <u>RRGG</u>WQPC*-<u>Hypt4</u>-WESWTFC*WDP |
| Seq032 | <u>RW</u>QPC*P<u>A</u>ESWT-<u>Cha</u>-C*WDP |
| Seq033 | <u>G</u>WQPC*P<u>A</u>ESWT-<u>Cha</u>-C*WDP |
| Seq034 | <u>RG</u>WQPC*P<u>A</u>ESWTFC*WDP |
| Seq035 | <u>RG</u>WQPC*P<u>A</u>ESWT-<u>Cha</u>-C*WDP |
| Seq036 | <u>RW</u>QPC*P<u>A</u>ESWTFC*WDP |

Y is, independently in each occurrence, a suitable linking moiety connecting A with at least one T moiety;
T is, independently in each occurrence, a diagnostically or therapeutically active moiety;
r is, independently in each occurrence, an integer from 1 to 8;
s is 1 or 2;
or a physiologically acceptable salt thereof.

As used therein in Table 1, and elsewhere in the present description, amino acid sequences are conventionally represented through the one letter code as per IUPAC-IUB rules (see, for instance, *Biochem. J.*, 1984, 219, 345-373; and *Biochemical Nomenclature and Related Documents,* 2nd edition, Portland Press, 1992, pages 39-69).

For a better understanding, the meanings of the selected amino acids conventionally intended according to both the one-letter or three-letter codes are reported in the following Table 2.

TABLE 2

Abbreviations for Amino Acids

| Amino Acid | 3-letter | 1-letter |
|---|---|---|
| alanine | ala | A |
| arginine | arg | R |
| asparagine | asn | N |
| aspartic acid | asp | D |
| cysteine | cys | C |
| glutamic acid | glu | E |
| glutamine | gln | Q |
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| threonine | thr | T |
| tryptophan | trp | W |
| tyrosine | tyr | Y |
| valine | val | V |

As per Table 1, the moiety A may also comprise non natural amino acids and additional residues such as, for instance, Cha, Ffe4, F34fe, S(Galnac), and the like, which meanings are specifically reported in the following Table 3.

TABLE 3

Abbreviations for non natural amino acid residues and moieties

| Residue Abbreviation | Structure |
|---|---|
| Cha | 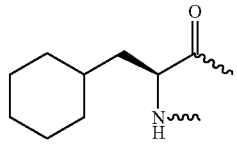 |
| Ffe4 | 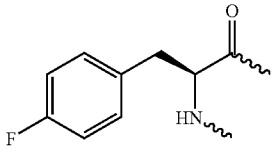 |
| F34fe | 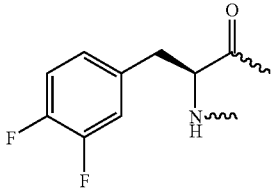 |
| S(Galnac) | 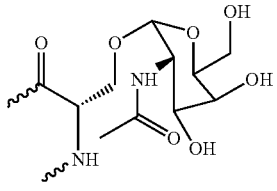 |
| Thf2ca | 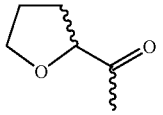 |

TABLE 3-continued

Abbreviations for non natural amino acid residues and moieties

| Residue Abbreviation | Structure |
|---|---|
| Hypt4 | 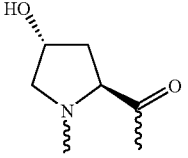 |

Moreover, within the amino acid sequences of Table 1, there are purposely underlined given variations with respect to the aforementioned prior art peptide disclosed in WO 02/055544, that is WQPCPWESWTFCWDP, presently and hereinbelow identified with SEQ ID NO:037.

Therefore, just as an example, within the peptide of the invention coded as SEQ ID NO:001, the amino acid therein defined as "A" replaces, in that same position, the corresponding amino acid "W" in the prior art peptide. Substantially analogous considerations apply for any remaining sequence.

Finally, the fibrin-binding peptide moieties of the invention, within formula (I), are preferably conformationally restrained by disulfide linkages between the two cysteine residues in their sequence. As per Table 1 and elsewhere herein, therefore, the designation "C*" just refers to a cysteine residue that contributes to a disulfide bond.

Other methods for constraining peptides which would retain a similar conformation and fibrin specificity for the peptide have been described in the art and may be used herein.

In addition to the above, and unless otherwise provided, within the compounds of formula (I) of the invention, any amino or carboxylic groups of the aforementioned amino acid sequences, not involved in carboxamido linkages so as to form the given peptides of Table 1, nor bound to the rest of the molecule, may be optionally present in a protected or anyway deactivated form through conjugation with any suitable protecting group (Pg), as per the following details.

According to one embodiment of the instant invention, within the compounds of formula (I) the fibrin peptide moiety A includes an amino acid sequence selected from the group of Table 1 in which one or both of the N-terminal (—NH$_2$) and the C-terminal (—COOH) groups of the peptide sequence are functionalized through formation of a carboxamido bond with Y.

In the present description, unless otherwise specified, with the expression "fibrin-binding peptide moiety" or, simply, "peptide moiety", as used herein interchangeably, we refer to that portion of the peptide unit remaining unchanged after the above conjugation.

On the other side, and as formerly said, if the C-terminal or the N-terminal group of the amino acid sequence is not functionalized trough formation of a bond with Y, it may be suitably protected or deactivated through conjugation with any suitable protecting group (Pg), and according to conventional means.

In this case, when saying "fibrin-binding peptide moiety", we intend to refer to that moiety resulting from the original amino acid sequence of the fibrin-binding peptide, following the said optional protection/deactivation and the said carboxamido bond formation.

Typically, for instance, in the case of the fibrin-binding peptide having the amino acid sequence SEQ ID NO:001, as shown in table 1 and as reported below

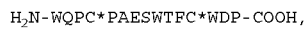

wherein the N-terminal (—NH₂) of tryptophan W and the C-terminal (—COOH) of proline groups are made explicit, the corresponding fibrin-binding peptide moiety A may include, for instance:

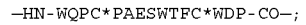

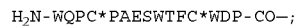

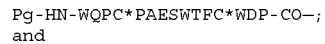

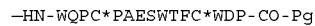

in which Pg is any suitable protecting or deactivating group.

In the present description, unless otherwise indicated, the term "protecting group" designates a protective group adapted to preserve the characteristic chemical function of the functional group to which it is bound. Specifically, in the present context, protective groups are used to preserve amino or carboxyl functions. Appropriate protective groups may thus include, for example, Fmoc, benzyl, benzyloxycarbonyl or alkyl esters or other groups commonly intended for the protection of such functions; for a general reference to protective groups see, as an example, T. W. Green, Protective Groups in Organic Synthesis (Wiley, N.Y. 1981).

Unless otherwise indicated, with the term "deactivating group" as used herein, we intend to refer to a chemical group that is able to chemically react with the N-terminal (—NH₂) or the C-terminal (—COOH) group of the peptide unit transforming it, through a chemical reaction, into a suitable derivative thereof that maintains the specificity of the corresponding peptide moiety toward fibrin, but is unable to chemically react with, respectively, a carboxyl or an amino functionality on a different moiety and, thus, may not be involved in carboxamido cross-linking reactions.

Suitable examples of deactivating groups may thus comprise acetyl [also referred to as CH₃(CO)— or even Ac], to be used to deactivate an amino terminal group of the peptide chain by converting it into the corresponding unreactive acetylated AcHN— group.

On the other side, amino groups themselves and derivatives thereof such as, for instance, —NH₂, —NH(CH₃) or H₂NOC—CH₂—NH— may be used to deactivate a terminal carboxyl group by providing the corresponding —CONH₂, —CONH(CH₃) or —CONH—CH₂—CONH₂ unreactive amides, respectively.

According to a preferred embodiment of the invention, within the compounds of formula (I), A is a fibrin-binding peptide moiety comprising the amino acid sequence being identified as (SEQ ID NO:001), as shown in Table 1, either as such or bearing any of the aforementioned Pg or deactivating groups, for instance as follows:

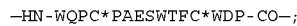

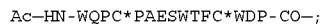

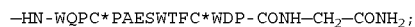

According to an additional embodiment of the invention, within the compounds of formula (I) the parameter "s" is selected from 1 and 2, thus giving rise to the compounds of the invention schematically represented as follows:

when s=1 A-Y(-T)ᵣ wherein A is bound to the rest of the molecule through any one of the terminal amino or carboxyl functions of the peptides of Table 1;

when s=2 (T)ᵣ-Y-A-Y(-T)ᵣ wherein A is bound to the rest of the molecule through the terminal amino group, at one side, and through the terminal carboxy group at the other side, being the two —Y(-T)ᵣ moieties the same or different from each other.

In addition to the above, and according to a still different embodiment of the invention, the parameter "r" represents an integer varying from 1 to 8; accordingly, one or more T groups may be present in the compounds of formula (I), each of which being properly bound to the moiety Y.

Preferably, within the compounds of formula (I) r is an integer from 1 to 4. According to another preferred aspect of the invention, within the compounds of formula (I), s is 1.

The compounds of the invention having s=1 include, independently in each occurrence, one or more diagnostically of therapeutically active moiety or moieties T conjugated, through a suitable linking moiety Y, to the N-terminal (—NH₂) or, conversely, to the C-terminal (—COOH) group of the peptide moiety, thus resulting in a compound of formula (I) in which A is functionalized at only one of its ending N- or C-terminal groups.

According to another preferred aspect of the invention, within the compounds of formula (I), s is 2.

The compounds of the invention having s=2 thus include, independently in each occurrence, one or more diagnostically or therapeutically active moiety or moieties T conjugated, through a suitable linking moiety Y, to each one of the two N-terminal (—NH₂) and the C-terminal (—COOH) groups of the peptide moiety, thus resulting in compounds of formula (I) in which A is functionalized at both of the N- and C-terminal groups.

As formerly reported, within the compounds of formula (I), the peptide moiety A is conjugated with one or more diagnostically or therapeutically active moieties T by means of linking moieties Y.

Besides acting as a linking group between moieties A and T, Y may provide for a proper distance between the diagnostically or therapeutically active moiety T and the fibrin-targeting moiety itself.

In fact, an optimal distance between these two units may represent an important factor so as to get and maintain the targeting capability of the compounds of the invention. It is well known, in fact, that any improper or anyway sub-optimal derivatization of a peptidic-based targeting moiety may often result in a significant loss of the peptide affinity for the targeted objective.

In addition to the above, the linker(s) Y may significantly contribute to improve the hydrophilicity of the diagnostic or therapeutic agent T, thus providing the desired pharmacokinetic or pharmacodynamic profile of the compounds of formula (I).

According to the present invention, Y is a linear or branched, at least divalent, linking moiety.

In one preferred embodiment of the invention, Y is a linear or branched divalent linking moiety.

With "divalent linking moiety" (or "divalent linking chain" or "divalent linker", as used herein interchangeably), we intend a chain including two functional groups allowing for its conjugation with the terminal amino or carboxyl groups of A, at one side, and its conjugation with the active moiety T, at the other side. Unless otherwise indicated, whit the term "functional group" as used herein we refer to specific groups of atoms within molecules or moieties that are responsible for the characteristic chemical reaction of those molecules or moieties. In the context of the present invention, the functional groups are the specific —$NH_2$ or —COOH terminal groups of the moiety A, of the linker(s) Y, and of the active moieties T allowing each other carboxamido cross-linking conjugation.

In addition to the above, however, these same linker(s) Y and active moieties T may optionally comprise additional functional groups such as, for instance, amino, thiol or carboxyl groups that may be present as free groups or as optionally activated or suitably protected groups.

In another preferred embodiment of the invention, Y is a linear or branched polyfunctional linking moiety.

Unless otherwise provided, with "polyfunctional linking moiety", or "polyfunctional linker", as used herein interchangeably, we intend a linear or branched chain including at least 3 functional groups, one of them connecting the said polyfunctional moiety with the N-terminal (—$NH_2$) or the C-terminal (—COOH) group of A, and the remaining functional groups connecting the polyfunctional moiety with at least 2, preferably, from 2 to 8 and, more preferably, from 2 to 4, equal or different, diagnostically or therapeutically effective moieties. Suitable examples of the said polyfunctional chains may include, for instance:

(a) N-branched lysine systems (see, f. i., Veprek, P et al., J. Pept. Sci. 5, 5 (1999); 5, 203 (1999),
(b) Polycarboxylic compounds and suitable derivative thereof in which the carboxylic group(s) are in a suitably activated or protected form,
(c) polyaminated compounds and suitable derivative thereof in which the amino group(s) are in a suitably activated or protected form,
(d) amino acids and poly-amino acids such as polyornithine, polyarginine, polyglutamic acid, polyaspartic acid.

Whether divalent or polyvalent, Y may include, without limitations: substituted or unsubstituted, either saturated or unsaturated, straight or branched alkylene chains; amino acids and peptides from straight, branched or cyclic amino acids (e.g., extensions of the N- or C-terminus of the binding moieties); derivatized or underivatized polyethylene glycol, polyoxyethylene or polyvinylpyridine chains; substituted or unsubstituted polyamide chains; derivatized or underivatized polyamine, polyester, polyethylenimine, polyacrylate, poly(vinylalcohol), polyglycerol, or oligosaccharide (e.g., dextran) chains; glycosylated amino acid residues, alternating block copolymers; malonic, succinic, glutaric, adipic and pimelic acids; caproic acid; simple diamines and dialcohols; any of the other linkers disclosed herein as well as any other simple polymeric linker known in the art, for instance as described in WO 98/18497 and WO 98/18496.

Preferably, the said linking moiety comprises a straight or branched $C_1$-$C_{100}$ and, more preferably, a $C_1$-$C_{50}$, and, even more preferably, a $C_1$-$C_{35}$ alkylene chain, that is optionally interrupted by one or more groups selected from —O—, —CO—, —CONH—, —NHCO—, —NH—, >NCO—, —OCN< or —N<, the said Y chain being optionally further substituted by one or more groups selected from optionally protected amino or carboxyl groups such as, for instance, —$CONH_2$ or —$NHCOCH_3$ groups, or, in general, by any side chain deriving from a natural alpha amino acid, when included in the said Y chain through carboxamido cross-linking reaction. In this reference, suitable examples of the said Y chain substituents include, for instance, a linear or branched ($C_1$-$C_5$) alkyl or alkylene group, optionally interrupted by one or more —S— units and optionally substituted by a suitably protected or optionally unprotected amino or carboxyl group, or by hydroxyl (—OH) or thiol (—SH) groups, or by one or more, optionally substituted, aryl or heteroaryl rings.

Unless otherwise provided, the term "($C_1$-$C_5$) alkyl or alkenyl" as used herein, designates a linear or branched, saturated or unsaturated alkyl or alkylene substituent comprising from 1 to 5 carbon atoms such as, for example, methyl, ethyl, propyl, isopropyl, butyl, tert-butyl, pentyl, vinyl, propenyl, and the like, wherein methyl, ethyl, propyl and isopropyl are preferred.

More preferably, the linking moiety Y includes one or more sub-units selected, for instance, from homobifunctional and heterobifunctional units and suitable combinations thereof.

Unless otherwise provided, the term homobifunctional or heterobifunctional unit or moiety, as used herein, refers to a unit or moiety having at least two reactive functional groups which are the same or different, respectively.

Suitable examples of homobifunctional units include, for instance, dicarboxylic and diamino moieties having formula:

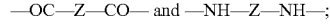
—OC—Z—CO— and —NH—Z—NH—;

whereas examples of heterobifunctional units include amino acids having formula:

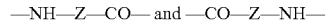
—NH—Z—CO— and —CO—Z—NH— wherein Z is an optionally interrupted and/or substituted straight or branched chain as formerly reported.

In a preferred aspect of the invention, Z comprises a group selected from:
—$(CH_2)_n$—,
—$CH_2$—$(CH_2O)_n$—,
—$CH_2O$—$(CH_2(CH_2)_pO)_n$—$(CH_2)_n$—,
—$(CH_2)_n$—NH—$(CH_2)_n$—,
—$N((CH_2)_n—)_2$
—$(CH_2)_p$—CH(NH—)—$(CH_2)_n$—,
—$(CH_2)_p$—CH($CONH_2$)—$(CH_2)_n$—,
—$(CH_2(CH_2)_pO)_n$—$(CH_2)_n$—,
—$(CH_2)_p$—CH(CO—)—$(CH_2)_n$—,
—$(CH_2)_p$—CH($NHCOCH_3$)—$(CH_2)_n$—
wherein n is, independently in each occurrence, an integer from 1 to 6 and p is zero or an integer from 1 to 5.

Preferably, the linking chain Y of the invention comprises one or more of the following groups, and any suitable repetition and combination thereof:
—HN—$(CH_2)_n$—CO—,
—OC—$(CH_2)_n$—CO—,
—HN—$(CH_2)_n$—NH—,
—HN—$(CH_2)_n$—NH—$(CH_2)_n$—NH—,
—OC—$(CH_2)_n$—NH—$(CH_2)_n$—CO—,
—HN—$[(CH_2)_n$—O$]_2$—$CH_2$—CO—,
—HN—CH(CO—)—$(CH_2)_n$—NH—,
—HN—CH(CO—)—$(CH_2)_n$—CO—,
—OC—CH(NH—)—$(CH_2)_n$—NH—,
—OC—$CH_2O$—$((CH_2)_2O))_n$—$(CH_2)_2$—NH—,
—$N((CH_2)_n$—CO—$)_2$,
—HN—CH($CONH_2$)—$(CH_2)_n$—NH—,
—OC—CH($NHCOCH_3$)—$(CH_2)_n$—NH—
wherein n is as defined above.

Even more preferably, within this class are:
—HN—$CH_2$—CO—,
—OC—$(CH_2)_2$—CO—,
—OC—$(CH_2)_3$—CO—,
—HN—$[(CH_2)_2$—O$]_2$—$CH_2$—CO—,
—OC—$CH_2O$—$(CH_2)_2O$—$(CH_2)_2$—NH—,
—HN—CH(CO—)—$(CH_2)_4$—NH—, —OC—CH(NH—)—(CH$_2$)$_4$—NH—,
—HN—CH(CO—)—(CH$_2$)$_2$—CO—,
—HN—CH(CONH$_2$)—(CH$_2$)$_4$—NH—,
—OC—CH(NHCOCH$_3$)—(CH$_2$)$_4$—NH—,
—N(CH$_2$—CO—)$_2$ From all of the above, it is clear to the skilled person that any of the aforementioned moieties bearing more than two functional groups allowing for additional functionalization may give rise to a branched system. In fact, just as an example, the moiety therein referred to as

—HN—CH(CO—)—(CH$_2$)$_4$—NH— may be properly represented through the chemical formula below

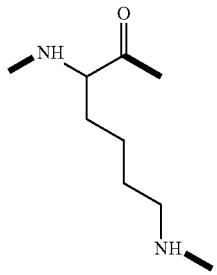

wherein the lines in bold represent possible points of attachment with additional moieties or groups.

Any intermediate compound according to the invention including, for instance, a peptide moiety A conjugated with a suitable, optionally protected, Y moiety or sub-unit of a Y moiety, at one or both of the N-terminal (—NH$_2$) or the C-terminal (—COOH) group of A, may thus constitute a further object of the present invention. According to an additional preferred aspect of the invention, within the compounds of formula (I) T is a diagnostically effective moiety.

With the expression "diagnostically effective moiety" or "imaging effective moiety" or "imaging moiety", as used herein interchangeably, we intend any moiety detectable by imaging diagnostic procedures, that is to say any moiety able to provide, to improve or, in any way, to advantageously modify the signal detected by an imaging diagnostic technique today in use including, for instance, magnetic resonance imaging (MRI), radioimaging, X-ray imaging, light imaging, thus enabling the registration of diagnostically useful, preferably contrasted, images when used in association with the said techniques.

Examples of diagnostically effective moieties according to the invention include, for instance, chelated gamma ray or positron emitting radionuclides; paramagnetic metal ions in the form of chelated or polychelated complexes, X-ray absorbing agents including atoms having atomic number higher than 20; a dye molecule; a fluorescent molecule; a phosphorescent molecule; a molecule absorbing in the UV spectrum; a quantum dot; a molecule capable of absorption within near or far infrared radiations and, in general, all the moieties which generate a detectable substance. From all of the above, it is known to the person skilled in the art that the imaging modality to be used has to be selected according to the imaging detectable moiety the diagnostic compounds of the invention include.

With the term "contrast imaging agent" or "contrast agent" as used herein interchangeably, we refer to any detectable entity that can be used to in vitro visualize or detect fibrin units or fibrin deposition into or on a biological element including cells, biological fluids and biological tissues originating from a live mammal patient, and preferably, from human patient, as well as to in vivo identify and locate fibrin and fibrin deposition in or on mammalian and, preferably, human body organs, regions or tissues when the said detectable entity are used in association with a suitable diagnostic imaging technique.

MRI Contrast Agents

In a particularly preferred embodiment of the invention, within the compound of formula (I), T is an MRI detectable moiety.

Compound of formula (I) in which T is an MRI detectable moiety are preferred for use as MRI contrast agents.

Accordingly, in one preferred aspect, the present invention relates to novel MRI contrast agents of formula (I) in which T is an MRI detectable moiety.

Preferably, the said MRI detectable moiety comprises the residue of a chelating ligand labelled with a paramagnetic metal element detectable by MRI techniques. Preferred paramagnetic metal elements are those having atomic number ranging between 20 and 31, 39, 42, 43, 44, 49 and between 57 and 83.

More preferred are paramagnetic metal ions selected from the following: Fe($^{2+}$), Fe($^{3+}$), Cu($^{2+}$), Ni($^{2+}$), Rh($^{2+}$), Co($^{2+}$), Cr($^{3+}$), Gd($^{3+}$), Eu($^{3+}$), Dy($^{3+}$), Tb($^{3+}$), Pm($^{3+}$), Nd($^{3+}$), Tm($^{3+}$), Ce($^{3+}$), Y($^{3+}$), Ho($^{3+}$), Er($^{3+}$), La($^{3+}$), Yb($^{3+}$), Mn($^{3+}$), Mn($^{2+}$; Gd($^{3+}$) being the most preferred.

With the term "chelator", "chelating ligand" or "chelating agent", as used herein interchangeably, we intend chemical moieties, agents, compounds, or molecules characterized by the presence of polar groups able to a form a complex containing more than one coordinate bond with a transition metal or another metal entity. In a preferred aspect of the invention the said chelating ligand includes cyclic or linear polyamino polycarboxylic or polyphosphonic acids and contains at least one amino, thiol or carboxyl group present as free or optionally activated functionality, that is suitable for use in the conjugation reaction with a suitable functional group of the linking chain Y.

With the expression a "residue of a chelating agent", or "residue of a chelating ligand", as used herein interchangeably, we intend that portion of the chelating ligand remaining after the above conjugation. Preferably, the said conjugation is from an acidic group (—COOH) on the chelating ligand, or a suitable reactive derivative thereof, with an amino group (—NH$_2$) of the linking moiety Y or, alternatively, between a suitable reactive amino group of the chelating ligand and a carboxyl group of the Y moiety, or a suitable derivative thereof, so as to give rise to a carboxamido linkage. The acidic or the amino group of the chelating ligand involved in the said crosslinking reaction is suitably selected in order not to reduce or modify the chelating capability of the ligand residue.

With the term "labelled" or "complexed" as used herein in the context of "chelating ligand labelled with a metal element" we refer to a ligand that is complexed with the said metal element, i.e. a ligand that is in the form of a chelate or coordinate complex with the metal element.

With the term "metal entity" or "metal element", as used herein interchangeably, we refer to a metal ion that is detectable by an imaging technique. Such metal entities specifically include paramagnetic metal ions that are detectable by imaging techniques such as Magnetic Resonance Imaging (MRI), or to a metal ion (e.g. a radionuclide) that is detectable by imaging techniques such as scintigraphic imaging, Single Photon Emission Computed Tomography (SPECT) and Positron Emission Tomography (PET), or even a radionuclide for therapy.

Suitable chelating ligands include those discussed herein, particularly chelating ligands selected from the group consisting of: a polyaminopolycarboxylic acid and the derivative thereof comprising, for example, diethylenetriamine pentaacetic acid(DTPA) and derivative thereof including benzo-DTPA, dibenzo-DTPA, phenyl-DTPA, diphenyl-DTPA, benzyl-DTPA and dibenzyl DTPA, N,N-Bis[2-[(carboxymethyl)[(methylcarbamoyl)methyl]ethyl]-glycine (DTPA-BMA), N-[2-[bis(carboxymethyl)amino]-3-(4-ethoxyphenyl)propyl)]-N-[2-[bis(carboxymethyl)amino]ethyl]glycine (EOB-DTPA), 4-carboxy-5,8,11-tris(carboxymethyl)-1-phenyl-2-oxa-5,8,11-triazatridecan-13-oic acid (BOPTA), N,N-bis[2-[bis(carboxymethyl)amino]ethyl]L-glutamic acid (DTPA-GLU); DTPA-Lys (see compound 1 of FIG. 3a); ethylenediaminetetraacetic acid (EDTA); 1,4,7,10-teraazacyclododecane 1,4,7,-triacetic acid (DO3A) and derivatives thereof including, for example, [10-(2-hydroxypropyl)-1,4,7,10-teraazacyclododecane 1,4,7,-triacetic acid (HPDO3A); 1,4,7-triazacyclononane N,N',N''-triacetic acid (NOTA); 6-[bis(carboxymethyl)amino]tetrahydro-6-methyl-1H-1,4-diazepine-1,4(5H)-diacetic acid (AAZTA) and derivative thereof, for instance as disclosed in WO 03/008390, incorporated herein by reference, 1,4,7,10-tetraazacyclotetradecane-1,4,7,10-tetraacetic acid (DOTA) and derivatives thereof including, for instance, benzo-DOTA, dibenzo-DOTA, (α,α', α'',α''')-tetramethyl-1,4,7,10-tetraazacyclotetradecane-1,4,7,10-tetraacetic acid (DOTMA); or 1,4,8,11-tetraazacyclotetradecane-N,N',N'',N'''-tetraacetic acid (TETA); or corresponding compounds wherein one or more of the carboxylic groups is replaced by a phosphonic and/or phosphinic group, including, for instance, N,N'-bis-(pyridoxal-5-phosphate) ethylenediamine-N.N'-diacetic acid (DPDP); ethylenedinitrilotetrakis(methylphosphonic) acid (EDTP), 1,4,7,10-tetraazacyclotetradecane-1,4,7,10-tetra (methylenephosphonic) acid (DOTP), the phosphonoalkylpolyaza macrocyclic compounds for instance disclosed in U.S. Pat. No. 5,362,476 and U.S. Pat. No. 5,409,689 and the linear phosphonoalkyl derivatives disclosed in U.S. Pat. No. 6,509,324; or of macrocyclic chelants such as texaphirines, porphyrins, phthalocyanines.

Preferred chelating ligands according to the present invention include those having structures from 1 to 21c, as comprised in FIGS. 3a to 3c, which also include suitable bibliographic references concerning their preparation.

Particularly preferred are: DTPA, DTPA-GLU, DTPA-Lys, DOTA, AAZTA, and the following AAZTA derivatives:

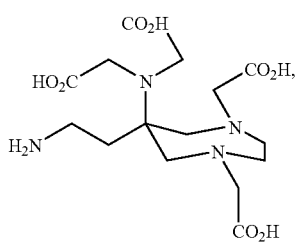

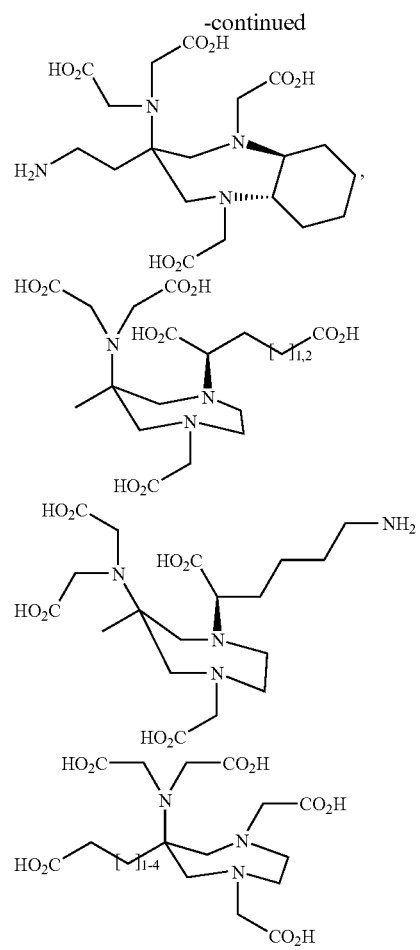

Nuclear Imaging (Radionuclide Imaging) and Radiotherapy

In another preferred embodiment of the invention, within the compounds of formula (I), T is a radioimaging detectable moiety or a radiotherapeutic moiety. Compounds of formula (I) in which T is a radioimaging detectable moiety are preferred for use as radiographic contrast agents.

Accordingly, in another preferred embodiment, the present invention relates to novel radiographic contrast agents of formula (I) in which T is a radioimaging detectable moiety.

Unless otherwise provided, with "radioimaging detectable moiety" as used herein we refer to a moiety that is detectable by imaging techniques such as scintigraphic imaging, Single Photon Emission Computed Tomography (SPECT) and Positron Emission Tomography (PET).

Preferably, the said radioimaging detectable moiety comprises the residue of a chelating agent labelled with a radionuclide detectable by the said scintigraphic, SPECT or PET imaging techniques.

When T is a radiotherapeutic moiety, it preferably comprises the residue of a chelating ligand labelled with a therapeutically active radionuclide.

Together with the chelating ligands discussed above, suitable examples of chelating ligands for radionuclides may be selected from linear, macrocyclic, terpyridine, and $N_3S$, $N_2S_2$, $N_2S_3$, $N_2S_4$, $N_3S_3$ or $N_4$ chelators including, for instance, the ligands disclosed in U.S. Pat. No. 5,367,080, U.S. Pat. No. 5,364,613, U.S. Pat. No. 5,021,556, U.S. Pat. No. 5,075,099 and U.S. Pat. No. 5,886,142, and other chelating ligands known in the art including, but not limited to, 6-Hydrazinopyridine-3-carboxylic acid (HYNIC), or 1,4,8,11-tetraazacyclotetradecane-N,N',N'',N'''-tetraacetic acid (TETA); and bis-amino bis-thiol (BAT) chelators such as, for instance, those disclosed in U.S. Pat. No. 5,720,934.

$N_4$ chelating ligands are also described, for instance, in U.S. Pat. No. 5,608,110, U.S. Pat. No. 5,665,329, U.S. Pat. No. 5,656,254 and U.S. Pat. No. 5,688,487. Certain $N_3S$ or $N_2S_2$ chelators are described, for instance, in U.S. Pat. No. 5,659,041, U.S. Pat. No. 5,574,140, U.S. Pat. No. 5,780,006, U.S. Pat. No. 5,662,885 and U.S. Pat. No. 5,976,495. The chelators may also include derivatives of the chelating ligand mercapto-acetyl-acetyl-glycyl-glycine (MAG3), which contains an $N_3S$ and $N_2S_2$ system such as MAMA (monoamide-monoaminedithiols), DADS ($N_2S$ diaminedithiols), CODADS, and the like. These ligand systems and a variety of others are described in Liu and Edwards, *Chem Rev,* 1999, 99, 2235-2268 and cited references therein.

The chelators may also include complexes containing ligand atoms that are not donated to the metal in a tetradentate array. These include the boronic acid adducts of technetium and rhenium dioximes, for instance described in U.S. Pat. No. 5,183,653, U.S. Pat. No. 5,387,409 and U.S. Pat. No. 5,118,797.

In another embodiment, disulfide bonds of a fibrin-binding polypeptide of the invention are used as two ligands for chelation of a radionuclide such as $^{99m}Tc$. In this way, the peptide loop is expanded by the introduction of Tc (peptide-S—S-peptide changed to peptide-S—Tc—S-peptide).

Preferred radionuclides according to the present invention include, for instance: $^{99m}Tc$, $^{51}Cr$, $^{67}Ga$, $^{68}Ga$, $^{47}Sc$, $^{167}Tm$, $^{141}Ce$, $^{111}In$, $^{113}In$, $^{168}Yb$, $^{175}Yb$, $^{140}La$, $^{90}Y$, $^{88}Y$, $^{153}Sm$, $^{166}Ho$, $^{165}Dy$, $^{166}Dy$, $^{61}Cu$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{105}Rh$, $^{109}Pd$, $^{117m}Sn$, $^{149}Pm$, $^{161}Tb$, $^{177}Lu$, $^{198}Au$, $^{111}Ag$, $^{199}Au$, $^{51}Mn$, $^{52m}Mn$, $^{52}Fe$, $^{60}Cu$, $^{72}As$, $^{94m}Tc$, or $^{110}In$, $^{142}Pr$, $^{159}Gd$.

The choice of the radionuclide will be based on the desired therapeutic or diagnostic application. For example, for therapeutic purposes (e.g., to provide radiotherapy for primary tumors and metastasis), the preferred radionuclides may include $^{64}Cu$, $^{90}Y$, $^{105}Rh$, $^{111}In$, $^{117m}Sn$, $^{149}Pm$, $^{153}Sm$, $^{161}Tb$, $^{166}Dy$, $^{166}Ho$, $^{175}Yb$, $^{177}Lu$, $^{186/188}Re$, and $^{199}Au$, with $^{186/188}Re$, $^{177}Lu$ and $^{90}Y$ being particularly preferred. For diagnostic purposes (e.g., to locate fibrin deposition and to monitor tumor therapy progress) the preferred radionuclides may include $^{64}Cu$, $^{67}Ga$, $^{68}Ga$, $^{99m}Tc$, and $^{111}In$. $^{99m}Tc$ is particularly preferred for diagnostic applications because of its low cost, availability, imaging properties and high specific activity. In particular, the nuclear and radioactive properties of $^{99m}Tc$ make this isotope an ideal scintigraphic imaging agent. This isotope, in fact, has a single photon energy of 140 keV and a radioactive half-life of about 6 hours, and is readily available from a $^{99}Mo$-$^{99m}Tc$ generator.

Preferred metal radionuclides for use in PET imaging are positron emitting metal ions such as, for instance: $^{51}Mn$, $^{52}Fe$, $^{60}Cu$, $^{68}Ga$, $^{72}As$, $^{94m}Tc$ or $^{110}In$.

The choice of the suitable ligand residue depends on the radionuclide used for the ligand labelling. Thus, preferred residues include those of the chelating ligands from 1 to 21c, of FIGS. 3a to 3c (for $^{111}In$ and radioactive lanthanides such as, for instance, $^{177}Lu$, $^{90}Y$, $^{153}Sm$, and $^{166}Ho$ or for $^{67}Ga$, $^{68}Ga$, $^{61}Cu$, $^{62}Cu$, $^{64}Cu$ or $^{67}Cu$) and those of the chelating ligand from 22 to 33, of FIGS. 4a to 4b (for radioactive $^{99m}Tc$, $^{186}Re$, $^{188}Re$).

In particular, for metal entities including $^{111}In$ and radioactive lanthanides such as, for example $^{177}Lu$, $^{90}Y$, $^{153}Sm$, and $^{166}Ho$, particularly preferred are the following ligand residues

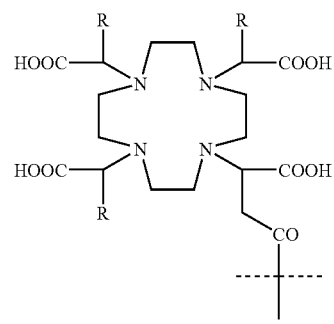

17

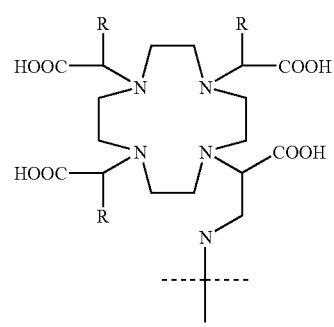

18

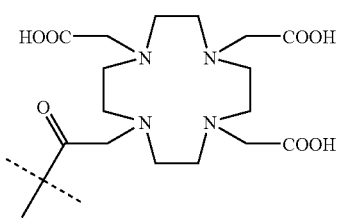

19

In the above formulae 17 and 18, R is alkyl, preferably methyl.

For radioactive $^{99m}Tc$, $^{186}Re$, $^{188}Re$, particularly preferred are the following ligand residues

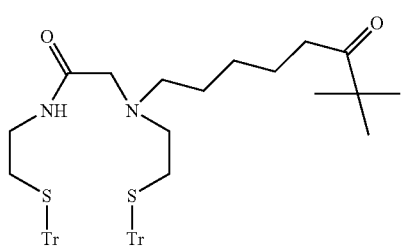

22

-continued

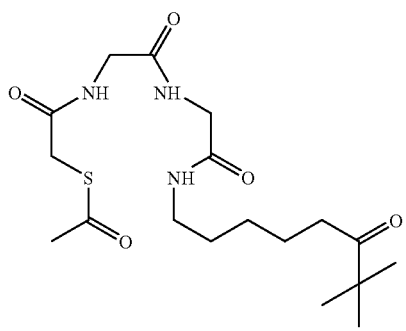
19

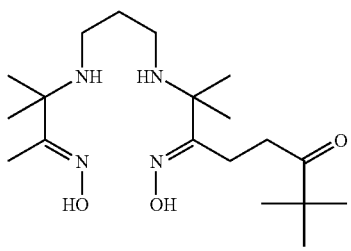
29

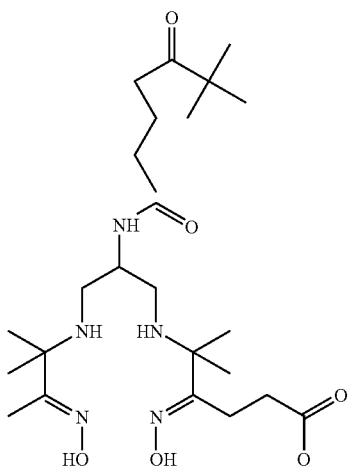
30

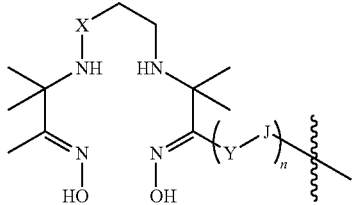
31

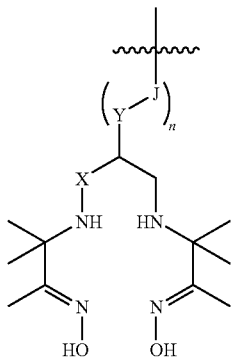
32

-continued

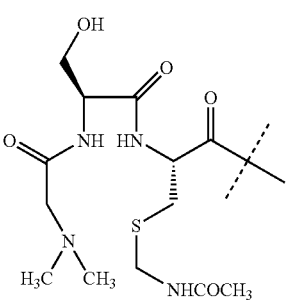
23

33

These and other metal chelating groups are for instance described in U.S. Pat. No. 5,608,110, U.S. Pat. No. 6,143,274, U.S. Pat. No. 5,627,286, U.S. Pat. No. 5,662,885, U.S. Pat. No. 5,780,006 and U.S. Pat. No. 5,976,495 which are incorporated by reference herein in their entirety.

Additionally, the above chelating group of formula 19 is described in U.S. Pat. No. 6,143,274; the chelating groups of the above formulae 31 and 32 are described in U.S. Pat. No. 5,627,286 and U.S. Pat. No. 6,093,382; and the chelating group of formula 33 is described in U.S. Pat. No. 5,662,885, U.S. Pat. No. 5,780,006 and U.S. Pat. No. 5,976,495.

In the formulae 31 and 32, X is either $CH_2$ or O, Y is either $C_1$-$C_{10}$ branched or unbranched alkyl; Y is aryl, aryloxy, arylamino, arylaminoacyl; Y is arylkyl where the alkyl group or groups attached to the aryl moiety are $C_1$-$C_{10}$ branched or unbranched alkyl groups, $C_1$-$C_{10}$ branched or unbranched hydroxy or polyhydroxyalkyl groups or polyalkoxyalkyl or polyhydroxy-polyalkoxyalkyl groups, J is >C(=O), —OC(=O)—, —SO$_2$—, >NC(=O)—, >NC(=S)—, —N(Y)—, —NC(=NCH$_3$)—, —NC(=NH)—, —N=N—, homopolyamides or heteropolyamines derived from synthetic or naturally occurring amino acids; all where n is 1-100. Other variants of these structures are described, for example, in U.S. Pat. No. 6,093,382. The disclosures of each of the foregoing patents, applications and references are incorporated by reference herein, in their entirety.

Thus, preferred for scintigraphic applications are radioimaging contrast agents of formula (I) wherein T is one of the above ligand residues from 22 to 33 labelled with $^{99m}$Tc.

PET Imaging

In a still further embodiment of the invention, within the compounds of formula (I) T is an optionally labelled sugar moiety for use, when labelled, in PET Imaging. Accordingly, in another preferred aspect, the present invention relates to compounds of formula (I) in which T is a suitably labelled sugar moiety.

Preferably, the said sugar moiety is labelled by halogenation with radionuclides such as, for instance: $^{124}$I, $^{125}$I, $^{131}$I, $^{123}$I, $^{77}$Br, $^{76}$Br and $^{18}$F; $^{18}$F being as particularly preferred.

Therapeutically Effective Agents

In another embodiment of the invention, within the compounds of formula (I) T is a therapeutic active moiety.

Therefore, compounds of formula (I) in which T is a therapeutically active moiety or a therapeutic agent, as used herein interchangeably, constitute a further object of the present invention.

Unless otherwise provided, the term "therapeutic" as used herein includes at least partial alleviation of symptoms of a given condition. The therapeutically active agents of formula (I) do not have to produce a complete alleviation of the symptoms to be useful. For example, treatment of an individual can result in a decrease in the size of a tumor or diseased area or a blood clot, or even prevention of an increase in size of the tumor or diseased area, as well as partial alleviation of other symptoms. Alternatively, treatment can also result in the reduction in the number of blood vessels in an area of interest or can prevent an increase in their number. Treatment can also prevent or lessen the number or size of metastatic outgrowths of the main tumor(s).

Suitable examples of therapeutic active moieties according to the present invention include anticoagulant-thrombolytic or fibrinolitic agents capable of clots lyses, anti-angiogenic agents, cytotoxic agents including chemotherapeutic or tumorcidal agents for selective killing and/or inhibiting the growth of cancer cells and, especially, radiotherapeutic agents.

In one embodiment of the invention T is a thrombolytic or fibrinolitic agent. Suitable examples of the said fibrinolitic agents comprise, for instance, fibrinolitic enzymes including plasminogen activators, urokinase, streptokinase, and anistreplase. The fibrin binding polypeptide portion of the therapeutically active compounds of the invention causes the thrombolytic agent to "home" to the sites of fibrin clots or sites of angiogenesis, and to improve the affinity of the conjugate for such sites, so that the thrombolytic or anti-angiogenic activity of the conjugate is more localized and concentrated at the sites of interest.

Thus, the compounds of formula (I) in which T is a thrombolytic or a fibrinolitic agent will be especially useful in treating thrombus associated diseases, especially acute myocardial infarction, stroke and pulmonary embolism in mammals, including humans.

In another embodiments of the invention, T is a chemotherapeutic or tumorcidal agent.

Suitable examples of the said tumor targeted therapeutic agents comprise, for instance, antineoplastic agents such as platinum compounds (e.g., spiroplatin, cisplatin and carboplatin), methotrexate, adriamycin, mitomycin, ansamitocin, bleomycin, cytosine, arabinoside, arabinosyl adenine, mercaptopolylysine, vincristine, busulfan, chlorambucil, melphalan (e.g., PAM, L-PAM, or phenylalanine mustard), mercaptopurine, mitotane, procarbazine hydrochloride, dactinomycin (actinomycin D), daunorubcin hydrochloride, doxorubicin hydrochloride, taxol, mitomycin, plicamycin (mithramycin), aminoglutethimide, estramustine phosphate sodium, flutamide, leuprolide acetate, megestrol acetate, tamoxifen citrate, testoiactone, trilostane, amsacrine (m-AMSA), aparaginase (L-aparaginase), Erwina aparaginase, etoposide (VP-16), interferon cx-2a, Interferon cx-2b, teniposide (VM-26, vinblastine sulfate (VLB), vincristine sulfate and bleomycin sulfate.

In a still further embodiment of the invention T is an anti-angiogenic agent such as a tyrosine kinase inhibitor with activity toward signaling molecules important in angiogenesis and/or tumor growth, for instance SU5416 and SU6668 (Sugen/Pharmacia & Upjohn), endostatin (EntreMed), angiostatin (EntreMed), Combrestatin (Oxigene), cyclosporine, 5-fluorouracil, vinblastine, doxorubicin, paclitaxel, daunorubcin, immunotoxins; coagulation factors; antivirals such as acyclovir, amantadine azidothymidine (AZT or Zidovudine), ribavirin and vidarabine monohydrate (adenine arahinoside, ara-A);

In an additional preferred embodiment of the invention, within the compounds of formula (I) T is a radiotherapeutic agent.

Preferably, the said radiotherapeutic agent comprises the residue of a chelating ligand that is labelled with a therapeutic radionuclide. These compounds are preferred for use as radiotherapeutic agents according to the invention.

Accordingly, in another embodiment, the invention relates to novel radiotherapeutic agents of formula (I) in which T is the residue of a chelating ligand suitably labelled with a radioactive nuclide that emits ionizing radiations such as beta particles, alpha particles and Auger or Coster-Kroning electrons.

Preferred radionuclides for use in radiotherapy include: $^{64}Cu$, $^{90}Y$, $^{105}Rh$, $^{111}In$, $^{117m}Sn$, $^{149}Pm$, $^{153}Sm$, $^{161}Tb$, $^{166}Dy$, $^{166}Ho$, $^{175}Yb$, $^{177}Lu$, $^{186/188}Re$, and $^{199}Au$; with $^{177}Lu$ and $^{90}Y$ being particularly preferred.

The selection of a proper radionuclide for use in a particular radiotherapeutic application depends on many factors, including:

a. Physical half-life—This should be long enough to allow synthesis and purification of the radiotherapeutic construct from the radiometal and the conjugate, and delivery of said construct to the site of injection, without significant radioactive decay prior to injection. Preferably, the radionuclide should have a physical half-life between about 0.5 and about 8 days.

b. Energy of the emission(s) from the radionuclide—Radionuclides that are particle emitters (such as alpha emitters, beta emitters and Auger electron emitters) are particularly useful, as they emit highly energetic particles that deposit their energy over short distances, thereby producing a highly localized damage. Beta emitting radionuclides are particularly preferred, as the energy from beta particle emissions from these isotopes is deposited within about 5 to about 150 cell diameters. Radiotherapeutic agents prepared from these nuclides are capable of killing diseased cells that are relatively close to their site of localization, but cannot travel long distances to damage adjacent normal tissues such as bone marrow.

c. Specific activity (i.e. radioactivity per mass of the radionuclide)—Radionuclides that have high specific activity (e.g., generator produced $^{90}Y$, $^{111}In$, $^{177}Lu$) are particularly preferred. The specific activity of a radionuclide is determined by its method of production, the particular target for which it is produced, and the properties of the isotope in question.

Many of the lanthanides and lanthanoids include radioisotopes that have nuclear properties that make them suitable for use as radiotherapeutic agents, as they emit beta particles. Some of these are listed in the following Table 4.

TABLE 4

| Isotope | Half-Life (days) | Max b-energy (MeV) | Gamma energy (keV) | Approximate range of b-particle (cell diameters) |
|---|---|---|---|---|
| $^{149}$-Pm | 2.21 | 1.1 | 286 | 60 |
| $^{153}$-Sm | 1.93 | 0.69 | 103 | 30 |
| $^{166}$-Dy | 3.40 | 0.40 | 82.5 | 15 |
| $^{166}$-Ho | 1.12 | 1.8 | 80.6 | 117 |
| $^{175}$-Yb | 4.19 | 0.47 | 396 | 17 |
| $^{177}$-Lu | 6.71 | 0.50 | 208 | 20 |
| $^{90}$-Y | 2.67 | 2.28 | — | 150 |
| $^{111}$-In | 2.810 | Auger electron emitter | 173, 247 | <5 * m | wherein: Pm is Promethium, Sm is Samarium, Dy is Dysprosium, Ho is Holmium, Yb is Ytterbium, Lu is Lutetium, Y is Yttrium, In is Indium.

The use of radioactive rhenium isotope as an alternative to the above lanthanides and lanthanoids is well known in the art.

Particularly $^{186/188}$Re isotopes have proved to be of particular interest in nuclear medicine, having a large number of applications in radiopharmaceutical therapy. Thus, in a preferred embodiment, the invention relates to novel radiotherapeutic agents of formula (I) wherein T is the residue of a suitably chelated radionuclide that emits ionizing radiations such as beta particles, alpha particles and Auger or Coster-Kroning electrons.

More preferably, T is the residue of a chelating ligand labelled with a lanthanide or a lanthanoid radionuclide selected from $^{90}$Y, $^{111}$In, $^{149}$Pm, $^{153}$Sm, $^{166}$Dy, $^{166}$Ho, $^{175}$Yb, and $^{177}$Lu. Examples of suitable chelating ligands may be selected from those of FIGS. 3a to 3c.

In a particularly preferred embodiment, the present invention relates to novel radiotherapeutic agents of formula (I) in which T is the residue of a chelating ligand of figures from 3a to 3c, labelled with a $^{90}$Y, $^{111}$In or $^{177}$Lu.

In another preferred aspect, the invention relates to novel radiotherapeutic agents of formula (I) in which T is the residue of a chelating ligand of formula from 22 to 33, as provided in FIGS. 4a and 4b, labelled with $^{186}$Re or $^{188}$Re.

The fibrin-targeted peptide moiety the radiotherapeutic agents of the invention comprise is able to bring the chelated radioactive isotope linked thereto to the pathologic fibrin deposition, for instance inside solid tumors and, hence, the beta or alpha-particles emitting radioisotope emits a cytotoxic amount of ionizing radiation causing the cell death.

Optical Imaging

In one further preferred embodiment of the invention, within the compounds of formula (I) T represents an optically active imaging moiety.

Compounds of formula (I) in which T is an optically active imaging moiety are also novel and constitute a further object of the present invention. These compounds are preferred for use as optical imaging contrast agents.

Thus, in a still further embodiment, the invention relates to novel contrast agents for optical imaging having formula (I) in which T is an optically active imaging moiety.

Suitable examples of optically active imaging moieties include, for instance, optical dyes, including organic chromophores or fluorophores, having extensive delocalized ring systems and having absorption or emission maxima in the range of 400-1500 nm; a fluorescent molecule such as, for example, fluorescein; a phosphorescent molecule; a molecule absorbing in the UV spectrum; a quantum dot; or a molecule capable of absorption of near or far infrared radiations.

Optical parameters to be detected in the preparation of an image may include, e.g., transmitted radiation, absorption, fluorescent or phosphorescent emission, light reflection, changes in absorbance amplitude or maxima, and elastically scattered radiation. For example, the biological tissue is relatively translucent to light in the near infrared (NIR) wavelength range of 650-1000 nm. NIR radiation can penetrate tissues up to several centimeters, permitting the use of the diagnostic agents of the invention comprising a NIR moiety to image target-containing tissues in vivo.

Near infrared dye may include, cyanine or indocyanine derivatives such as, for example, Cy5.5, IRDye800, indocyanine green (ICG), indocyanine green derivatives including the tetrasulfonic acid substituted indocyanine green (TS-ICG), and combinations thereof.

In another embodiment, the compounds of the invention may include photolabels, such as optical dyes, including organic chromophores or fluorophores, having extensively conjugated and hence delocalized ring systems and having absorption or emission maxima in the range of 400-1500 nm. The compounds of the invention may alternatively be derivatized with a bioluminescent molecule. The preferred range of absorption maxima for photolabels is between 600 and 1000 nm to minimize interference with the signal from hemoglobin. Preferably, photoabsorption labels have large molar absorptivities, e.g. >$10^5$ cm$^{-1}$M$^{-1}$, while fluorescent optical dyes will have high quantum yields. Examples of optical dyes include, but are not limited to, those described in U.S. Pat. No. 6,051,207, U.S. Pat. No. 6,083,485, U.S. Pat. No. 6,534,041, WO 96/23524 and references cited therein.

After injection of the optically-labelled diagnostic derivative according to the invention, the patient is scanned with one or more light sources (e.g., a laser) in the appropriate wavelength range for the photolabel employed in the agent. The light used may be monochromatic or polychromatic and continuous or pulsed. Transmitted, scattered, or reflected light is detected via a photodetector tuned to one or multiple wavelengths to determine the location of target-containing tissue (e.g. angiogenic tissue) in the subject. Changes in the optical parameter may be monitored over time to detect accumulation of the optically-labelled reagent at the target site. Standard image processing and detecting devices may be used in conjunction with the optical imaging reagents of the present invention.

In a preferred embodiment, within the compounds of formula (I) T represents the residue of a 5-carboxyfluorescein (CF5)

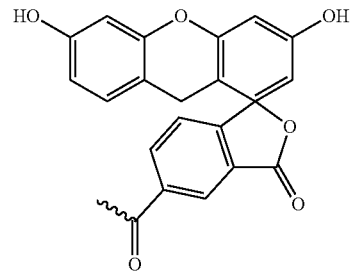

A number of compounds of formula (I) including a fibrin-binding peptide moiety according to the present invention conjugated with 5-carboxyfluorescein have been prepared and used for in vitro fibrin detection assays.

Obtained results, provided in Table 5 below, show that all of the 5-carboxyfluorescein labelled fibrin-binding peptides described therein have equivalent or far superior binding than the comparative fibrin-binding peptide of the art being equally labelled.

Salts

The compounds of formula (I) of the invention wherein T is a therapeutically or diagnostically active moiety including a paramagnetic or radionuclide chelated compound of the invention, as well as the unlabelled precursor thereof, can also be in the form of a pharmaceutically acceptable salt.

The term "pharmaceutically acceptable salt", as used herein, refers to derivatives of the compounds of the invention wherein the parent compound is modified by making the acid or basic groups not yet internally neutralized in the form of non-toxic, stable salts which do not destroy the activity of the parent compound.

Suitable examples of the said salts include: mineral or organic acid salts of basic residues such as amines; alkali or organic salts of acidic residues such as carboxylic acids, and the like.

Preferred cations of inorganic bases which can be suitably used to salify the compounds of the invention comprise ions of alkali or alkaline-earth metals such as potassium, sodium, calcium or magnesium. Preferred cations of organic bases comprise, inter alia, those of primary, secondary and tertiary amines such as ethanolamine, diethanolamine, morpholine, glucamine, N-methylglucamine, N,N-dimethylglucamine.

Preferred anions of inorganic acids which can be suitably used to salify the complexes of the invention comprise the ions of halo acids such as chlorides, bromides, iodides or other ions such as sulfate.

Preferred anions of organic acids comprise those of the acids routinely used in pharmaceutical techniques for the salification of basic substances such as, for instance, acetate, succinate, citrate, fumarate, maleate or oxalate.

Preferred cations and anions of amino acids comprise, for example, those of taurine, glycine, lysine, arginine, ornithine or of aspartic and glutamic acids.

From all of the above, specific examples of compounds of formula (I) of the invention are reported below including, in particular, the following MRI contrast agents:

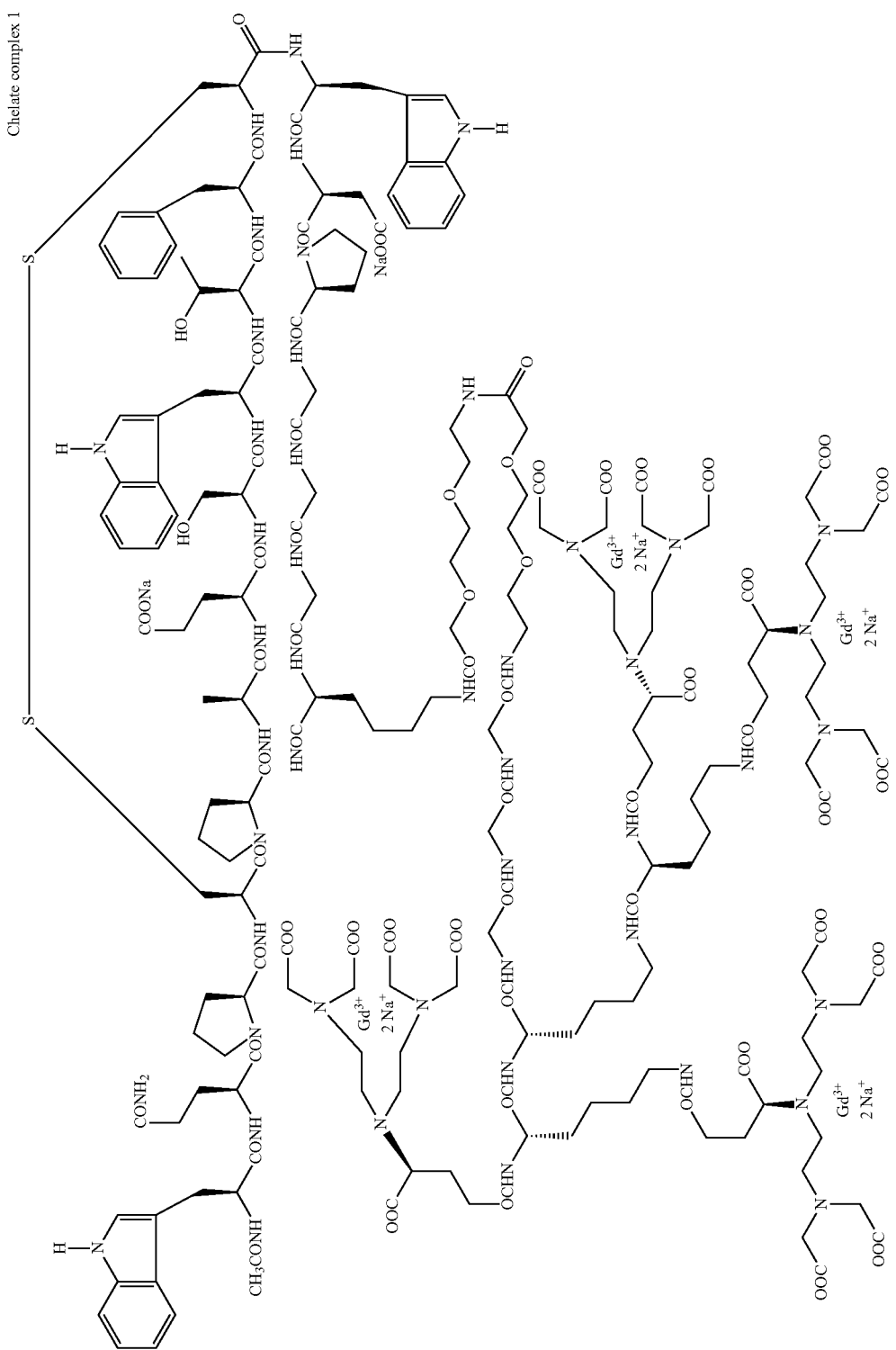

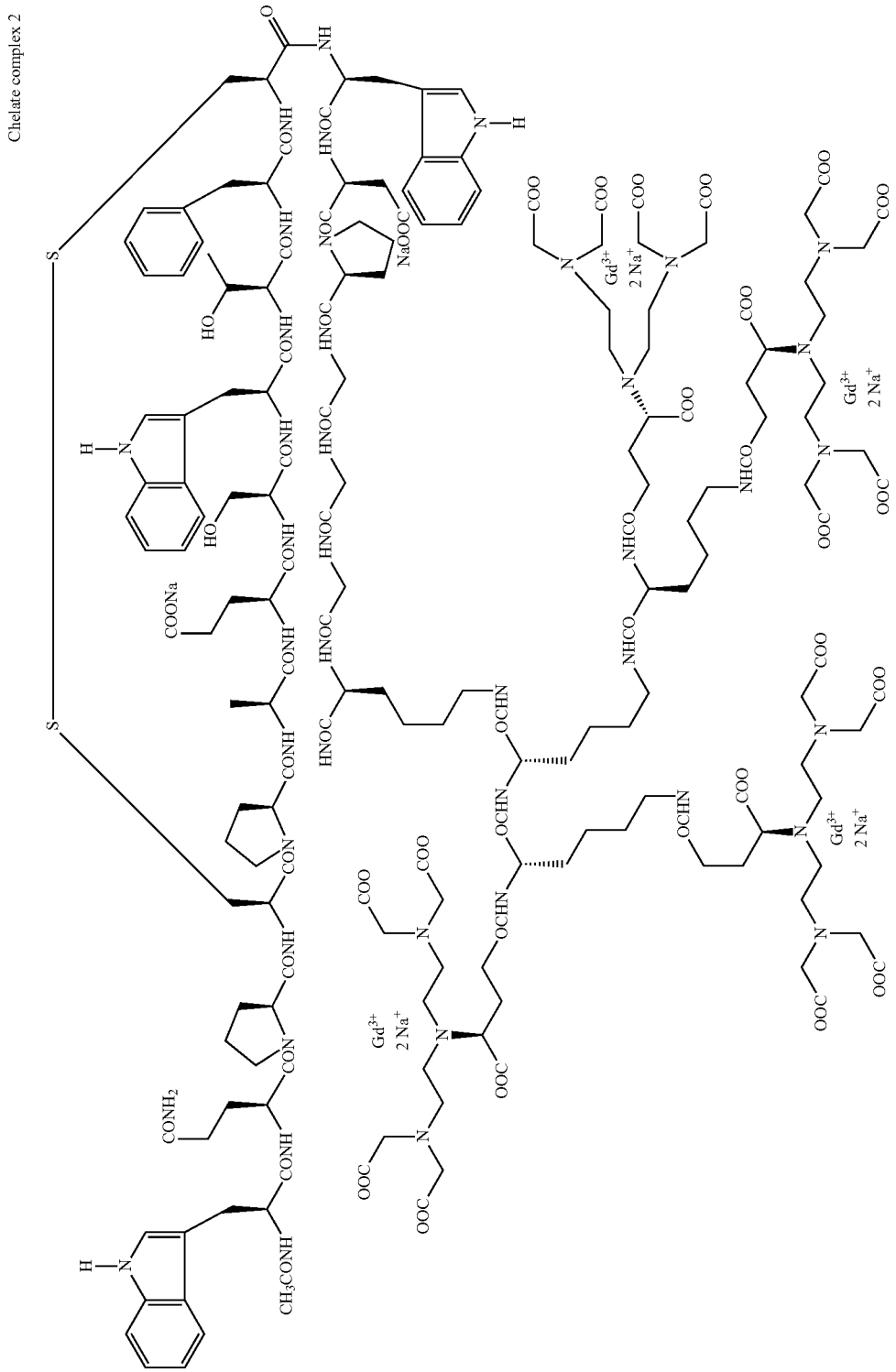

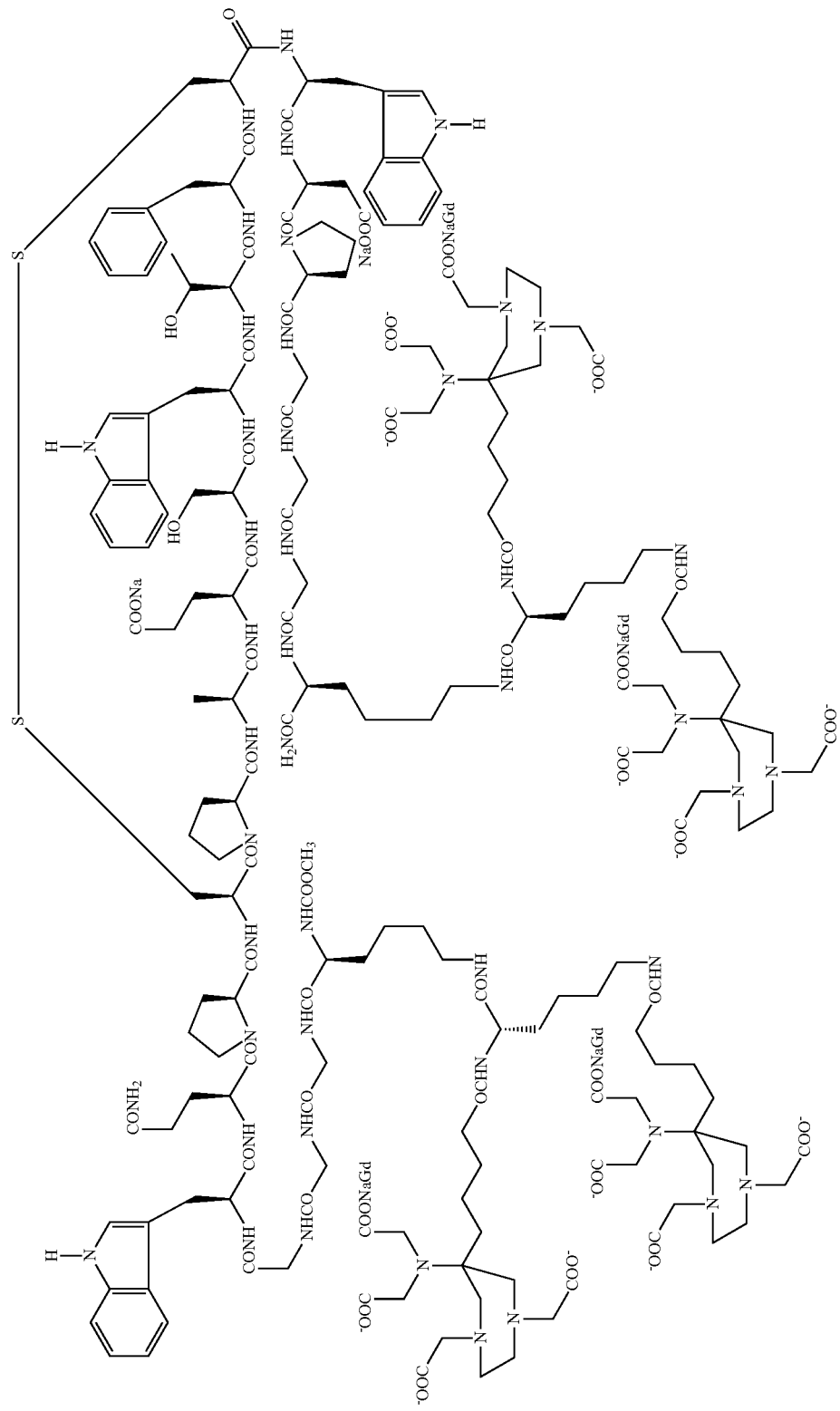

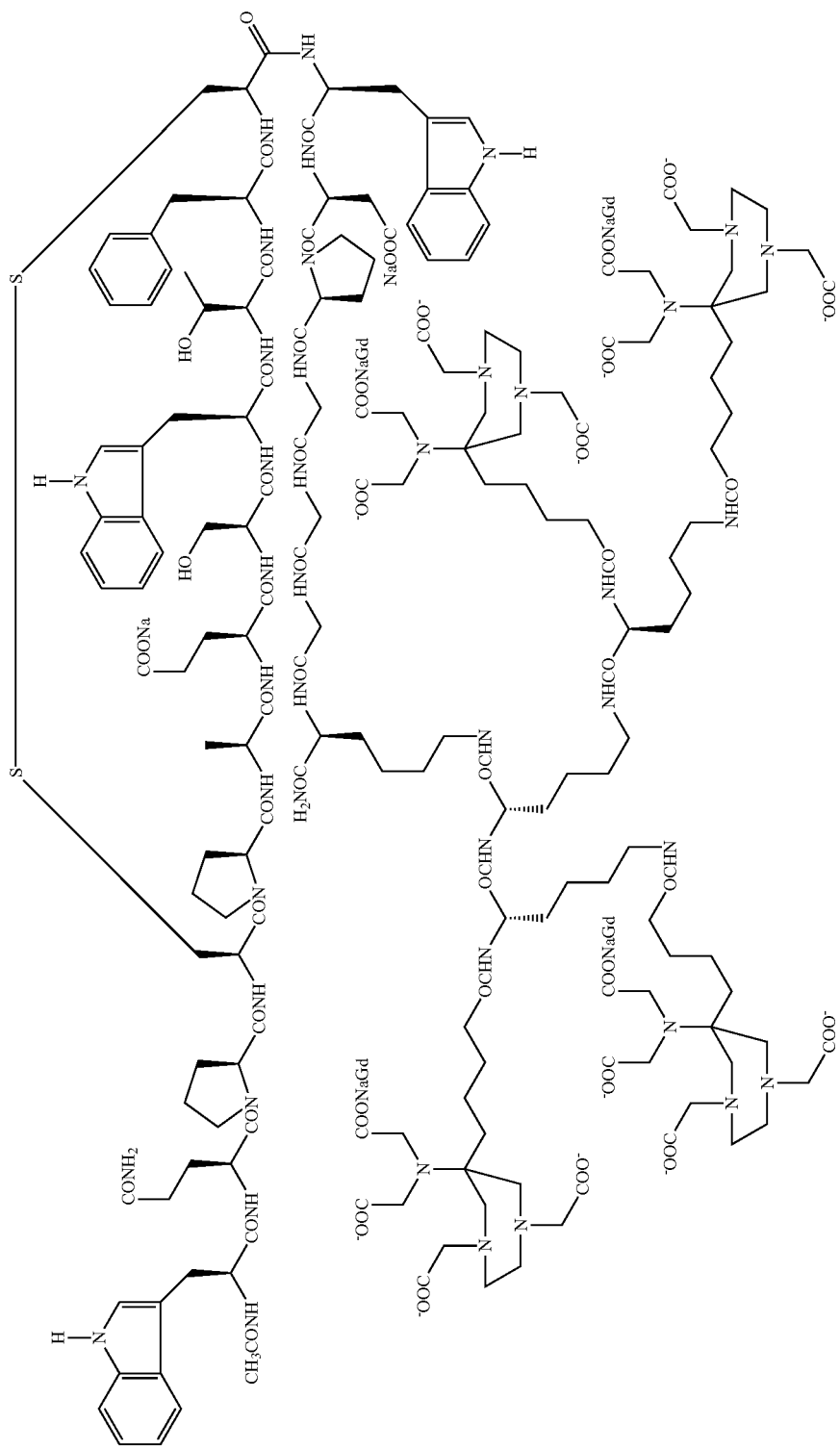
Chelate complex 4

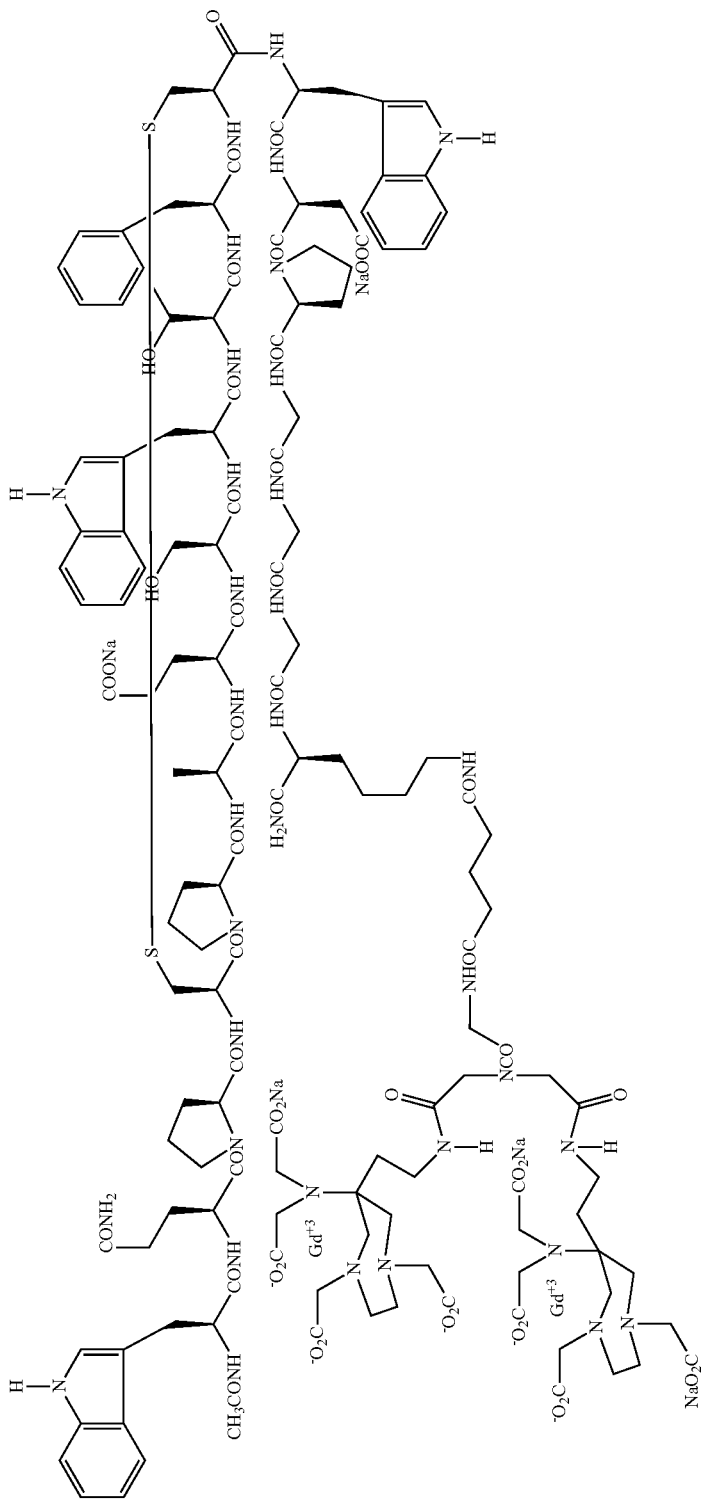

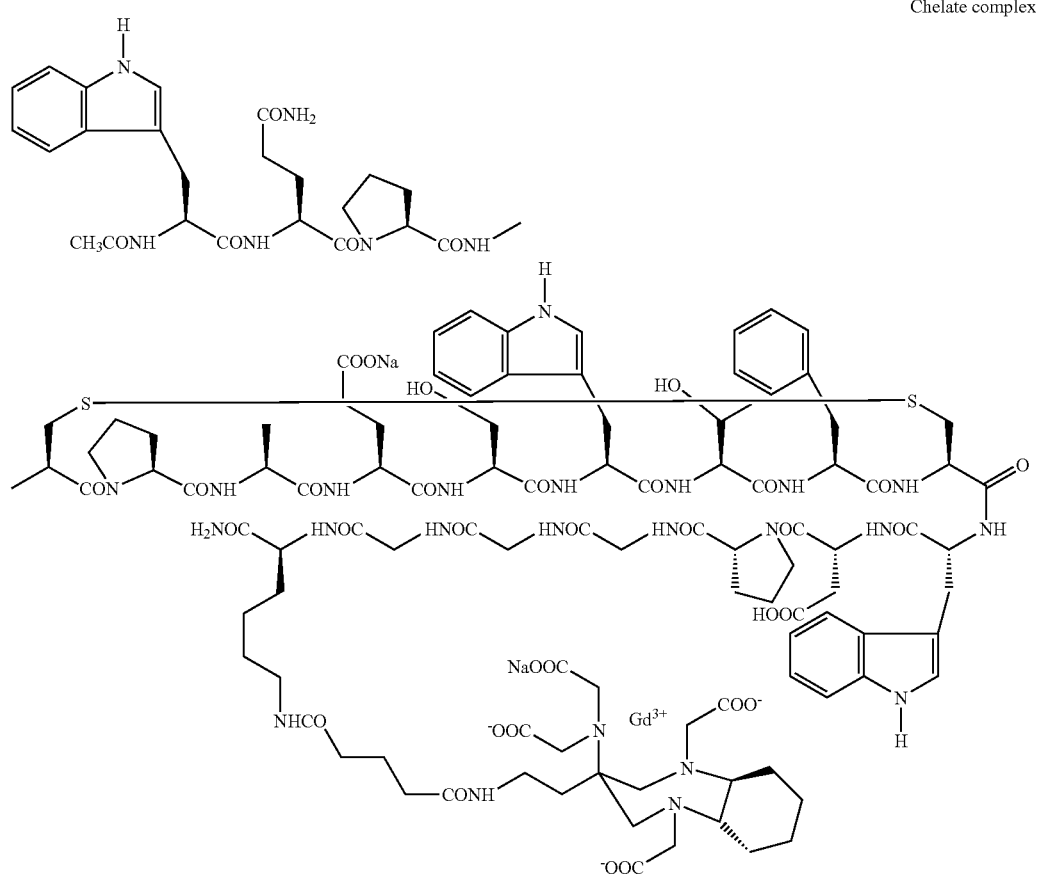
Chelate complex 6

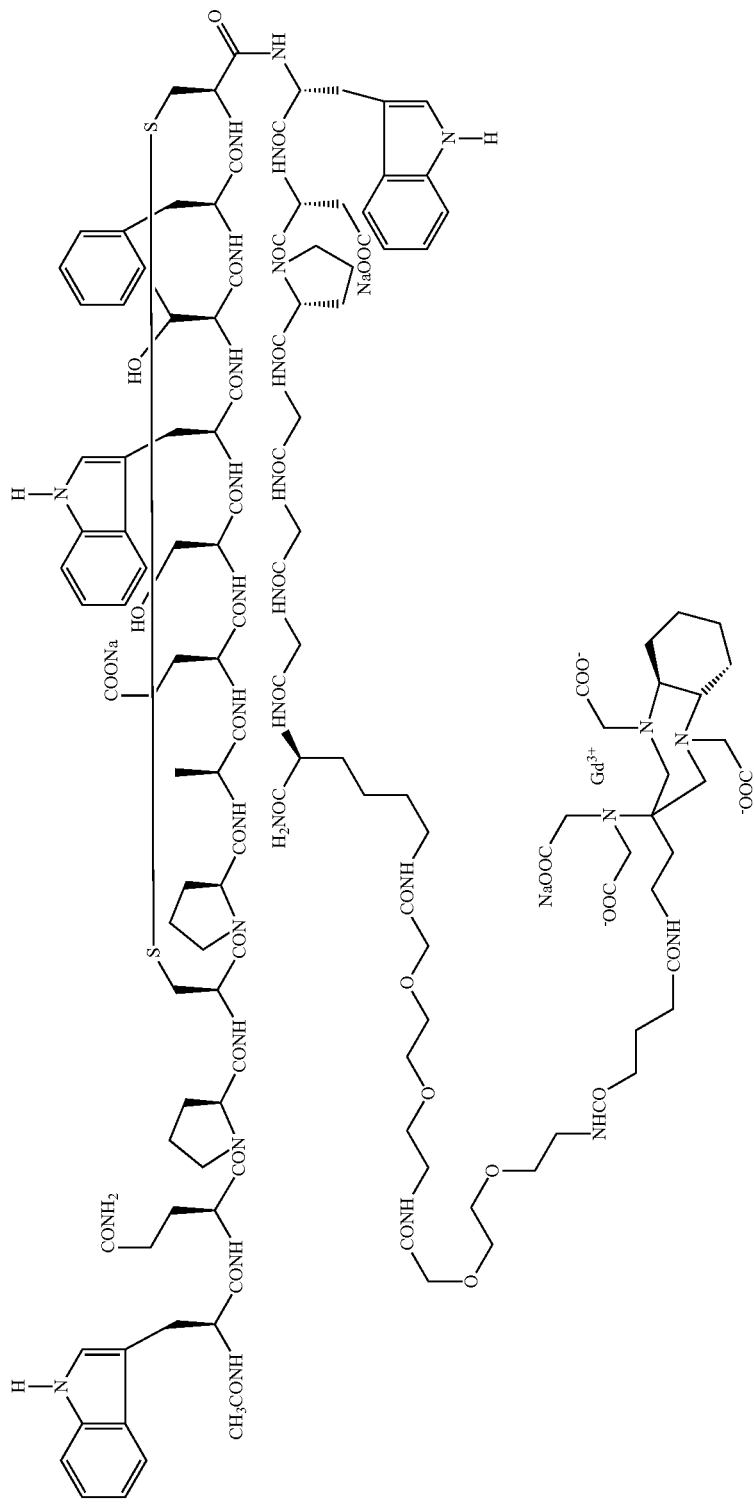

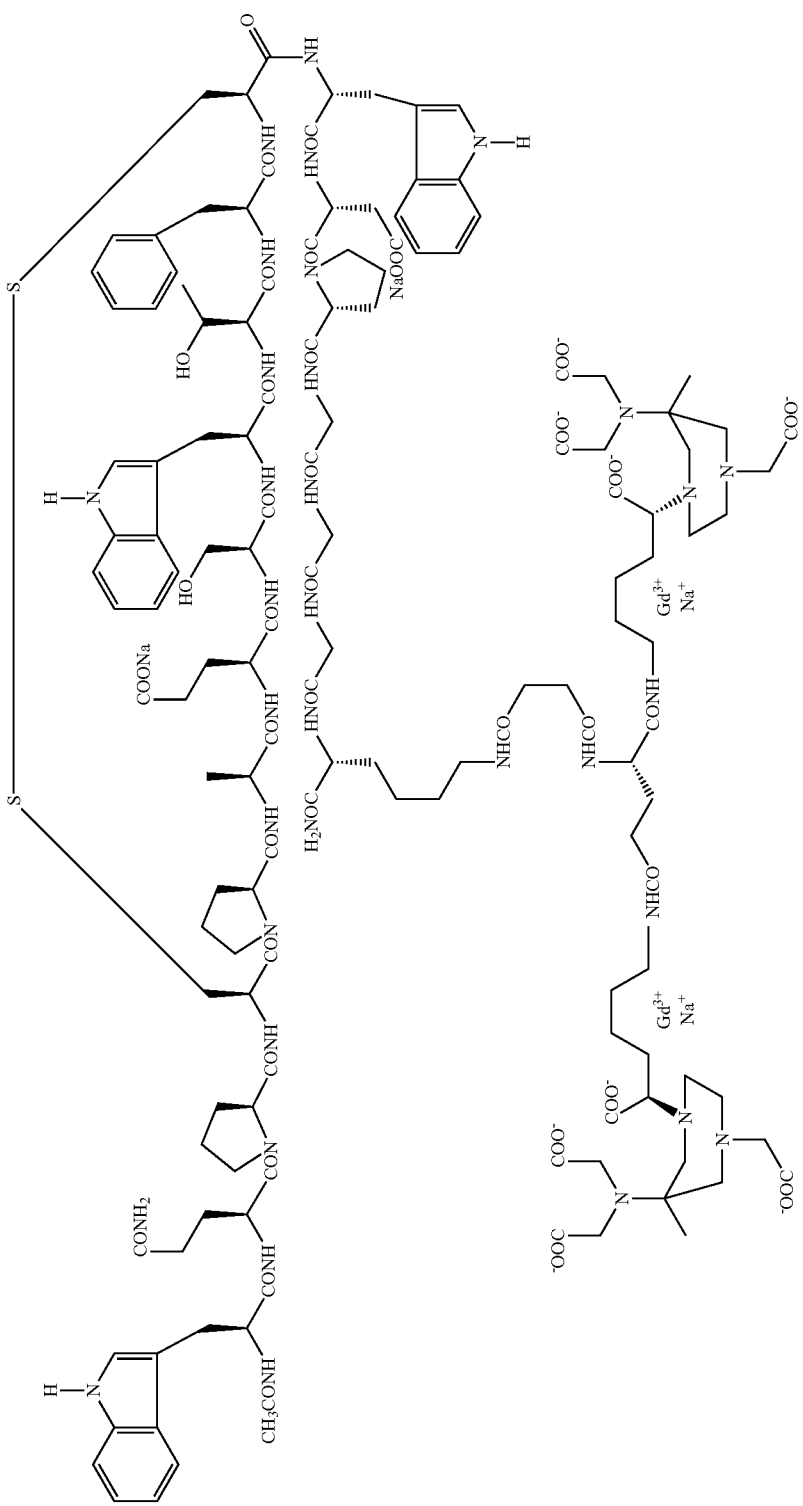

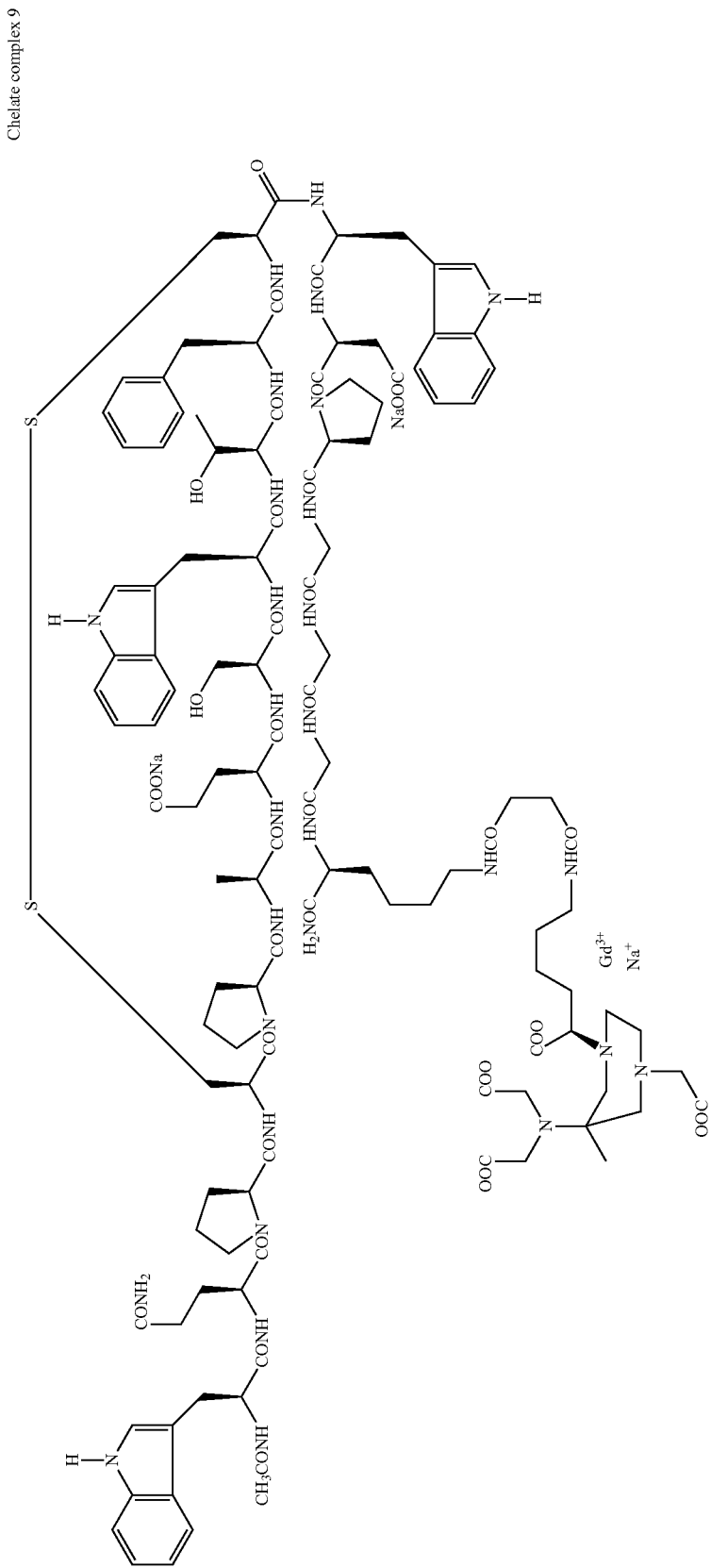
Chelate complex 9

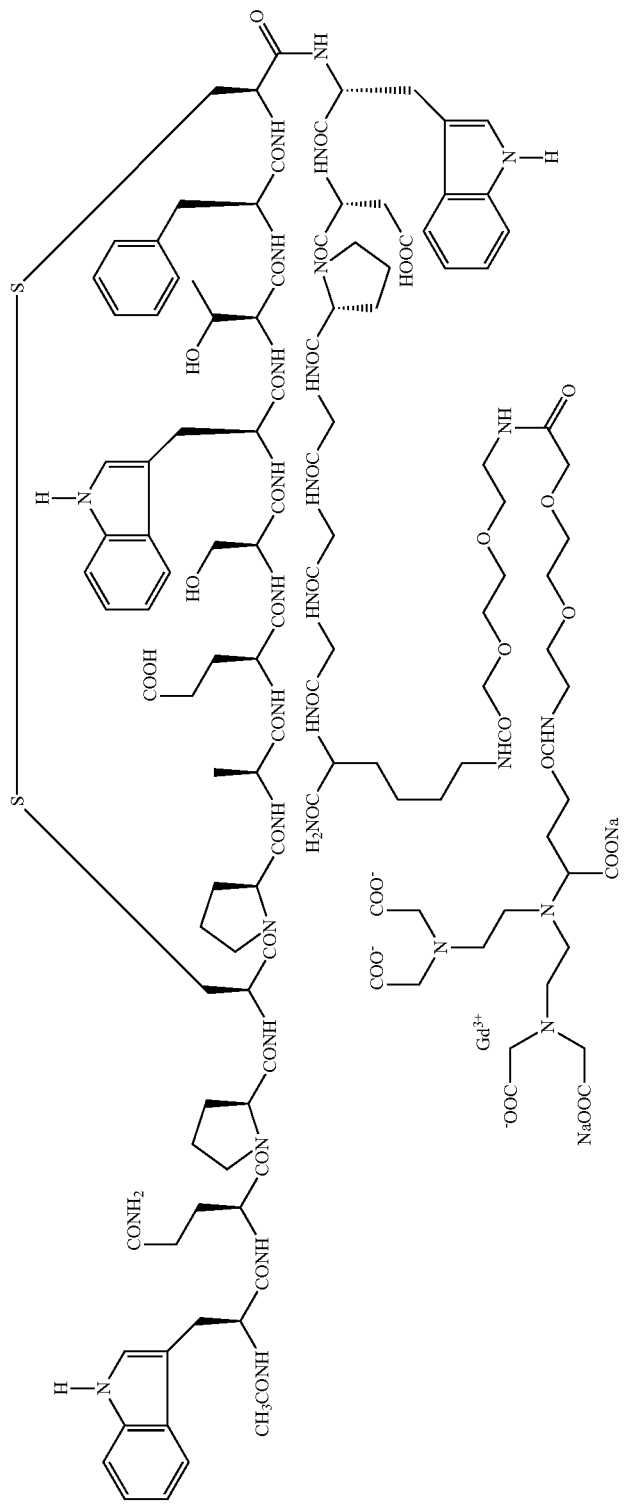
Chelate complex 10

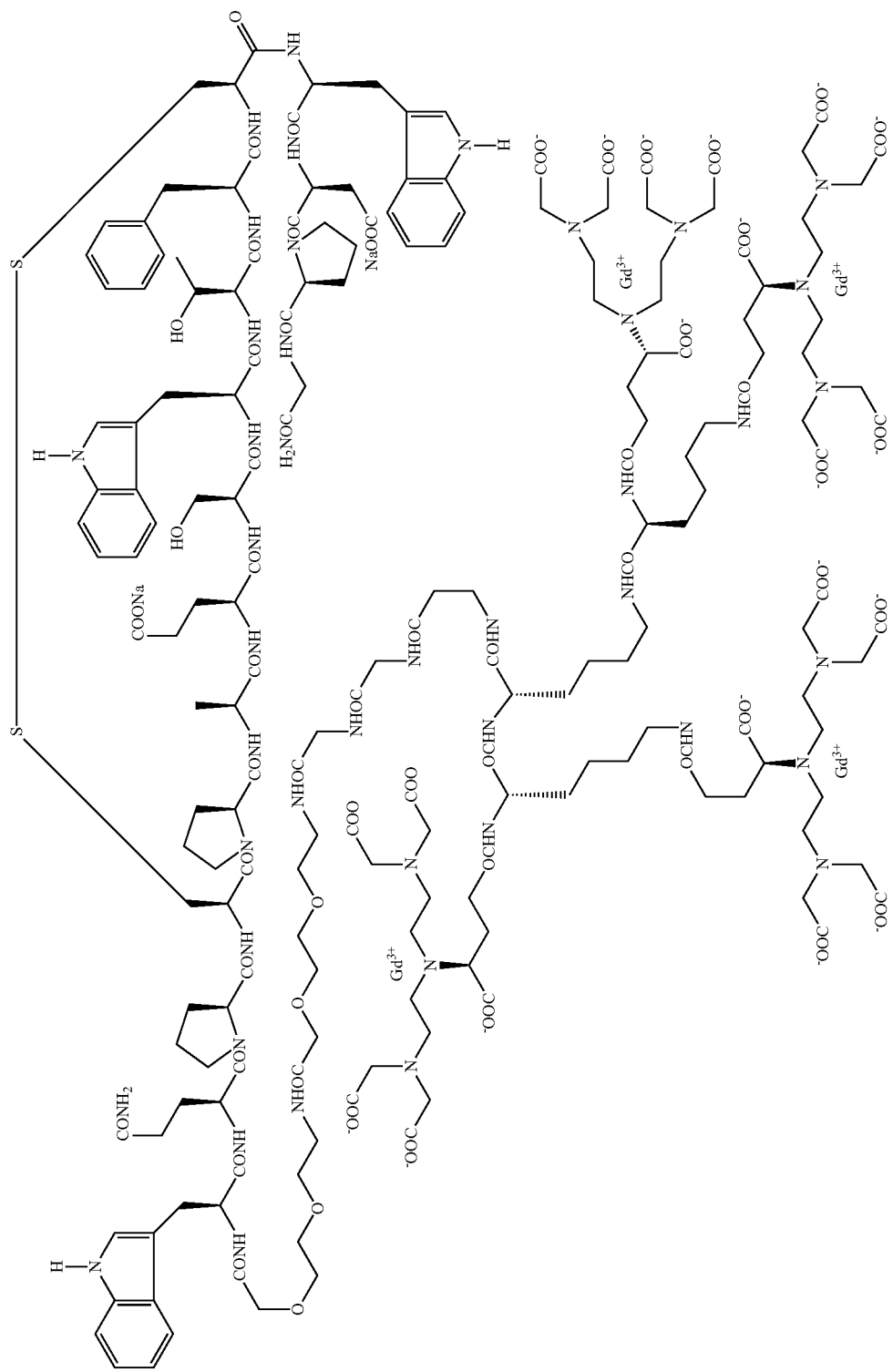
Chelate complex 11

Preparation

Precursor

In a still further embodiment thereof, the present invention relates to an unlabelled precursor of the compounds of formula (I) in which T represents an unlabelled chelating ligand residue according to the invention, or a physiologically acceptable salt thereof.

Preparation

The preparation of the compounds of formula (I), either as such or in the form of a physiologically acceptable salt, represents a further object of the invention.

Peptide Synthesis

The preparation of the novel compounds of formula (I) includes the preparation of the optimized fibrin-binding peptide moiety A.

Direct synthesis of the fibrin-binding peptide moieties of the invention may be accomplished using conventional techniques, including solid-phase peptide synthesis, solution-phase synthesis, and the like; solid-phase synthesis being as preferred; see, as an example: Stewart et al., Solid-Phase Peptide Synthesis, W. H. Freeman Co., San Francisco, 1989; Merrifield, J. Am. Chem. Soc., 1963, 85:2149-2154; Bodanszky and Bodanszky, The Practice of Peptide Synthesis, Springer-Verlag, New York, 1984; all of which are incorporated herein by reference.

For a reference to the peptide synthesis see, for instance, procedures A-L reported in the following experimental section.

A fibrin-binding peptide according to the present invention is preferably purified once it has been isolated or synthesized. For purification purposes, there are many standard methods that may be employed, including reversed-phase high-pressure liquid chromatography (RP-HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate peptides based on their charge. The degree of purity of the polypeptide may be determined by various methods, including identification of a major large peak on HPLC. A polypeptide that produces a single peak that is at least 95% of the input material on an HPLC column is preferred. Even more preferable is a polypeptide that produces a single peak that is at least 97%, at least 98%, at least 99% or even 99.5% or more of the input material on an HPLC column.

In order to ensure that the fibrin-binding peptide obtained is the desired peptide for use within the compounds of formula (I) according to the invention, analysis of the peptide composition may be carried out. Such analysis may be conducted using high resolution mass spectrometry to determine the molecular weight of the peptide. Alternatively, the amino acid content of the peptide can be confirmed by hydrolyzing the peptide in aqueous acid, and separating, identifying and quantifying the components of the mixture through HPLC or an amino acid analyzer. Protein sequencers, which sequentially degrade the peptide and identify the amino acids in order, may also be used to determine definitely the sequence of the peptide.

Modification or Optimization of Binding Polypeptides

Modification or optimization of the fibrin-binding polypeptides, thus providing optimized peptide moieties, is within the scope of the present invention. Specifically, a polypeptide sequence of the invention can be further modified to optimize its potency, pharmacokinetic behaviour, stability and/or other biological, physical and chemical properties.

Linkers

The linking moieties Y of the invention are known or they may be easily prepared according to know procedures, starting from commercially available sub-units.

As a non limiting example, FIG. 1 includes the synthetic pathway for the preparation of a linker functionalized peptide moiety of the invention, in which the peptide moiety is the one comprising the amino acid SEQ ID NO:001, as shown in Table 1, and the conjugated linking moiety is -GGGKJJ-, wherein J is the Fmoc-8-amino-3,6-dioxaoctanoic acid (see Aldrich Neosystem and Peptides International catalogue).

Chelate Compounds

The preparation of the compounds of formula (I) wherein T is a chelating ligand residue labelled (or to be labelled) with a paramagnetic or a radioactive metal ion, or a physiologically acceptable salt thereof, is described in detail over the course of the present description making reference, in particular, to the synthetic schemes 2-4 included in the following experimental section.

From the above, it is clear to the skilled person that the above method may apply as well to the preparation of the compounds of formula (I) bearing different T moieties.

General Procedure

In general terms, the synthetic pathway that may be adopted for the preparation of the compounds of formula (I) may, for instance, include the following main steps:

1) Preparation of the chelating ligand(s) in a suitable form, wherein any functional group, either involved or not in the metal coordination and covalent binding with the rest of the molecule, can be suitably and independently protected or activated, as the case may be. In this respect, the prepared chelating moiety can be already complexed with the selected paramagnetic or radioactive metal or, alternatively, and according to a preferred embodiment, it may be unlabelled. In this case, the ligand is first reacted and conjugated with the rest of the molecule, and the resulting conjugate compound is then complexed with the selected paramagnetic metal ion or radionuclide, as per known methods.

In this latter case, the compounds of formula (I) wherein T represents the residue of the chelating agent to be labelled with the paramagnetic metal ion or radionuclide represent a further object of the invention.

2) Loading of the suitably protected peptide moiety or of the selected amino acid on a suitably deprotected/activated resin and subsequent sequential couplings with additional amino acids, peptide or linker sub-units so as to properly assemble the peptide moiety A conjugated with the linker or linkers Y. Alternatively, a proper sub-unit of the linker Y may be suitably loaded on the above resin and, then, sequentially reacted with additional linker and peptide sub-units and amino acids, according to known methods, so as to obtain the resin supported A-Y moieties.

It is clear to the skilled person that the above coupling reactions may occur through a variety of possibilities of sequential couplings, all to be intended as comprised within the scope of the invention.

In each of the above coupling reactions, functional groups may be suitably deprotected or activated, once taking part of the reaction or, otherwise, protected or deactivated, so as to avoid undesired side reactions.

Thus, for instance, a given amino acid or sub-unit could be first subjected to a protection or deactivation step, aimed to preserve the functional group not involved in the coupling reaction that, subsequently, may purposely be deprotected or activated so as to take part of a subsequent coupling step.

Preferably, after each of the above steps including, as said, deprotection/activation, coupling and protection/deactivation, any resulting "loaded-peptide-intermediate" is subjected to a purification step, for instance including a washing step with suitable solvents.

3) Coupling of the suitably deprotected/activated resin supported A-Y moiety with the selected moiety or moieties T.

4) Cleavage of the coupled compound from the resin, cyclization of the peptide so as to convert the —SH groups of cysteine into disulphide bonds —S—S—, and, in case T represents any suitable chelating agent to be labelled, subsequent complexation with the selected paramagnetic metal ion or radionuclide, so as to obtain the desired compound of formula (I).

As formerly said, "protecting group" is a group adapted to preserve the function to which it is bound. In the present contest, Fmoc ((9H-fluoren-9-ylmethoxy)carbonyl) is preferably used as amino-protecting group for amino acid(s), peptide moiety(ies), poly-amino-acidic resin(s) involved with the preparation of the complex compounds of the invention. Fmoc protected amino acids, Y unit(s) or subunit(s) and peptide moiety(ies) may thus be considered as useful intermediates-building blocks for the preparation of the compounds of formula (I).

The above schematic procedure, comprehensive of any variant thereof, either in the reaction order, in any of the steps of deprotection/protection, in the steps of purification and washing of the intermediates, as well as in the loading to, and cleavage from, the resin, advantageously allows to isolate the chelated complexes, or the salts thereof, of formula (I) and, hence, is to be intended as comprised within the scope of the present invention.

Likewise, by working in a substantially analogous way, the said method may also provide for the preparation of the compounds of formula (I) wherein the moiety or moieties T represent groups other than the aforementioned complex compounds such as, for instance, optical imaging moieties or therapeutically effective moieties.

Preparation of the Suitably Protected Chelating Ligand(s)

The majority of the ligand residues according to the compounds of the invention is well known to a skilled person in the art and some of them are already marketed. The non-marketed chelators may be prepared according to known methods, for example as per the accompanying bibliographic references.

Among them, the AAZTA derivative having the following structure

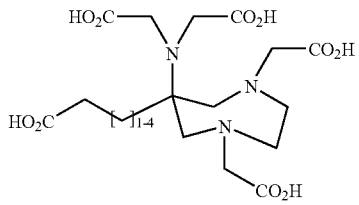

is novel and, hence, represents a further object of the invention.

Its preparation, particularly of its corresponding tert-butyl ester, is detailed in the experimental section below.

Loading of the Peptide, Deprotection/Activation and Coupling of the Loaded Peptide.

Preferably, the resin on which the peptide moiety is appended is a suitably protected PAL-PEG-PS resin. More preferably, it is a Fmoc-PAL-PEG-PS resin.

Before coupling the peptide moiety, once loaded onto the resin, with the linker Y or any sub-unit thereof, the functional group undergoing coupling reaction is deprotected according to conventional methods and the resulting intermediate properly washed.

Complexation of the Isolated Ligand

The complexation of the isolated ligand may be performed by properly labelling it with the proper metal or radionuclide, according to well known methods.

For example, the paramagnetic complexes of the invention such as, in particular, the Gd(III) chelates may be prepared by stoichiometric addition of suitable Gd(III) derivatives, particularly Gd(III) salts or oxides. See, for instance, EP 230893 disclosing labelling with paramagnetic metal ions, and WO 98/52618, U.S. Pat. No. 5,879,658, and U.S. Pat. No. 5,849,261 disclosing labelling with radioactive metals.

Chelates for Radioimaging or Radiodiagnostic Applications

The above process, comprehensive of any variant thereof, may be also advantageously used to prepare the chelated complex of lanthanides or lanthanoids radioisotopes of formula (I).

On the other side, for instance when forming a complex of radioactive technetium, a salt of $^{99m}$Tc, preferably a $^{99m}$Tc pertechnetate, is reacted with the unlabelled compounds of the invention in the presence of a reducing agent. Preferred reducing agents are dithionite and stannous and ferrous ions, stannous chloride being the most preferred one.

Means for preparing such complexes are conveniently provided in a kit form comprising a sealed vial containing a predetermined quantity of compound of the invention to be labelled and a sufficient amount of reducing agent to label the reagent with $^{99m}$Tc. A single or multi-vial kit that contains all of the components needed to prepare the radiopharmaceuticals of this invention, other than the radionuclide, is an integral part of this invention. A single-vial kit preferably contains a chelating ligand (if a metal radionuclide is used), a source of a stannous salt (if reduction is required, e.g., when using technetium), or other pharmaceutically acceptable reducing agent, and it is appropriately buffered with pharmaceutically acceptable acids or bases to adjust the pH to a value of about 3 to about 9. The quantity and type of reducing agent used would depend mainly on the nature of the exchange complex to be formed. The proper conditions are well known to those skilled in the art. Preferably, the kit contents is in lyophilized form. Such a single vial kit may optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or α-, β-, or γ-cyclodextrin that serve to improve the radiochemical purity and stability of the final product. The kit may also contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial may contain all of the ingredients that are required to form a labile Tc(V) complex on addition of pertechnetate (e.g., the stannous source or other reducing agent). Pertechnetate is added to this vial, and after waiting for a suitable period of time, the contents of this vial are added to a second vial that contains the ligand, as well as proper buffers to adjust pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. may be present in either or both vials.

Among the $^{99m}$Tc pertechnetate salts useful with the present invention are included the alkali metal salts such as the sodium salt or ammonium salts or lower alkyl ammonium salts.

Radioactively-labelled imaging agents provided by the present invention must contain a suitable amount of radioactivity. In forming $^{111}$In or $^{99m}$Tc complexes, for instance, it is generally preferred to form radioactive complexes in solutions containing radioactivity at concentrations of from about 0.01 millicurie (mCi) to about 100 mCi per mL.

Chelates for Radiotherapy.

Methods for the preparation of radiometals such as beta-emitting lanthanide radioisotopes are known to those skilled in the art, and have been described elsewhere [e.g., Cutler C S, Smith C J, Ehrhardt G J.; Tyler T T, Jurisson S S, Deutsch E. "Current and potential therapeutic uses of lanthanide radioisotopes." Cancer Biother. Radiopharm. 2000; 15(6): 531-545]. Many of beta-emitting isotopes can be produced in high yields for relatively low cost and many (e.g. $^{90}$Y, $^{149}$Pm, $^{177}$Lu) can be produced at close to carrier-free specific activities (i.e. the vast majority of atoms are radioactive) according to the above cited procedures of the art. Since non-radioactive atoms can compete with their radioactive analogs for binding to receptors on the target tissue, the use of high specific activity radioisotope is important to allow delivery of as high a dose of radioactivity to the target tissue as possible.

Preparation of the complexes of the present invention where the metal is radioactive rhenium may be accomplished, for instance, using as starting materials rhenium compounds wherein the metal is in the +5 or +7 oxidation state. Examples of compounds in which rhenium is in the Re(VII) state are $NH_4ReO_4$ or $KReO_4$. Re(V) is available for instance as [ReOCl$_4$](NBu$_4$), [ReOCl$_4$](AsPh$_4$), ReOCl$_3$(PPh$_3$)$_2$ and as ReO$_2$(pyridine)$_4^+$. Other rhenium reagents capable of forming a rhenium complex may also be used.

Activity

As formerly reported, the novel compounds of formula (I) of the invention comprise a novel fibrin-binding peptide moiety A which amino acid sequence differs form that of the known fibrin-targeted peptide sequences of the prior art. Unexpectedly, the compounds of the invention are endowed with a superior fibrin-selective binding over previously known fibrin targeted peptides and, particularly, over WQPC*PWESWTF*CWDP (SEQ ID NO:037) being functionalized through a linker GGGK—NH$_2$(SEQ ID NO:039), along with excellent physical properties.

In particular, substitution of Ala for Trp at position 6 of the previously known peptide, resulted in an improved potency as well as in a more hydrophilic peptide as demonstrated by fibrin binding affinity data provided herein below, in Tables 5 and 6. The improved properties of this substitution were unexpected, particularly because by replacing either of the other Trp residues in the peptide lead to no or reduced fibrin binding.

Another method that was used to modify the prior-art peptide was by means of attaching amino acids at the N- or C-terminus. In general, attachment of amino acids at the C-terminus did not dramatically change the potency of the peptides. However, when polar amino acids (such as Arg) were added to the N-terminus, improvement in binding was observed. Considering the importance of the Trp at position 1, the introduction of polarity with beneficial effects was thus unexpected. Moreover, the introduction of the unusual amino acid cyclohexylalanine (Cha) for Phe, at position 11, additionally lead to improvements in potency. Considering that substituted phenylalanine derivatives led to weaker binding, it was not expected that changing to the more bulky, less aromatic residues would improve potency. Thus, the combination of these three modifications led to peptides of Table 1 that are endowed, unexpectedly, with superior fibrin-specific binding and improved potency along with excellent physical properties as compared to previously known peptides.

In the practice of the present invention, a determination of the affinity of the fibrin-binding moiety for fibrin relative to fibrinogen is a useful measure, and is referred to as specificity for fibrin. Standard assays for quantitating binding and determining affinity include equilibrium dialysis, equilibrium binding, gel filtration, or the monitoring of numerous spectroscopic changes (such as a change in fluorescence polarization) that may result from the interaction of the binding moiety and its target. These techniques measure the concentration of bound and free ligand as a function of ligand (or protein) concentration. The concentration of bound polypeptide ([Bound]) is related to the concentration of free polypeptide ([Free]) and the concentration of binding sites for the polypeptide, i.e., on fibrin, (N), as described in the following equation:

$$[Bound]=N\times[Free]/((1/K_a)+[Free]).$$

A solution of the data to this equation yields the association constant, $K_a$, a quantitative measure of the binding affinity. The association constant, $K_a$ is the reciprocal of the dissociation constant, $K_D$. The $K_D$ is more frequently reported in measurements of affinity. A peptide having a $K_D$ 1.5 times higher for fibrinogen than for fibrin would be considered low-specificity fibrin binder. A peptide having a $K_D$ 10 times greater for fibrinogen than fibrin would be a moderate-specificity fibrin binder, and a peptide having a $K_D$ 100 times or more greater for fibrinogen than for fibrin would be termed highly specific for fibrin. Preferably, within the present invention the peptides and the diagnostically or therapeutically active agents including them have a $K_D$ at least 1.5 times higher for fibrinogen than for fibrin, more preferably at least 10 times higher, even more preferably at least 100 times, and most preferably at least 1000 times higher. Preferred fibrin binding polypeptides have a $K_D$ for fibrin in the range of 1 nanomolar (nM) to 100 micromolar (μM) and includes $K_D$ values of at least 10 nM, at least 20 nM, at least 40 nM, at least 60 nM, at least 80 nM, at least 1 μM, at least 5 μM, at least 10 μM, at least 20 μM, at least 40 μM, at least 60 μM, and at least 80 μM.

In the practice of the present invention, binding assay tests have been performed using 5-carboxyfluorescein labelled peptides of the invention. Obtained $K_D$ values, determined by fluorescence polarization measurements, are included in Table 5 below providing, for each of the prepared 5-carboxyfluorescein derivative, the sequence ID of the peptide moiety they include, the extended peptide sequence and the linker comprised by the prepared compound, HPLC and mass spectral data (see details in the experimental section) and, for most them, binding affinity measurements compared to the previously known fibrin-binding peptide, equally functionalized and labelled, and thus having the sequence Ac-WQPC*PWESWTFC*WDPGGGK-NH$_2$[Ac-SEQ ID NO:037-GGGK(CF5)-NH$_2$].

TABLE 5

5-Carboxyfluorescein Labelled Peptides

| Seq. ID | Sequence | HPLC Data (System, t$_R$) | Mass Spectral Data (Mode; Ions) | K$_D$ (µM) Direct Binding (n = 2) |
|---|---|---|---|---|
| Ac-Seq000-GGGK(CF5)-NH$_2$ | Ac-WQPC*PWESWTFC*WDPGGGK(CF5)-NH$_2$ | F, 14.78 | Neg. ion; [M − 2H]/2: 1330.9; [M − 3H]/3: 886.9; [M − 4H]/4: 665.0 | 0.39 |
| Ac-Seq002-GGGK(CF5)-NH$_2$ | Ac-GPPGWQPC*PWESWTFC*WDPGGGK(CF5)-NH$_2$ | D, 4.31 | Neg. ion; [M − 2H]/2: 1485.2, [2M − 3]/3: 1981.8 | 0.25 |
| Ac-Seq003-GGGK(CF5)-NH$_2$ | Ac-GGRGWQPC*PWESWTFC*WDPGGGK(CF5)-NH$_2$ | D, 4.10 | Neg. ion: [M − 2H]/2: 1494.9, [2M − 3H]/3: 1993.5, [3M + Na − 5H]/4: 2249.1 | 0.29 |
| Ac-Seq004-GGGK(CF5)-NH$_2$ | Ac-GWQPC*PWESWTFC*WDPGGGK(CF5)-NH$_2$ | D, 4.35 | Neg. ion; [M − 2H]/2: 1359.4, [2M − 3H]/3: 1812.9 | 0.23 |
| Ac-Seq005-GGGK(CF5)-NH$_2$ | Ac-SGSGJWQPC*PWESWTFC*WDPGGGK(CF5)-NH$_2$ | D, 4.15 | Neg. ion; [M − 2H]/2: 1547.8 | 0.45 |
| Ac-Seq006-GGGK(CF5)-NH$_2$ | Ac-WQPC*PWESWT-Cha-C*WDPGGGK(CF5)-NH$_2$ | D, 4.49 | Neg. ion; [M − H]: 2670.3, [M − 2H]/2: 1333.9, [M − 3H]/3: 888.7 | 0.20 |
| Ac-Seq007-GGGK(CF5)-NH$_2$ | Ac-WQPC*PWESWT-Ffe4-C*WDPGGGK(CF5)-NH$_2$ | D, 4.50 | Neg. ion; [M − 2H]/2: 1339.8 | 1.02 |
| Ac-Seq008-GGGK(CF5)-NH$_2$ | Ac-WQPC*PWESWT-F34fe-C*WDPGGGK(CF5)-NH$_2$ | D, 4.56 | Neg. ion; [2M − 3]/3: 1798.5; [M − 2H]/2: 1348.7 | 0.70 |
| Seq004-GGGK(CF5)-NH$_2$ | GWQPC*PWESWTFC*WDPGGGK(CF5)-NH$_2$ | D, 4.31 | Neg. ion; [M − 2H]/2: 1338.9, [M − 3H]/3: 892.0 | N/D |
| Seq009-GGGK(CF5)-NH$_2$ | RGWQPC*PWESWTFC*WDPGGGK(CF5)-NH$_2$ | D, 3.99 | Neg. ion; [2M − 3H]/3: 1889.3, [M − 2H]/2: 1416.4, [M − 3H]/3: 944.0 | 0.28 |
| Seq010-GGGK(CF5)-NH$_2$ | RWQPC*PWESWTFC*WDPGGGK(CF5)-NH$_2$ | D, 4.00 | Neg. ion; [M − 2H]/2: 1387.9, [M − 3H]/3: 925.0 | 0.11 |
| Ac-Seq011-GGGK(CF5)-NH$_2$ | Ac-SGSGSGSGWQPC*PWESWTFC*WDPGGGK(CF5)-NN$_2$ | D, 4.11 | Neg. ion; [M − 2H]/2: 1619.1, [2M − 3H]/3: 2158.5 | 0.47 |
| Ac-Seq012-GGGK(CF5)-NH$_2$ | Ac-KKGWQPC*PWESWTFC*WDPGGGK(CF5)-NH$_2$ | D, 3.94 | Neg. ion; [M − 2H]/2: 1487.7, [2M − 3H]/3: 1984.5 | 0.71 |
| Ac-Seq013-GGGK(CF5)-NH$_2$ | Ac-KGKGKGWQPC*PWESWTFC*WDPGGGK(CF5)-NH$_2$ | D, 3.79 | Neg. ion; [M − 2H]/2: 1608.6, [2M − 3H]/3: 2145.1 | 0.76 |
| Ac-Seq014-GGGK(CF5)-NH$_2$ | Ac-S(Galnac)-WQPC*PWESWT | D, 4.16 | Neg. ion; [M − 2H]/2: 1476.4, [2M − 3H]/3: | 0.50 |

TABLE 5-continued

5-Carboxyfluorescein Labelled Peptides

| Seq. ID | Sequence | HPLC Data (System, $t_R$) | Mass Spectral Data (Mode; Ions) | $K_D$ (µM) Direct Binding (n = 2) |
|---|---|---|---|---|
| | FC*WDPGGGK(CF5)-NH$_2$ | | 1968.6, [2M − 6H]/6: 984.5 | |
| Seq015-GGGK(CF5)-NH$_2$ | Thf2ca-WQPC*PWESWT FC*WDPGGGK(CF5)-NH$_2$ | D, 4.13 | Neg. ion; [M + Na − 2H]: 2740.2; [M + Na − 3H]/2: 1370.1 [M − 2H]/2: 1359.0, [M − 3H]/3: 905.4 | 1.21 |
| Ac-Seq016-GGGK(CF5)-NH$_2$ | Ac-RRGGWQPC*PW ESWTFC*WDPGG GK(CF5)-NH$_2$ | D, 4.15 | Neg. ion; [M − 2H]/2: 1543.7, [2M − 3H]/3: 2059.8, [M − 3H]/3: 1029.0 | N/D |
| Ac-Seq019-GGGK(CF5)-NH$_2$ | Ac-GPPGWQPC*PAE SWTFC*WDPGG GK(CF5)-NH$_2$ | D, 3.45 | Neg. ion; [M − H]: 2857.4; [M − 2H]/2: 1228.0 | 0.31 |
| Ac-Seq020-GGGK(CF5)-NH$_2$ | Ac-GGRGWQPC*PAE SWTFC*WDPGG GK(CF5)-NH$_2$ | D, 3.88 | Neg. Ion; [2M − 3H]/3: 1916.3, [M − 2H]/2: 1437.4 | 0.52 |
| Seq023-GGGK(CF5)-NH$_2$ | GWQPC*PAESWT FC*WDPGGGK(CF5)-NH$_2$ | D, 3.87 | Neg. ion; [M − 2H]/2: 1280.8 | 0.24 |
| Ac-Seq023-GGGK(CF5)-NH$_2$ | Ac-GWQPC*PAESWT FC*WDPGGGK(CF5)-NH$_2$ | D, 4.04 | Neg. ion; [M − 2H]/2: 1302.7 | 0.24 |
| Ac-Seq024-GGGK(CF5)-NH$_2$ | Ac-SGSGSGSGWQPC *PAESWTFC*WD PGGGK(CF5)-NH$_2$ | D, 3.82 | Neg. ion; [2M − 3H]/3: 2083.1, [M − 2H]/2: 1561.8, [M − 3H]/: 1040.7 | 0.53 |
| Ac-Seq026-GGGK(CF5)-NH$_2$ | Ac-WQPC*PAESWT-Cha-C*WDPGGGK(CF5)-NH$_2$ | D, 4.29 | Neg. ion; [M − H]: 2554.6, [M − 2H]/2: 1276.9 | 0.17 |
| Ac-Seq029-GGGK(CF5)-NH$_2$ | Ac-SGSGJWQPC*PA ESWTFC*WDPGG GK(CF5)-NH$_2$ | D, 3.90 | Neg. ion; [M − H]: 2982.0, [M − 2H]/2: 1489.9 | 0.57 |
| Ac-Seq030-GGGK(CF5)-NH$_2$ | Ac-RRGGWQPC*PAE SWTFC*WDPGG GK(CF5)-NH$_2$ | D, 3.50 | Pos. ion; [M + 2H]/2: 1488.9, [M + 3H]/3: 992.7 | 0.22 |
| Ac-Seq010-GGGK(CF5)-NH$_2$ | Ac-RWQPC*PWESW TFC*WDPGGGK(CF5)-NH$_2$ | D, 4.26 | Neg. ion; [M − 2H]/2: 1409.1, [2M − 3H]/3: 1879.1 | 0.11 |
| Ac-Seq032-GGGK(CF5)-NH$_2$ | Ac-RWQPC*PAESWT FC*WDPGGGK(CF5)-NH$_2$ | D, 3.94 | Neg. ion; [M − H]: 2704.5, [2M − 3H]/3: 1802.6, [M − 2H]/2: 1351.3 | 0.21 |
| Ac-Seq033-GGGK(CF5)-NH$_2$ | Ac-RWQPC*PAESWT-Cha-C*WDPGGGK(CF5)-NH$_2$ | D, 4.04 | Neg. ion; [M − H]: 2710.9, [2M − 3H]/3: 1806.4, [M − 2H]/2: 1354.5 | 0.08 |

TABLE 5-continued

5-Carboxyfluorescein Labelled Peptides

| Seq. ID | Sequence | HPLC Data (System, $t_R$) | Mass Spectral Data (Mode; Ions) | $K_D$ (μM) Direct Binding (n = 2) |
|---|---|---|---|---|
| Ac-Seq035-GGGK(CF5)-NH$_2$ | Ac-RGWQPC*PAESWT-Cha-C*WDPGGGK(CF5)-NH$_2$ | D, 4.04 | Neg. ion; [M − H]: 2767.5, [2M − 3H]/3: 1844.1, [M − 2H]/2: 1383.0 | 0.10 |
| Seq035-GGGK(CF5)-NH$_2$ | RGWQPC*PAESWT-Cha-C*WDPGGGK(CF5)-NH$_2$ | D, 3.91 | Neg. ion; [M − H]: 2726.1, [2M − 3H]/3: 1816.9, [M − 2H]/2: 1362.0 | 0.05 |
| Seq036-GGGK(CF5)-NH$_2$ | RWQPC*PAESWTFC*WDPGGGK(CF5)-NH$_2$ | D, 3.81 | Neg. ion; [M − H]: 2663.1, [2M − 3H]/3: 1774.2, [M − 2H]/2: 1330.3 | 0.06 |

As shown in Table 5, all of the 5-carboxyfluorescein labelled fibrin-binding peptides described therein have equivalent or far superior binding than the comparative fibrin-binding peptide.

In addition, Table 6 below provides, for the fibrin-binding peptides of Table 1, the sequence ID, the extended sequence of the fibrin-binding moiety prepared and tested, analytical data including HPLC and mass spectral data (see details in the experimental section) and, for most of the peptides, binding affinity measurements carried out according to conventional methods (expressed as $IC_{50}$) compared to a previously known fibrin-binding peptide, equally functionalized and having the sequence Ac-WQPC*PWESWTFC*WDPGGGK-NH$_2$, (Ac-SEQ ID NO:037-GGGK—NH$_2$) (relative $IC_{50}$=1).

A relative $IC_{50}$ lower than 1 indicates better binding than the comparative peptide.

TABLE 6

Peptides fibrin-binding properties

| Seq. ID | Sequence | Prepared Sequence | Prepared Sequnce ID | HPLC Data (System, $t_R$) | Mass Spectral Data (Mode: Ions) | Rel $IC_{50}$ (n = 2, Competition FP assay) |
|---|---|---|---|---|---|---|
| Seq001 | WQPC*PAESWTFC*WDP | Ac-WQPC*PAESWTFC*WDPGGGK-NH$_2$ | Ac-Seq001-GGGK-NH$_2$ | B, 4.93 | Neg. ion: [M − H]: 2189.6; [M − 2H]/2: 1094.4 | 0.875 |
| Seq002 | GPPGWQPC*PWESWTFC*WDP | Ac-GPPGWQPC*PWESWTFC*WDPGGGK-NH$_2$ | Ac-Seq002-GGGK-NH$_2$ | A, 4.70 | Neg. ion: [M + Na − 2H]: 2636.8; [M − 2H]/2: 1306.2 | 0.235 |
| Seq003 | GGRGWQPC*PWESWTFC*WDP | Ac-GGRGWQPC*PWESWTFC*WDPGGGK-NH$_2$ | Ac-Seq003-GGGK-NH$_2$ | A, 4.44 | Pos. ion: [2M + 3H]/3: 1756.9; [M + 2H]/2: 1317.3; [M + 3H]/3: 876.1 | 0.370 |
| Seq004 | GWQPC*PWESWTFC*WDP | Ac-GWQPC*PWESWTFC*WDPGGGK-NH$_2$ | Ac-Seq004-GGGK-NH$_2$ | B, 4.08 | Neg. ion: [M − H]: 2160.2; [M − 2H]/2: 1180.5; [M − 3H]/3: 786.8 | 1.04 |
| Seq005 | SGSGJWQPC*PWESWTFC*WDP | Ac-SGSGJWQPC*PWESWTFC*WDPGGGK-NH$_2$ | Ac-Seq005-GGGK-NH$_2$ | B, 3.96 | Neg. ion: [M − H]: 2738.7; [M − 2H]/2: 1369.1 | 0.714 |
| Seq006 | WQPC*PWESWT-Cha-C*WDP | Ac-WQPC*PWESWT-Cha-C*WDPGGGK-NH$_2$ | Ac-Seq006-GGGK-NH$_2$ | B, 4.27 | Neg. ion: [M − H]: 2311.8; [M − 2H]/2: 1154.8 | 0.494 |

TABLE 6-continued

Peptides fibrin-binding properties

| Seq. ID | Sequence | Prepared Sequence | Prepared Sequnce ID | HPLC Data (System, $t_R$) | Mass Spectral Data (Mode: Ions) | Rel IC$_{50}$ (n = 2, Competition FP assay) |
|---|---|---|---|---|---|---|
| Seq007 | WQPC*PWESWT-Ffe4-C*WDP | Ac-WQPC*PWESWT-Ffe4-C*WDPGGGK-NH$_2$ | Ac-Seq007-GGGK-NH$_2$ | B, 4.26 | Neg. ion: [M − H]: 2322.6; [M − 2H]/2: 1160.4 | 0.601 |
| Seq008 | WQPC*PWESWT-F34fe-C*WDP | Ac-WQPC*PWESWT-F34fe-C*WDPGGGK-NH$_2$ | Ac-Seq008-GGGK-NH$_2$ | B, 4.33 | Neg. ion: [M − H]: 2341.2; [M − 2H]/2: 1169.8 | 0.428 |
| Seq004 | GWQPC*PWESWTFC*WDP | GWQPC*PWESWTFC*WDPGGGK-NH$_2$ | Seq004-GGGK-NH$_2$ | B, 3.94 | Neg. ion: [M − H]: 2319.6; [M − 2H]/2: 1159.3 | 0.622 |
| Seq009 | RGWQPC*PWESWTFC*WDP | RGWQPC*PWESWTFC*WDPGGGK-NH$_2$ | Seq009-GGGK-NH$_2$ | B, 3.79 | Pos. ion [M + 2H]/2: 1239.3; [M + 3H]/3: 826.8 | 0.511 |
| Seq010 | RWQPC*PWESWTFC*WDP | RWQPC*PWESWTFC*WDPGGGK-NH$_2$ | Seq010-GGGK-NH$_2$ | B, 3.77 | Pos. ion [M + 2H]/2: 1211.6; [M + 3H]/3: 807.6 | 0.47 |
| Seq011 | SGSGSGSGWQPC*PWESWTFC*WDP | Ac-SGSGSGSGWQPC*PWESWTFC*WDPGGGK-NH$_2$ | Ac-Seq011-GGGK-NH$_2$ | B, 3.89 | Neg. ion: [M − 2H]/2: 1439.8 | 0.527 |
| Seq12 | KKGWQPC*PWESWTFC*WDP | Ac-KKGWQPC*PWESWTFC*WDPGGGK-NH$_2$ | Ac-Seq012-GGGK-NH$_2$ | A, 4.26 | Neg. ion: [M − H]: 2618.8; [M − 2H]/2: 1308.1 | 0.357 |
| Seq013 | KGKGKGWQPC*PWESWTFC*WDP | Ac-KGKGKGWQPC*PWESWTFC*WDPGGGK-NH$_2$ | Ac-Seq013-GGGK-NH$_2$ | A, 4.11 | Neg. ion: [M − H]: 2860.5; [M − 2H]/2: 1429.6 | 0.595 |
| Seq014 | S(Galnac)-WQPC*PWESWTFC*WDP | Ac-S(Galnac)-WQPC*PWESWTFC*WDPGGGK-NH$_2$ | Ac-Seq014-GGGK-NH$_2$ | B, 3.95 | Neg. ion: [M − H]: 2595.5; [M − 2H]/2: 1297.0 | 0.5595 |
| Seq015 | Thf2ca-WQPC*PWESWTFC*WDP | Thf2ca-WQPC*PWESWTFC*WDPGGGK-NH$_2$ | Seq015-GGGK-NH$_2$ | B, 4.23 | Neg. ion: [M − H]: 2416.8; [M − 2H]/2: 1208.6 | 0.616 |
| Seq016 | RRGGWQPC*PWESWTFC*WDP | Ac-RRGGWQPC*PWESWTFC*WDPGGGK-NH$_2$ | Ac-Seq016-GGGK-NH$_2$ | A, 4.32 | Pos. ion [M + 2H]/2: 1366.4; [M + 3H]/3: 911.8; [M + 3H + Na]/4: 689.8 | 0.125 |
| Seq017 | S(Galnac)-JWQPC*PWESWTFC*WDP | Ac-S(Galnac)-JWQPC*PWESWTFC*WDPGGGK-NH$_2$ | Ac-Seq017-GGGK-NH$_2$ | B, 3.95 | Neg. ion: [M − H]: 2740.4; [M − 2H]/2: 1369.3 | 1.15 |
| Seq018 | WQPC*-Hypt4-WESWTFC*WDP | Ac-WQPC*-Hypt4-WESWTFC*WDPGGGK-NH$_2$ | Ac-Seq018-GGGK-NH$_2$ | B, 4.12 | Mode: Neg. - ion: [M − H]: 2320.7; [M − 2H]/2: 1159.4 | 0.55 |

TABLE 6-continued

Peptides fibrin-binding properties

| Seq. ID | Sequence | Prepared Sequence | Prepared Sequnce ID | HPLC Data (System, $t_R$) | Mass Spectral Data (Mode: Ions) | Rel IC$_{50}$ (n = 2, Competition FP assay) |
|---|---|---|---|---|---|---|
| Seq019 | GPPGWQPC*PAESWTFC*WDP | Ac-GPPGWQPC*PAESWTFC*WDPGGGK-NH$_2$ | Ac-Seq019-GGGK-NH$_2$ | D, 3.49 | Neg. Ion - [M - H]: 2498.9, [M - 2H]/2: 1248.4 | § |
| Seq020 | GGRGWQPC*PAESWTFC*WDP | Ac-GGRGWQPC*PAESWTFC*WDPGGGK-NH$_2$ | Ac-Seq020-GGGK-NH$_2$ | D, 3.29 | Neg. Ion - [M - H]: 2516.7, [M + TFA - 2H]/2: 1314.7, [M - 2H]/2: 1257.9 | § |
| Seq021 | KKGWQPC*PAESWTFC*WDP | Ac-KKGWQPC*PAESWTFC*WDPGGGK-NH$_2$† | Ac-Seq021-GGGK-NH$_2$ | D, 4.91 | Neg. Ion - [M - H]: 2916.4, [2M - 3H]/3: 1943.6, [M - 2H]/2: 1457.6 | § |
| Seq022 | KGKGKGWQPC*PAESWTFC*WDP | Ac-KGKGKGWQPC*PAESWTFC*WDPGGGK-NH$_2$† | Ac-Seq022-GGGK-NH$_2$ | D, 5.26 | Neg. Ion - [2M - 3H]/3: 2242.8, 2225.4, [M - 2H]/2: 1681.2 | § |
| Seq023 | GWQPC*PAESWTFC*WDP | GWQPC*PAESWTFC*WDPGGGK-NH$_2$† | Seq023-GGGK-NH$_2$ | D, 3.76 | Neg. Ion - [M - H]: 2288.6, [M - 2H]/2: 1143.9 | § |
| Seq023 | GWQPC*PAESWTFC*WDP | Ac-GWQPC*PAESWTFC*WDPGGGK-NH$_2$ | Ac-Seq023-GGGK-NH$_2$ | D, 3.44 | Neg. Ion - [M - H]: 2247.9, [M - 2H]/2: 1122.9 | § |
| Seq024 | SGSGSGSGWQPC*PAESWTFC*WDP | Ac-SGSGSGSGWQPC*PAESWTFC*WDPGGGK-NH$_2$ | Ac-Seq024-GGGK-NH$_2$ | D, 3.25 | Neg. Ion - [2M - 3H]/3: 1844.3, [M - 2H]/2: 1382.8 | § |
| Seq025 | WQPC*PAESWT-Ffe4-C*WDP | Ac-WQPC*PAESWT-Ffe4-C*WDPGGGK-NH$_2$ | Ac-Seq025-GGGK-NH$_2$ | D, 3.65 | Neg. Ion - [M - H]: 2207.7, [M - 2H]/2: 1103.4 | § |
| Seq026 | WQPC*PAESWT-Cha-C*WDP | Ac-WQPC*PAESWT-Cha-C*WDPGGGK-NH$_2$ | Ac-Seq026-GGGK-NH$_2$ | D, 3.69 | Neg. Ion - [M - H]: 2195.7, [M - 2H]/2: 1097.4 | § |
| Seq027 | WQPC*PAESWT-F34fe-C*WDP | Ac-WQPC*PAESWT-F34fe-C*WDPGGGK-NH$_2$ | Ac-Seq027-GGGK-NH$_2$ | D, 3.73 | Neg. Ion - [M - H]: 2225.4, [M - 2H]/2: 1111.9 | § |
| Seq028 | Thf2ca-WQPC*PAESWTFC*WDP | Thf2ca-WQPC*PAESWTFC*WDPGGGK-NH$_2$ | Seq028-GGGK-NH$_2$ | D, 3.71 | Neg. Ion - [M - H]: 2245.6, [M - 2H]/2: 1122.3. | § |
| Seq029 | SGSGJWQPC*PAESWTFC*WDP | Ac-SGSGJWQPC*PAESWTFC*WDPGGGK-NH$_2$ | Ac-Seq029-GGGK-NH$_2$ | D, 3.34 | Neg. ion - [M - 2H]/2: 1311.3 | § |

TABLE 6-continued

Peptides fibrin-binding properties

| Seq. ID | Sequence | Prepared Sequence | Prepared Sequnce ID | HPLC Data (System, $t_R$) | Mass Spectral Data (Mode: Ions) | Rel IC$_{50}$ (n = 2, Competition FP assay) |
|---|---|---|---|---|---|---|
| Seq030 | RRGGWQPC*PAESWTFC*WDP | Ac-RRGGWQPC*PAESWTFC*WDPGGGK-NH$_2$ | Ac-Seq030-GGGK-NH$_2$ | D, 3.12 | Pos. ion - [2M + 3H]/3: 1745.4, [M + 2H]/2: 1309.5, [M + 3H]/3: 873.3 | § |
| Seq031 | RRGGWQPC*-Hypt4-WESWTFC*WDP | Ac-RRGGWQPC*-Hypt4-WESWTFC*WDPGGGK-NH$_2$ | Ac-Seq031-GGGK-NH$_2$ | G, 4.5 | Mode: Pos. ion; [M + 2H]/2: 1375.0, [M + 3H]/3: 917.3, [M + Na + 3H]/4: 693.8, [M + 2Na + 3H]/5: 558.9 | 0.75 |
| Seq010 | RWQPC*PWESWTFC*WDP | Ac-RWQPC*PWESWTFC*WDPGGGK-NH$_2$ | Ac-Seq010-GGGK-NH$_2$ | B, 3.72 | Neg. Ion: [M − H]: 2461.8, [M − 2H]/2: 1230.0, [M + TFA − 2H]/2: 1286.8 | § |
| Seq032 | RWQPC*PAESWT-Cha-C*WDP | Ac-RWQPC*PAESWT-Cha-C*WDPGGGK-NH$_2$ | Ac-Seq032-GGGK-NH$_2$ | D, 3.43 | Neg. ion: [M − H]: 2352.9, [M − 2H]/2: 1175.4, [M + TFA − 2H]/2: 1232.2 | § |
| Seq033 | GWQPC*PAESWT-Cha-C*WDP | GWQPC*PAESWT-Cha-C*WDPGGGK-NH$_2$† | Seq033-GGGK-NH$_2$ | D, 3.92 | Neg. ion: [M − H]: 2294.7, [M − 2H]/2: 1146.9 (as Aloc peptide) | § |
| Seq009 | RGWQPC*PWESWTFC*WDP | Ac-RGWQPC*PWESWTFC*WDPGGGK-NH$_2$ | Ac-Seq009-GGGK-NH$_2$ | D, 3.64 | Neg. ion: [M − H]: 2517.9, [M − 2H]/2: 1258.8, [M + TFA − 2H]/2: 1315.5 | § |
| Seq034 | RGWQPC*PAESWTFC*WDP | Ac-RGWQPC*PAESWTFC*WDPGGGK-NH$_2$ | Ac-Seq034-GGGK-NH$_2$ | D, 3.46 | Neg. Ion: [M − H]: 2403.3, [M − 2H]/2: 1200.9 | § |
| Seq035 | RGWQPC*PAESWT-Cha-C*WDP | Ac-RGWQPC*PAESWT-Cha-C*WDPGGGK-NH$_2$ | Ac-Seq035-GGGK-NH$_2$ | D, 3.48 | Neg. ion: [M − H]: 2409.0, [M − 2H]/2: 1204.1, [M + TFA − 2H]/2: 1261.1 | § |
| Seq035 | RGWQPC*PAESWT-Cha-C*WDP | RGWQPC*PAESWT-Cha-C*WDPGGGK-NH$_2$† | Seq035-GGGK-NH$_2$ | D, 3.91 | Neg. ion: [M − H]: 2451.0, [M − 2H]/2: 1224.7, [M + TFA − 2H]/2: 1282.2 (as Aloc peptide) | § |
| Seq033 | GWQPC*PAESWT-Cha-C*WDP | Ac-GWQPC*PAESWT-Cha-C*WDPGGGK-NH$_2$ | Ac-Seq033-GGGK-NH$_2$ | D, 3.59 | Neg. ion: [[M − H]: 2253.1, [M − 2H]/2: 1125.9 | § |
| Seq036 | RWQPC*PAESWTFC*WDP | RWQPC*PAESWTFC*WDPGGGK-NH$_2$‡ | Seq036-GGGK-NH$_2$ | D, 3.71 | Neg. ion: [M − H]: 2388.0, [M − 2H]/2: 1193.4, [M + TFA − 2H]/2: 1250.8 (as Aloc peptide) | § |

TABLE 6-continued

Peptides fibrin-binding properties

| Seq. ID | Sequence | Prepared Sequence | Prepared Sequnce ID | HPLC Data (System, $t_R$) | Mass Spectral Data (Mode: Ions) | Rel IC$_{50}$ (n = 2, Competition FP assay) |
|---|---|---|---|---|---|---|
| Seq032 | RWQPC*P<u>AE</u>SWT-<u>Cha</u>-C*WDP | RWQPC*P<u>A</u>ESWT-<u>Cha</u>-C*WDPGGGK-NH$_2$‡ | Seq032-GGGK-NH$_2$ | D, 3.71 | Neg. ion: [M − H]: 2394.0, [M − 2H]/2: 1196.4, [M + TFA − 2H]/2: 1252.9 (as Aloc peptide) | § |

IC$_{50}$ the half maximal inhibitory concentration, represents the concentration of an inhibitor that is required for 50% inhibition of its target
†= Analytical data reported for peptide bearing the ivDde group on N$^ε$ of all lysine groups of the peptide except for the C-terminal lysine.
‡= Analytical data reported for N-terminal Aloc-protected peptide.

As shown in Table 6, all of the fibrin-binding peptides described therein have equivalent or far superior binding than the comparative fibrin-binding peptide.

Where a fibrin binding moiety is employed as targeting vector able to direct a diagnostically or therapeutically effective moiety linked thereto to the targeted site, as per the present invention, other aspects of binding specificity may become more important. That is because imaging and therapeutic agents operate in a dynamic system, in which the binding of the imaging agent to the target is not in a stable equilibrium state throughout the imaging procedure. For example, when the agent is initially injected, the concentration of agent and of agent-target complex rapidly increases. Shortly after injection, however, the circulating (free) agent starts to clear through the kidneys or liver, and the plasma concentration of imaging agent begins to drop. This drop in the concentration of free agent in the plasma eventually causes the agent-target complex to dissociate. The usefulness of a diagnostic (or therapeutic) agent thus depends, on one side, on the difference in rate of agent-target dissociation relative to the clearing rate of the agent. On the other side, poor diffusion or transport, limited in vivo availability, and/or lack of in vivo specificity all result in a modest contrast enhancement or poor therapeutic efficacy.

With the aim to test the specificity and efficiency of the compounds of the invention two protocols have been prompted and used for in vitro MRI tests on human plasma clots and for the in vivo MRI tests on neuro-2A-blastoma mouse model, respectively.

Imaging tests have been then performed, either in vitro or in vivo, in which the MRI signal enhancement provided by some representative chelate complexes of the invention was registered and compared with the signal provided by analogous chelate compounds including the prior-art peptide Ac-WQPCWESWTFCWDP, SEQ ID NO:037, disclosed in WO02/055544. As indicated in the above referred protocols, included below in the experimental section, ProHance® was always used as a reference compound. Thus, in particular, in vitro tests have been performed comparing the signal enhancement recovered from each of the tested compounds incubated in human plasma clots at different incubation concentration. Obtained results, comprised, for instance, in Tables 7 and 8 as reported in the Experimental section below, and graphically resumed in FIG. 5, show that the compounds of the invention provided the highest signal enhancement register in clots, in particular, and advantageously, when used at low incubation concentration.

Moreover, in vivo MR imaging tests performed on animals carrying both subcutaneous inoculated or spontaneous tumors demonstrates the suitability of the diagnostic agents of the invention to detect fibrin inside the tumor.

For instance, in vivo tests have been performed in a mouse model using some representative chelate compounds of the invention and ProHance® as reference compound. Obtained data and images, some of which are included, for instance, in FIG. 6-10, demonstrate that the novel fibrin-targeted MRI contrast agents of the invention accumulate selectively within tumor in a realistically short time (their targeting time is less than 6 hours) consenting the imaging of the fibrin substrate for a reasonable length of time. Tested agents was then completely washed out of all tissues over few days. As confirmed by histological examination of administered animals, the targeting they provided was proportional to fibrin concentration with a good correlation between MR registered signal and fibrin concentration.

Together with high fibrin affinity, the MRI contrast agents of the invention are further advantageously endowed with high relaxivity, wherein this consented the detection of very small accumulations of fibrin in vivo.

As shown for instance in FIG. 10, comparison tests performed in vivo between a representative chelate complex of the invention and the analogous compound including the above prior-art peptide demonstrated the superior tumor enhancement provided by the agents of the invention. In particular, while a high signal enhancement inside tumor was registered 4 hours post injection of the Chelate Complex 1 of used as a representative chelate complex of the instant invention, a lower signal enhancement and present in a lower number of tumor slices was recovered in animal treated with the analogous prior art peptide derivative.

Furthermore, MRI experiments carried out on tumor animal model treated with Warfarin as anticoagulant agent, demonstrate the suitability of the use of the compounds of the present invention to evaluate the reduction of tumor fibrin content as result of a tumor therapy.

Uses

The compounds of the present invention may find advantageous application for localizing, measuring and treating fibrin and all pathological conditions associated with fibrin, including, for instance, clots and thromboembolic diseases, and, especially, tumors and metastatic processes, as well as for evaluating and monitoring therapeutic effect of different anticancer drugs and anticoagulant-antithrombotic agents.

In particular, the compounds of formula (I) in which T is a diagnostically active moiety may find advantageous application in the detection and diagnosis of fibrin deposition associated with, for example, embolism (PE), deep-vein thrombosis (DVT), stroke, atherosclerosis and plaque formation as well as with inflammatory processes, including demyelization processes and axonal damage involved in Multiple Sclerosis, rheumatoid arthritis, lupus, hypoxia or ischemia of the heart, kidney, liver, brain, or other organs and, in general, of all inflammatory conditions associated with angiogenic processes in which fibrin plays a role. Preferably, the novel contrast agents of the invention may advantageously be used for localizing and imaging fibrin in cancerous and metastatic tissues, and, especially in solid tumors and in the evaluation of therapeutic effect of different anticancer drugs from antiangiogenesis to anticoagulant-antithrombotic agents. Moreover, as fibrin content is related to tumor stage and grade, the diagnostic agents of the invention may find application in the non invasive histopathologic grading of solid tumors.

On the other side, the compounds of formula (I) in which T is a therapeutically active moiety find advantageous application for prevention and treatment of all pathological conditions associated with fibrin deposition, and, especially, for prevention and treatment of solid tumors and metastatic processes associated thereto.

The compounds of the invention have a wide range of applications as they can be used for intravasal, (for instance intravenous, intraarterial, intracoronaric, intraventricular administration and the like), intrathecal, intraperitoneal, intralymphatic and intracavital administrations. Furthermore, they are suitable for the oral or parenteral administration and, therefore, specifically for the imaging of the gastrointestinal tract.

In a preferred embodiment thereof, the invention concerns pharmaceutical compositions containing, as active ingredient, at least one compound of formula (I), including pharmaceutically acceptable salts thereof, in combination with one or more pharmaceutically acceptable carriers or excipients.

Compositions for the desired route of administration can be prepared by any of the methods well known in the art. Details concerning dosages, dosage forms, modes of administration, compositions and the like are further discussed in a standard pharmaceutical text, such as *Remington's Pharmaceutical Sciences,* 18th ed., Alfonso R. Gennaro, ed. (Mack Publishing Co., Easton, Pa. 1990), which is hereby incorporated by reference.

For instance, for parenteral administration they can be preferably formulated as sterile aqueous solutions or suspensions, whose pH can range from 6.0 to 8.5.

These aqueous solutions or suspensions can be administered in concentrations ranging between 0.002 and 1.0 M. These formulations can be lyophilized and supplied as they are, to be reconstituted before use.

For the gastrointestinal use or for injection in the body cavities, these agents can be formulated as a solution or suspension optionally containing suitable excipients in order, for example, to control viscosity.

For the oral administration they can be formulated according to preparation methods routinely used in the pharmaceutical technique or as coated formulations to gain additional protection against the stomach acidic pH, thus preventing the chelated metal ion from release, which takes place particularly at the typical pH values of gastric fluids.

Other excipients, for example including sweeteners and/or flavouring agents, can also be added, according to known techniques of pharmaceutical formulations.

The solutions or suspensions of the compounds of this invention can also be formulated as aerosol to be used in aerosol-bronchography and instillation. For example, they can be also encapsulated into liposomes or even constitute the liposomes themselves, and thus can be used as uni- or multilamellar vesicles.

Preferably, a suitable pharmaceutical composition according to the invention is formulated in accordance with routine procedures as a pharmaceutical composition adapted for intravenous administration to human being.

For example, the paramagnetic contrast agents of the invention, for use in MRI techniques, are administered to the patient in the form of an injectable compositions. The method of administering the MRI contrast agent is preferably parenterally, meaning intravenously, intraarterially, intrathecally, interstitially, or intracavitarilly. For imaging fibrin deposition and, especially, solid tumors intravenous or intraarterial administration is preferred.

For instance, for MRI, it is contemplated that the subject will receive a dosage of contrast agent sufficient to enhance the MR signal at the target (e.g., a site of angiogenesis) at least 10%. After injection of the fibrin targeted MRI contrast agent of the invention, the patient is scanned in the MRI machine to determine the location of any sites containing the target. In therapeutic settings, upon target localization, a cytotoxic or therapeutic agent can be immediately administered, if necessary, and the patient can be subsequently scanned to visualize the therapeutic effect.

MRI contrast agents according to the present invention, may, for instance, be used in the same manner as conventional MRI contrast reagents. When the target is, for example, a tumorous site in a tissue, certain MR techniques and pulse sequences may be preferred to enhance the contrast of the site to the background blood and tissues. These techniques include (but are not limited to), for example, black blood angiography sequences that seek to make blood dark, such as fast spin echo sequences (see, e.g., Alexander et al., *Magnetic Resonance in Medicine,* 40(2): 298-310 (1998)) and flow-spoiled gradient echo sequences (see, e.g., Edelman et al., *Radiology,* 177(1): 45-50 (1990)). These methods also include flow independent techniques that enhance the difference in contrast, such as inversion-recovery prepared or saturation-recovery prepared sequences that will increase the contrast between target containing tissue, such as an angiogenic tumor, and background tissues.

In case of radiotherapy, proper dose schedules known in the art may be used for the radiotherapeutic compounds of the present invention.

The compounds can be administered using many methods which include, but are not limited to, a single or multiple IV or IP injections, using a quantity of radioactivity that is sufficient to cause damage or ablation of the targeted tissue, but not so much that substantive damage is caused to non-target (normal tissue). The quantity and dose required is different for different constructs, depending on the energy and half-life of the isotope that is used, the degree of uptake and clearance of the agent from the body and the mass of the tumor. In general, doses can range from about 0.01 mCi to about 100 mCi, preferably from 1 mCi to 50 mCi. Typically, a single dose of about 30-50 mCi to a cumulative dose of up to about 3 Curies may apply.

The radiotherapeutic compositions of the invention can include physiologically acceptable buffers, and can require radiation stabilizers to prevent radiolytic damage to the compound prior to injection. Radiation stabilizers are known to those skilled in the art, and may include, for example, para-aminobenzoic acid, ascorbic acid, gentisic acid and the like.

In case of radionuclide imaging, the compound of the invention may be administered to the patient through injection. A PET camera or a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabelled peptide is injected into a patient. In most instances, a sufficient amount of the administered dose will accumulate in the area to be imaged within about 0.1 of an hour to permit the taking of scintiphotos. In order to obtain the desired prophylactic, therapeutic or diagnostic effect, a therapeutically or diagnostically effective dose or amount of the active ingredient is advantageously administered in the form of a unit dose, one or more times daily. The daily dosages are obviously selected by the health professional depending on the biologically active molecule introduced.

The term "effective dose or amount", as used herein, refers to any amount of a diagnostic or a therapeutic molecule of the invention, or pharmaceutical composition thereof, that is sufficient to fulfil its intended diagnostic or therapeutic purpose(s): i.e., for example, to visualize a patient biological element including cells, biological fluids and biological tissues as well as human body organs, regions or tissues affected by fibrin deposition, or its intended therapeutic purpose(s); or to delay or to prevent to onset of a pathological condition associated with fibrin; or to slow down or stop the progression, aggravation, or deterioration of the symptoms.

In a further embodiment thereof the invention relates to the use of the compounds of formula (I) wherein T is a diagnostically active moiety for the preparation of a diagnostic formulation for use in the diagnostic imaging, both in vitro and in vivo, of pathological systems, including cells, biological fluids and biological tissues originating from a live mammal patient, and preferably, human patient, as well as of human body organ, regions or tissues, including tumors or cancerous tissues, inflammations, wherein fibrin deposition occurs as well as for monitoring the progress and results of therapeutic treatment of the said pathologies.

In yet another aspect the invention provides a method for imaging solid tumors or tumorous cells both in vitro, for instance by contacting a suitable compound of formula (I) with biological samples and tissues, for example of ex vivo samples, and also in vivo, by administering to a mammalian patient a compound of formula (I) wherein T is a diagnostically active moiety.

In a further embodiment, the invention relates to the use of the compounds of formula (I) wherein T is a therapeutically active moiety for the preparation of a therapeutic formulation for use in the prevention and/or treatment, both in vitro and in vivo, of pathological systems, including cells, biological fluids and biological tissues originating from a live mammal patient, and preferably, human patient, as well as of human body organ, regions or tissues, including tumorous or cancerous tissues, inflammations, wherein fibrin deposition occurs.

In still further aspect the invention provides a method of in vivo preventing or inhibiting tumor growth comprising contacting a pathological systems, including human cells, fluids, or body organ, tissue or area affected by fibrin deposition with a therapeutic agent of the invention.

BRIEF DESCRIPTION OF THE DRAWINGS

FIG. 1 illustrates a method for the preparation of a representative linker-functionalized peptide according to the present invention.

FIG. 2 illustrates a method for the preparation of a representative 5-carboxyfluorescein labelled peptide according to the present invention.

FIGS. 3a, 3b, 3c illustrate examples of preferred chelators for either $^{111}$In and lanthanides such as paramagnetic $Gd^{3+}$ or radioactive lanthanides such as, for example, $^{177}$Lu, $^{90}$Y, $^{153}$Sm, and $^{166}$Ho.

FIGS. 4a, 4b illustrate examples of preferred chelators of radioactive metal ion such as $^{99m}$Tc, $^{186}$Re and $^{188}$Re;

EXPERIMENTAL SECTION

Figure 3C:
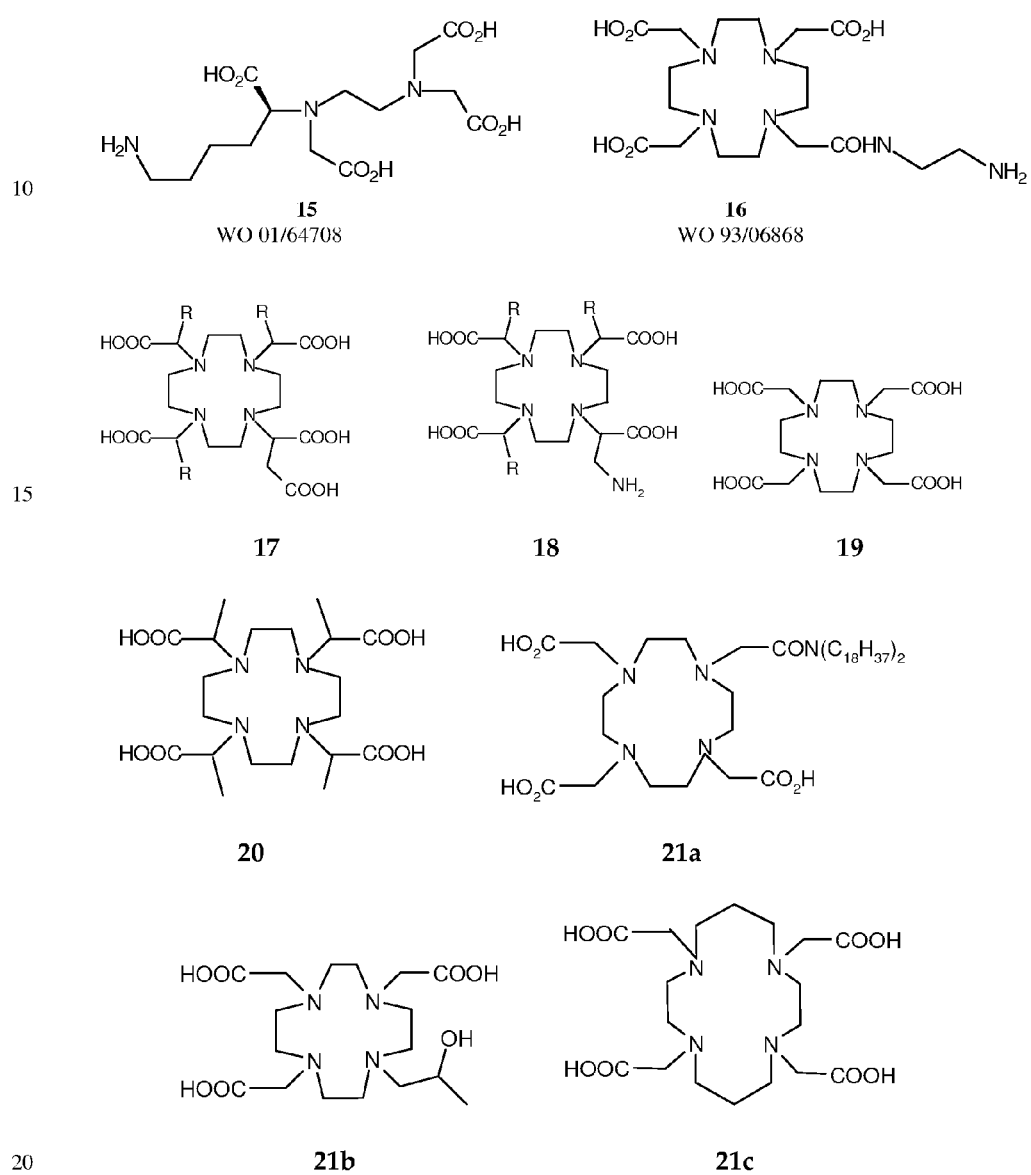

Isolation, conjugation and use of fibrin binding moieties and conjugates thereof with diagnostically or therapeutically active moieties in accordance with this invention will be further illustrated in the following examples. The specific parameters included in the following examples are intended to illustrate the practice of the invention, and they are not presented to limit in any way the scope of the invention.

A skilled technician may understand that different preparation approaches may equally be adopted based on synthetic procedures well known in the art.

Abbreviations

The following common abbreviations are used throughout the specification and the following experimental section; several others are not herewith reported as being conventionally adopted.

FBS Foetal Bovine Serum
DMEM: Dulbecco's Modified Eagle's Medium
FCS: Foetal Calf Serum
AA amino acid
ACN acetonitrile,
$Ac_2O$ acetic anhydride,
Adoa (J) 8-amino-3,6-dioxaoctanoic acid,
Aloc Allyloxycarbonyl,
API-ES Atmospheric pressure ionization electrospray,
Boc t-butyloxycarbonyl,
CE Capillary Electrophoresis
CF5-NHS 5 carboxyfluorescein, succinimidyl ester (single isomer),
Cha 2-Cyclohexyl-L-alanine,
DCM dichloromethane,
DIC N,N'-diisopropylcarbodiimide,
DIEA N,N-diisopropylethylamine, DMAC N,N-Dimethylacetamide,
DMF N,N-dimethylformamide,
DMSO dimethyl sulfoxide,
DSG Di-N-hydroxysuccinimidyl-glutarate
$Et_2O$ diethyl ether,
EtOAc Ethyl acetate,
Ffe4 L-4-Fluorophenylalanine,
F34fe L-3,4-difluorophenylalanine,
Fmoc 9-fluorenylmethyloxycarbonyl,
Fmoc-J (or Fmoc-Adoa) Fmoc-8-amino-3,6-dioxaoctanoic acid,
G Glycine,
$GdCl_3$ Gadolinium chloride
Glut glutaric acid,
HATU O-(7-azabenzotriazol-1-yl)-N,N,N',N'-tetramethyluronium hexafluorphosphate,
HBTU (2-(1H-Benzotriazol-1-yl)-1,2,3,3-tetramethyluronium hexafluorophosphate),
HOBt N-Hydroxybenzotriazole,
Hypt4 trans-4-hydroxy-L-proline,
ICP-AES Inductively coupled plasma atomic emission spectroscopy,
ivDde (4,4-dimethyl-2,6-dioxocyclohex-1-ylidene)-3-methylbutyl, Lys Lysine,
MALDI Matrix Assisted Laser Desorption Ionization,
Mr Molecular Weight,
MS Mass Spectroscopy
NHS N-hydroxysuccinimide,
NMM N-Methylmorpholine
NMP N-Methylpirrolidone,
PB phosphate buffer
PBS Dulbecco's Phosphate Buffered Saline without Ca++ and Mg++
Pip Piperidine,
$Pd(PPh_3)_4$ Tetrakis(triphenyl-phosphine)palladium(0),
Pmc 2,2,5,7,8-pentamethylchroman-6-sulfonyl,
Reagent B ($TFA:H_2O$:phenol:triisopropylsilane, 88:5:5:2),
SATA S-Acetylthiolacetyl,
S(Galnac)O-(2-Acetamido-2-deoxy-α-D-galactopyranosyl)-L-serine,
SPPS Solid phase peptide synthesis,
TFA trifluoroacetic acid,
TIPS Triisopropylsilane,
Tris Tris(hydroxymethyl)aminomethane
Trt Trityl, Starting Materials Fmoc-protected amino acids used were obtained from Nova-Biochem (San Diego, Calif., USA), Advanced ChemTech (Louisville, Ky., USA), Chem-Impex International (Wood Dale Ill., USA), and Multiple Peptide Systems (San Diego, Calif., USA). DPPE, DSPE-PG4-$NH_2$, and DPPE-PG4-$NH_2$ were obtained from Avanti Polar Lipids (Alabaster, Ala.). Fmoc-PEG3400-NHS was obtained from Shearwater Polymers (Huntsville, Ala.). Other reagents were obtained from Aldrich Chemical Co. (Milwaukee, Wis.) and VWR Scientific Products (Bridgeport, N.J.). Solvents for peptide synthesis were obtained from Pharmco Co. (Brookfield, Conn.).

Synthesis and Purification of the Peptide Moiety

Procedure A: Automated Peptide Solid Phase Peptide Synthesis

Individual peptides were prepared using an ABI 433A instrument (Applied Biosystems, Foster City, Calif.). PAL-Peg-PS-Resin (1.2 g, 0.18 mmol/g) or NovaSyn TGR resin (1.25 g, 0.20 mmol/g) (NovaBiochem, Novato, Calif.) was used for all syntheses. The peptides were assembled on resin using the FastMoc™ protocol. After the synthesis, the resin was washed with DCM (2×) and dried.

Procedure B: Manual Coupling of Amino Acids

DMF was used as the coupling solvent unless otherwise stated. The appropriate Fmoc-amino acid in DMF (0.25M solution, 3 equiv) was treated with HATU (0.5M in NMP, 3.0 equiv) and DIEA (6.0 equiv). The mixture was shaken for ~2 min and then was transferred to the synthesis vessel containing the resin. The vessel was then shaken overnight at ambient temperature. The resin was filtered to remove excess reagents and then washed (4×) with DMF.

Procedure C: Manual Removal of the Fmoc Protecting Group

The resin containing the Fmoc-protected amino acid was treated with 20% piperidine in DMF (v/v, 15.0 mL/g resin) for 10 min. The solution was drained from the resin. This procedure was repeated once and then followed by washing the resin with DMF (4×).

Procedure D: Removal of the ivDde Group (Solid Phase)

The resin containing the ivDde-protected amino acid was treated with 10% (v/v) hydrazine in DMF (10 mL/g resin) for 10 min. The solution was drained from the resin. This procedure was repeated once and then followed by washing the resin with DMF (4×).

Procedure E: Removal of the ivDde Group from Peptides in Solution

The peptide (50 mg) was dissolved in DMF (2.0 mL) and treated with neat hydrazine (40-200 µL) for 10 min. The mixture was diluted with water to a volume of 10 mL and this was directly applied to a C18 reverse phase column and purified by preparative HPLC as described in the general procedures.

Procedure F: Coupling of Fmoc-Adoa (Fmoc-I)

Fmoc-Adoa (2 equiv) and HATU (2 equiv) were dissolved in DMF and DIEA (4 equiv) was added to the mixture. The mixture was stirred for 1 min before transferring the activated acid to the resin. The concentration of reagents was as discussed above for standard peptide couplings. The coupling was continued for 12 h at ambient temperature. The resin was drained of the reactants and washed with DMF (4×). In cases where two Adoa units were appended to the resin, the Fmoc group of the first appended Fmoc-Adoa unit was removed (procedure C), the resin washed with DMF (4×) and followed by coupling of the second Adoa moiety.

Procedure G: Cleavage and Side-Chain Deprotection of Resin Bound Peptides

Reagent B (88:5:5:2—TFA:water:phenol:TIPS—v/v/wt/v), 15 mL/g resin, was added to ~1.0 g of the resin and the vessel was shaken for 4.5 h at ambient temperature. The resin was filtered and washed twice with TFA (5 mL/g resin). The filtrates were combined, concentrated to give a syrup which upon Trituration with 20 mL of $Et_2O$/g of resin gave a solid residue which was stirred for 5-15 min and then centrifuged. The supernatant was decanted and the process was repeated three times. The resulting solid was dried under high vacuum or with a stream of dry nitrogen gas.

Procedure H: Disulfide Cyclization

The precipitate obtained from trituration of the crude cleavage mixture with $Et_2O$ was transferred to a beaker and DMSO (5-10 µL/mg crude peptide) was added. The pH of the solution was adjusted to 8 by adding N-methyl-D-glucamine (10-100 mM in $H_2O$). The mixture was stirred for 48 h and was then purified by preparative HPLC.

Procedure I: Preparation of 5-Carboxyfluorescein (CF5) Derivatives of Peptides

To a solution of a peptide in DMF (15 µL/mg) and DIEA (20 equiv/equiv peptide) was added 5-carboxyfluorescein NHS ester (1.3-1.5 equiv.) in DMF (20 μL/mg). The mixture was stirred for 1-3 h. The reaction was monitored by mass spectroscopy and analytical HPLC. Upon completion of the reaction, the crude was filtered and purified by preparative HPLC.

Procedure J: Preparation of Aloc-Gly-OH

Gly-O-t-Bu.AcOH (1 g, 5.24 mmol) was dissolved in DCM (15 mL), and diallyl pyrocarbonate (1.1 g, 5.91 mmol, 1.13 equiv) was added dropwise. The mixture was stirred at ambient temperature for 0.5 h. Then DIEA (3.7 g, 5 mL, 28.68 mmol, 5.47 equiv) was added. The mixture was stirred at ambient temperature overnight. The volatiles were removed and the crude residue was dissolved in EtOAc (100 mL/g of crude) and the organic layer was washed with 1N HCl (2×). The volatiles were removed and the crude was dried at high vacuum. NMR (500 MHz, $CDCl_3$) indicated a pure product and was consistent with the structure. The crude was then dissolved in a solution of TFA/DCM (1/1, v/v, 25 mL) and the solution was stirred overnight. The volatiles were removed, EtOAc was added to wash any residue from the wall of the flask and then the volatiles were removed on the rotary evaporator. This was repeated. The resulting product was dried overnight at high vacuum. NMR spectroscopy of the material ($CDCl_3$, 500 MHz) was consistent with the expected structure and the purity was found to be sufficient for use in manual coupling protocols.

Procedure K: Preparation of Aloc-Arg(Pmc)-OH

H-Arg(Pmc)-OH (5 g, 11.35 mmol) was dissolved in a mixture of $H_2O$ and Dioxane (1/1, v/v, 125 mL), and diallyl pyrocarbonate (6.34 g, 34.05 mmol, 3.0 equiv) was added. The pH of the mixture was adjusted to >10.0 by adding $Na_2CO_3$. The mixture was stirred and kept at reflux overnight. The volatiles were removed by rotary evaporation, the crude was dissolved in EtOAc (100 mL/g of crude) and the solution was washed with 1N HCl (2×). The volatiles were removed by rotary evaporation, the crude was dissolved in $CHCl_3$ and the solution was loaded onto a silica gel column. The column was eluted with two column volumes of $CHCl_3$ and then similarly eluted with a 5% solution of MeOH in $CHCl_3$. Fractions containing the desired compound were combined and the volatiles were removed by rotary evaporation and pumping at high vacuum to provide 4.2 g (70% yield) of Aloc-Arg(Pmc)-OH. The proton NMR spectrum ($CDCl_3$, 500 MHz) was consistent with the expected structure and required purity.

Procedure L: Removal of the Aloc Protecting Group from Peptides

The Aloc-protected peptide was dissolved in 5-20 mL/100 mg peptide of a solution of NMM:acetic acid:DMF (1:2:10). $Pd(PPh_3)_4$ (1-10 equiv/equiv peptide) was added. The mixture was stirred for 0.5-4 h. MS and analytical HPLC were used to check the reaction. After the reaction was complete, the crude reaction mixture was diluted to twice its volume with 10%-25% $CH_3CN$ in $H_2O$, filtered and purified by preparative HPLC.

General Procedures for Analysis and Purification
Analytical HPLC

Column: Waters Corp. X-Terra, MS-$C_{18}$; 4.6 mm i.d.×50 mm; 5 μm particle;

Eluent A: Water (HPLC Grade with 0.1% TFA by weight); Eluent B: Acetonitrile (0.1% TFA by weight). Initial conditions and gradient elution profiles employed are described in the respective experimental procedures for analysis of the title compounds. Elution rate: 3 mL/min; Detection: LTV at 220 nm.

Preparative HPLC Purification

Column: Waters Corp. X-Terra MS-$C_{18}$; 50 mm i.d.×250 mm; 10 μm particle; Eluents: Eluent A: Water (HPLC Grade with 0.1% TFA by weight); Eluent B: Acetonitrile (0.1% TFA by weight); Initial conditions and gradient elution profiles employed are described in the respective experimental procedures for analysis of the title compounds. Elution rate: 100 mL/min; Detection: UV at 220 nm.

HPLC Methods Employed for Analysis of Peptides

System A: Column: Waters XTerra MS-C18 4.6×50 mm; Particle size: 5 microns; Eluents: A: Water (0.1% TFA), B: Acetonitrile (0.1% TFA); Elution: linear gradient 5-55% B in 7 min; Flow rate: 3 mL/min; Detection: UV, $\lambda$=220 nm.

System B: Column: Waters XTerra MS-C18 4.6×50 mm; Particle size: 5 microns; Eluents: A: Water (0.1% TFA), B: Acetonitrile (0.1% TFA); Elution: linear gradient 5-65% B in 7 min; Flow rate: 3 mL/min; Detection: UV, $\lambda$=220 nm.

System C: Column: Waters XTerra MS-C18 4.6×50 mm; Particle size: 5 microns; Eluents: A: Water (0.1% TFA), B: Acetonitrile (0.1% TFA); Elution: linear gradient 15-65% B in 7 min; Flow rate: 3 mL/min; Detection: UV, $\lambda$=220 nm.

System D: Column: Waters XTerra MS-C18 4.6×50 mm; Particle size: 5 microns; Eluents: A: Water (0.1% TFA), B: Acetonitrile (0.1% TFA); Elution: linear gradient 15-70% B in 6 min; Flow rate: 3 mL/min; Detection: UV, $\lambda$=220 nm.

System E: Column: Waters XTerra MS-C18, 4.6 mm i.d.× 50 mm; Particle size: 5 microns; Eluents: A: Water (0.1% TFA), B: Acetonitrile (0.1% TFA); Elution: linear gradient 15-60% B in 6 min; Flow rate: 3.0 mL/min; Detection: UV, $\lambda$=220 nm.

System F: Column: YMC C18, 4.6×250 mm; Eluents: A: Water (0.1% TFA), B: Acetonitrile (0.1% TFA), Initial condition: 20% B, Elution: linear gradient 20-80% B in 20 min; Flow rate: 1.0 mL/min; Detection: UV, $\lambda$=220 nm.

System G: Column: Waters XTerra MS-C18, 4.6 mm i.d.× 50 mm; Particle size: 5 microns; Eluents: A:Water (0.1% TFA), B: acetonitrile (0.1% TFA); Elution: Initial condition: 10% B, linear gradient 10-50% B over 8 min; Flow rate: 3 mL/min; Detection: UV, $\lambda$=220 nm.

System H: Column: Waters XTerra MS-C18 4.6×50 mm; Particle size: 5 microns; Eluents: A: Water (0.1% TFA), B: Acetonitrile (0.1% TFA); Elution: Initial condition: 5% B, linear gradient 5-65% B in 8 min; Flow rate: 3 ml/min; Detection: UV $\lambda$=220 nm.

EXAMPLES

Example 1

Preparation of Ac-GWQPC*PWESWTFC*WDPGGGK-$NH_2$ cyclic (5→13) (GGGK Linker Functionalized Ac-SEQ ID NO:004 Peptide)

The peptide sequence was prepared by SPSS from Fmoc-PAL-PEG-PS resin (0.18 mmol/g, 1.38 g, 0.25 mmol) as described in procedure A using an ABI peptide synthesizer employing Fmoc chemistry which was implemented using the FastMoc™ protocol. Cleavage and side-chain deprotection was conducted as described in procedure G and disulfide cyclization was accomplished as described in procedure H. HPLC purification provided 105 mg (17.8% yield) of the purified cyclic peptide.

Example 2

Preparation of
Ac-SGSGJWQPC*PWESWTFC*WDPGGGK-NH$_2$
(Cyclic 9→17) (GGGK Linker Functionalized
Ac-SEQ ID NO:005 Peptide)

Procedures A, G and H were employed to prepare the peptide on a 0.266 mmol scale and HPLC purification provided 130 mg (18.8% yield) of the pure product.

Example 3

Preparation of
Ac-RWQPC*PAESWT-Cha-C*WDPGGGK-NH$_2$
Cyclic (5→13) (GGGK Linker Functionalized
Ac-SEQ ID NO:032 Peptide)

The peptide was prepared using the methods of procedures A, G and H. HPLC purification provided a 140 mg (27.5% yield) portion of the product as a fluffy white solid.

Example 4

Preparation of
Ac-WQPC*PAESWTFC*WDPGGGK(JJ)-NH$_2$
Cyclic (4→12) Peptide, (Ac-SEQ ID
NO:001-GGGKJJ)

The ivDde-protected peptide Ac-W(N$^{in}$-Boc)-Q(Trt)-P-C(Trt)-P-A-E(OtBu)-Ser(tBu)-W(N$^{in}$-Boc)-T(tBu)-F-C(Trt)-W(N$^{in}$-Boc)-D(OtBu)-P-GGGK(ivDde)-NH-TGR was assembled on a 130 μmol scale (0.65 g resin) (procedure A). The ivDde group was removed (procedure D) by treatment of the resin with 10% hydrazine in DMF (6.5 mL) for 10 min (2×). Then the resin was washed with DMF (4×). In a separate flask Fmoc-Adoa (100 mg, 0.26 mmol, 2.0 equiv) in NMP (1 mL) was treated with HATU (99 mg, 0.26 mmol, 2 equiv) in DMF (0.5 mL) and DIEA (67 mg, 91 μL, 0.52 mmol, 4 equiv) for 2 min after which the solution was transferred to the vessel containing the resin followed by agitation of the vessel for 12 h at ambient temperature (procedure F).

The resin was washed with DMF (4×5 mL) and the Fmoc group was removed by treatment with 20% piperidine in DMF (10 mL, 2×10 min) followed by washing (4×10 mL) with DMF (procedure C). Then Fmoc-Adoa was coupled to the resin as described (vide supra) followed by removal of the Fmoc protecting group (vide supra) and washing of the resin. Cleavage and side-chain deprotection (procedure G) was conducted for 4.5 h using Reagent B (10 mL). The resin was drained and washed with TFA (5 mL) and the combined solutions were evaporated and triturated with ether to provide the crude linear peptide as an off-white solid. The solid was dissolved in DMSO (3 mL) after which the pH of the solution was adjusted to 8 by addition of 0.1M aqueous N-methylglucamine. The mixture was stirred for 48 h (procedure H) during which time the reaction was monitored by analytical HPLC and mass spectroscopy. At the end of the reaction period the entire solution was diluted to 15 mL with 10% CH$_3$CN in H$_2$O and the pH was adjusted to 2 by addition of aqueous TFA.

The resulting solution was applied to a preparative reverse-phase C18 column and purified using a linear gradient of 10% CH$_3$CN (0.1% TFA) into H$_2$O (0.1% TFA). Fractions (15 mL) were collected and the pure product-containing fractions were pooled, frozen and lyophilized to provide 42 mg (13% yield) of the peptide as a fluffy white solid which was characterized by HPLC and mass spectroscopy.

HPLC: t$_R$ 3.83 min; Column: Waters XTerra MS-C18 4.6×50 mm; Particle size: 5 microns; Eluents: A: Water (0.1% TFA), B: Acetonitrile (0.1% TFA); Elution: linear gradient 5-65% B in 7 min; Flow rate: 3 mL/min; Detection: UV, λ=220 nm. Mass spectrum (API-ES): Neg. ion: [M-H]: 2480.6; [M-2H]/2: 1239.9

Examples 5 and 6 below describe the preparation of peptides bearing N-terminal Aloc-Arginine.

Example 5

Preparation of
Aloc-RWQPC*PWESWTFC*WDPGGGK-NH$_2$
Cyclic (5→13) Peptide (GGGK Linker
Functionalized Aloc-SEQ ID NO:010)

A 0.54 mmol (3 g) portion of W(N$^{in}$-Boc)-Q(Trt)-P-C(Trt)-P-W(N$^{in}$-Boc)-E(OtBu)-S(tBu)-W(N$^{in}$-Boc)-T(tBu)-F-C(Trt)-W(N$^{in}$-Boc)-D(OtBu)-P-GGG-K(Boc)-PAL-PEG-PS resin was prepared by automated SPSS (procedure A). Aloc-Arg(Pmc) was appended to the N-terminus using a modification of procedure B as follows. The resin was added to a manual solid phase synthesis vessel and suspended in DMF (20 mL) by brief agitation. Aloc-Arg(Pmc)-OH (524 mg, 1.00 mmol, 1.85 equiv), HATU (380 mg, 1.0 mmol, 1.85 equiv) and DIEA (257 mg, 347 L, 1.98 mmol, 3.67 equiv) were added successively with intervening agitation of the vessel and the vessel was shaken overnight. The coupling reaction was complete as indicated by a negative ninhydrin test. The resin was washed with DCM (3×20 mL) and dried. Reagent B (88:5:5:2—TFA:water:phenol:TIPS—v/v/wt/v) (25 mL) was added to the vessel and the vessel was shaken at ambient temperature for 5 h. The resin was filtered and washed with TFA (2×5 mL). The combined filtrates were concentrated to a syrup which was triturated with Et$_2$O (20 mL) and the resulting solid was pelleted by centrifugation. The supernatant liquid was decanted and the process was repeated three times (procedure G). The resulting solid was collected and cyclized (48 h) as described (procedure H) and purified by HPLC on a reverse phase C18 column. The product-containing fractions were pooled, frozen and lyophilized to provide 290 mg (21% yield) of the desired product.

Example 6

Preparation of
Aloc-RWQPC*PAESWT-Cha-C*WDPGGGK-NH$_2$
(GGGK Linker Functionalized Aloc-SEQ ID
NO:032)

The peptide was prepared by the methods of procedure A, B, G and H to give 230 mg (26.7% yield) portion of the product as a fluffy white solid.

Example 7 below and FIG. 2 describe and illustrate the preparation of 5-carboxyfluorescein derivatives of peptides.

Example 7

Preparation of the 5-Carboxyfluorescein Labelled
Derivative RWQPC*PAESWTFC*WDPGGGK
(CF5)-NH$_2$ Cyclic (5→13) Peptide Compound
(GGGK(CF5) Linker Functionalized SEQ ID
NO:036-CF5)

The peptide Aloc-RWQPC*PAESWTFC*WDPGGGK-NH$_2$ cyclic (5→13) peptide (Aloc-SEQ ID NO:036) was prepared by the methods of procedures A, B, G and H and purified by HPLC. The N-terminal Aloc $N^{\epsilon20}$-CF5 derivative was prepared according to procedure I as follows. The peptide (70 mg, 0.029 mmol) was dissolved in anhydrous DMF (1 mL) with stirring, after which DIEA (0.074 g, 100 μL, 0.572 mmol, 19.7 equiv) was added followed by a solution of CF5-NHS (20 mg, 0.042 mmol, 1.45 equiv) in anhydrous DMF. The mixture was stirred 1 h at ambient temperature. The reaction mixture was diluted to twice its volume with 20% $CH_3CN$ in $H_2O$ and purified on a C18 reverse phase preparative HPLC column to provide 50 mg (62.8% yield) of Aloc-RWQPC*PAESWTFC*WDPGGGK(CF5)—$NH_2$ cyclic (5-13) peptide.

The Aloc group of this intermediate was removed according to procedure L as follows. The intermediate was dissolved in a solution of NMM:HOAc:DMF (1:2:10, v/v/v, 5 mL), the mixture was stirred and $Pd(PPh_3)_4$ (21 mg, 0.018 mmol, 1.0 equiv) was added. The mixture was stirred 1 h at ambient temperature. Then the reaction mixture was diluted to twice its volume with 10% $CH_3CN$ in $H_2O$ and purified on a preparative reverse phase C18 column using a linear gradient of $CH_3CN$ (0.1% TFA) into $H_2O$ (0.1% TFA). The pure product-containing fractions were pooled, frozen and lyophilized to provide 29 mg (60.4% yield) of the product as an orange solid.

Example 8

Preparation of 6-[Bis[2-(1,1-dimethylethoxy)-2-oxoethyl]amino]-6-(5-carboxypentyl)tetrahydro-1H-1,4-diazepine-1,4(5H)-diacetic acid α,α'-bis(1,1-dimethylethyl)ester The preparation of the title AAZTA ligand is synthetically represented according to Scheme 1 below.

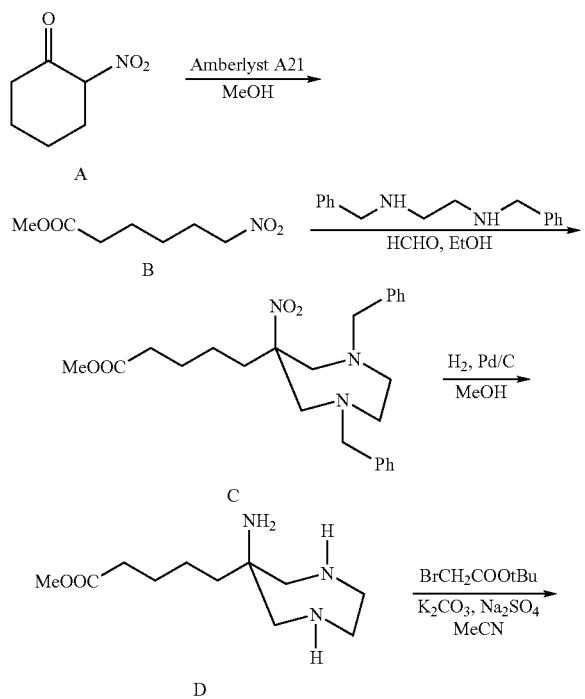

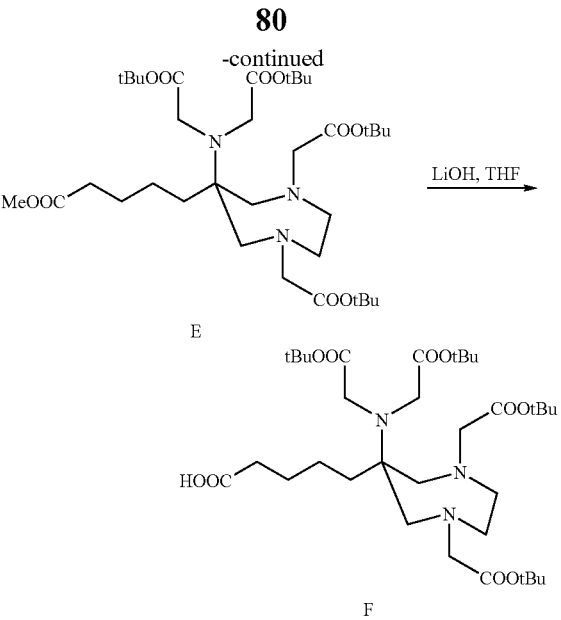

a) Preparation of the Intermediate B: 6-Nitrohexanoic acid methyl ester

2-Nitrocyclohexanone (6.77 g; 47.3 mmol) was dissolved in dried MeOH (150 mL) and a two fold excess by weight of Amberlyst® A21 (13.5 g) was added. The mixture was refluxed under nitrogen for 1.5 h then filtered and evaporated to give 6-nitrohexanoic acid methyl ester (7.72 g; 42 mmol). Yield: 89%.

Analytical Data
HPLC: 95.4% (area %)
Mr: 175.18 ($C_7H_{13}NO_4$)
$^1$H-NMR: obtained data are consistent with the structure of intermediate B
$^{13}$C-NMR: obtained data are consistent with the structure of intermediate B
MS: obtained data are consistent with the structure of intermediate B b) Preparation Of Intermediate C: Hexahydro-6-nitro-1,4-bis(phenylmethyl)-1H-1,4-diazepine-6-pentanoic acid methyl ester N,N'-Dibenzylethylenediamine diacetate (14.67 g; 40.7 mmol) was suspended in EtOH (50 mL) and the mixture was heated at 50° C. until a clear solution was obtained. Paraformaldehyde (3.67 g; 122.1 mmol) was added and the suspension was heated at 80° C. for 1.5 h to give a dark orange clear solution. A solution of 6-nitrohexanoic acid methyl ester B (7.13 g; 40.7 mmol) in EtOH (10 mL) was added dropwise. The new solution was left to cool down to room temperature, stirred for 18 h at room temperature then for 4.5 h at 50° C. The mixture was evaporated, the residue dissolved in EtOAc (100 mL) and the solution washed with aq. $Na_2CO_3$ and brine. The aqueous phase was separated and extracted with EtOAc (1×50 mL; 1×30 mL). The organic phases were collected, dried ($Na_2SO_4$), filtered and evaporated. The crude (21.7 g) was purified by flash chromatography to give C as a pale yellow oil (10.8 g; 24.6 mmol). Yield: 60%.

Analytical Data
HPLC: 99.5% (area %)
Mr: 439.55 ($C_{25}H_{33}N_3O_4$)

¹H-NMR: obtained data are consistent with the structure of intermediate C

¹³C-NMR: obtained data are consistent with the structure of intermediate C

MS: obtained data are consistent with the structure of intermediate C c) Preparation of the Intermediate E: 6-[Bis[2-(1,1-dimethylethoxy)-2-oxoethyl]amino]-6-(5-methoxy-5-oxopentyl)tetrahydro-1H-1,4-diazepine-1,4(5H)-diacetic acid α,α'-bis(1,1-dimethylethyl)ester 10% Pd/C (1.5 g) was added to a solution of compound C (10 g; 22.8 mmol) in MeOH (400 mL) and the suspension was stirred at 40° C. for 5 h under hydrogen atmosphere. The suspension was filtered (Millipore filter FT 0.45 μm) and the solution evaporated. The residue was dissolved in MeCN (100 mL) and freshly ground $K_2CO_3$ (16.8 g; 122 mmol) and $Na_2SO_4$ (3 g; 21 mmol) were added. t-Butyl bromoacetate (20.8 g; 107 mmol) was added and the orange mixture was stirred and heated at 80° C. for 7 h. The mixture was filtered, more $K_2CO_3$ (16.8 g; 122 mmol), $Na_2SO_4$ (3 g; 21 mmol) and t-butyl bromoacetate (0.88 g; 4.5 mmol) were added and the new mixture heated at 80° C. for 9.5 h. The mixture was filtered, evaporated and the residue purified by column chromatography to give E as a pale yellow oil (7.8 g; 11.4 mmol). Yield: 50%.

Analytical Data

Mr: 685.90 ($C_{35}H_{63}N_3O_{10}$)

¹H-NMR: obtained data are consistent with the structure of intermediate E

¹³C-NMR: obtained data are consistent with the structure of intermediate E

MS: obtained data are consistent with the structure of intermediate E d) Preparation Of Intermediate F: 6-[Bis[2-(1,1-dimethylethoxy)-2-oxoethyl]amino]-6-(5-carboxypentyl)tetrahydro-1H-1,4-diazepine-1,4(5H)-diacetic acid α,α'-bis(1,1-dimethylethyl)ester A 1 M solution of LiOH (95.4 mL; 95.4 mmol) was added drop by drop to a solution of compound E (8.17 g; 11.9 mmol) in THF (200 mL) cooled at 0° C. The solution was then stirred at room temperature for 28 h. The pH of the solution was brought to 7 by addition of glacial AcOH (4 mL). Water (50 mL) was added and the THF was evaporated. The aqueous residue was extracted with EtOAc (3×75 mL). The organic phases were collected, dried ($Na_2SO_4$), filtered and evaporated. The crude (6.24 g) was purified by flash chromatography to give F as a pale yellow oil (3.76 g; 5.6 mmol). Yield: 47%.

Analytical Data

Mr: 671.87 ($C_{34}H_{61}N_3O_{10}$)

¹H-NMR: obtained data are consistent with the structure of intermediate F

¹³C-NMR: obtained data are consistent with the structure of intermediate F

MS: obtained data are consistent with the structure of intermediate F.

If desired, the tert-butoxycarbonyl groups of intermediate F may be removed according to well known methods of deprotection.

Example 9

Preparation of the Chelate Complex 1

The preparation of the Chelated Complex 1 is represented in Scheme 2 below.

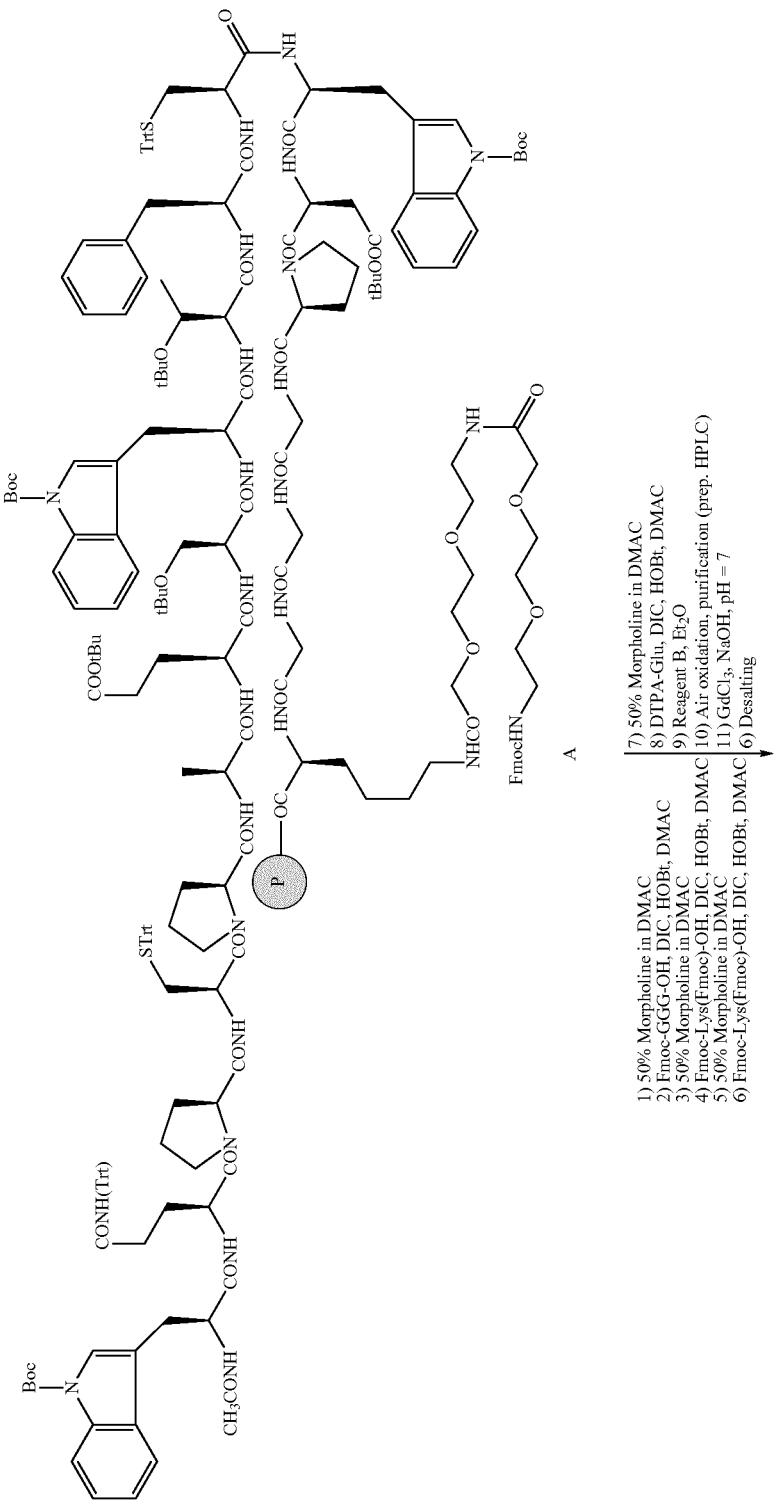
Scheme 2

-continued
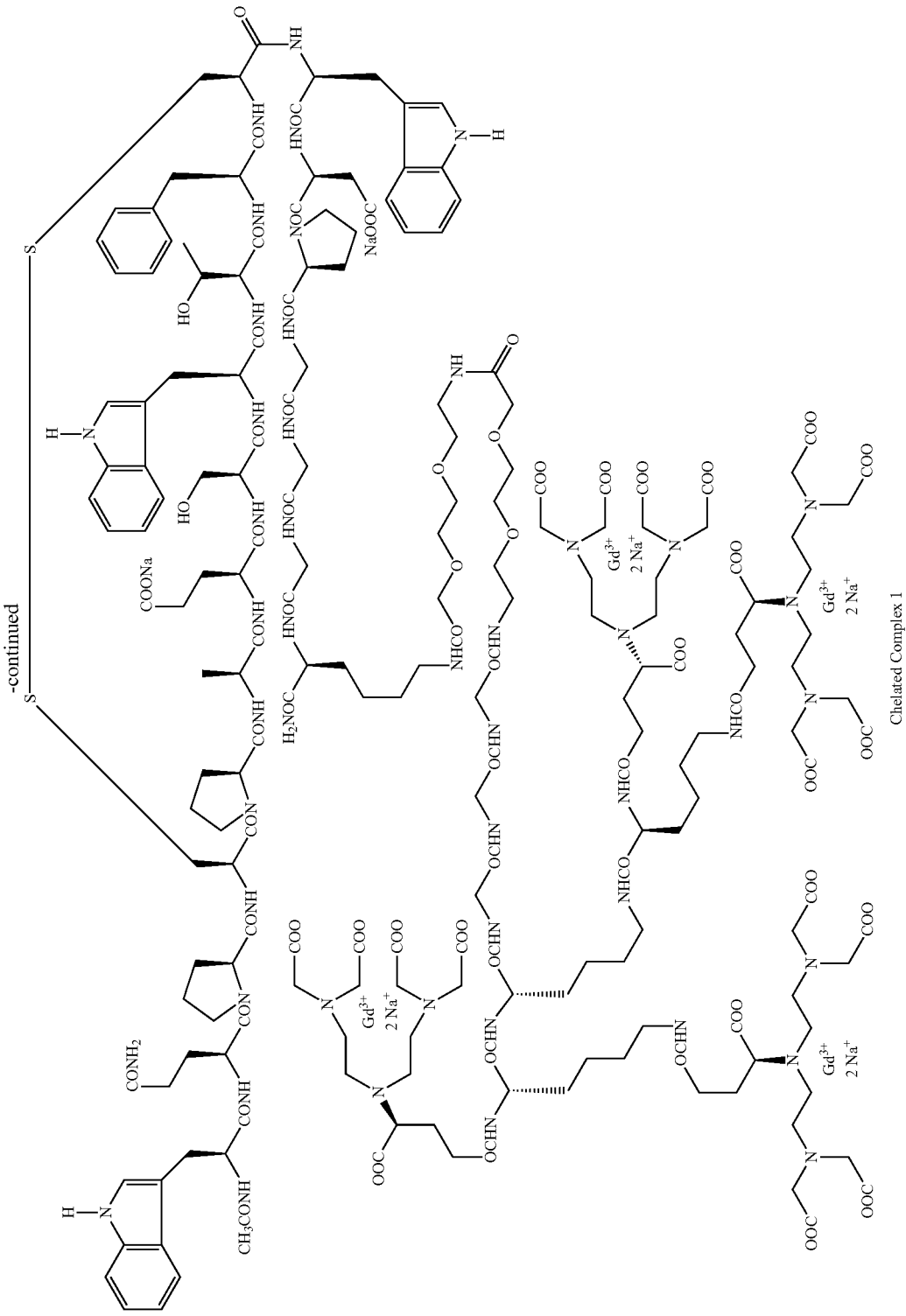
Chelated Complex 1

Fmoc-PAL-PEG-PS resin supported intermediate A prepared as schematized in FIG. 1 (5.00 g; 0.90 mmol) was shaken in a SPPS vessel with 50% morpholine in DMAC (40 mL) for 1 h to swell the resin and cleave the Fmoc group. After the solvent was filtered, Fmoc-GGG-OH (1.48 g; 3.60 mmol), HOBt (0.55 g; 3.60 mmol), DIC (0.56 mL; 3.60 mmol) and DMAC (40 mL) were added to the resin, the suspension shaken for 6 h at room temperature, the mixture filtered and the resin washed with DMAC (5×40 mL). The resin was then shaken with 50% morpholine in DMAC (7 mL) for 10 min, the mixture filtered and fresh 50% morpholine in DMAC (7 mL) was added. The suspension was stirred for 20 min then the mixture was filtered and the resin washed with DMAC (5×40 mL). Fmoc-Lys(Fmoc)-OH (2.13 g; 3.60 mmol), HOBt (0.55 g; 3.60 mmol), DIC (0.56 mL; 3.60 mmol) and DMAC (40 mL) were added to the resin, the suspension shaken for 6 h at room temperature, filtered and the resin washed with DMAC (5×40 mL). The resin was then shaken with 50% morpholine in DMAC (7 mL) for 10 min, the mixture filtered and fresh 50% morpholine in DMAC (7 mL) was added. The suspension was stirred for 20 min then the mixture was filtered and the resin washed with DMAC (5×40 mL). Fmoc-Lys(Fmoc)-OH (4.26 g; 7.20 mmol), HOBt (1.10 g; 7.20 mmol), DIC (1.12 mL; 7.20 mmol) and DMAC (40 mL) were added to the resin, the suspension shaken for 6 h at room temperature, filtered and the resin washed with DMAC (5×40 mL). The resin was then shaken with 50% morpholine in DMAC (7 mL) for 10 min, the mixture filtered and fresh 50% morpholine in DMAC (7 mL) was added. The suspension was stirred for 20 min then the mixture was filtered and the resin washed with DMAC (5×40 mL). DTPA-Glu (10.7 g; 14.4 mmol), HOBt (2.20 g; 14.4 mmol), DIC (2.26 mL; 14.4 mmol), DIEA (4.90 mL; 28.8 mmol) and DMAC (40 mL) were added to the resin. The suspension was shaken for 24 h at room temperature, filtered and the resin washed with DMAC (5×40 mL), $CH_2Cl_2$ (5×40 mL) and then vacuum dried. The resin was shaken in a flask with "Reagent B" (150 mL) for 4.5 h. The resin was filtered and the solution was evaporated under reduced pressure to afford an oily crude that, after treatment with $Et_2O$ (40 mL), gave a precipitate. The precipitate was centrifuged, decanted and washed with $Et_2O$ (4×40 mL) to give a white solid (2.10 g). This product (2.10 g) was dissolved in a mixture of DMSO (36 mL) and $H_2O$ (4.0 mL) and the pH adjusted to 8 with D-(–)-N-methyl glucamine (1.23 g). The solution was stirred for 96 hours at room temperature and then purified by preparative HPLC. The fractions containing the product were lyophilized to afford the desired chelating ligand (0.280 g; 0.058 mmol) as a white solid. The ligand (0.240 g; 0.050 mmol) was suspended in $H_2O$ (80 mL) and dissolved by addiction of 0.1 N NaOH (8.50 mL; 0.85 mmol) up to pH 6.5. 5.187 mM aq. $GdCl_3$ (38.3 mL; 0.202 mmol) was added maintaining pH 6.5 by means of 0.1 N NaOH (6.0 mL; 0.60 mmol). The solution was adjusted to pH 7.0 with 0.1 N NaOH and then loaded onto a XAD 1600 column and eluted with a gradient $H_2O$/ACN (the desired product elutes with a percentage of ACN=30) to give, after evaporation, compound the Chelated complex 1, as sodium salt, (0.167 g; 0.029 mmol) as a white solid. Overall yield 3.8%.

Analytical Data for Chelate Complex 1

Mr: 5663.73 ($C_{205}H_{276}Gd_4N_{48}Na_{10}O_{83}S_2$)

CE: 88.5% (Area %)

MS: obtained data are consistent with Chelate Complex 1 structure.

Example 10

Preparation of the Chelate Complex 2

The preparation of the Chelated Complex 2 is represented in Scheme 3 below.

Scheme 3
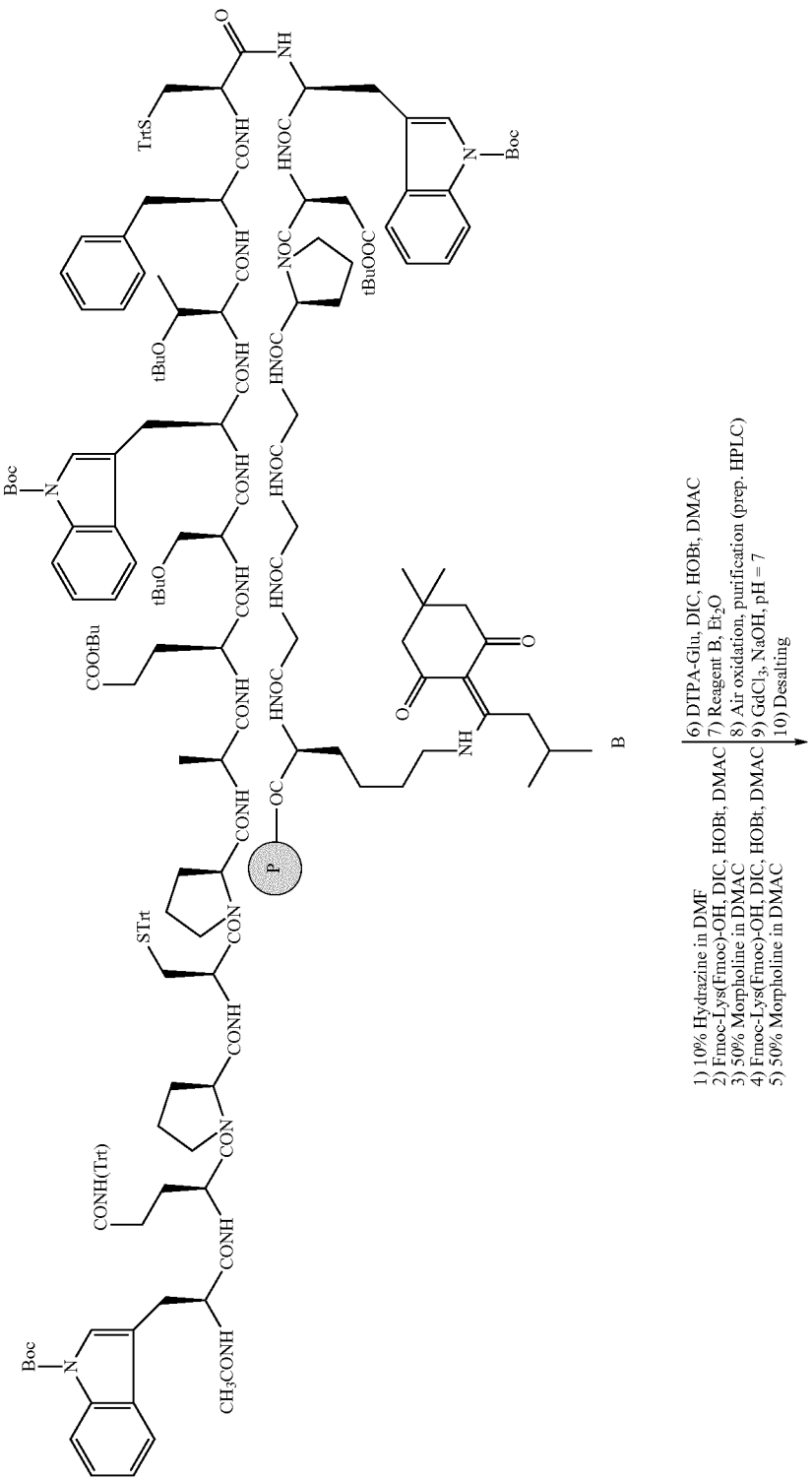
1) 10% Hydrazine in DMF
2) Fmoc-Lys(Fmoc)-OH, DIC, HOBt, DMAC
3) 50% Morpholine in DMAC
4) Fmoc-Lys(Fmoc)-OH, DIC, HOBt, DMAC
5) 50% Morpholine in DMAC
6) DTPA-Glu, DIC, HOBt, DMAC
7) Reagent B, Et₂O
8) Air oxidation, purification (prep. HPLC)
9) GdCl₃, NaOH, pH = 7
10) Desalting -continued
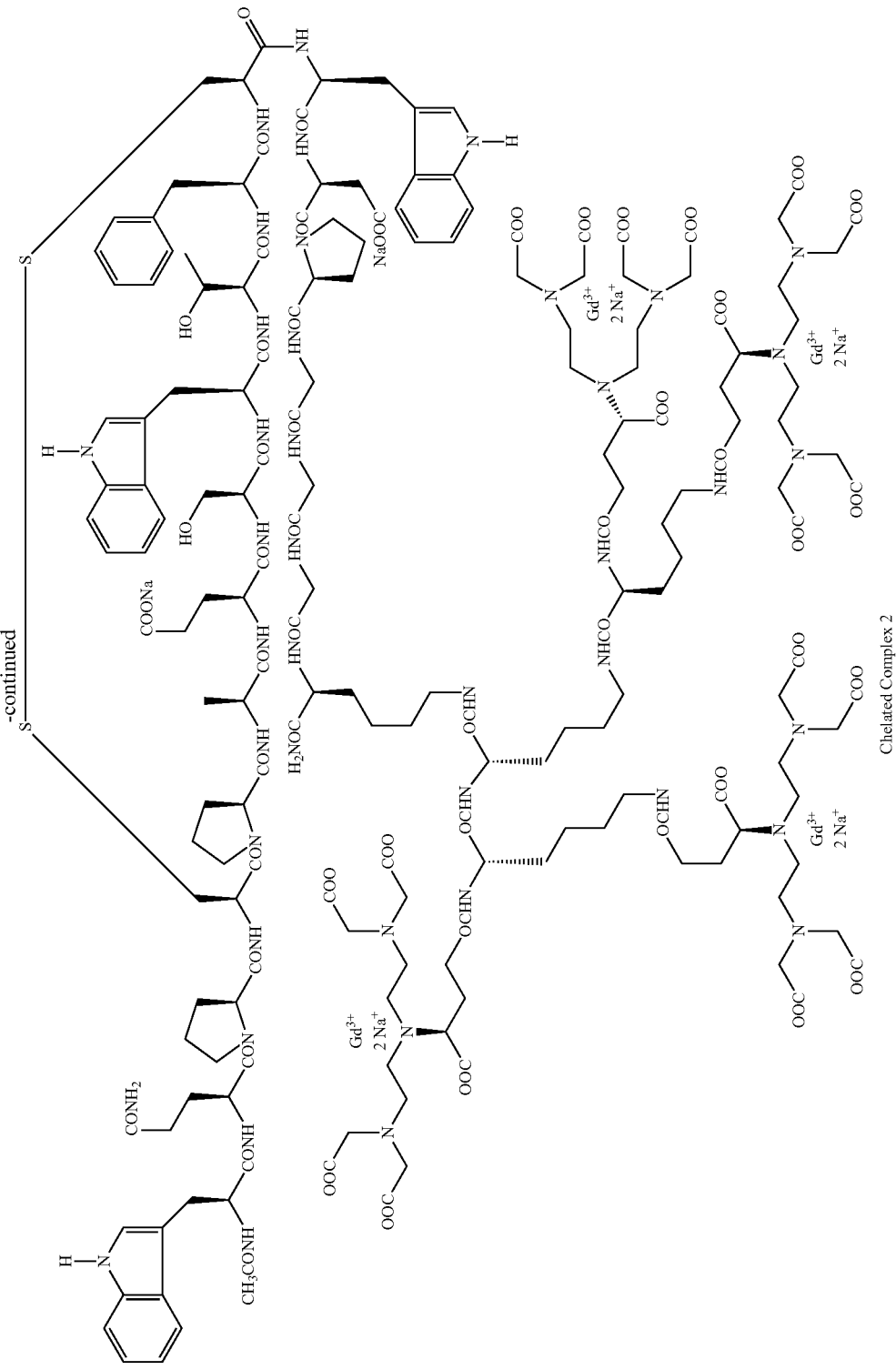
Chelated Complex 2

To Fmoc-PAL-PEG-PS resin supported intermediate B (3.00 g; 0.60 mmol) obtained according to Procedure A, described above, was shaken in a SPPS vessel with DMAC (25 mL) for 1 h to swell the resin. After the solvent was filtered, the resin was washed with DMF (5×25 mL). The resin was then shaken with 10% hydrazine in DMF (25 mL) for 15 min, the solvent filtered and fresh 10% hydrazine in DMF (25 mL) was added. The suspension was stirred for more 20 min then the mixture was filtered and the resin washed with DMF (5×25 mL) and then DMAC (5×25 mL). Fmoc-Lys(Fmoc)-OH (1.42 g; 2.40 mmol), HOBt (0.36 g; 2.40 mmol), DIC (0.37 mL; 2.40 mmol) and DMAC (25 mL) were added to the resin, the suspension shaken for 24 h at room temperature, filtered and the resin washed with DMAC (5×25 mL). The resin was then shaken with 50% morpholine in DMAC (25 mL) for 10 min, the mixture filtered and fresh 50% morpholine in DMAC (25 mL) was added. The suspension was stirred for 20 min then the mixture was filtered and the resin washed with DMAC (5×25 mL). Fmoc-Lys(Fmoc)-OH (2.84 g; 4.80 mmol), HOBt (0.73 g; 4.80 mmol), DIC (0.75 mL; 4.80 mmol) and DMAC (25 mL) were added to the resin, the suspension shaken for 24 h at room temperature, filtered and the resin washed with DMAC (5×25 mL). The resin was then shaken with 50% morpholine in DMAC (25 mL) for 10 min, the mixture filtered and fresh 50% morpholine in DMAC (25 mL) was added. The suspension was stirred for 20 min then the mixture was filtered and the resin washed with DMAC (5×25 mL). DTPA-Glu (7.17 g; 9.60 mmol), HOBt (1.47 g; 9.60 mmol), DIC (1.50 mL; 9.60 mmol), DIEA (3.26 mL; 9.60 mmol) and DMAC (25 mL) were added to the resin. The suspension was shaken for 24 h at room temperature, filtered and the resin washed with DMAC (5×25 mL), $CH_2Cl_2$ (5×25 mL) and then vacuum dried. The resin was shaken in a flask with "Reagent B" (100 mL) for 4.5 h. The resin was filtered and the solution was evaporated under reduced pressure to afford an oily crude that, after treatment with $Et_2O$ (40 mL), gave a precipitate. The precipitate was centrifuged, decanted and washed with $Et_2O$ (4×40 mL) to give a white solid (1.60 g). This product (1.60 g) was dissolved in a mixture of DMSO (27 mL) and $H_2O$ (3.0 mL) and the pH adjusted to 8 with D-(−)-N-methyl glucamine (0.94 g). The solution was stirred for 96 hours at room temperature and then purified by preparative HPLC. The fractions containing the product were lyophilized to afford the desired chelating ligand (0.260 g; 0.060 mmol) as a white solid. The ligand (0.220 g; 0.050 mmol) was suspended in $H_2O$ (80 mL) and dissolved by addiction of 0.1 N NaOH (7.40 mL; 0.74 mmol) up to pH 6.5. 6.21 mM aq. $GdCl_3$ (32.60 mL; 0.202 mmol) was added maintaining pH 6.5 by means of 0.1 N NaOH (6.10 mL; 0.61 mmol). The solution was adjusted to pH 7.0 with 0.1 N NaOH and then loaded onto a XAD 1600 column and eluted with a gradient $H_2O$/ACN (the desired product elutes with a percentage of ACN=30) to give, after evaporation, the Chelated complex 2, sodium salt, (0.174 g; 0.033 mmol) as a white solid. Yield 6.6%.

Analytical Data for Chelate Complex 2
Mr: 5202.26 ($C_{187}H_{245}Gd_4N_{43}Na_{10}O_{74}S_2$)
CE: 87.8% (Area %)
MS: Obtained data are consistent with Chelate Complex 2 structure

Example 11

Preparation of the Chelate Complex 4

By following the synthetic procedure of Scheme 3, and by using the suitable AAZTA ligand instead of the corresponding DTPA ligand, the Chelate Complex 4 has been also prepared.

Chelate complex 4
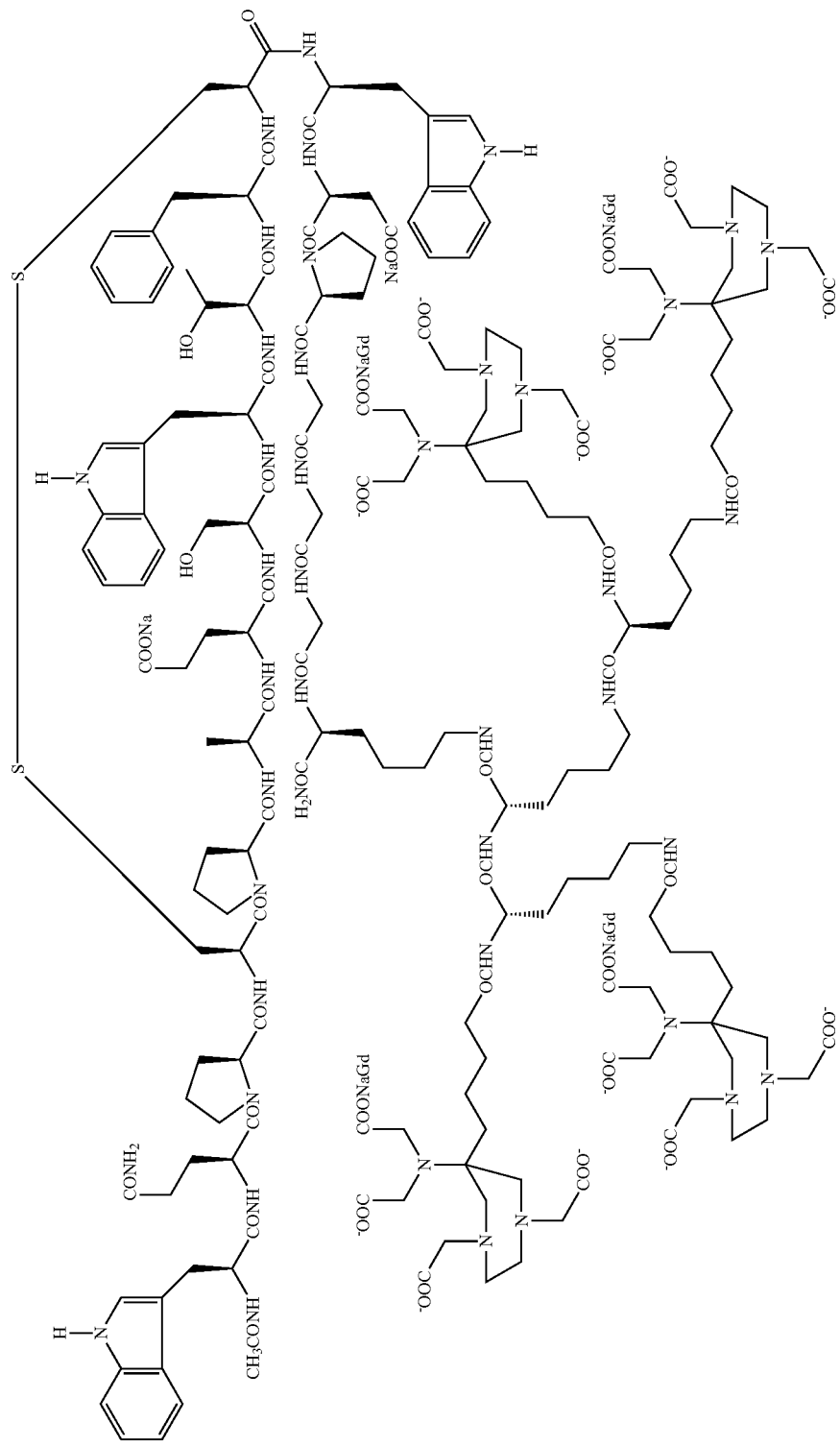

Mr: 5042.44 ($C_{191}H_{257}Gd_4N_{43}Na_6O_{66}S_2$)
MS: Obtained data are consistent with Chelate Complex 4 structure

Example 12

Preparation of the Chelate Complex 3

The preparation of the Chelate complex 3 is represented in Scheme 4 below.

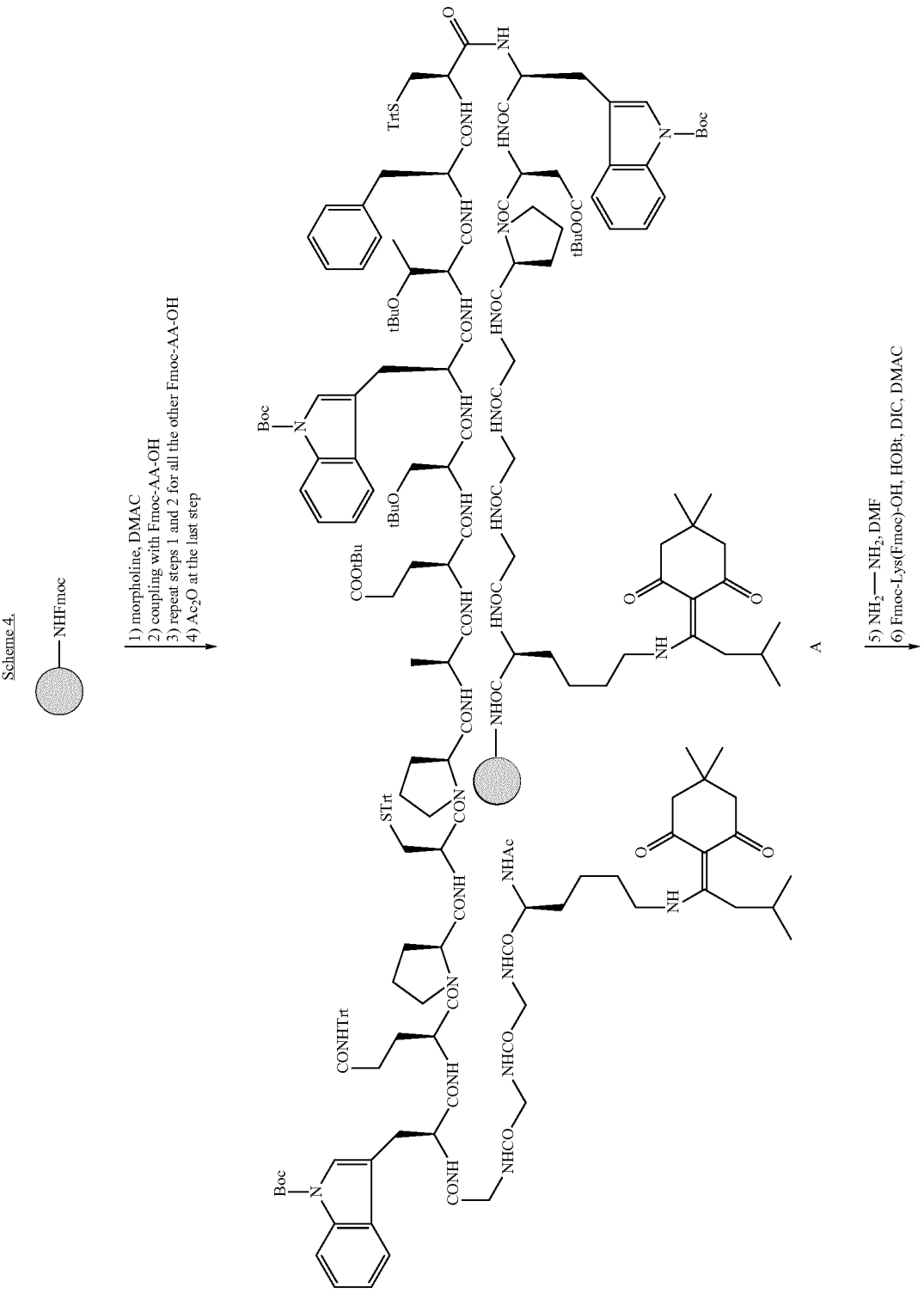
Scheme 4.

-continued
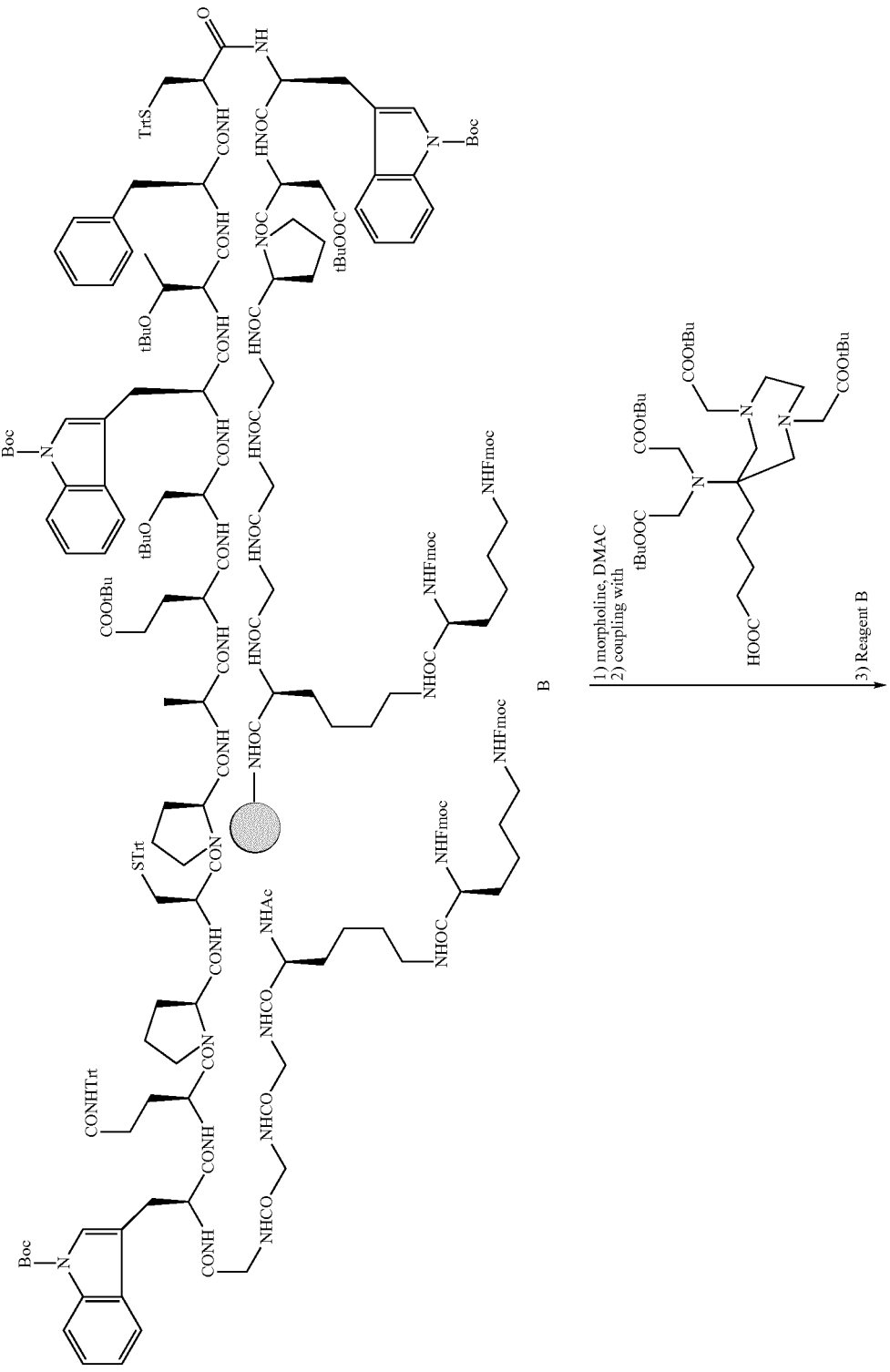

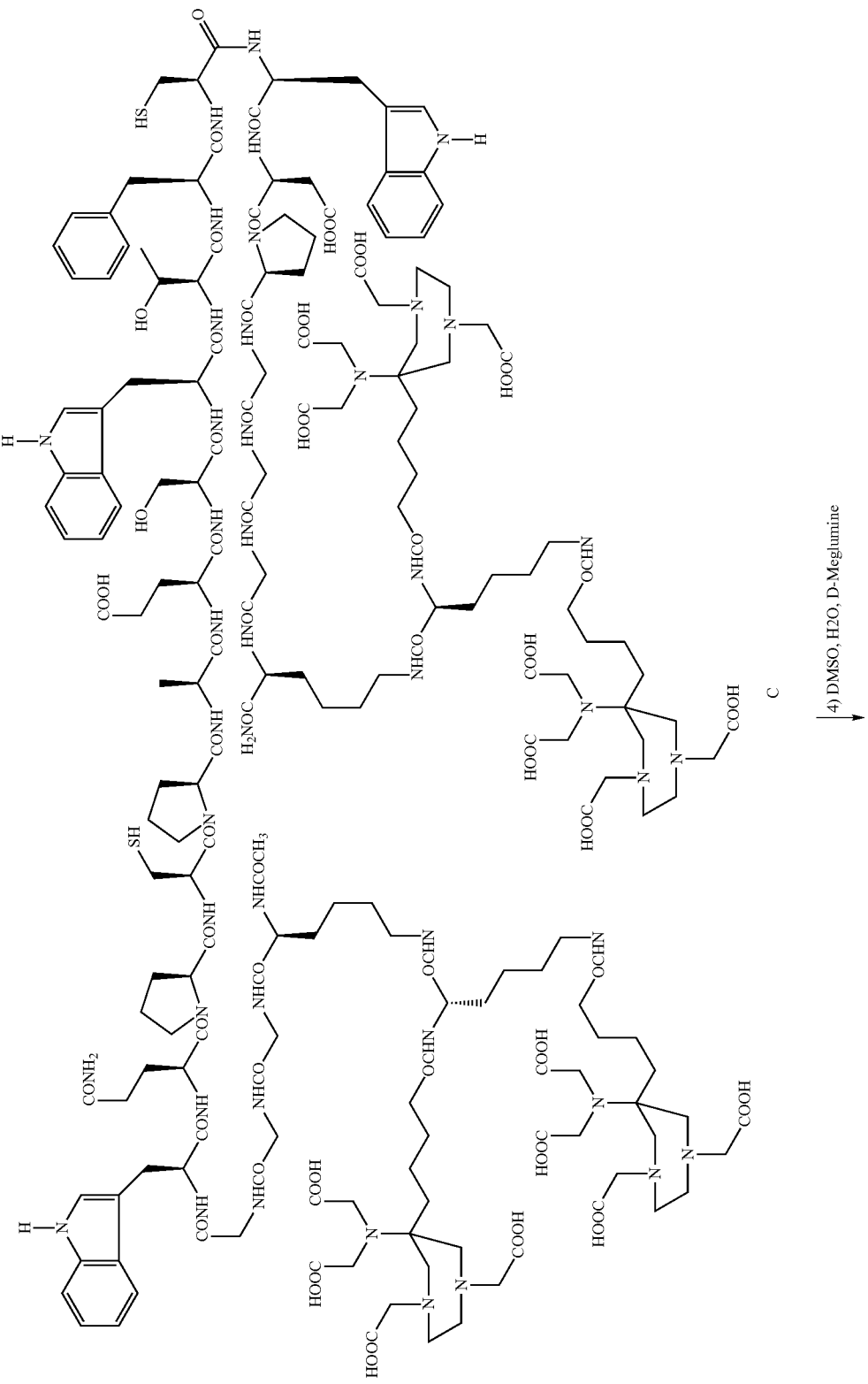

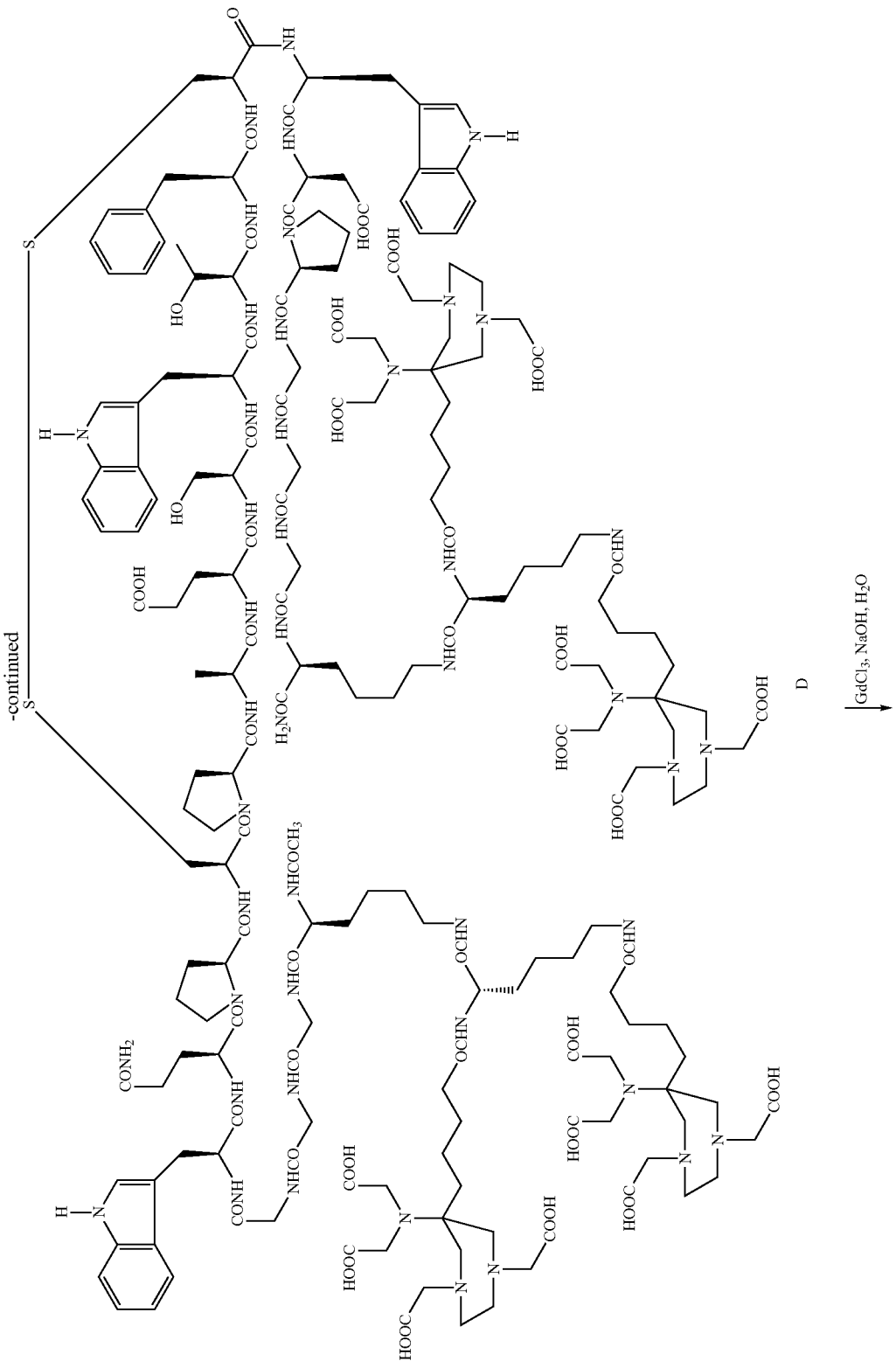

-continued
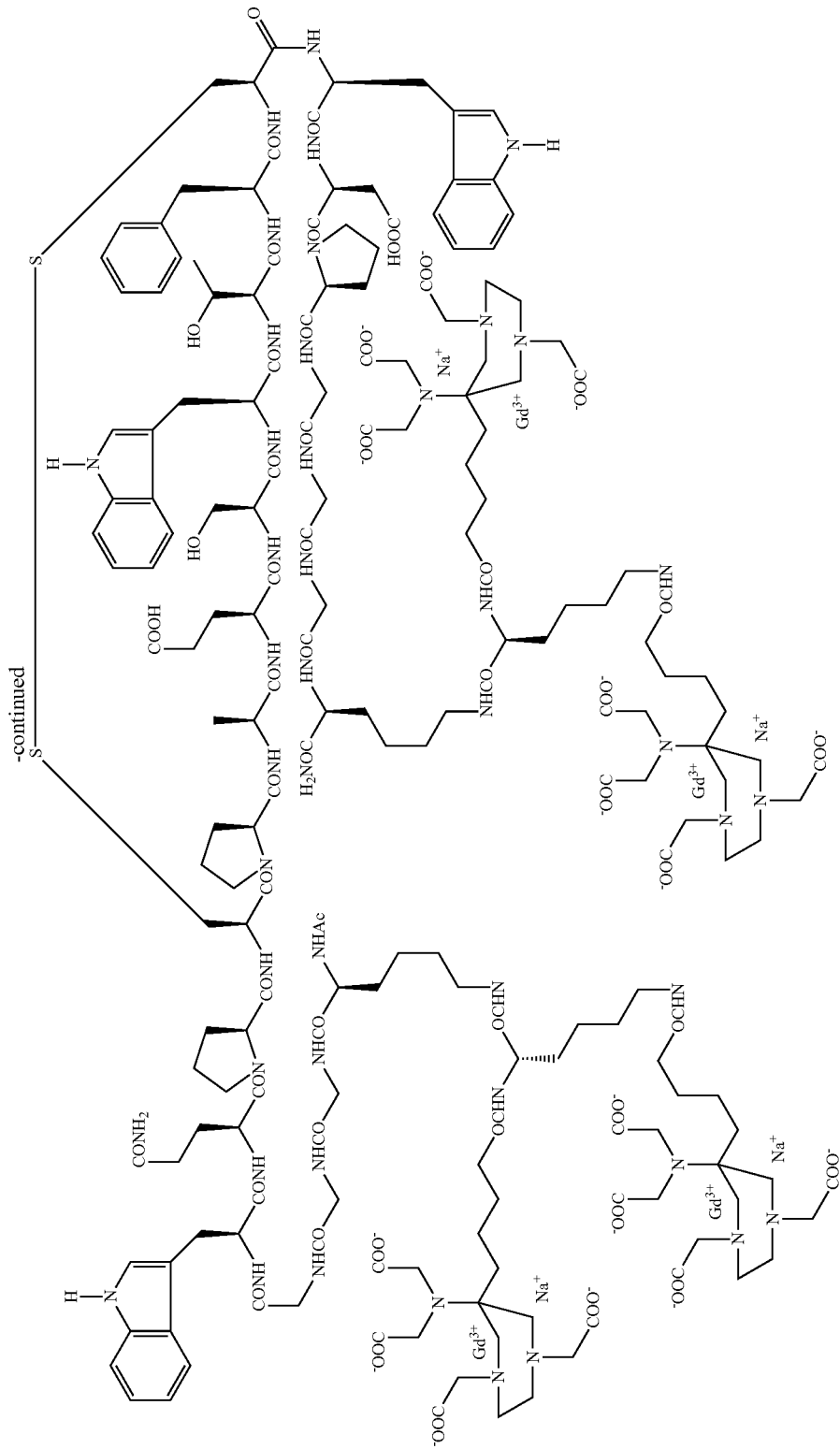
Chelated complex 3 a) The ligand suitably protected as tert-butil ester is prepared as previously reported in example 8.

b) Preparation of Intermediate A

To Fmoc-PAL-PEG-PS resin supported intermediate A described above in Scheme 4, was synthesised from PAL-PEG-PS resin using conventional Fmoc solid phase peptide synthesis.

c) Preparation of the Intermediate B

The Fmoc-PAL-PEG-PS resin supported intermediate A, being prepared as above described, was shaken in a SPPS vessel with DMAC (25 mL) for 1 h to swell the resin. After the solvent was filtered, the resin was washed with DMF (5×20 mL). The resin was then shaken with 10% hydrazine in DMF (25 mL) for 15 min, the solvent filtered and fresh 10% hydrazine in DMF (25 mL) was added. The suspension was stirred for more 20 min then the mixture was filtered and the resin washed with DMF (3×25 mL) and then DMAC (4×25 mL). The resin was then shaken Fmoc-Lys(Fmoc)-OH (2.84 g; 4.80 mmol), HOBt (0.73 g; 4.80 mmol), DIC (0.75 mL; 4.80 mmol) and DMAC (25 mL) were added to the resin, the suspension shaken for 24 h at room temperature, filtered and the resin washed with DMAC (5×25 mL) thus providing the intermediate B.

d) Preparation of the Intermediate C

The Fmoc-PAL-PEG-PS resin supported intermediate B (2.6 g; 0.43 mmol) was shaken in a SPPS vessel with DMAC (25 mL) for 1 h to swell the resin. After the solvent was filtered, the resin was washed with DMF (5×20 mL). The resin was then shaken with 50% morpholine in DMAC (25 mL) for 15 min, the mixture filtered and fresh 50% morpholine in DMAC (25 mL) was added. The suspension was stirred for 20 min then filtered and the resin washed with DMAC (5×20 mL). The suitably protected AAZTA ligand (Compound F) (3.5 g; 5.21 mmol), HOBt (799 mg; 5.21 mmol), DIC (816 µL; 5.21 mmol) and DMAC (25 mL) were added to the resin. The suspension was shaken for 96 h at room temperature, filtered and the resin washed with DMAC (5×25 mL), $CH_2Cl_2$ (5×25 mL) and then vacuum dried. The resin was shaken in a flask with "Reagent B" (100 mL) for 5 h. The resin was filtered and washed with DMAC (30 mL) and the solution was evaporated under reduced pressure to afford an oily crude that, after treatment with $Et_2O$ (30 mL), gave a precipitate. The precipitate was centrifuged, decanted and washed with $Et_2O$ (4×40 mL) to give a white solid (1.70 g).

e) Preparation of the Intermediate D

The intermediate C (1.70 g) was dissolved in a mixture of DMSO (27 mL) and $H_2O$ (3.0 mL) and the pH adjusted to 8 with D-(−)-N-methyl glucamine (0.94 g). The solution was stirred for 96 hours at room temperature and then purified by preparative HPLC. The fractions containing the product were lyophilized to afford 1e ligand D (0.300 g; 0.067 mmol) as a white solid.

f) Preparation of the Chelate Complex 3

Ligand D (0.300 g; 0.067 mmol) was suspended in $H_2O$ (80 mL) and dissolved by addiction of 0.1 N NaOH up to pH 6.5. 5.18 mM aq. $GdCl_3$ (51.9 mL; 0.27 mmol) was added maintaining pH 6.5 by means of 0.1 N NaOH. The solution was adjusted to pH 7.0 with 0.1 N NaOH (total NaOH=10 mL; 1.0 mmol) and then loaded onto a XAD 1600 column and eluted with a gradient $H_2O$/ACN to give, after evaporation, the Chelate Complex 3 (0.110 g; 0.021 mmol) as a white solid.

Mr: 5213.60 ($C_{197}H_{266}Gd_4N_{46}Na_6O_{69}S_2$)

MS: Obtained data are consistent with Chelate Complex 3 structure

Example 13

Preparation of the Chelate Complex 11

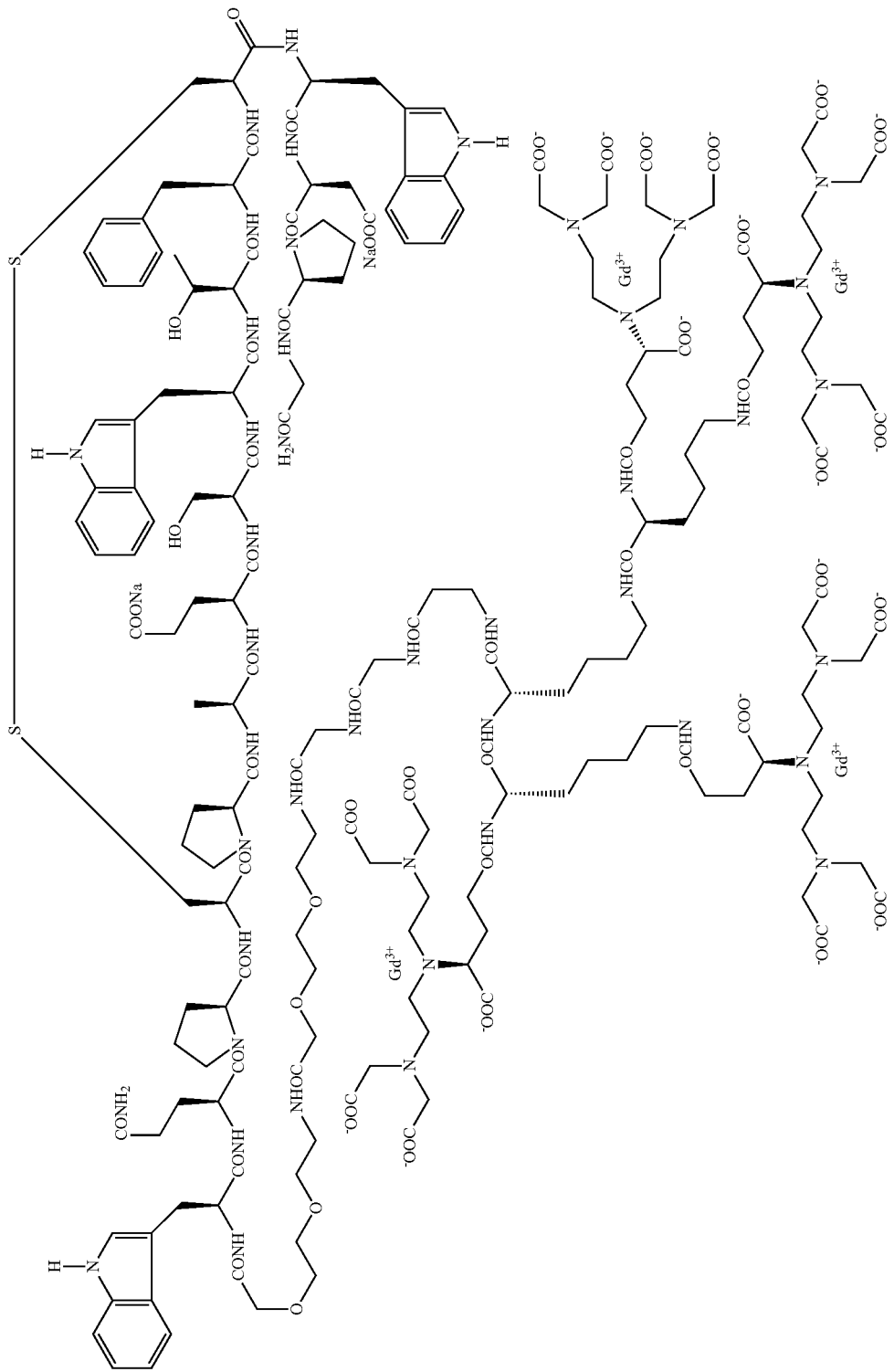

The title compound was prepared by working as per the previous examples and by carrying out all of the synthetic steps on 100 mg of Fmoc-PAL-PEG-PS resin (loading 0.2 mmol/g), by using the standard Fmoc procedure previously disclosed and including piperidine deprotection, aminoacid coupling with 4 equivalents of AA and HBTU/HOBt/DIPEA, using DMF as solvent. The last step was carried out with a manual system using HATU as acid activator. The cleavage of the peptide from the resin was then obtained using a mixture of TFA/Triisopropylsilane/Ethandithiol (95:3:2, v:v) for two hours. The peptide was then precipitated and washed with diethyl ether and the solid obtained was dissolved in a mixture of a 5% solution of AcOH and DMSO (50 ml, 49:1, v:v) and stirred for 24 h to afford both the complete deprotection of the tryptophan and the cyclization of the two central cysteines. The solution was then lyophilised to yield the final product which was purified by HPLC.

There were thus obtained 45 mg of pure product (9.7 μmol, 48% overall yield). A 10 mM solution of $GdCl_3$ in $H_2O$ was added in portion to a water solution of the ligand maintained at pH 6.5 with NaOH solution. A relaxivity measurement was carried out after each addition until the measured value was out from the linearity. At this point the requested amount of ligand was added bringing back the point on the rect. The residual free Gd(III) ion was quantified by Orange Xylenol UV method. A stoichiometric amount of free ligand was then added to reduce the free Gd(III) ion under 0.3% (mol/mol). Lyophilisation yielded the desired chelate complex 11.

By working in a substantially analogous way and by properly selecting any suitable reactant and operative conditions thereof, the following chelate complexes of the invention were also prepared:

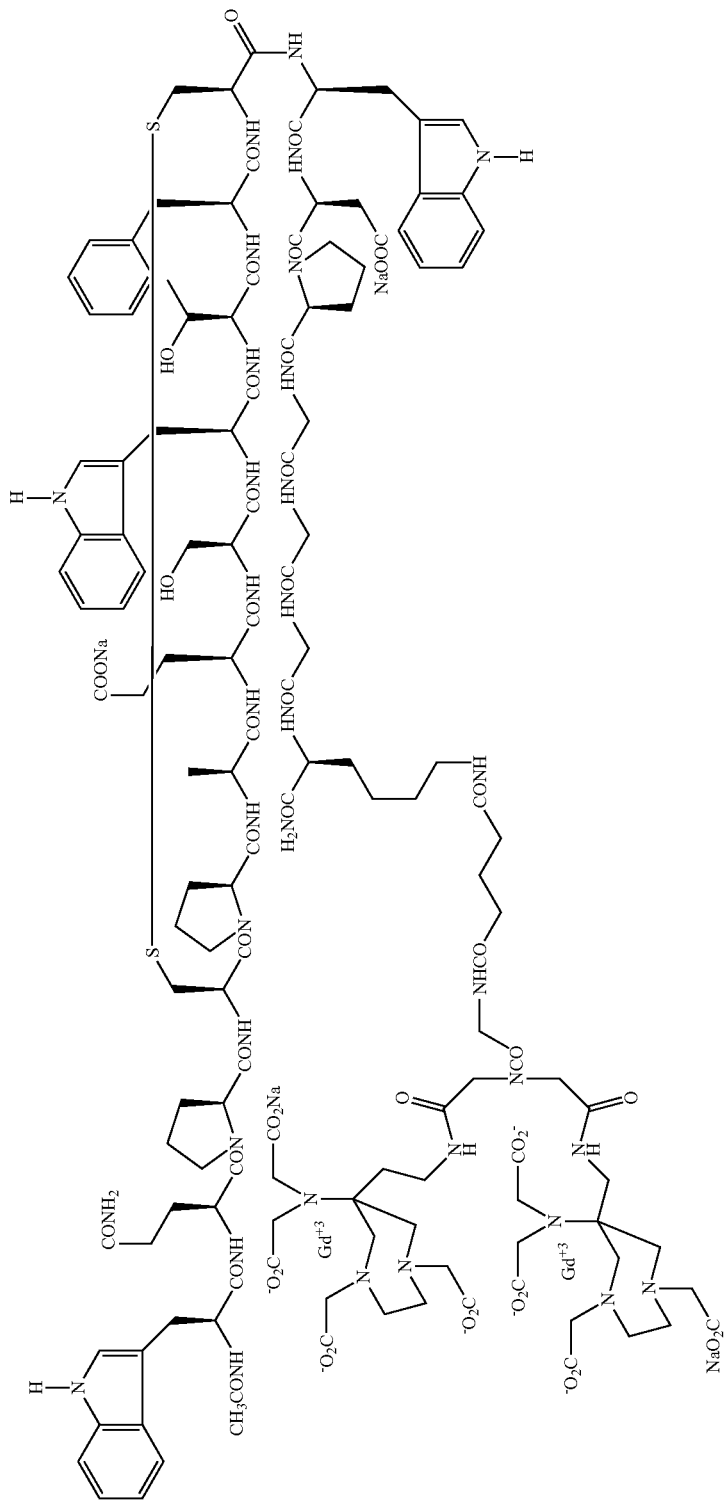
Chelate complex 5

Mr: 3618.79 ($C_{142}H_{183}Gd_2N_{35}Na_4O_{48}S_2$)
MS: Obtained data are consistent with Chelate Complex 5 structure

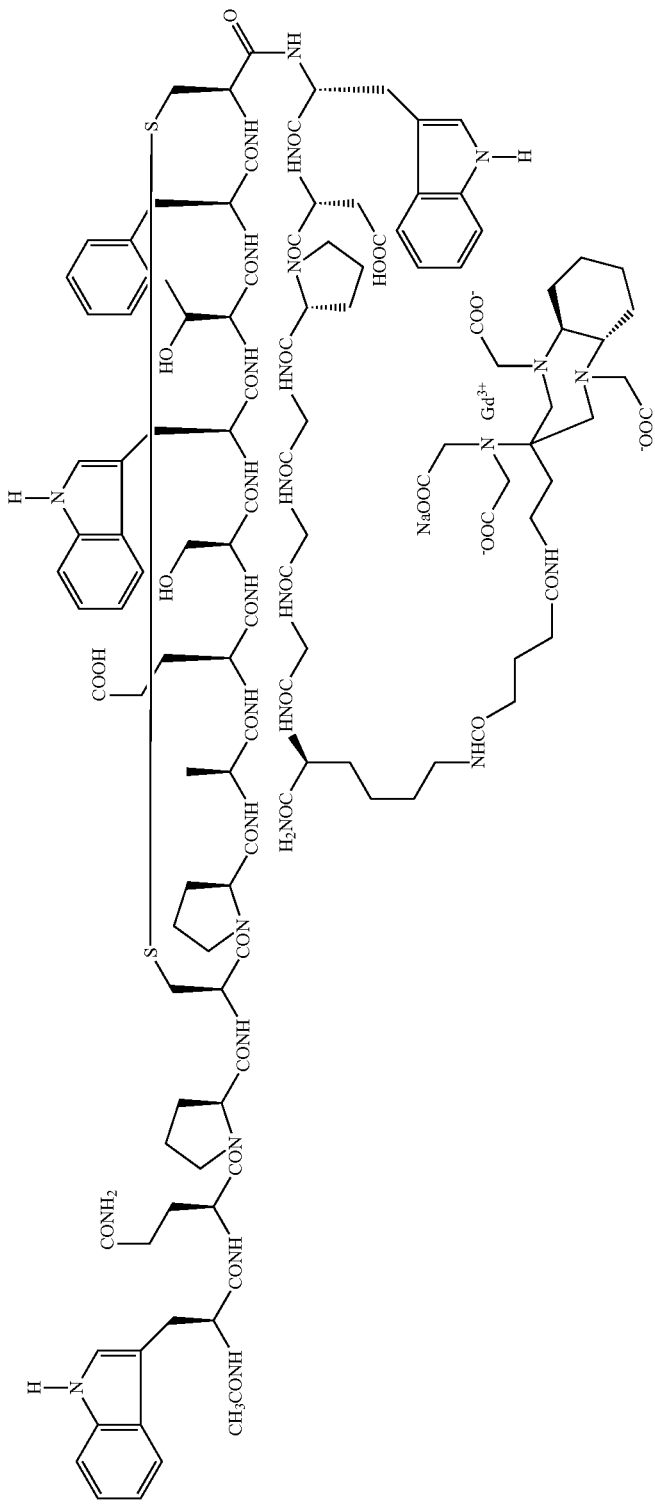

Mr: 2952.16 ($C_{125}H_{161}GdN_{29}Na_3O_{37}S_2$)
MS: Obtained data are consistent with Chelate Complex 6 structure

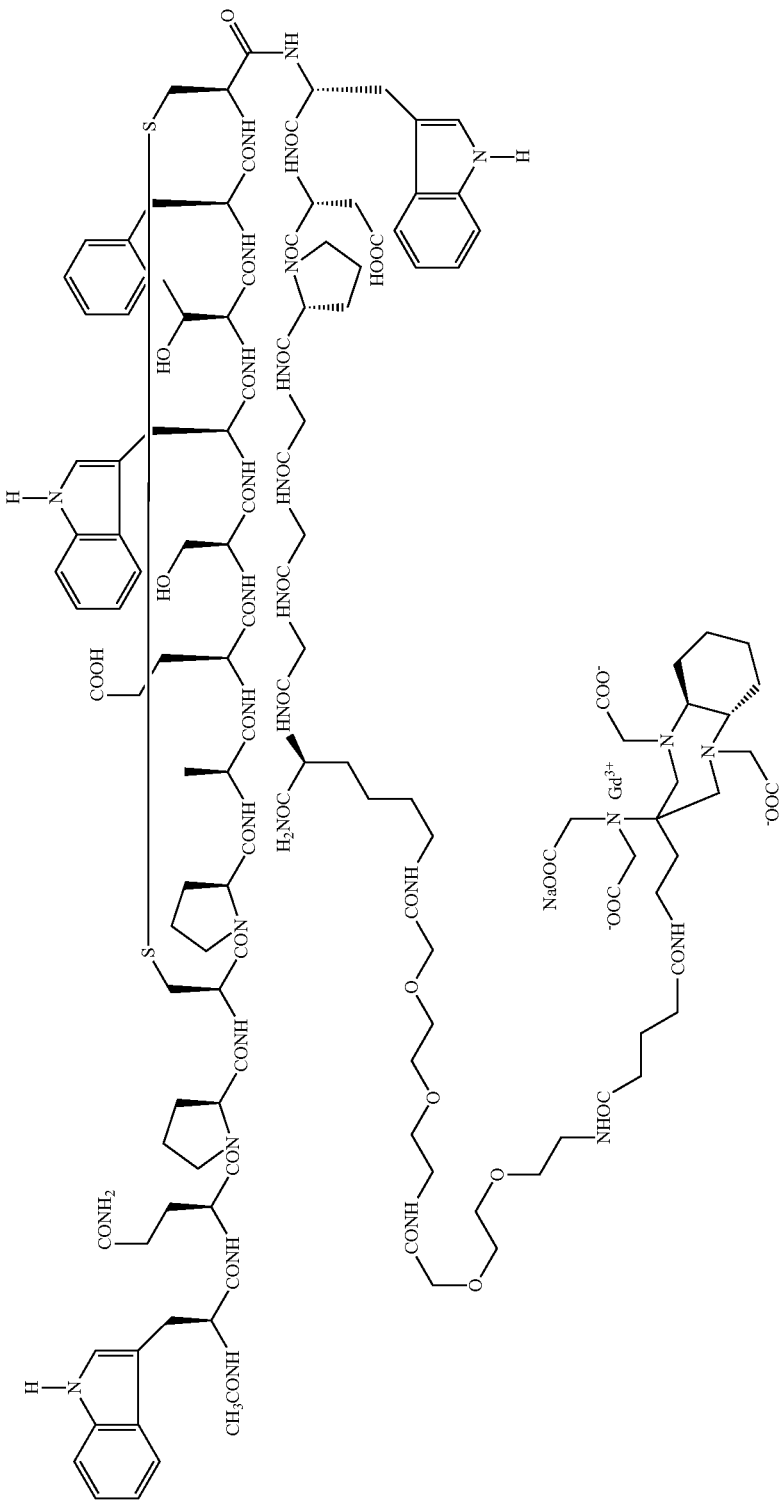
Chelate complex 7

Mr: 3242.48 ($C_{137}H_{183}GdN_{31}Na_3O_{43}S_2$)
MS: Obtained data are consistent with Chelate Complex 7 structure

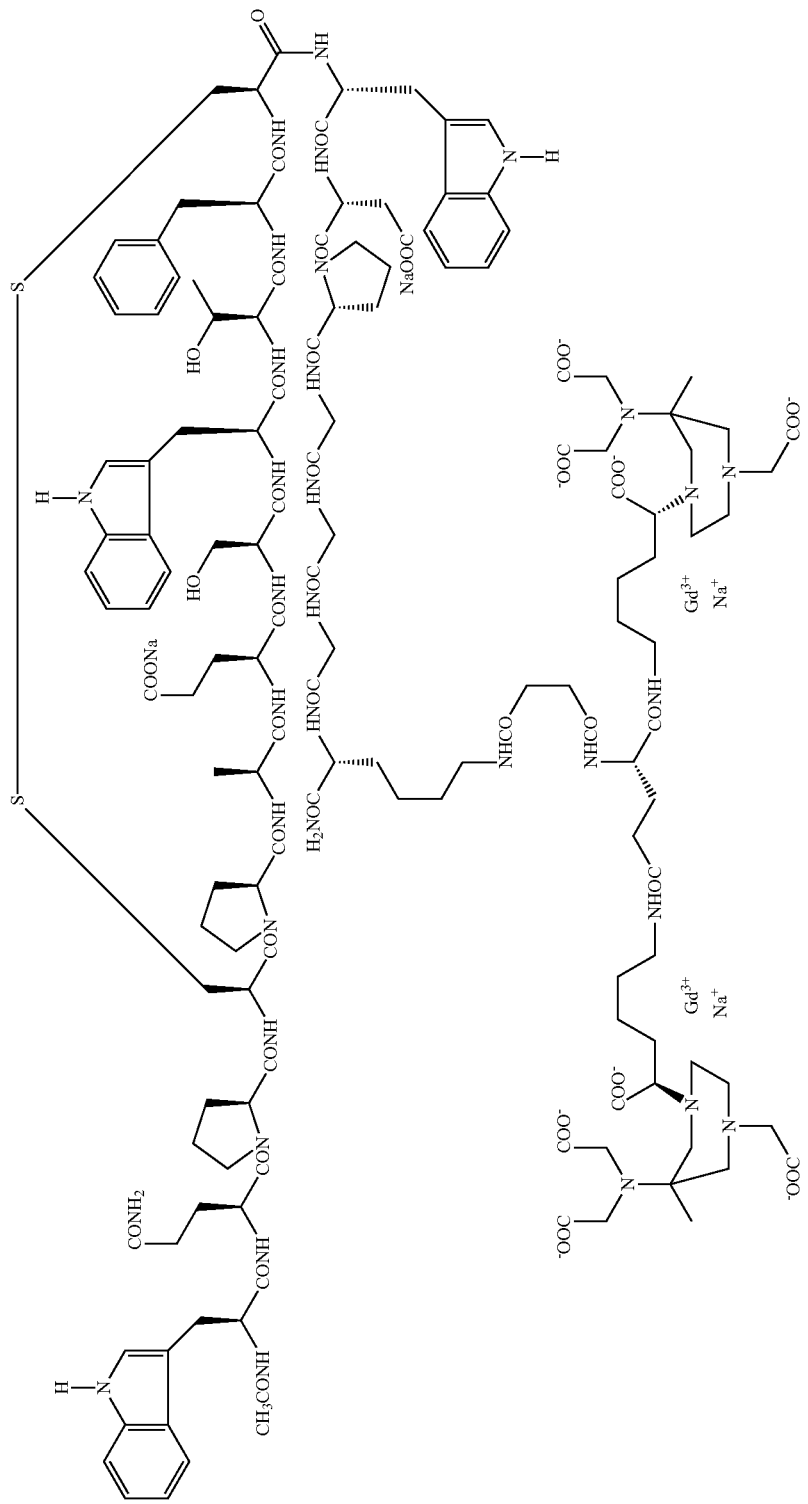
Chelate complex 8

Mr: 3645.90 ($C_{146}H_{192}Gd_2N_{34}Na_4O_{47}S_2$)
MS: Obtained data are consistent with Chelate Complex 8 structure

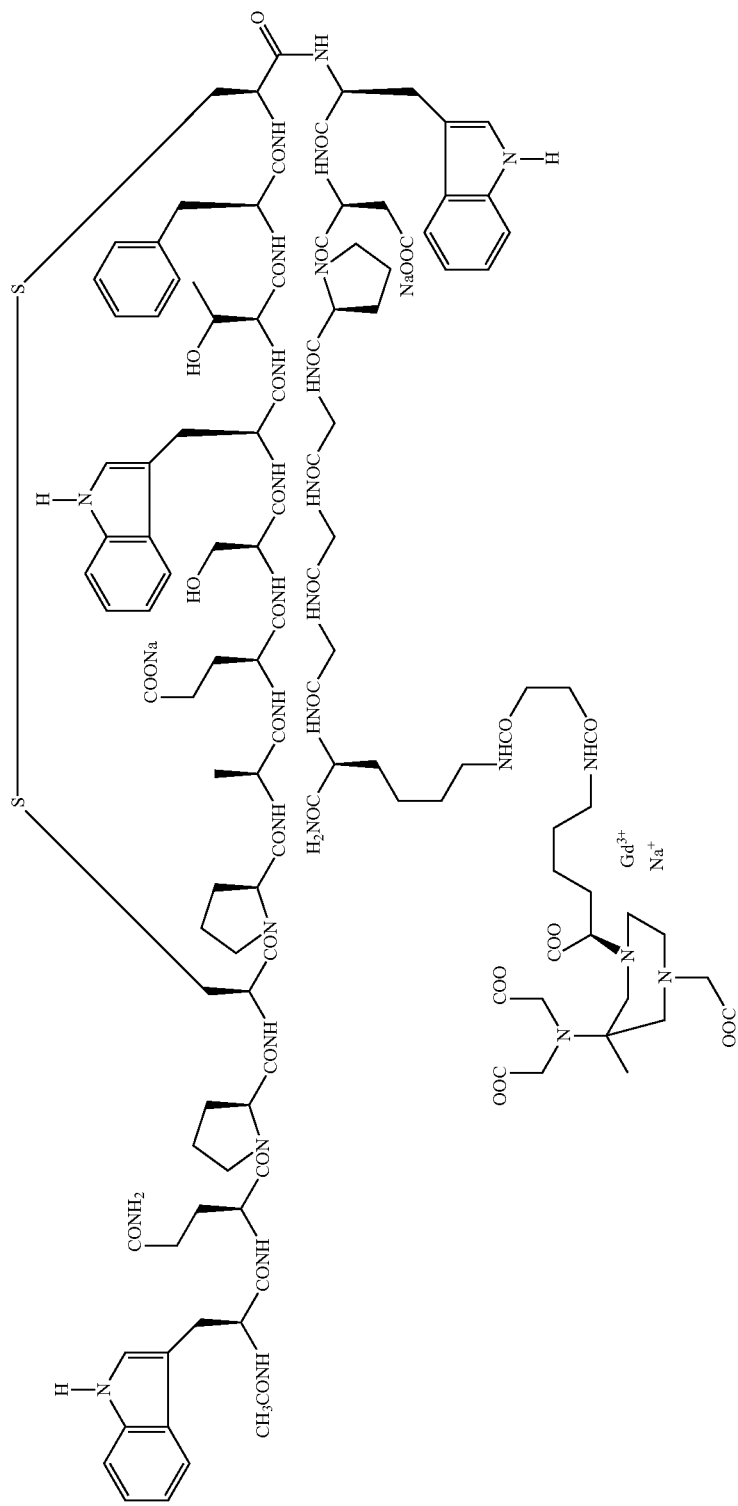
Chelate complex 9

Mr: 2926.12 ($C_{123}H_{159}GdN_{29}Na_3O_{37}S_2$)
MS: Obtained data are consistent with Chelate Complex 9 structure

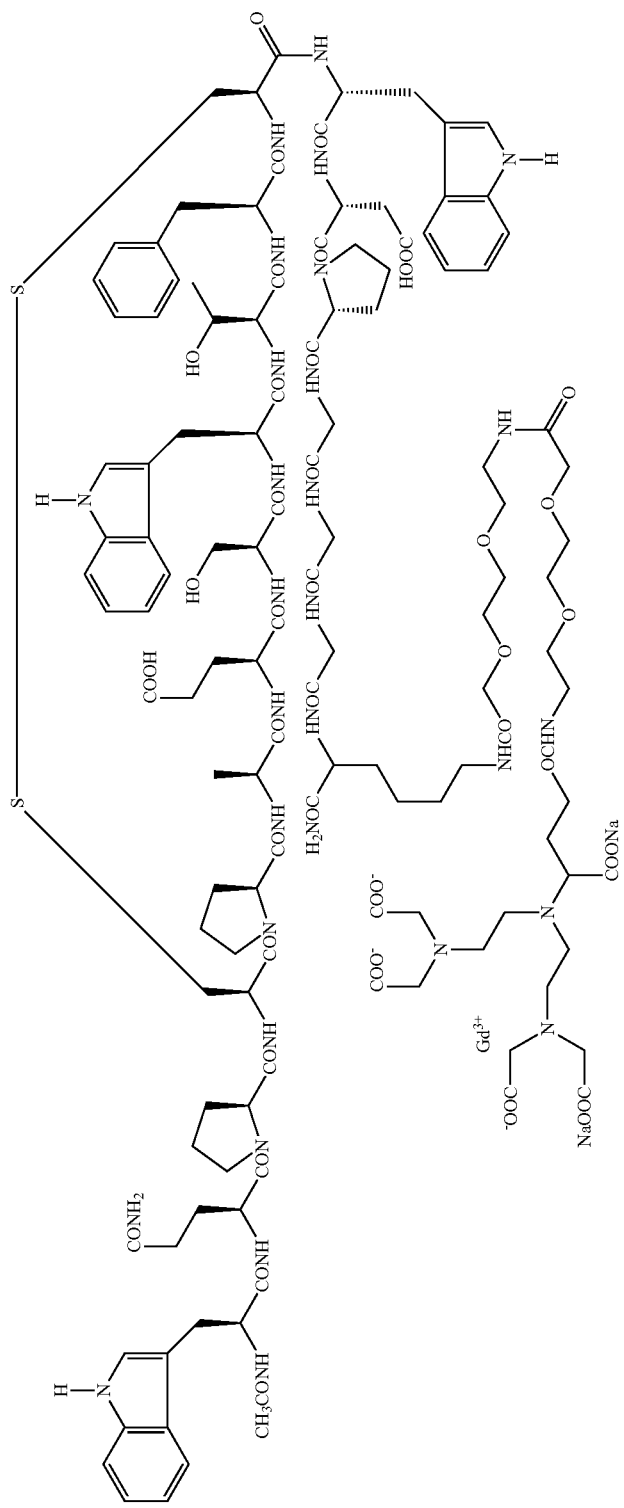

Mr: 3171.29 ($C_{130}H_{171}GdN_{30}Na_4O_{44}S_2$)

MS: Obtained data are consistent with Chelate Complex 10 structure

Reference Complexes

By starting from the previously known peptide Ac-WQPC*PWESWTFC*WDGGGK-NH$_2$, SEQ ID NO:038, provided by WO 02/055544, by following the synthetic procedures of previous schemes, and by suitably changing the chelating ligand moiety to be conjugated to linker-functionalized peptide intermediates, some chelated compounds have been prepared as Reference Compounds for in vivo and in vitro tests.

The following reference compounds have, in particular, been prepared:

Reference 1

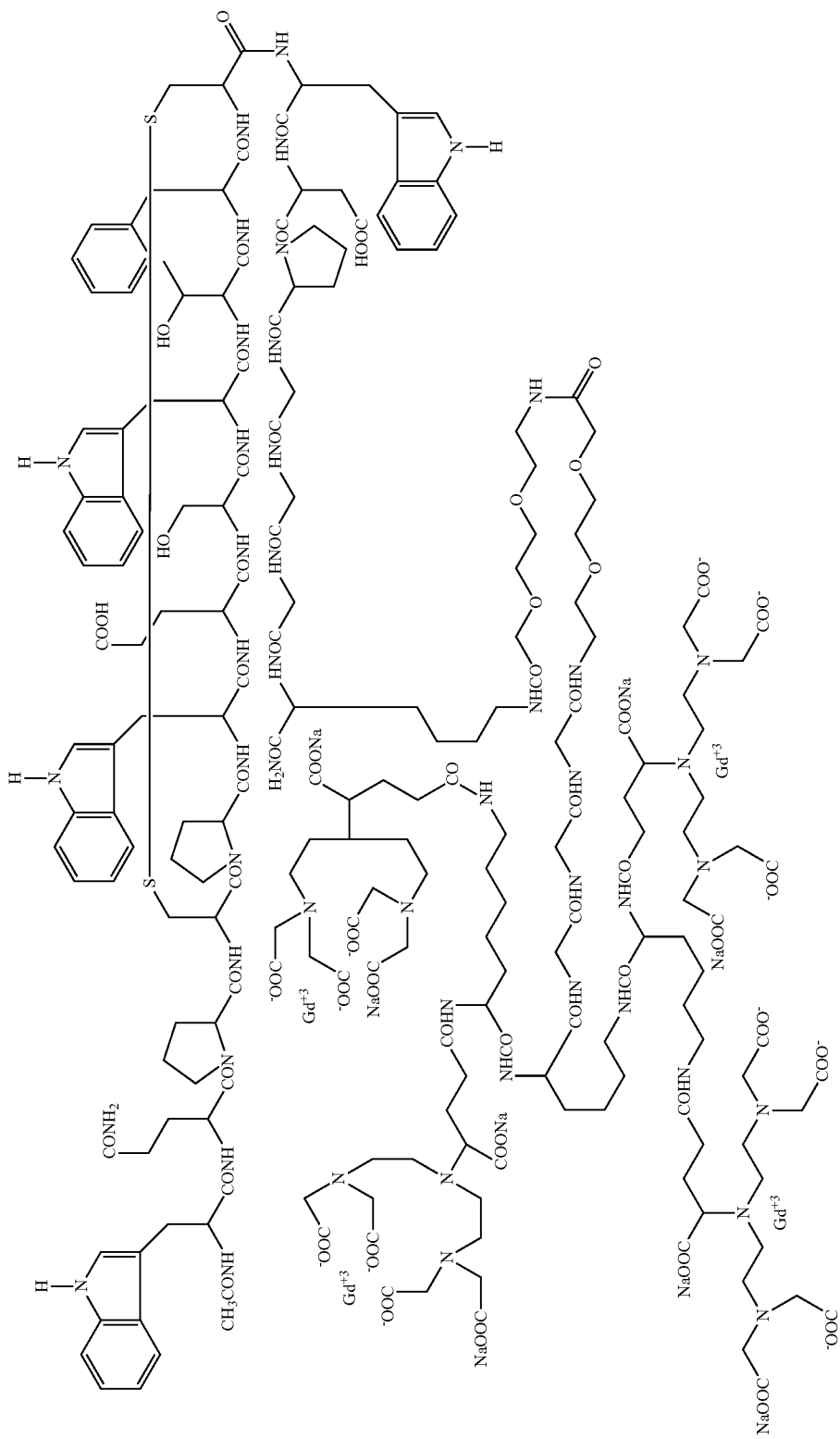

Mr: 5778.87 ($C_{213}H_{281}Gd_4N_{49}Na_{10}O_{83}S_2$)
MS: Obtained data are consistent with Reference 1 structure Reference 2

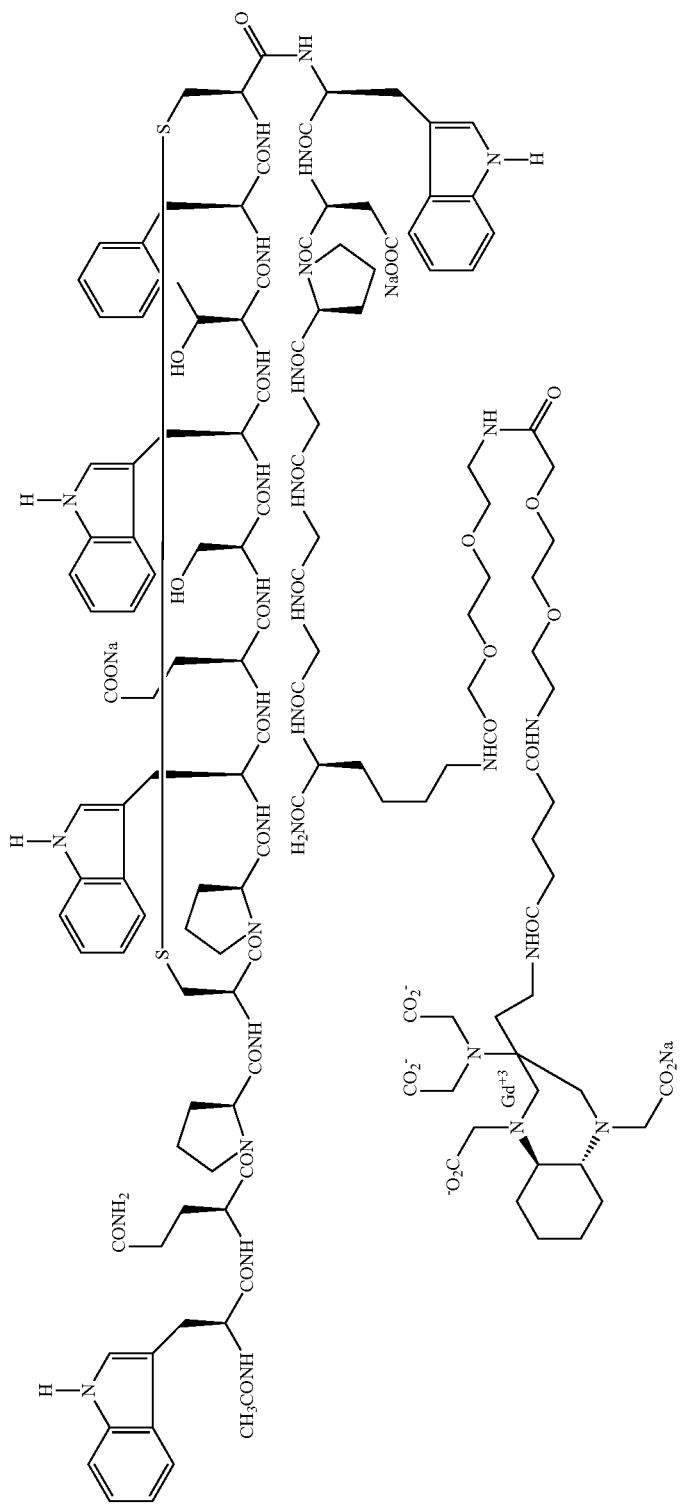

Mr: 3357.61 ($C_{145}H_{188}GdN_{32}Na_3O_{43}S_2$)
MS: Obtained data are consistent with Reference 2 structure Reference 3

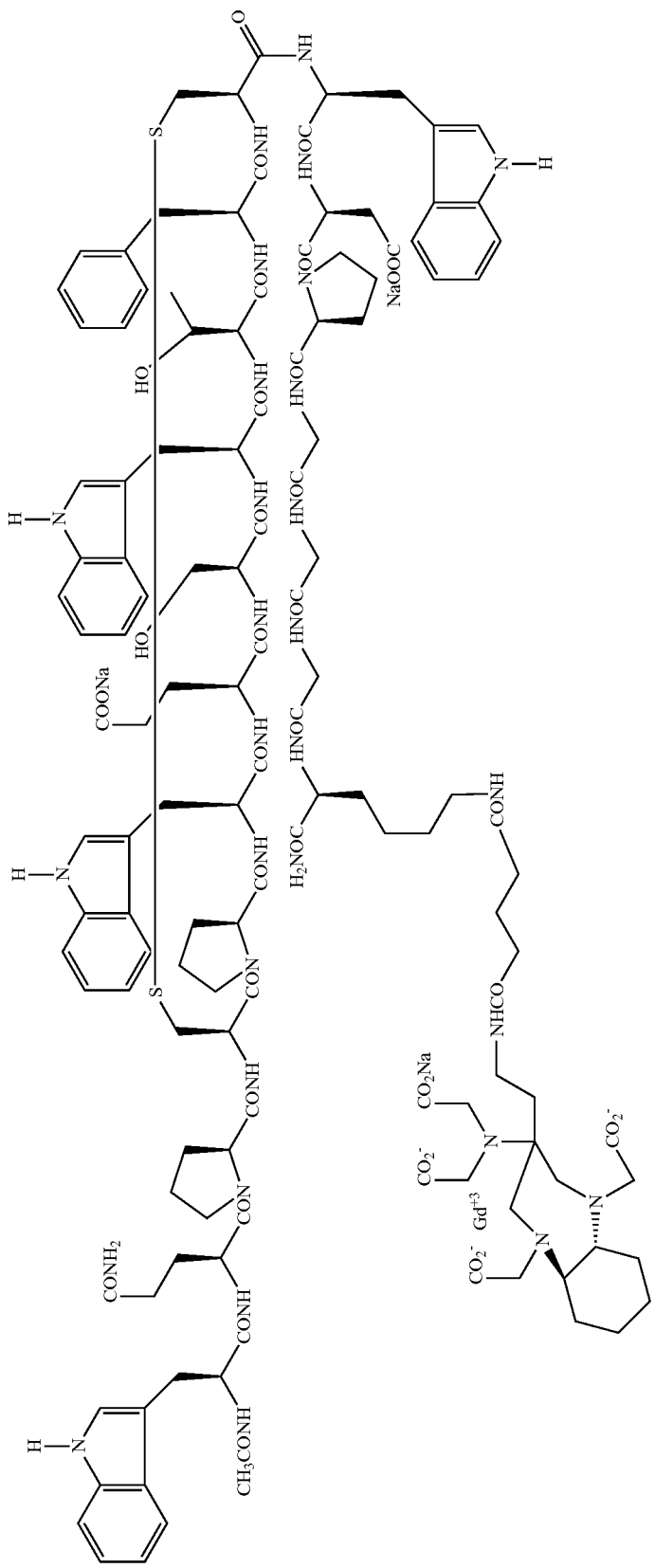

Mr: 2952.16 ($C_{125}H_{161}GdN_{29}Na_3O_{37}S_2$)
MS: Obtained data are consistent with Reference 3 structure Reference 4

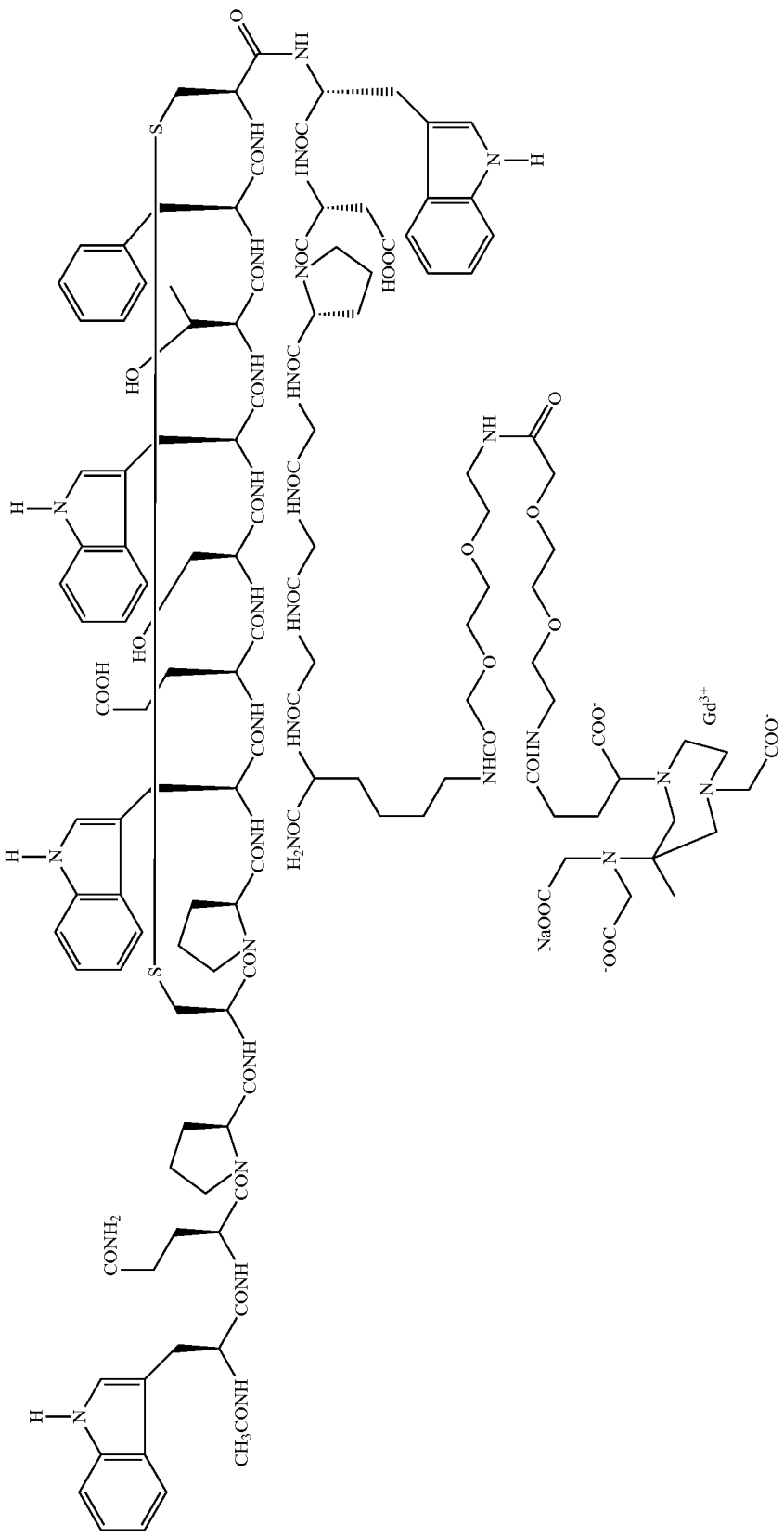

Mr: 3232.44 ($C_{138}H_{177}GdN_{31}Na_3O_{42}S_2$)
MS: Obtained data are consistent with Reference 4 structure Reference 5

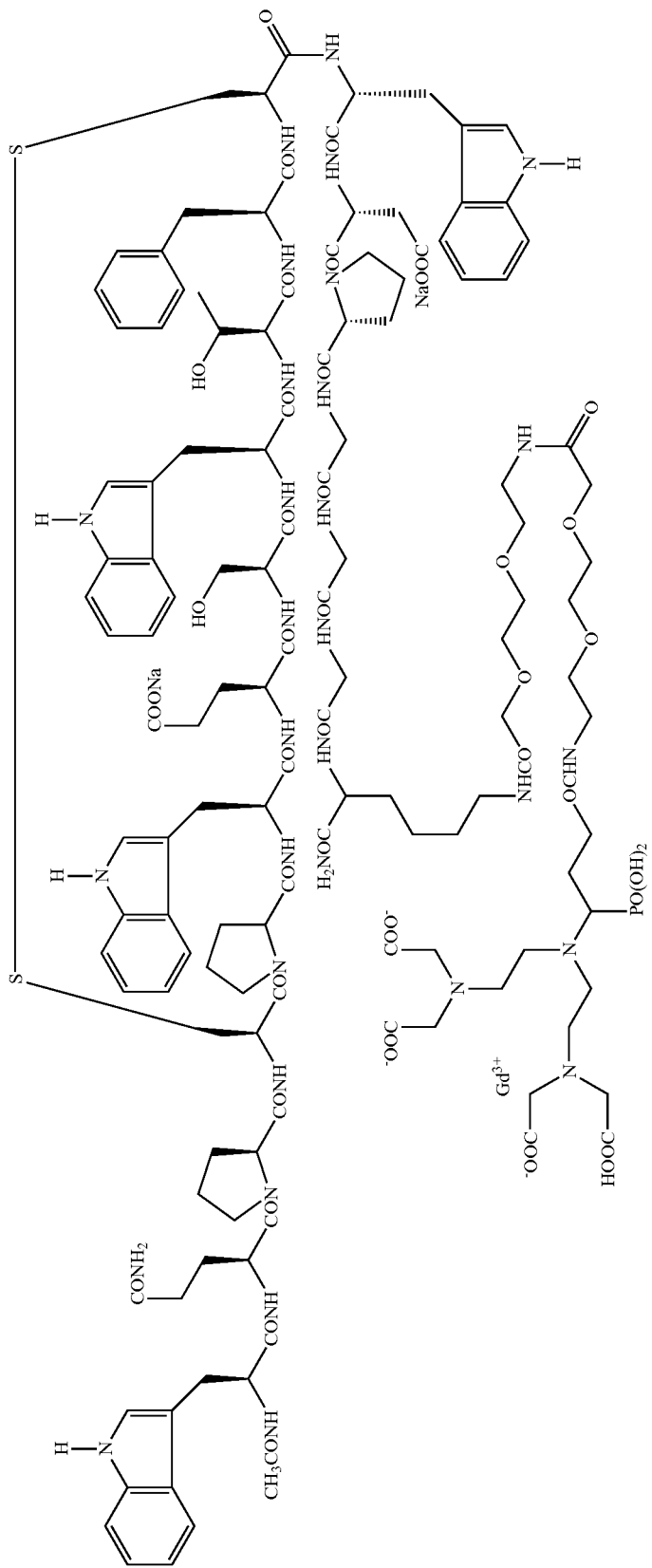

Mr: 3344.37 ($C_{137}H_{176}GdN_{31}Na_5O_{45}PS_2$)
MS: Obtained data are consistent with Reference 5 structure Reference 6

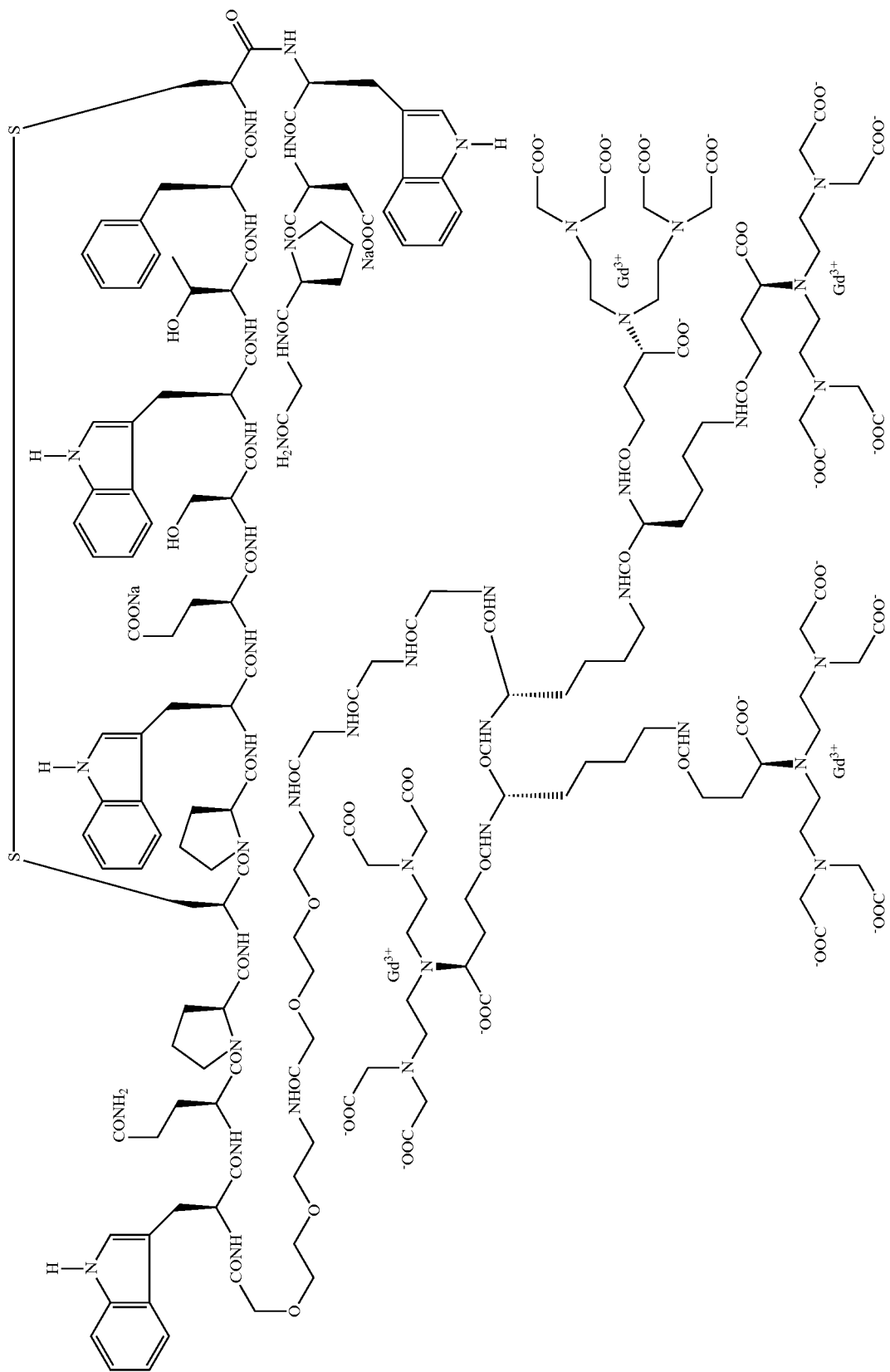

Mr: 5494.55 ($C_{201}H_{261}Gd_4N_{45}Na_{10}O_{79}S_2$)

MS: Obtained data are consistent with Reference 6 structure

All of the synthesized chelate compounds of the invention and the reference compounds were characterized by means of electrophoresis according to methods widely known in the art.

Example 14

Fibrin MRI Imaging in Human/Mouse Clots

In Vitro MRI Tests

All the procedure steps are described in detail in the In vitro Protocol, below.

Methods

Small plasma clots from different species (human, guinea pig and mouse) were formed by combining citrate plasma (1:3,v/v) phospholipids (Reagent Pathromtin) and CaCl2 0.008 M (Dade Behring, Germany) into small 2 ml vials at 37° C. Clots were washed 3 times with TBS 1× and incubated with contrast agents at a concentration of 100 µM of complex, for 30 minutes at 37° C. Two clots were prepared for each solution of incubation. After the incubation clots were washed 4 times with TBS 1× and placed into small vials filled with TBS 1× for MRI analysis. T1-weighted 2D Spin-Echo (SE) images were acquired on a 2T MRI system, by use of the following parameters: TR/TE=400/8 ms, spatial resolution=430 µm and slice thickness=2 mm. Maximum signal intensity of each clot was measured in recovered MR images and compared to the signal from clots incubated with TBS. After MRI, clots were prepared for ICP analysis.

Results

By comparing the signal enhancement in clots obtained with the tested compounds including Chelated Complex 1 of the invention, Reference compound 1, Reference compound 2, Reference compound 4, and Reference compound 5, obtained results, could be classified in term of performance as follows:

TABLE 7

| Compound | Max signal Enhancement at 100 µM |
|---|---|
| Chelate Complex 1 | 100% |
| Reference Compound 2 | 68% |
| Reference Compound 1 | 44% |
| Reference Compound 5 | 41% |
| Reference Compound 4 | 23% |

In Table 7 the Max signal enhancement recovered for Reference compounds is reported as normalized to the chelate complex 1. Obtained results indicate that the Chelate Complex 1, as a representative compound of formula (I) of the invention, provides the maximum signal enhancement, while the enhancement provided by all tested Reference compounds is always significantly lower.

Example 15

By following the above procedure, a second wider group of chelate compounds of the invention including, for instance, Chelate Complexes from 1 to 7 and the Reference Compounds from 1 to 6 were tested on human clots at different incubation concentration (25 to 400 µM of complex). Signal enhancement (%) was then determined for each clots by MR Imaging at 2T and corresponding Gd content in clots was measured by ICP.

Results

By comparing the signal enhancement in clots, for instance at incubation concentration of 100 µM of peptide, tested compounds could be classified in term of performance as follows (Max signal enhancement was normalized to the chelate complex 4):

TABLE 8

| Compound | Max signal Enhancement (%) at 100 µM |
|---|---|
| Chelate Complex 4 | 100% |
| Chelate Complex 1 | 93.2% |
| Chelate Complex 5 | 91.5% |
| Chelate Complex 3 | 87.6% |
| Ref. Compound 2 | 61.9% |
| Chelate Complex 2 | 56.5% |
| Ref. Compound 1 | 47.7% |
| Chelate Complex 7 | 41.6% |
| Chelate Complex 6 | 40.08% |
| Ref. Compound 5 | 39.6% |
| Ref. Compound 6 | 39.5% |
| Ref. Compound 3 | 38.3% |
| Ref. Compound 4 | 16.7% |

Obtained results indicate that, in general, the compounds of the invention provide the higher signal enhancement and, at incubation concentration of 100 µM, Chelate Complex 4, Chelate Complex 1 and Chelate Complex 5 provide the best results.

Figure 5:
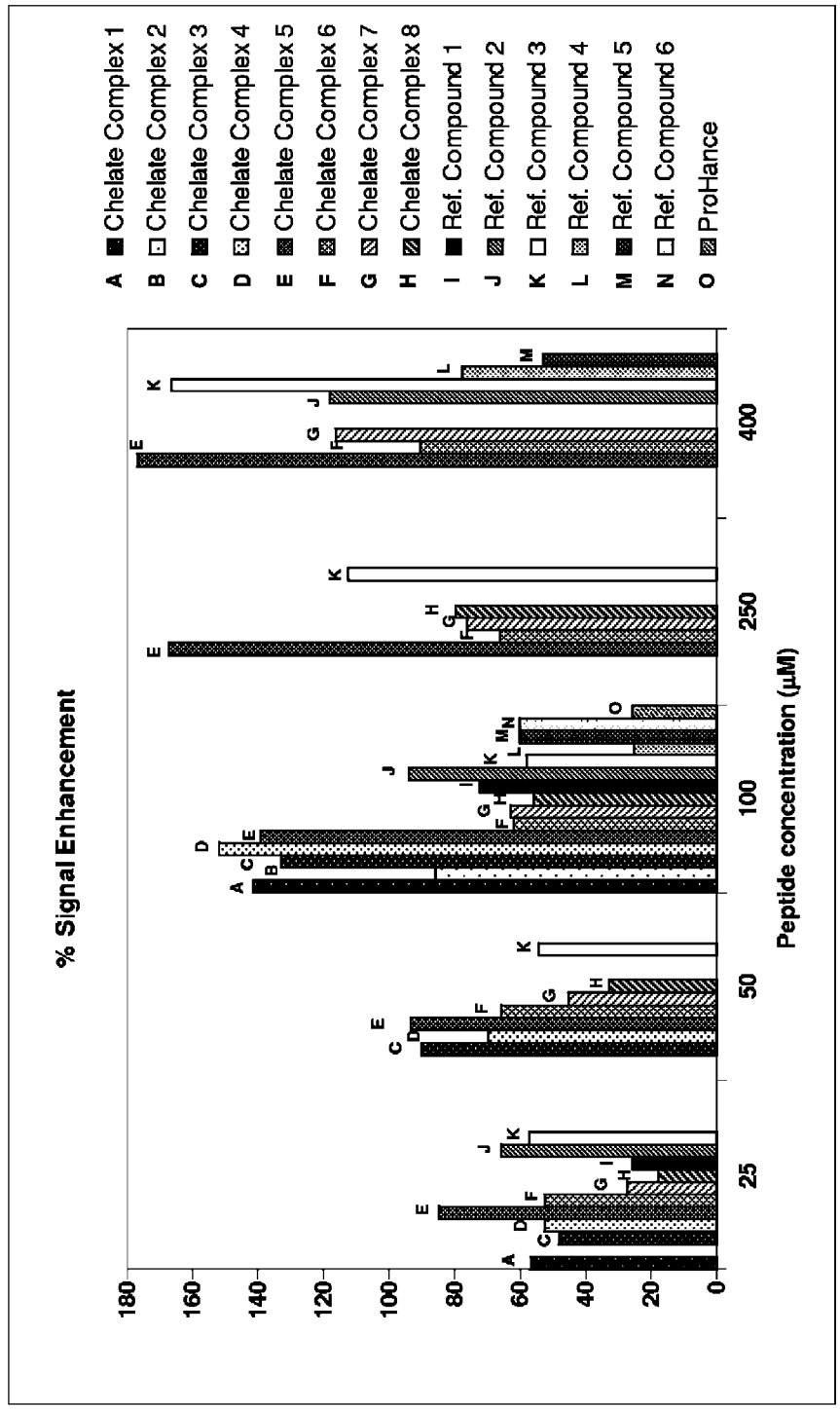
FIG. 5 provides, for each tested compound, a graphical presentation of the percentage of the registered signal enhancement (% Enh) in clots, measured on T1 weighted MR images recovered at 2T and at a concentration from 25 to 400 µM of peptide.

In FIG. 5 there are reported additional data on signal enhancement measured at different concentrations, as obtained with some representative compounds of the invention, references, and ProHance (control).

Advantageously, the obtained data do confirm the better enhancement obtained with the compounds of the invention, in particular when used at lower concentrations.

Example 16

Fibrin MRI Imaging in Tumor Models

In Vivo MRI Tests:

All the procedure steps are described in detail in the In vivo Protocol, below.

Methods:

The test has been performed in a mammary tumor mouse model (BALB-neuT). Mice were treated with Chelate Complex 2 of the invention, 25 µmol/kg, injected iv, and with ProHance® at 100 µmol/kg. Signal enhancement of the tumor was followed up to 3 h after contrast administration.

Results

High signal spots were found inside and at the borders of tumors up to 3 h after injection of the chelate compound of the invention. A different kinetics was shown with ProHance®, with signal distribution only on the border and no signal enhancement inside the tumors after 55 min.

Figure 6:
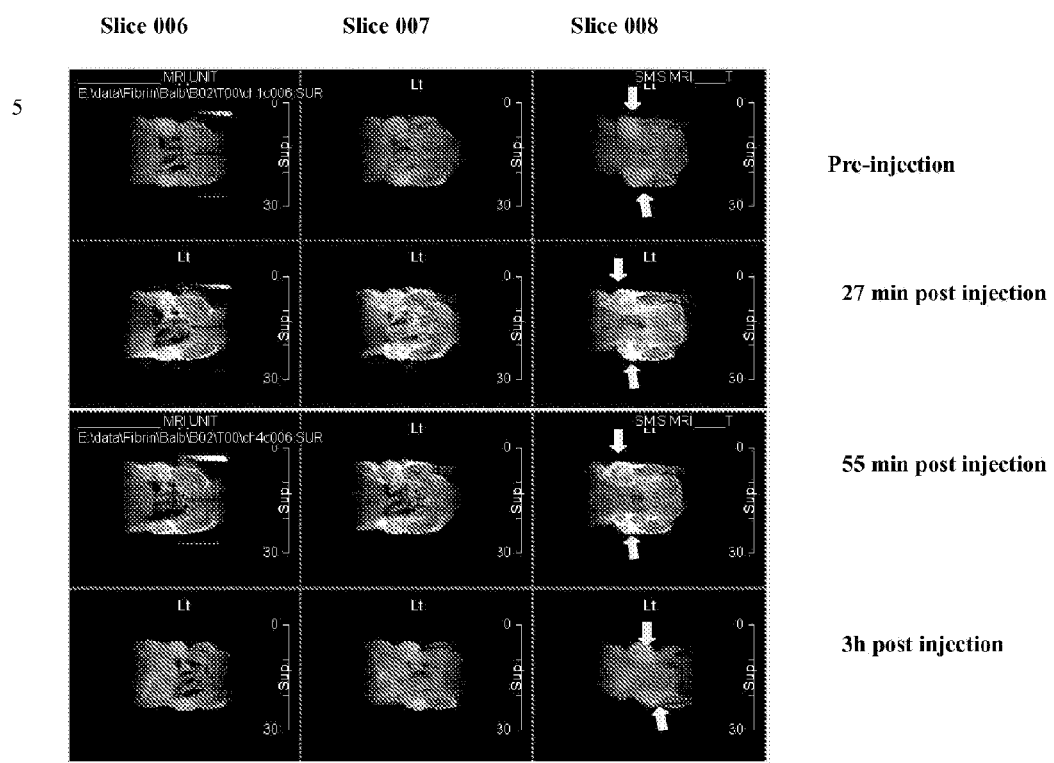
FIG. 6 relates to successive slices obtained at different time post-injection of Chelate Complex 2, 25 µmol/kg, as obtained in Example 16. Arrows indicate tumors.
Figure 7:
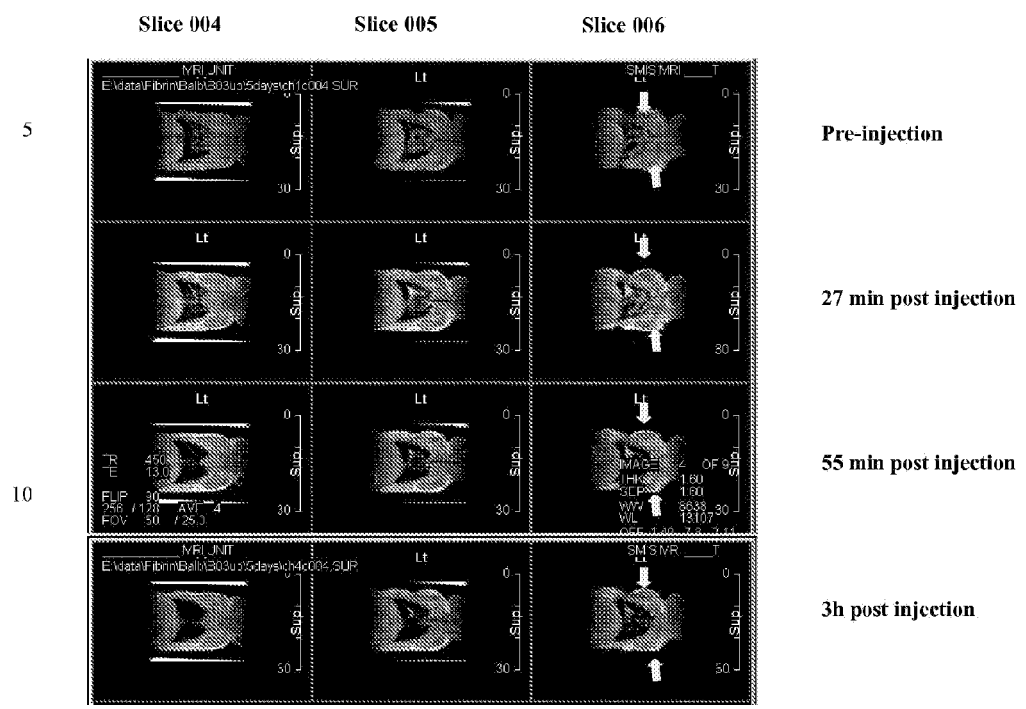
FIG. 7 relates to successive T1 weighted slices obtained at different time post-injection of ProHance®, 100 µmol/kg, used as reference compound in Example 16. Arrows indicate tumors.

Successive T1 weighted SE images were acquired pre- and post-injection of the test compounds and some examples are reported in FIGS. 6 and 7. Images are related to successive slices from the same mouse acquired at different time points post contrast. In particular, FIG. 6 includes images post-injection of chelate Complex 2 at 25 µmol/kg (arrows indicate tumor) and FIG. 7 includes analogous images post administration of ProHance®.

Example 17

This test has been performed in a transgenic adenocarcinoma mouse prostate model (TRAMP) developed by introducing a PB promoter—SV40 T antigen fusion transgene (PB-Tag) into the germ line of C57BL/6 inbred mice.

Methods:

Two TRAMP mice were treated with ProHance® at 100 μmol/kg iv (control), and the day after with Chelate Complex 2 or with Chelate Complex 5 at 25 μmol/kg iv. T1 weighted SE images were acquired pre- and post-contrast injection and the kinetic of enhancement in the tumor was followed up to 3 h post-test compound administration.

Results

High signal spots were found inside and at the borders of the tumors delineating enlarged seminal vesicles and prostate carcinoma within 5 and 30 min after injection of the Chelate Compounds of the invention, whereas, a very weak signal enhancement was found after injection of ProHance®.

Figure 8:
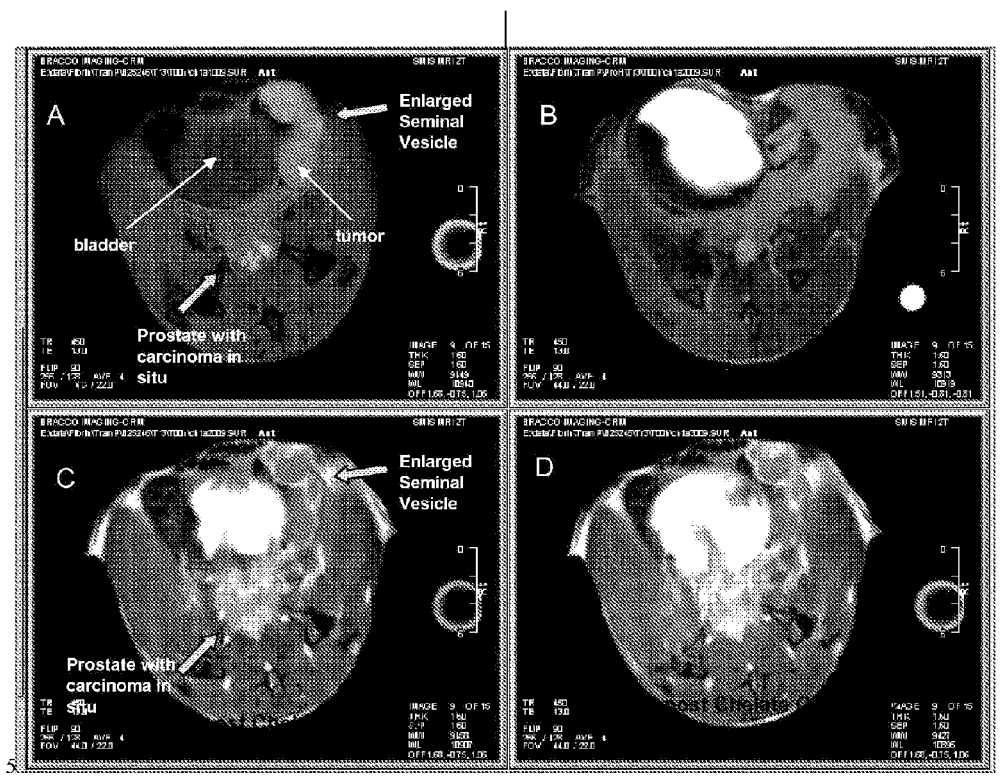
FIG. 8 refers to T1 weighted images, acquired before (Pre) and at different time post-injection of Chelate Complex 2, (25 µmol/kg), and ProHance® (100 µmol/kg) of as obtained in example 17. Tumor area (TRAMPT) is indicated by an arrow.
Figure 9:
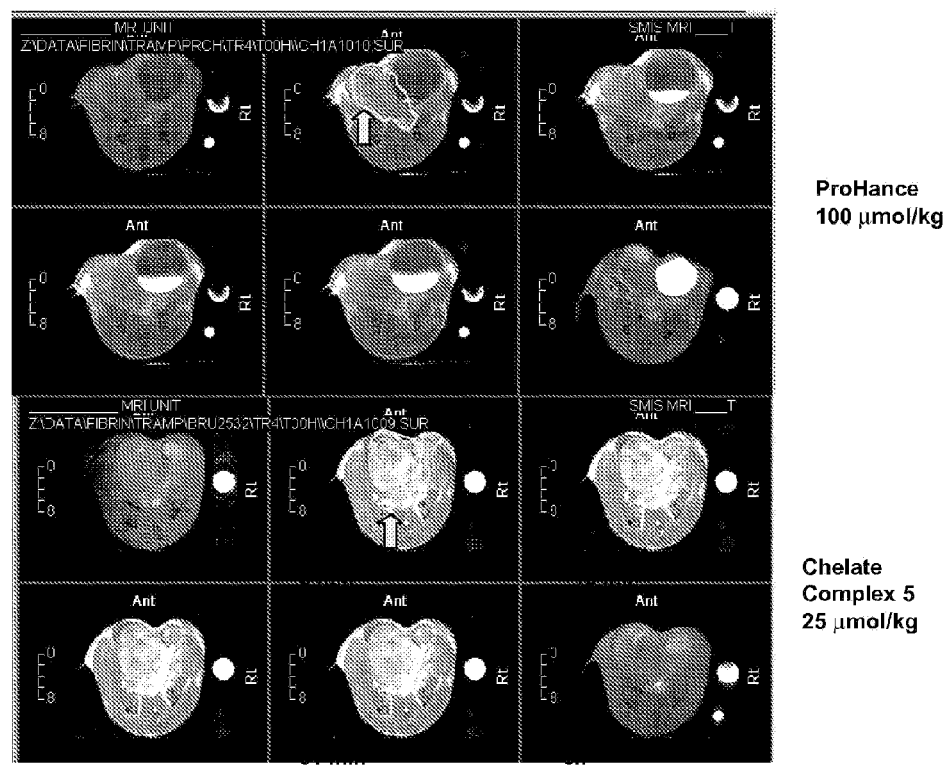
FIG. 9 refers to T1 weighted images collected at different time post-injection of Chelate Complex 5, 25 µmol/kg, and 100 µmol/kg of ProHance® as obtained in example 17. Tumor area is indicated by an arrow.

Some examples of the signal enhancement obtained in tumors are reported in FIGS. 8 and 9.

In particular, FIG. 8 refers to images from a mouse with a small prostate tumor, treated with Chelate Complex 2 (25 μmol/kg) and with ProHance® (100 μmol/kg of). The arrow indicate tumor area.

FIG. 9 refers to T1 weighted images from a mouse with a large prostate tumor treated with Chelate Complex 5 (25 μmol/kg) and with ProHance® (100 μmol/kg). The arrow indicate tumor area.

Example 18

This test has been performed on mice with neuroblastoma tumor induced by inoculation of $2.10^6$ Neuro 2A cells.

Methods

Two groups of 5 mice each inoculated were formed to test the Reference compound 2 and the Chelate complex 1.

At day-10 post tumor cells inoculation, mice with similar tumor size (5-10 mm in diameter) were selected for the in vivo MRI tests. Before and post contrast administration, T1 and T2 high resolution 2D spin-echo and 3D gradient echo images were acquired. MRI was performed at 4 h and 24 h post injection. The maximum signal intensity was measured in the entire tumor area and in each image post contrast covering the whole tumor and compared to the pre-contrast images. At the end of MRI exams, all animals were sacrificed and the tumor, blood, liver, kidneys and femoral bone were removed and prepared for Gd assay by ICP.

Results

Figure 10:
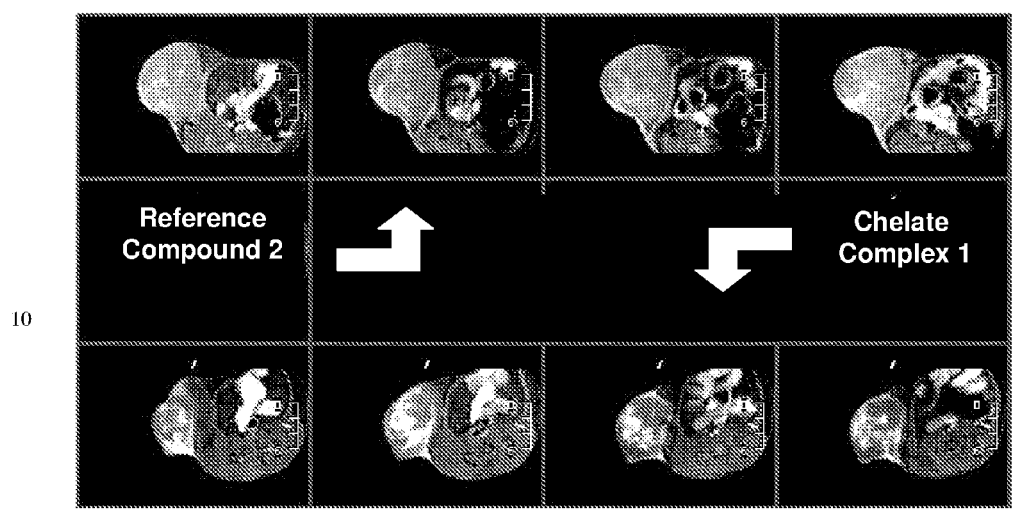
FIG. 10 relates to T1 weighted MRI images (successive slices) acquired 4 h post injection (25 µmol/kg of complex) of Chelate Complex 1 (bottom) and Reference Compound 2 (top) as obtained in Example 18.

A significant tumor signal enhancement was observed 4 h post chelate complex 1 injection whereas with the Reference Compound 2 the enhancement was low and less present in the whole tumor. FIG. 10 shows T1 weighted MRI images obtained at 2T, after injection of 25 μmol/kg of the complex.

Protocols

Screening of Fibrin Targeted Compounds of the Invention.

In Vitro Tests

Introduction

This protocol has been set up and used to test the specificity and efficiency of the fibrin targeted contrast agents of the invention for sensitive detection of thrombus by MRI.

The study was performed on clots generated in vitro from different plasma species. Signal enhancement from each sample incubated with the fibrin targeted contrast agent was evaluated and compared to a standard contrast agent Pro-Hance®.

Materials

Test Article

Compounds: The contrast agents under test are compounds of the present invention comprising a fibrin peptide, an optional linker and at least one chelated complex of gadolinium.

Reagents

Compounds: Biological Samples (species, biological fluid and strain): guinea pig plasma (Dunkin Hartley), mouse plasma CD®-1(ICR)BR IGS, rabbit plasma (New Zealand White).

Test System

The test system used was clots generated in-vitro from different plasma species (Human, guinea pig, mouse and rabbit), chosen as they are a suitable model and easy to replicate for this study.

Equipment

All MRI experiments were performed on a 2T Oxford magnet (bore=45 cm i.d.), equipped with a gradient set of maximum strength of 110 mT/m and slew rate of 75 μs, and interfaced to an MRRS console (MR Research Systems Ltd, Surrey UK). A bird-cage resonator antenna (7.3 cm i.d.) was used.

Methods

In-Vitro Test

The delivered Control Plasma N was obtained from pooled plasma collected from healthy blood donors, stabilized with HEPES buffer solution (12 g/L) and lyophilized. Before use, Plasma Control N was reconstituted in distilled water by shaking carefully the suspension to dissolve the lyophilized plasma. Clots were formed, in a 2 mL vial, in which were added 300 μl of reconstituted plasma and 300 μL of Pathromtin**SL (silicon dioxide particles, vegetable phospholipids, sodium chloride 2.4 g/L, Hepes 14.3 g/L, pH 7.6). The mixture was incubated for 2 minutes at 37° C., and then 300 μL of calcium chloride solution, previously incubated at 37° C., were added to obtain a new mixture that was further incubated for 30 minutes at 37° C. The obtained clot were transferred in a 5 mL tube, washed 3 times with 3 mL of TBS and incubated with the test article at the final concentration ranging from 0.0 to 0.2 mM for 30 minutes at 37° C. At the end of incubation, clots were rinsed 4 times with 3 mL of TBS to remove the unbounded test article and then placed in 1.5 ml vials for MRI procedure.

High resolution MRI was then performed at 2 Tesla by using T1-weighted Spin-Echo (SE) sequences. T1 maps were also calculated from the acquisitions of 2D gradient echo images or inversion recovery spin echo images.

At the end of experiment the clots were sent at the Analytical Laboratory for ICP-AES analysis.

Assay of Gadolinium in Biological Samples

Apparatus

The assays were carried out on a Jobin-Yvon Mod 24 spectrometer operating with the following instrumental parameters:

sample flow: 1 mL/min
plasma flame: 6000 to 10000° C.
wavelength: 342.247 nm
Argon flow: nebulizer 0.3 L/min, transport gas 0.2 L/min, cooling gas 12 L/min. Sample digestion was performed by a microwave system (MDS-2000 CEM Corporation).

Sample Preparation and Analytical Conditions

Clots solutions were prepared by suspending the clot in 1.5 mL of nitric acid (65% v/v). 1.5 mL of nitric acid (65% v/v) was added to solutions of incubation (before and after incubation) and to washing solutions. The destruction of the organic matrix was performed by subjecting the samples to a wet ashing process with a microwave oven system. Finally the dried residues were dissolved with 3.0 mL of HCL 5% (v/v) and then analysed by ICP-AES.

Data Processing.

Briefly, linearity was evaluated for two standards, low and high, ranging from 0.00 to 20 mg(Gd)/L in HCl 5% (v/v), respectively. The total content of gadolinium in the test sample was calculated by using the instrumental calibration straight line and express as µg(Gd)/mL.

MRI Data Analysis

The maximum signal intensity was measured within a region of interest (ROI) including a clot, drawn by an operator on each MR image using a dedicated software (MR Research Systems Ltd, Surrey UK). Max signal intensity enhancement (Enh %) was determined as:

$$Enh \% = 100*(SI_x - SI_0)/SI_0$$

where $SI_0$ and $SI_x$ are the signal intensity of clots incubated without and with test compounds, respectively.

In Vivo Tests

Introduction

The study aim was to evaluate the specificity and efficiency of fibrin targeted agents of the invention as contrast agents for sensitive detection of fibrin within solid tumors.

The study was performed on a mouse model of neuroblastoma induced by Neuro-2a cells subcutaneously injected in the right flank of a A/J mouse (See for instance: Y. Chen et al., J. Pediatr Surg. 2003. 37(9), 1298-1304; Anthony D. Sandler et al., Cancer Research 2003, 63, 394-399).

Signal enhancement kinetic within tumors was evaluated after injection of a fibrin targeted contrast agent of the invention and compared to a standard agent ProHance®.

Materials

Test Article

Compound: Tested contrast agents comprise a fibrin targeted peptide, an optional linker and at least one chelated complex of gadolinium.

Reference Article

Compound: ProHance®

Concentration: 0.5 M

Reagents

Compound: Penicillin/Streptomycin (10000 µg/mL), supplier: Biochrom KG, Berlin, Germany Compound: L-Glutamine (200 mM), supplier: SIGMA-ALDRICH, Steinheim, Germany Compound: Foetal bovine serum, supplier: HyClone®, Logan, Utah, USA Compound: Minimum Essential Medium Eagle, supplier: SIGMA-ALDRICH, Steinheim, Germany Compound: Dulbecco's Phosphate Buffered Saline (PBS), supplier: SIGMA Chemicals, St. Louis, Mo., U.S.A.

Compound: Zoletil 100, supplier: Virbac, Carros, France

Compound: Rompun®, supplier: Bayer AG, Laverkusen, Germany

Test System

Animals

Species and strain: mouse A/J (Harlan Italy, S. Pietro al Natisone (UD), Italy)

Equipment

All the experiments were performed on a MRRS console (MR Research Systems Ltd, Surrey UK) interfaced to a 2T Oxford magnet (bore=45 cm i.d.), equipped with a self-shielded gradient set with a maximum strength of 110 mT/m and slew rate of 75 µs. As R.F. coil, a quadrature resonator optimized to the mouse size was used.

Methods

Experimental Design

Mouse neuroblastoma cell line (BS TCL 128 Neuro-2a) was supplied by the Istituto Zooprofilattico Sperimentale della Lombardia e dell'Emilia, Brescia. The cells were grown in 90% MEM medium and 10% fetal bovine serum, collected, washed two times with physiological saline and resuspended in PBS ($10^6$ cells/0.2 mL). $10^6$ cells were injected subcutaneously in the right flank of each animal.

The tumor development was followed every other day after inoculation by measuring the tumor diameter until the day of the MRI experiment. Animals with a tumor diameter ranging from 300 to 700 mm were selected for in vivo imaging. Signal enhancement of the tumor was followed by MRI up to 24 h after the administration of the test article and it was compared with that of the reference article. Animals were anaesthetized with 0.4 mL/kg of Zoletil® and 0.25 mL/kg of Rompun® i.m The test articles and ProHance® (reference article) were administered at the following doses: 0.025 and 0.1 mmol/kg, respectively.

High resolution T1-weighted Spin-Echo and Gradient Echo sequences were used to achieve images with a suitable contrast to detect tumors and to follow the contrastographic effects of test and reference articles.

At the end of the experiment, animals were sacrificed by an intramuscular injection of tiletamine/zolazepam (Zoletil)® 0.2 mL/kg plus Xilazine (Rompun)® 0.25 mL/kg.

Tumor, blood, kidneys, liver and femoral bones were then taken, weighed and stored at about 4° C. until analyzed by ICP-AES.

Assay of Gadolinium in Biological Samples

Apparatus

The assays was carried out on a Jobin-Yvon Mod 24 spectrometer operating with the following instrumental parameters:

sample flow: 1 mL/min plasma flame: 6000 to 10000° C.

wavelength: 342.247 nm

Argon flow: nebulizer 0.3 L/min, transport gas 0.2 L/min, cooling gas 12 L/min.

Sample digestion was performed by a microwave system (MDS-2000 CEM Corporation).

Sample Preparation and Analytical Conditions

Tumor solutions were prepared by suspending the tumor, accurately weighed, in 1.5 mL of nitric acid (65% v/v). Liver was prepared by measuring the liver, accurately weighed, in 1.5 mL of nitric acid (65% v/v). Kidney solutions were prepared by suspending each kidney, accurately weighed, in 1.5 mL of nitric acid (65% v/v). Blood solutions were prepared by mixing 1 mL of blood in 1.5 mL of nitric acid (65% v/v). Bone solutions were prepared by suspending each femur, accurately weighed, in 1.5 mL of nitric acid (65% v/v).

The destruction of the organic matrix was performed by subjecting the samples to a wet ashing process with a microwave oven system.

Finally the dried residues were dissolved with 3.0 mL of HCL 5% (v/v) and then analysed by ICP-AES.

Data Processing.

Briefly, linearity was evaluated for two standards, low and high, ranging from 0.00 to 20 mg(Gd)/L in HCl 5% (v/v), respectively. The total content of gadolinium in the test sample was calculated by using the instrumental calibration straight line and express as µg(Gd)/mL.

MRI Data Analysis

The signal intensity was measured within a region of interest (ROI) including the entire tumor, drawn by an operator on each MR image using a dedicated software (MR Research Systems Ltd, Surrey UK). Signal intensity enhancement (Enh %) was determined as:

$$\text{Enh \%} = 100 * (SI_x(t) - SI_0)/SI_0$$

where $SI_0$ and $SI_x(t)$ were the signal intensity of tumor pre and post injection of the contrast agent (test articles or reference), respectively.

Data collected (bodyweight, clinical signs, gross pathology examination) were subjected to qualitative analysis.

The invention claimed is:

1. A compound of formula (I)

$$A[-Y(-T)_r]_s \quad (I)$$

wherein
- A is a fibrin-binding peptide moiety comprising the amino acid sequence WQPC*PAESWTFC*WDP (SEQ ID NO: 001), wherein C* is a cysteine residue that contributes to a disulfide bond;
- Y is, independently in each occurrence, a suitable linking moiety connecting A with at least one T moiety;
- T is, independently in each occurrence, a diagnostically or therapeutically active moiety;
- r is, independently in each occurrence, an integer from 1 to 8;
- s is 1 or 2;
or a physiologically acceptable salt thereof.

2. A compound according to claim 1 wherein Y comprises one or more moieties selected from the list consisting of:
—OC—Z—CO—,
—NH—Z—NH—,
—NH—Z—CO—,
—CO—Z—NH—,
and any suitable repetition and combination thereof,
wherein Z is a unit comprising a group selected from:
—(CH$_2$)$_n$—,
—CH$_2$—(CH$_2$O)$_n$—,
—CH$_2$O—(CH$_2$(CH$_2$)$_p$O)$_n$—(CH$_2$)$_n$—,
—(CH$_2$)$_n$—NH—(CH$_2$)$_n$—,
—N((CH$_2$)$_n$—)$_2$
—(CH$_2$)$_p$—CH(NH—)—(CH$_2$)$_n$—,
—(CH$_2$)$_p$—CH(CONH$_2$)—(CH$_2$)$_n$—,
—(CH$_2$(CH$_2$)$_p$O)$_n$—(CH$_2$)$_n$—,
—(CH$_2$)$_p$—CH(CO—)—(CH$_2$)$_n$—, and
—(CH$_2$)$_p$—CH(NHCOCH$_3$)—(CH$_2$)$_n$—
wherein n is, independently in each occurrence, an integer from 1 to 6 and p is zero or an integer from 1 to 5.

3. A compound according to claim 1 wherein Y comprises one or more groups selected from the list consisting of:
—HN—(CH$_2$)$_n$—CO—,
—OC—(CH$_2$)$_n$—CO—,
—HN—(CH$_2$)$_n$—NH—,
—HN—(CH$_2$)$_n$—NH—(CH$_2$)$_n$—NH—,
—OC—(CH$_2$)$_n$—NH—(CH$_2$)$_n$—CO—,
—HN—[(CH$_2$)$_2$—O]$_2$—CH$_2$—CO—,
—HN—CH(CO—)—(CH$_2$)$_n$—NH—,
—HN—CH(CO—)—(CH$_2$)$_n$—CO—,
—OC—CH(NH—)—(CH$_2$)$_n$—NH—,
—OC—CH$_2$O—((CH$_2$)$_2$O))$_n$—(CH$_2$)$_2$—NH—,
—N((CH$_2$)$_n$—CO—)$_2$,
—HN—CH(CONH$_2$)—(CH$_2$)$_n$—NH—, and
—OC—CH(NHCOCH$_3$)—(CH$_2$)$_n$—NH—
and any suitable repetition and combination thereof, wherein n is an integer from 1 to 6.

4. A compound according to claim 3 wherein Y comprises one or more groups selected from the list consisting of:
—HN—CH$_2$—CO—,
—OC—(CH$_2$)$_2$—CO—,
—OC—(CH$_2$)$_3$—CO—,
—HN—[(CH$_2$)$_2$—O]$_2$—CH$_2$—CO—,
—OC—CH$_2$O—(CH$_2$)$_2$O—(CH$_2$)$_2$—NH—,
—HN—CH(CO—)—(CH$_2$)$_4$—NH—,
—OC—CH(NH—)—(CH$_2$)$_4$—NH—,
—HN—CH(CO—)—(CH$_2$)$_2$—CO—,
—HN—CH(CONH$_2$)—(CH$_2$)$_4$—NH—,
—OC—CH(NHCOCH$_3$)—(CH$_2$)$_4$—NH—, and
—N(CH$_2$—CO—)$_2$ and any suitable repetition and combination thereof.

5. A compound according to claim 1 wherein s is 1.

6. A compound according to claim 1 wherein s is 2.

7. A compound according to claim 1 wherein r is an integer from 1 to 4.

8. A compound according to claim 1 wherein T is a diagnostically active moiety selected from the group consisting of: chelated gamma ray or positron emitting radionuclides, paramagnetic metal ions in the form of chelated or polychelated complexes and X-ray absorbing agents.

9. A compound according to claim 8 wherein T is an MRI detectable moiety comprising the residue of a chelating ligand labelled with a paramagnetic metal element detectable by MRI techniques.

10. A compound according to claim 9 wherein the chelating ligand is selected from the group consisting of: a polyaminopolycarboxylic acid and the derivative thereof comprising DTPA, benzo-DTPA, dibenzo-DTPA, phenyl-DTPA, diphenyl-DTPA, benzyl-DTPA and dibenzyl DTPA, DTPA-BMA, EOB-DTPA, BOPTA, DTPA-GLU, DTPA-Lys, EDTA, DO3A, HPDO3A, NOTA, AAZTA and derivatives thereof, DOTA and derivatives thereof, benzo-DOTA, dibenzo-DOTA, DOTMA, TETA, DPDP, EDTP and DOTP.

11. A compound according to claim 10 wherein the chelating ligand is selected from the group consisting of: DTPA, DTPA-GLU, DTPA-Lys, DOTA, AAZTA and any of the following AAZTA derivatives of formula:

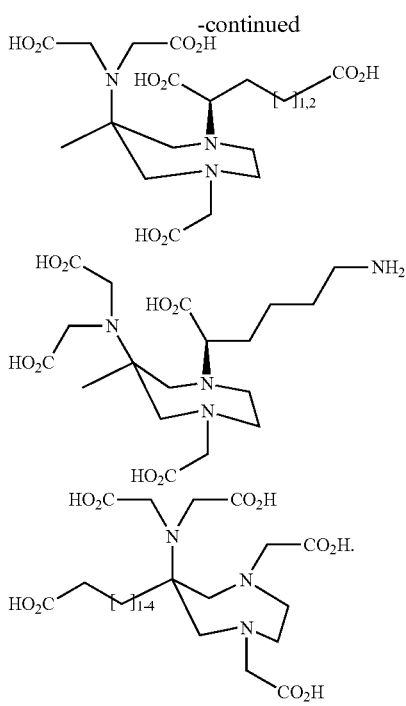

12. A compound of formula (I) according to any one of claims 9 to 11 wherein the paramagnetic metal element is a paramagnetic metal ion selected from the group consisting of: $Fe^{2+}$, $Fe^{3+}$, $Cu^{2+}$, $Ni^{2+}$, $Rh^{2+}$, $Co^{2+}$, $Cr^{3+}$, $Gd^{3+}$, $Eu^{3+}$, $Dy^{3+}$, $Tb^{3+}$, $Pm^{3+}$, $Nd^{3+}$, $Tm^{3+}$, $Ce^{3+}$, $Y^{3+}$, $Ho^{3+}$, $Er^{3+}$, $La^{3+}$, $Yb^{3+}$, $Mn^{3+}$ and $Mn^{2+}$.

13. A compound according to claim 12 wherein the paramagnetic metal ion is $Gd^{3+}$.

14. A compound according to claim 8 wherein T is a Radio imaging detectable moiety comprising the residue of a chelating ligand labelled with a radionuclide detectable by scintigraphic, SPECT or PET imaging techniques.

15. A compound according to claim 14 wherein the radionuclide is selected from the group consisting of: $^{99m}Tc$, $^{51}Cr$, $^{67}Ga$, $^{68}Ga$, $^{47}Sc$, $^{167}Tm$, $^{141}Ce$, $^{111}In$, $^{113}In$, $^{168}Yb$, $^{175}Yb$, $^{140}La$, $^{90}Y$, $^{88}Y$, $^{153}Sm$, $^{166}Ho$, $^{165}Dy$, $^{166}Dy$, $^{61}Cu$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{105}Rh$, $^{109}Pd$, $^{117m}Sn$, $^{149}Pm$, $^{161}Tb$, $^{177}Lu$, $^{198}Au$, $^{111}Ag$, $^{199}Au$, $^{51}Mn$, $^{52m}Mn$, $^{52}Fe$, $^{60}Cu$, $^{72}As$, $^{94m}Tc$, or $^{110}In$, $^{142}Pr$, $^{159}Gd$.

16. A compound according to claim 15 wherein the radionuclide is selected from $^{64}Cu$, $^{67}Ga$, $^{68}Ga$, $^{99m}Tc$, and $^{111}In$.

17. A compound according to any one of claims 14 to 16 wherein the chelating ligand is selected from those of formula 1 to 13, 15 to 20, 21a, 21b, 21c, and 22 to 33 set forth in FIGS. 3a-4b, wherein in formulas 17 and 18 R is alkyl, and wherein in formulas 31 and 32

X is either $CH_2$ or O;

Y is either $C_1$-$C_{10}$ branched or unbranched alkyl; Y is aryl, aryloxy, arylamino, arylaminoacyl; Y is arylkyl where the alkyl group or groups attached to the aryl moiety are $C_1$-$C_{10}$ branched or unbranched alkyl groups, $C_1$-$C_{10}$ branched or unbranched hydroxy or polyhydroxyalkyl groups or polyalkoxyalkyl or polyhydroxy-polyalkoxyalkyl groups;

J is —C(=O)—, —OC(=O)—, —$SO_2$—, —NC(=O)—, —NC(=S)—, —N(Y)—, —NC(=$NCH_3$)—, —NC(=NH)—, —N=N—, homopolyamides or heteropolyamines derived from synthetic or naturally occurring amino acids; and n is 1-100.

18. A compound according to any one of claims 1 to 7 wherein T is a therapeutically active moiety selected from the group consisting of: anticoagulant-thrombolytic agents, fibrinolitic agents, anti-angiogenic agents, cytotoxic agents, chemotherapeutic agents, tumoricidal agents and radiotherapeutic agents.

19. A compound according to claim 18 wherein T is a radiotherapeutic agent comprising the residue of a suitable chelating ligand labelled with a radionuclide selected from the group consisting of $^{64}Cu$, $^{90}Y$, $^{105}Rh$, $^{111}In$, $^{117m}Sn$, $^{149}Pm$, $^{153}Sm$, $^{161}Tb$, $^{166}Dy$, $^{166}Ho$, $^{175}Yb$, $^{177}Lu$, $^{186/188}Re$, and $^{199}Au$.

20. A compound according to claim 1, selected from the group consisting of

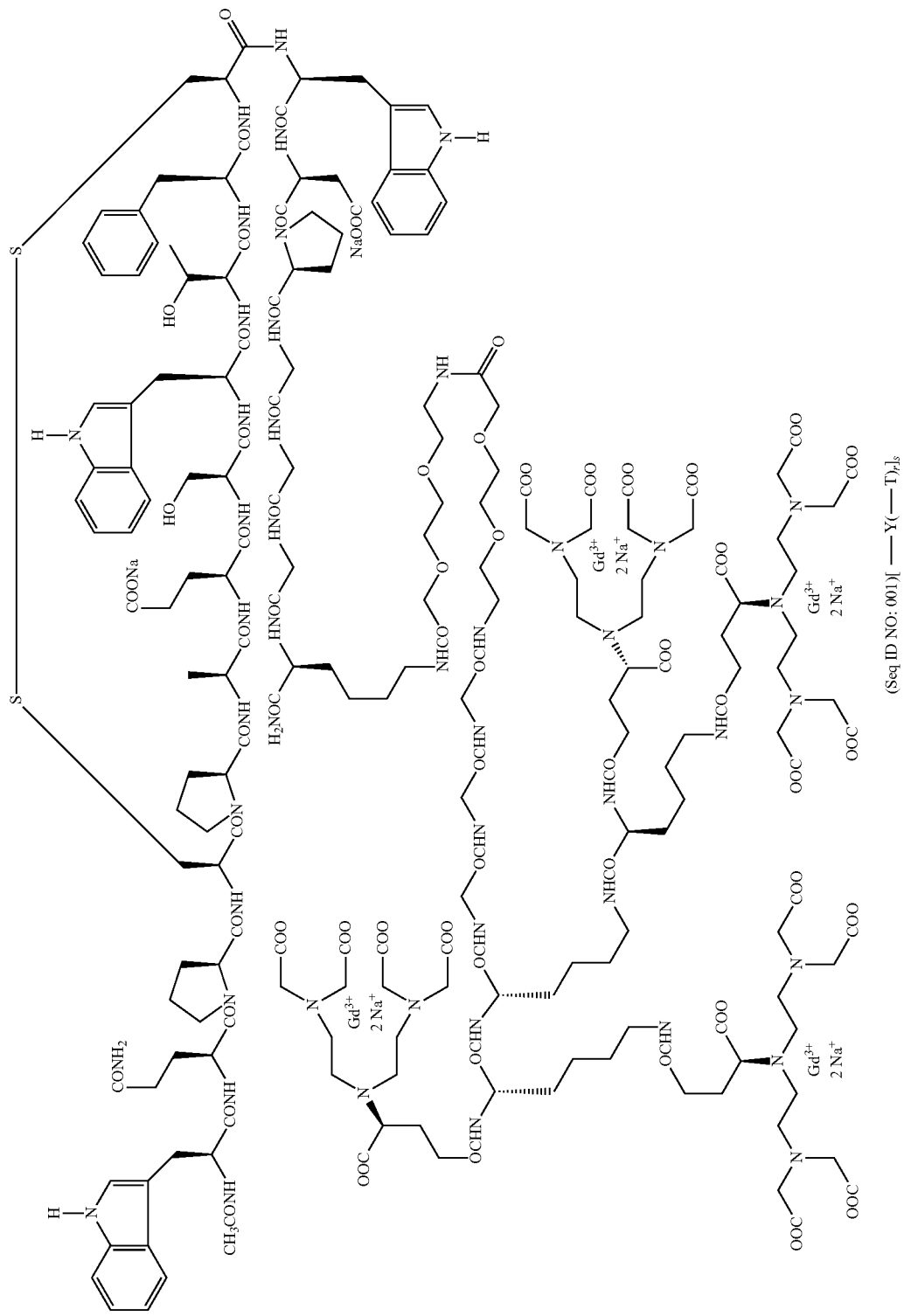

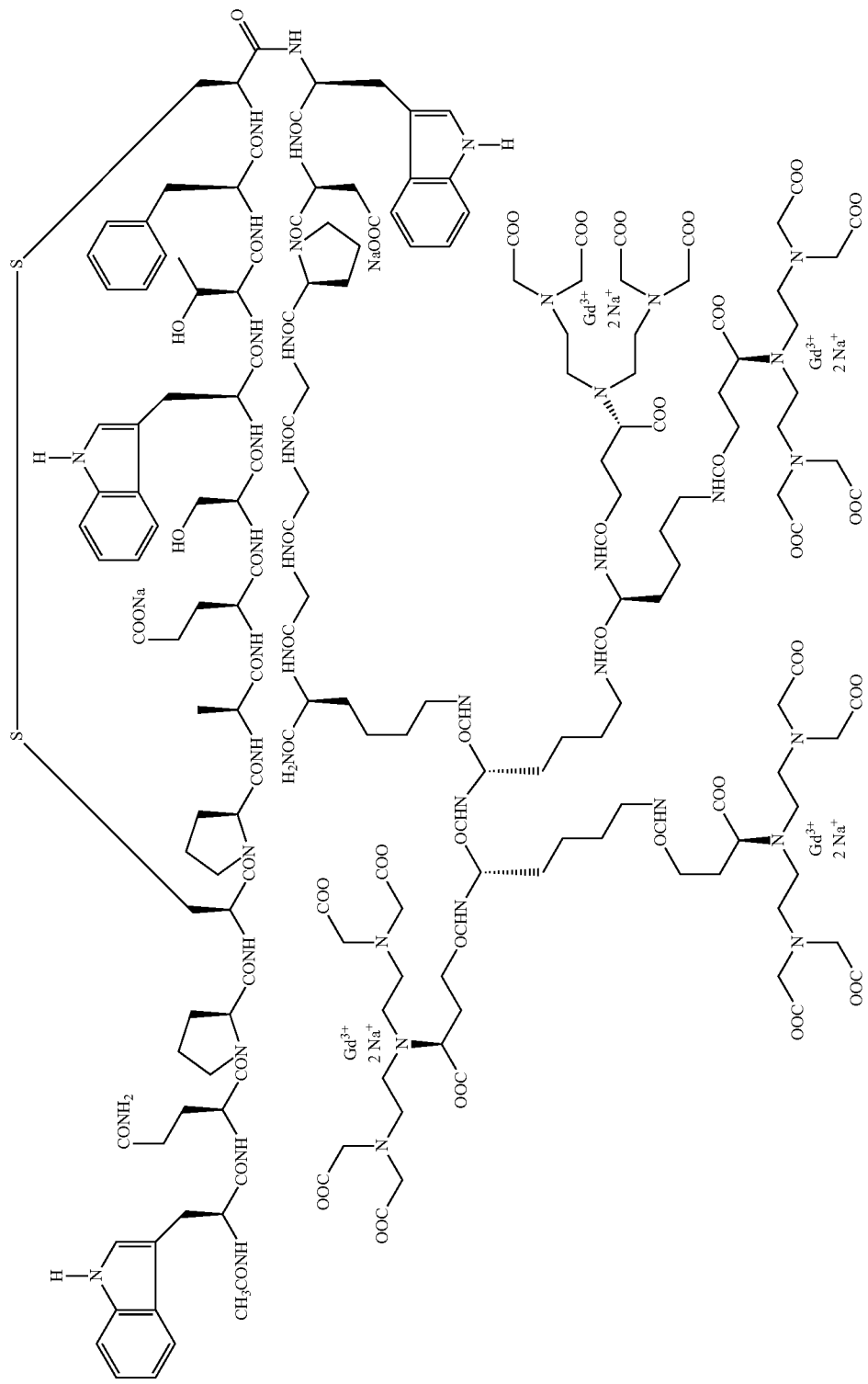
Chelate complex 2
(Seq ID NO: 001)[—Y(—T)$_r$]$_s$

Chelate complex 3
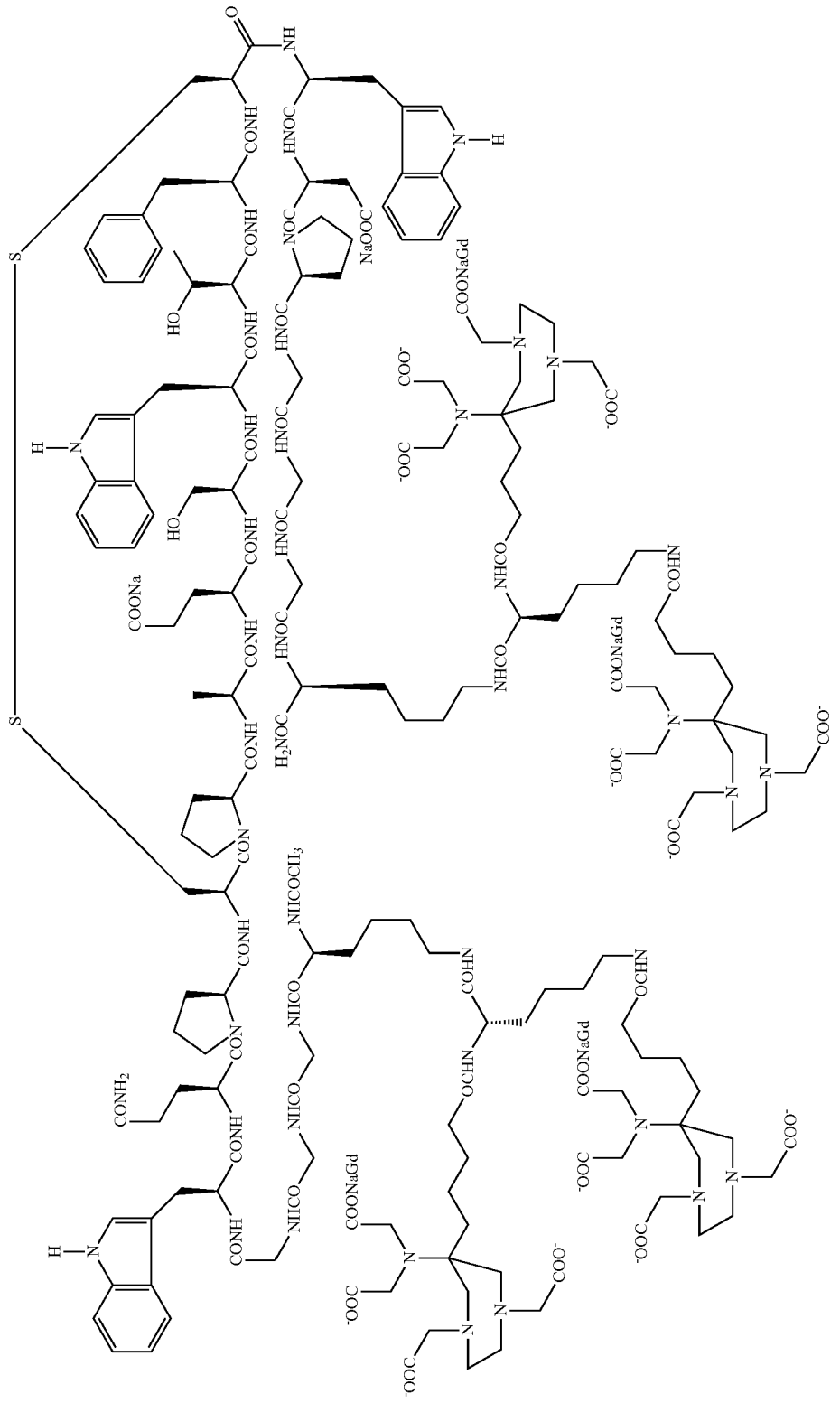
(Seq ID NO: 001)[—Y(—T)r]s

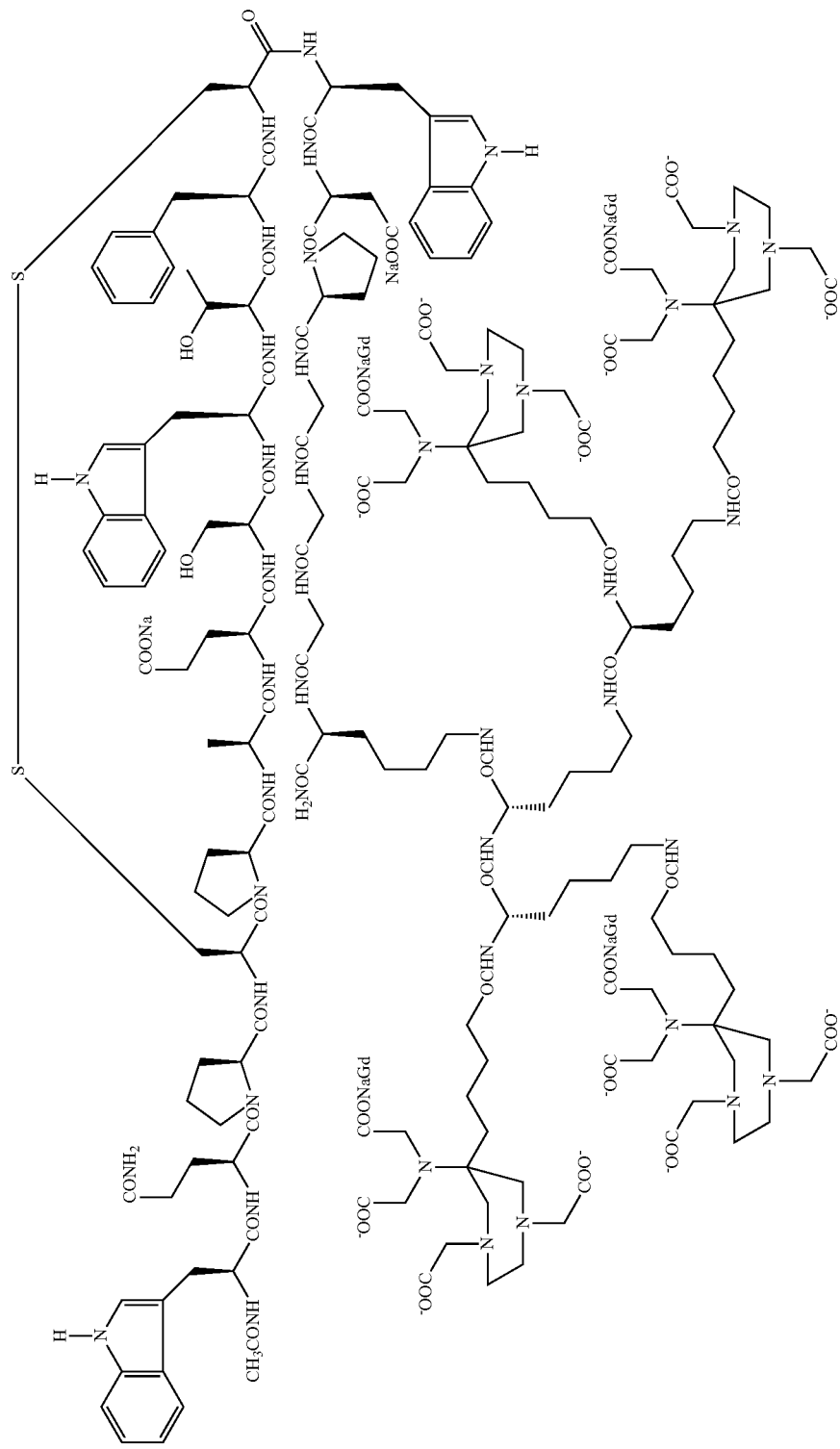

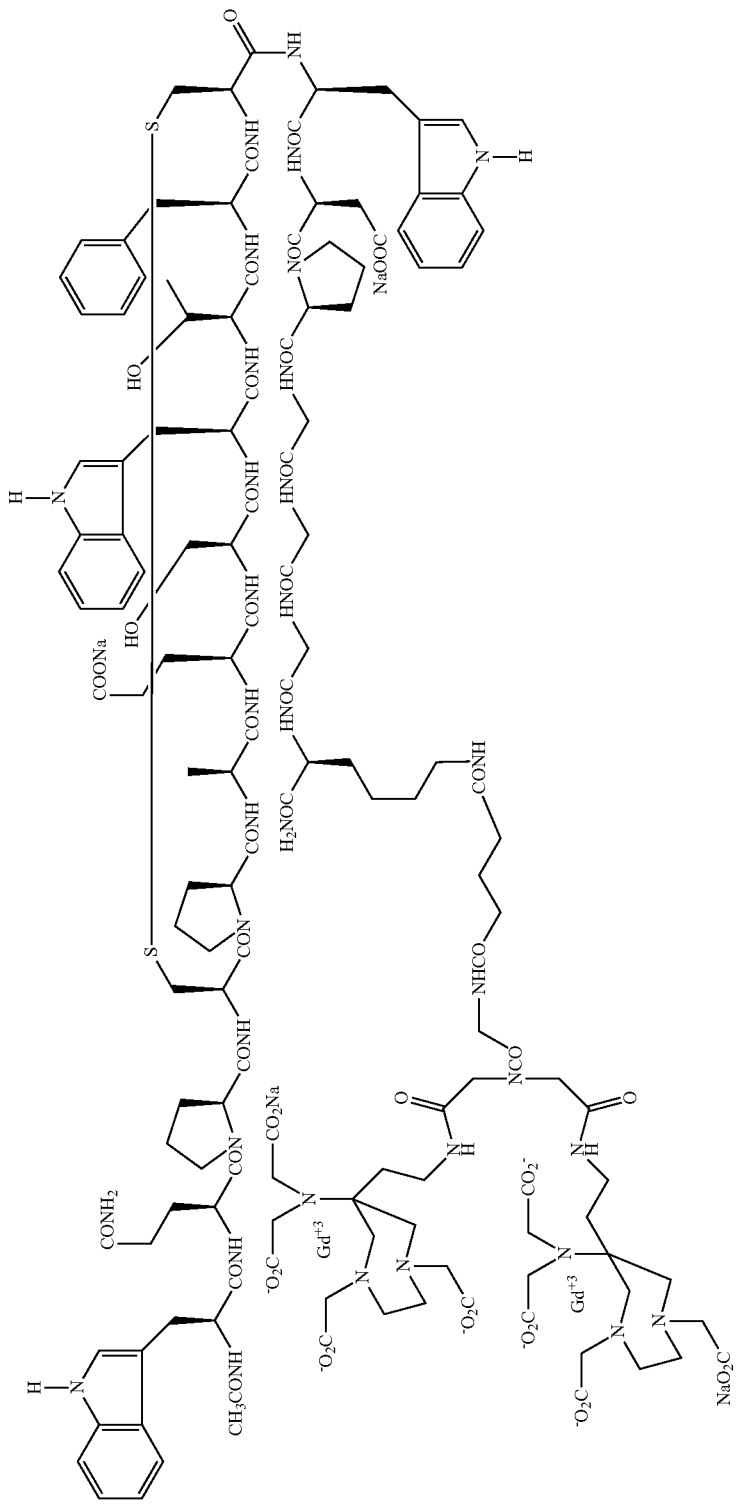

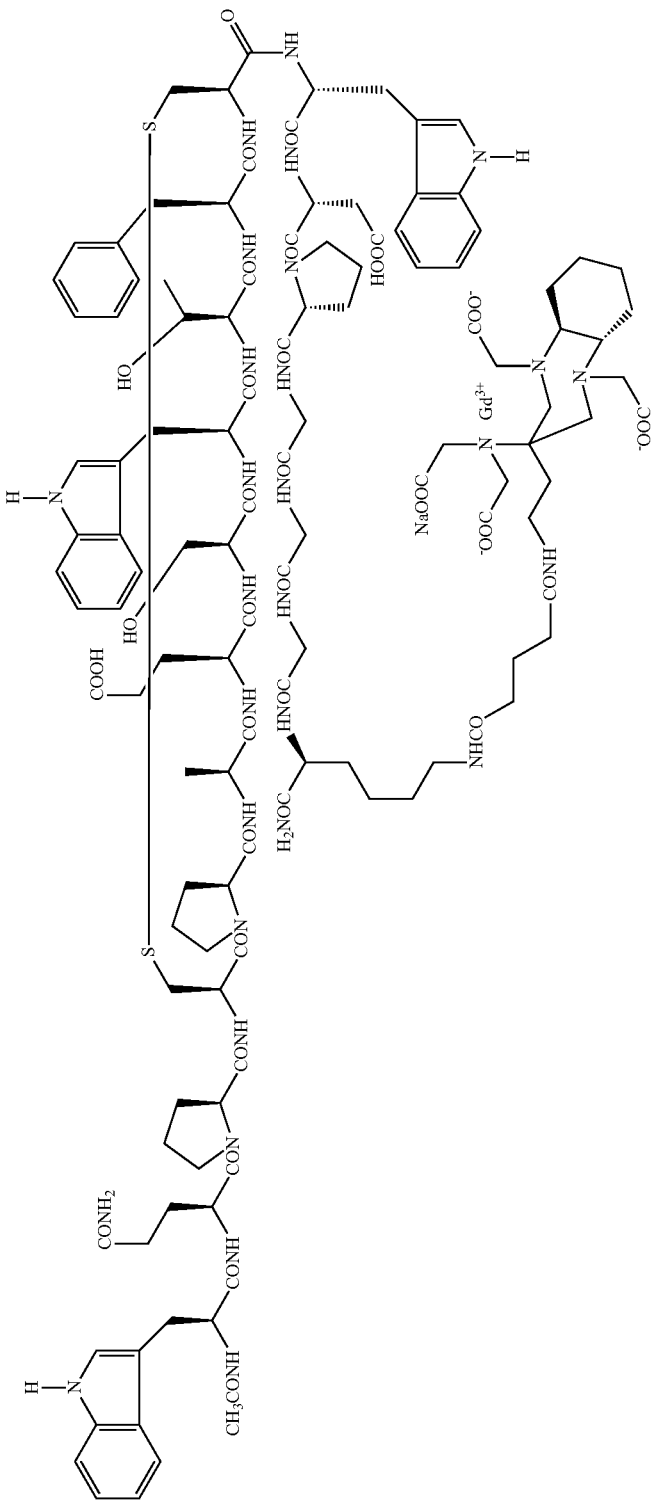
Chelate complex 6
(Seq ID NO: 001)[—Y(—T)$_r$]$_s$

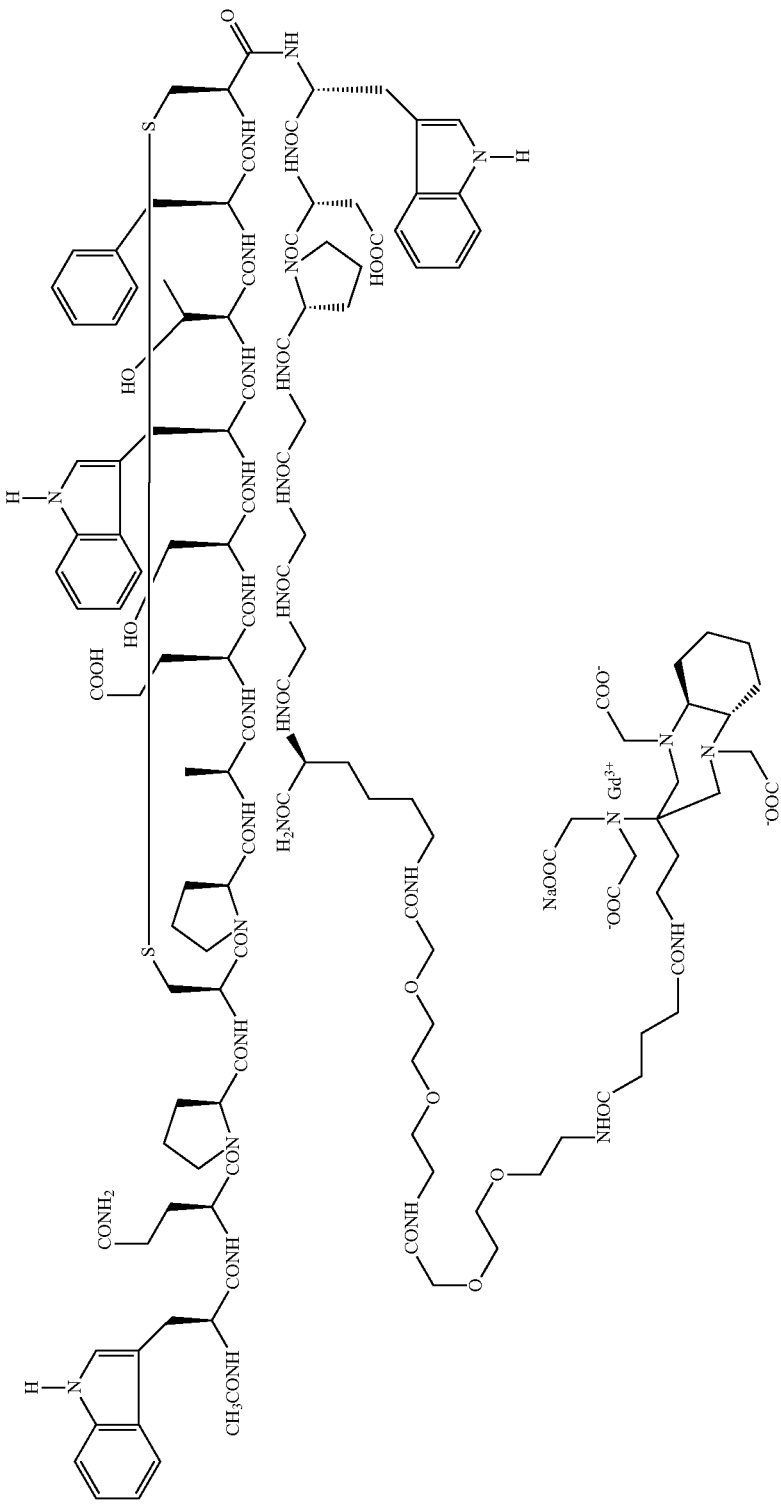

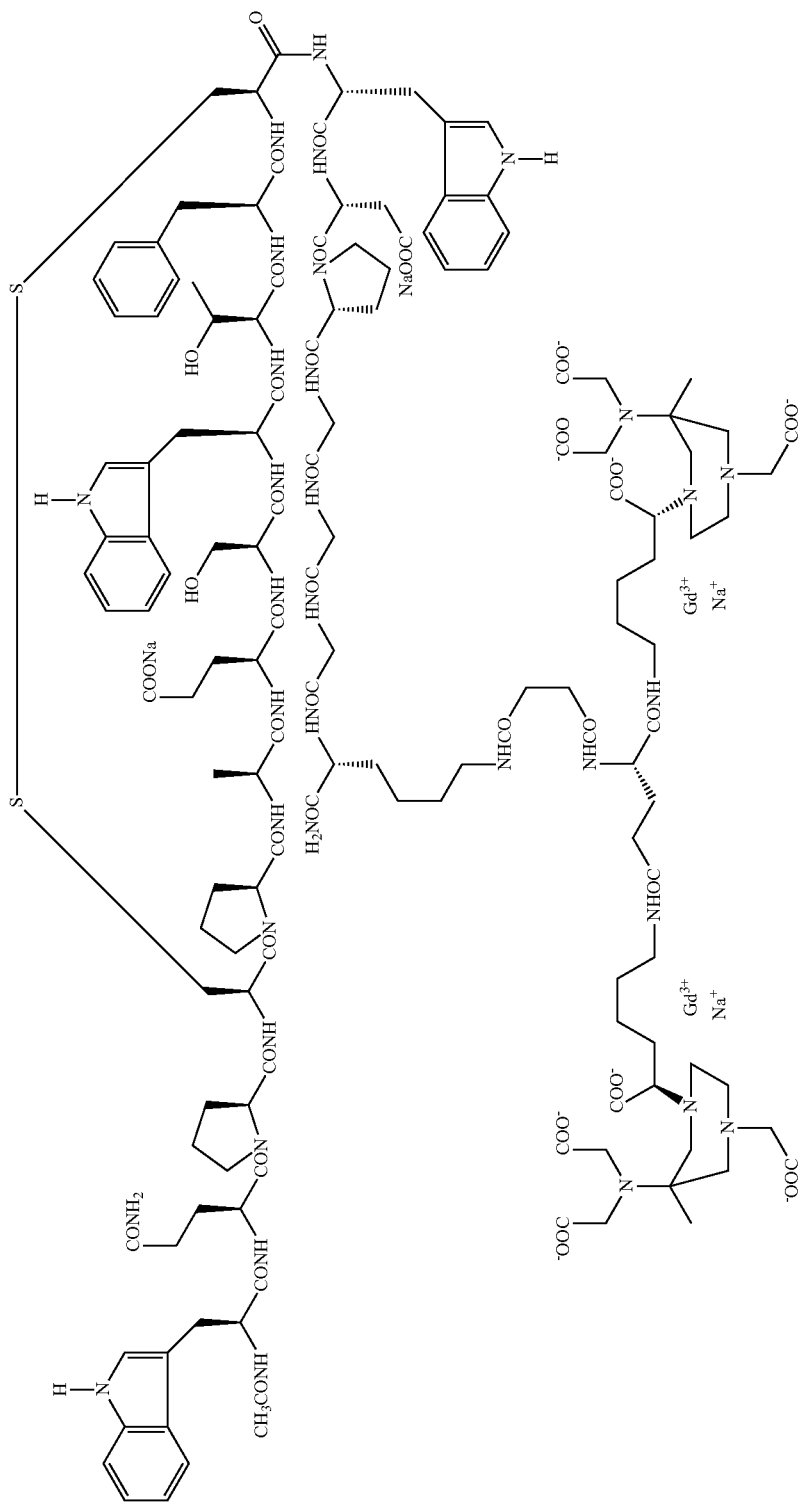

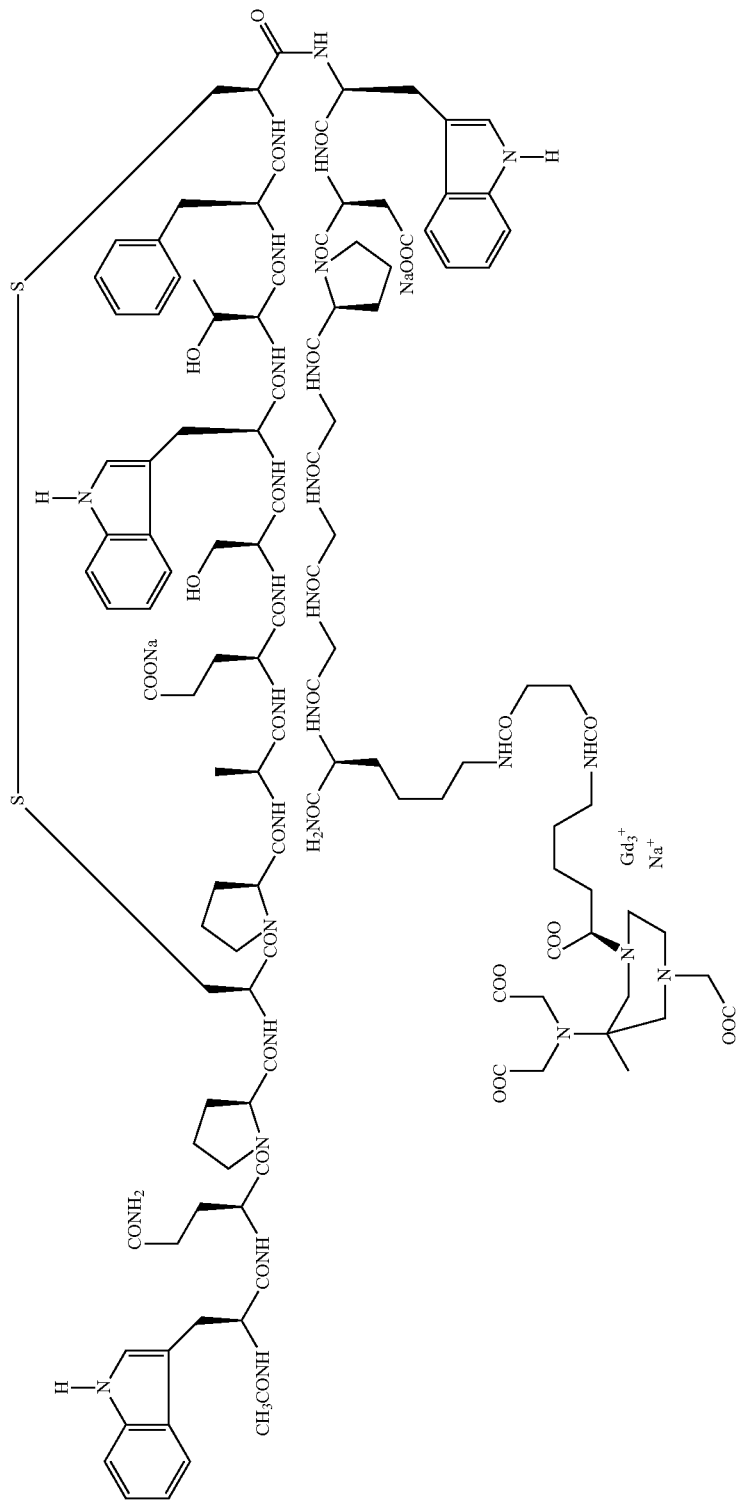
Chelate complex 9
(Seq ID NO: 001)[—Y(—T$_r$)$_s$]

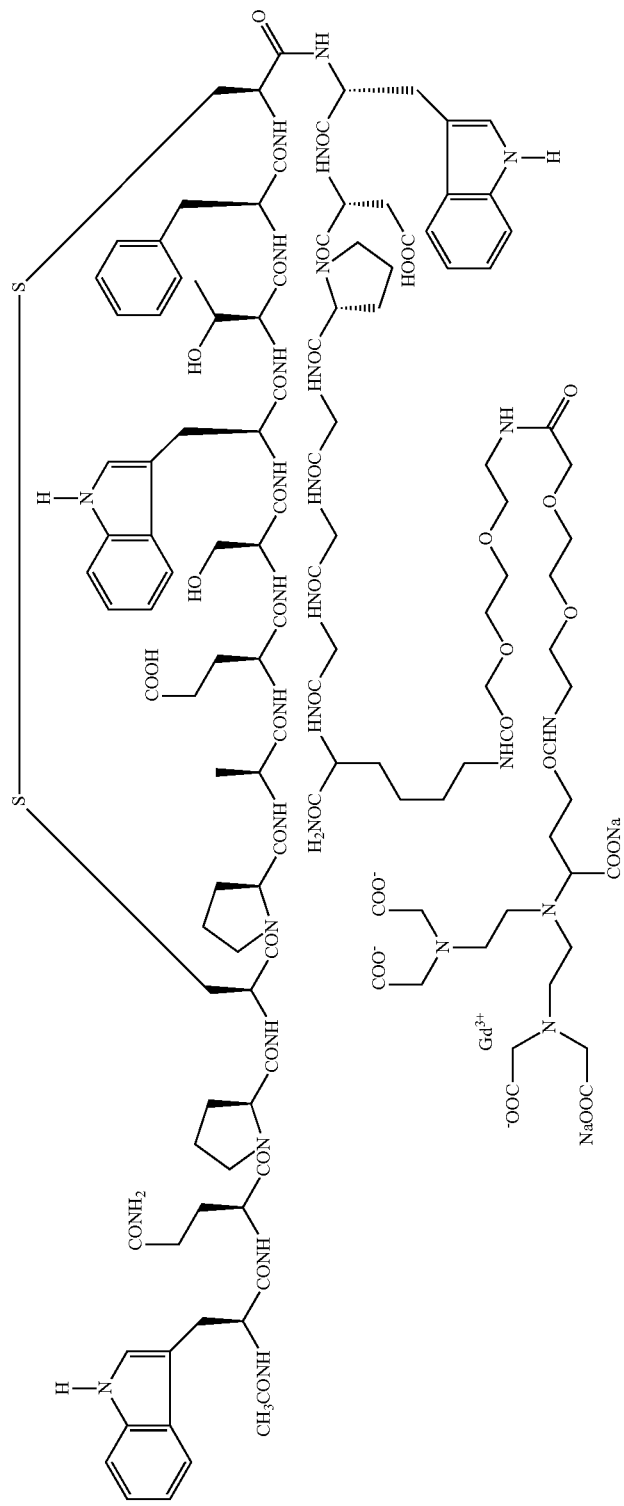

and

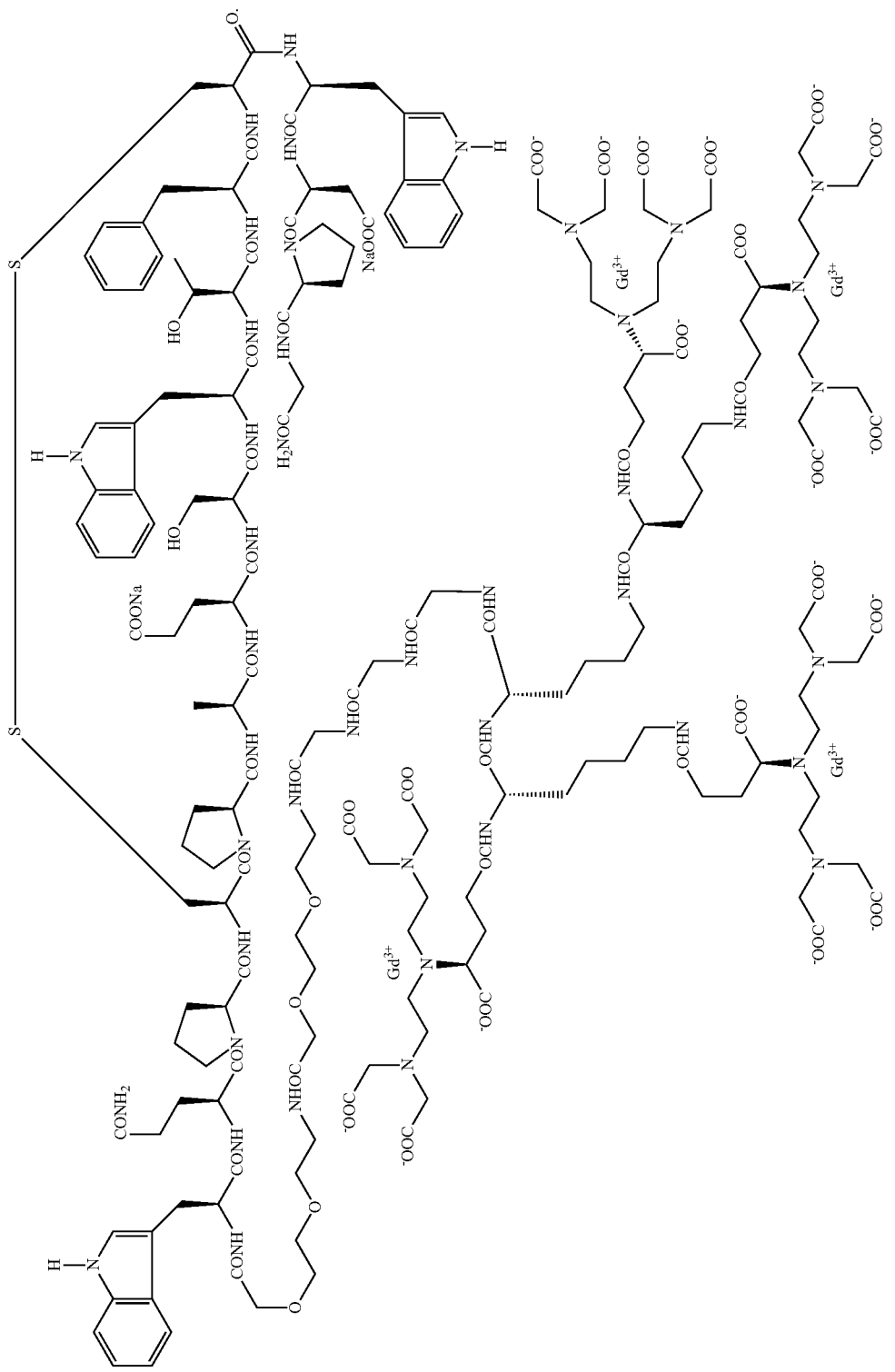
Chelate complex 11
(Seq ID NO: 001)[—Y(—T)$_r$]$_s$

21. A process for the preparation of a compound as defined in claim 1, and of the physiologically acceptable salts thereof, which process comprises:
- a) loading a suitably protected peptide moiety or a selected amino acid on a suitably deprotected/activated resin, followed by subsequent sequential couplings with additional amino acids, peptides or linker sub-units so as to properly assemble the peptide moiety A conjugated with the linker or linkers Y;
- b) coupling the suitably deprotected/activated resin supported A-Y moiety with the selected moiety or moieties T;
- c) cleaving of the coupled compound of step b) from the resin, cyclizing of the peptide so as to convert the —SH groups of cysteine into disulphide bonds —S—S—, and, in case T represents any suitable chelating agent to be labelled, optional subsequent complexation, so as to obtain the desired compound and, optionally, converting it into a physiologically acceptable salt thereof.

22. A pharmaceutical composition comprising, as the active ingredient, an effective amount of a compound of claim 1 or a physiologically acceptable salt thereof, in combination with one or more pharmaceutically acceptable carriers, diluents or excipients.

23. A method for the in vitro detection or measurement of fibrin deposition in biological samples, which method comprises contacting the biological samples with an effective amount of a compound as defined in claim 1, wherein T is a diagnostically active moiety, or a physiologically acceptable salt thereof.

24. A compound according to claim 1 wherein A is a fibrin-binding peptide moiety consisting of the amino acid sequence WQPC*PAESWTFC*WDP (SEQ ID NO: 001).

* * * * *

```
                              SEQUENCE LISTING

<160> NUMBER OF SEQ ID NOS: 39

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (4)..(12)

<400> SEQUENCE: 1

Trp Gln Pro Cys Pro Ala Glu Ser Trp Thr Phe Cys Trp Asp Pro
1               5                   10                  15

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (8)..(16)

<400> SEQUENCE: 2

Gly Pro Pro Gly Trp Gln Pro Cys Pro Trp Glu Ser Trp Thr Phe Cys
1               5                   10                  15

Trp Asp Pro

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (5)..(13)

<400> SEQUENCE: 3

Gly Gly Arg Gly Trp Gln Pro Cys Pro Trp Glu Ser Trp Thr Phe Cys
1               5                   10                  15

Trp Asp Pro

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (5)..(13)

<400> SEQUENCE: 4

Gly Trp Gln Pro Cys Pro Trp Glu Ser Trp Thr Phe Cys Trp Asp Pro
```

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: MISC_FEATURE
<222> LOCATION: (5)..(5)
<223> OTHER INFORMATION: Xaa is 8-Amino-3, 6-dioxaoctanoic acid
<220> FEATURE:
<221> NAME/KEY: DISULFID
<222> LOCATION: (9)..(17)

<400> SEQUENCE: 5

Ser Gly Ser Gly Xaa Trp Gln Pro Cys Pro Trp Glu Ser Trp Thr Phe
1               5                   10                  15

Cys Trp Asp Pro
            20

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (4)..(12)
<220> FEATURE:
<221> NAME/KEY: MISC_FEATURE
<222> LOCATION: (11)..(11)
<223> OTHER INFORMATION: Xaa is Cha (2-Cyclohexyl-L-alanine)

<400> SEQUENCE: 6

Trp Gln Pro Cys Pro Trp Glu Ser Trp Thr Xaa Cys Trp Asp Pro
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (4)..(12)
<220> FEATURE:
<221> NAME/KEY: MISC_FEATURE
<222> LOCATION: (11)..(11)
<223> OTHER INFORMATION: Xaa is Ffe4 (L-4-Fluorophenylalanine)

<400> SEQUENCE: 7

Trp Gln Pro Cys Pro Trp Glu Ser Trp Thr Xaa Cys Trp Asp Pro
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (4)..(12)

```
<220> FEATURE:
<221> NAME/KEY: MISC_FEATURE
<222> LOCATION: (11)..(11)
<223> OTHER INFORMATION: Xaa is F34fe (L-3, 4-difluorophenylalanine)

<400> SEQUENCE: 8

Trp Gln Pro Cys Pro Trp Glu Ser Trp Thr Xaa Cys Trp Asp Pro
 1               5                  10                  15

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (6)..(14)

<400> SEQUENCE: 9

Arg Gly Trp Gln Pro Cys Pro Trp Glu Ser Trp Thr Phe Cys Trp Asp
 1               5                  10                  15

Pro

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (5)..(13)

<400> SEQUENCE: 10

Arg Trp Gln Pro Cys Pro Trp Glu Ser Trp Thr Phe Cys Trp Asp Pro
 1               5                  10                  15

<210> SEQ ID NO 11
<211> LENGTH: 23
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (12)..(20)

<400> SEQUENCE: 11

Ser Gly Ser Gly Ser Gly Ser Gly Trp Gln Pro Cys Pro Trp Glu Ser
 1               5                  10                  15

Trp Thr Phe Cys Trp Asp Pro
            20

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (7)..(15)

<400> SEQUENCE: 12
```

```
Lys Lys Gly Trp Gln Pro Cys Pro Trp Glu Ser Trp Thr Phe Cys Trp
1               5                   10                  15

Asp Pro

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (10)..(18)

<400> SEQUENCE: 13

Lys Gly Lys Gly Lys Gly Trp Gln Pro Cys Pro Trp Glu Ser Trp Thr
1               5                   10                  15

Phe Cys Trp Asp Pro
            20

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: MISC_FEATURE
<222> LOCATION: (1)..(1)
<223> OTHER INFORMATION: Xaa is S(Galnac)
      (O-(2-Acteoamido-2-deoxy-alpha-D-galactopyranosyl)-L-serine
<220> FEATURE:
<221> NAME/KEY: DISULFID
<222> LOCATION: (5)..(13)

<400> SEQUENCE: 14

Xaa Trp Gln Pro Cys Pro Trp Glu Ser Trp Thr Phe Cys Trp Asp Pro
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: MISC_FEATURE
<222> LOCATION: (1)..(1)
<223> OTHER INFORMATION: Xaa is Thf2ca (tetrahydro-furan-2-
      carboxaldehyde)
<220> FEATURE:
<221> NAME/KEY: DISULFID
<222> LOCATION: (5)..(13)

<400> SEQUENCE: 15

Xaa Trp Gln Pro Cys Pro Trp Glu Ser Trp Thr Phe Cys Trp Asp Pro
1               5                   10                  15

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence:  synthetic
      peptide
<220> FEATURE:
```

<221> NAME/KEY: DISULFID
<222> LOCATION: (8)..(16)

<400> SEQUENCE: 16

Arg Arg Gly Gly Trp Gln Pro Cys Pro Trp Glu Ser Trp Thr Phe Cys
1               5                   10                  15

Trp Asp Pro

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: MISC_FEATURE
<222> LOCATION: (1)..(1)
<223> OTHER INFORMATION: Xaa is S(Galnac)
      (O-(2-Acteoamido-2-deoxy-alpha-D-galactopyranosyl)-L-serine
<220> FEATURE:
<221> NAME/KEY: MISC_FEATURE
<222> LOCATION: (2)..(2)
<223> OTHER INFORMATION: Xaa is 8-Amino-3, 6-dioxaoctanoic acid
<220> FEATURE:
<221> NAME/KEY: DISULFID
<222> LOCATION: (6)..(14)

<400> SEQUENCE: 17

Xaa Xaa Trp Gln Pro Cys Pro Trp Glu Ser Trp Thr Phe Cys Trp Asp
1               5                   10                  15

Pro

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (4)..(12)
<220> FEATURE:
<221> NAME/KEY: MISC_FEATURE
<222> LOCATION: (5)..(5)
<223> OTHER INFORMATION: Xaa is Hypt4 (trans-4-hydroxy-L-proline)

<400> SEQUENCE: 18

Trp Gln Pro Cys Xaa Trp Glu Ser Trp Thr Phe Cys Trp Asp Pro
1               5                   10                  15

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (8)..(16)

<400> SEQUENCE: 19

Gly Pro Pro Gly Trp Gln Pro Cys Pro Ala Glu Ser Trp Thr Phe Cys
1               5                   10                  15

Trp Asp Pro

```
<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (8)..(16)

<400> SEQUENCE: 20

Gly Gly Arg Gly Trp Gln Pro Cys Pro Ala Glu Ser Trp Thr Phe Cys
1               5                  10                  15

Trp Asp Pro

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (7)..(15)

<400> SEQUENCE: 21

Lys Lys Gly Trp Gln Pro Cys Pro Ala Glu Ser Trp Thr Phe Cys Trp
1               5                  10                  15

Asp Pro

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (10)..(18)

<400> SEQUENCE: 22

Lys Gly Lys Gly Lys Gly Trp Gln Pro Cys Pro Ala Glu Ser Trp Thr
1               5                  10                  15

Phe Cys Trp Asp Pro
            20

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (5)..(13)

<400> SEQUENCE: 23

Gly Trp Gln Pro Cys Pro Ala Glu Ser Trp Thr Phe Cys Trp Asp Pro
1               5                  10                  15

<210> SEQ ID NO 24
<211> LENGTH: 23
<212> TYPE: PRT
<213> ORGANISM: Artificial Sequence
```

```
<220> FEATURE:
<223> OTHER INFORMATION: Description of Artificial Sequence:  synthetic
      peptide
<220> FEATURE:
<221> NAME/KEY: DISULFID
<222> LOCATION: (12)..(20)

<400> SEQUENCE: 24

Ser Gly Ser Gly Ser Gly Ser Gly Trp Gln Pro Cys Pro Ala Glu Ser
1               5                   10                  15

Trp Thr Phe Cys Trp Asp Pro
            20

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (4)..(12)
<220> FEATURE:
<221> NAME/KEY: MISC_FEATURE
<222> LOCATION: (11)..(11)
<223> OTHER INFORMATION: Xaa is Ffe4 (L-4-Fluorophenylalanine)

<400> SEQUENCE: 25

Trp Gln Pro Cys Pro Ala Glu Ser Trp Thr Xaa Cys Trp Asp Pro
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (4)..(12)
<220> FEATURE:
<221> NAME/KEY: MISC_FEATURE
<222> LOCATION: (11)..(11)
<223> OTHER INFORMATION: Xaa is Cha (2-Cyclohexyl-L-alanine)

<400> SEQUENCE: 26

Trp Gln Pro Cys Pro Ala Glu Ser Trp Thr Xaa Cys Trp Asp Pro
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (4)..(12)
<220> FEATURE:
<221> NAME/KEY: MISC_FEATURE
<222> LOCATION: (11)..(11)
<223> OTHER INFORMATION: Xaa is F34fe (L-3, 4-difluorophenylalanine)

<400> SEQUENCE: 27

Trp Gln Pro Cys Pro Ala Glu Ser Trp Thr Xaa Cys Trp Asp Pro
1               5                   10                  15
```

```
<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: MISC_FEATURE
<222> LOCATION: (1)..(1)
<223> OTHER INFORMATION: Xaa is Thf2ca (tetrahydro-furan-2-
      carboxaldehyde)
<220> FEATURE:
<221> NAME/KEY: DISULFID
<222> LOCATION: (5)..(13)

<400> SEQUENCE: 28

Xaa Trp Gln Pro Cys Pro Ala Glu Ser Trp Thr Phe Cys Trp Asp Pro
1               5                   10                  15

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: MISC_FEATURE
<222> LOCATION: (5)..(5)
<223> OTHER INFORMATION: Xaa is 8-Amino-3, 6-dioxaoctanoic acid
<220> FEATURE:
<221> NAME/KEY: DISULFID
<222> LOCATION: (9)..(17)

<400> SEQUENCE: 29

Ser Gly Ser Gly Xaa Trp Gln Pro Cys Pro Ala Glu Ser Trp Thr Phe
1               5                   10                  15

Cys Trp Asp Pro
            20

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (8)..(15)

<400> SEQUENCE: 30

Arg Arg Gly Gly Trp Gln Pro Cys Pro Ala Glu Ser Trp Thr Phe Cys
1               5                   10                  15

Trp Asp Pro

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence:  synthetic
      peptide
<220> FEATURE:
<221> NAME/KEY: DISULFID
<222> LOCATION: (8)..(15)
<220> FEATURE:
<221> NAME/KEY: MISC_FEATURE
<222> LOCATION: (9)..(9)
<223> OTHER INFORMATION: Xaa is Hypt4 (trans-4-hydroxy-L-proline)
```

<400> SEQUENCE: 31

Arg Arg Gly Gly Trp Gln Pro Cys Xaa Trp Glu Ser Trp Thr Phe Cys
1               5                   10                  15

Trp Asp Pro

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (5)..(13)
<220> FEATURE:
<221> NAME/KEY: MISC_FEATURE
<222> LOCATION: (12)..(12)
<223> OTHER INFORMATION: Xaa is Cha (2-Cyclohexyl-L-alanine)

<400> SEQUENCE: 32

Arg Trp Gln Pro Cys Pro Ala Glu Ser Trp Thr Xaa Cys Trp Asp Pro
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (5)..(13)
<220> FEATURE:
<221> NAME/KEY: MISC_FEATURE
<222> LOCATION: (12)..(12)
<223> OTHER INFORMATION: Xaa is Cha (2-Cyclohexyl-L-alanine)

<400> SEQUENCE: 33

Gly Trp Gln Pro Cys Pro Ala Glu Ser Trp Thr Xaa Cys Trp Asp Pro
1               5                   10                  15

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (6)..(14)

<400> SEQUENCE: 34

Arg Gly Trp Gln Pro Cys Pro Ala Glu Ser Trp Thr Phe Cys Trp Asp
1               5                   10                  15

Pro

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID

```
<222> LOCATION: (6)..(14)
<220> FEATURE:
<221> NAME/KEY: MISC_FEATURE
<222> LOCATION: (13)..(13)
<223> OTHER INFORMATION: Xaa is Cha (2-Cyclohexyl-L-alanine)

<400> SEQUENCE: 35

Arg Gly Trp Gln Pro Cys Pro Ala Glu Ser Trp Thr Xaa Cys Trp Asp
1               5                   10                  15

Pro

<210> SEQ ID NO 36
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (5)..(13)

<400> SEQUENCE: 36

Arg Trp Gln Pro Cys Pro Ala Glu Ser Trp Thr Phe Cys Trp Asp Pro
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (4)..(12)

<400> SEQUENCE: 37

Trp Gln Pro Cys Pro Trp Glu Ser Trp Thr Phe Cys Trp Asp Pro
1               5                   10                  15

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: DISULFID
<222> LOCATION: (4)..(12)

<400> SEQUENCE: 38

Trp Gln Pro Cys Pro Trp Glu Ser Trp Thr Phe Cys Trp Asp Pro
1               5                   10                  15

Gly Gly Gly Lys

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: synthetic
      linker
<220> FEATURE:
<221> NAME/KEY:
<222> LOCATION:
```

```
<400> SEQUENCE: 39

Gly Gly Gly Lys
1
```